US012490980B2

(12) United States Patent
Shelton, IV et al.

(10) Patent No.: US 12,490,980 B2
(45) Date of Patent: Dec. 9, 2025

(54) SURGICAL INSTRUMENT HAVING CONTROLLABLE ARTICULATION VELOCITY

(71) Applicant: Cilag GmbH International, Zug (CH)

(72) Inventors: Frederick E. Shelton, IV, Hillsboro, OH (US); David C. Yates, West Chester, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 221 days.

(21) Appl. No.: 15/628,154

(22) Filed: Jun. 20, 2017

(65) Prior Publication Data

US 2018/0360456 A1 Dec. 20, 2018

(51) Int. Cl.

| | |
|---|---|
| ***A61B 17/072*** | (2006.01) |
| ***A61B 17/00*** | (2006.01) |
| ***A61B 17/29*** | (2006.01) |
| ***A61B 17/295*** | (2006.01) |

(Continued)

(52) U.S. Cl.

CPC ...... *A61B 17/07207* (2013.01); *A61B 17/295* (2013.01); *A61B 34/20* (2016.02); *A61B 2017/00017* (2013.01); *A61B 2017/00022* (2013.01); *A61B 2017/00154* (2013.01); *A61B 2017/0019* (2013.01); *A61B 2017/00398* (2013.01); *A61B 2017/2927* (2013.01); *A61B 2034/2051* (2016.02); *A61B 2034/2059* (2016.02); *A61B 2090/067* (2016.02)

(58) Field of Classification Search

CPC . A61B 17/07207; A61B 34/20; A61B 17/295; A61B 2034/2051; A61B 2090/067

USPC .......................................................... 318/560

See application file for complete search history.

(56) References Cited

U.S. PATENT DOCUMENTS

| | | | |
|---|---|---|---|
| 66,052 | A | 6/1867 | Smith |
| 662,587 | A | 11/1900 | Blake |
| 670,748 | A | 3/1901 | Weddeler |

(Continued)

FOREIGN PATENT DOCUMENTS

| | | | |
|---|---|---|---|
| AU | 2012200594 | A1 | 2/2012 |
| AU | 2012203035 | A1 | 6/2012 |

(Continued)

OTHER PUBLICATIONS

Motor-driven surgical stapler improvements, Published in Feb. 2008, Kenneth Mason Publications Ltd, Research Disclosure journal, ISSN 0374-4353 (Year 2008) (Year: 2008).*

(Continued)

*Primary Examiner* — Kawing Chan

(74) *Attorney, Agent, or Firm* — Lempia Summerfield Katz LLC

(57) ABSTRACT

A motorized surgical instrument is disclosed. The surgical instrument includes a motor configured to drive an end effector between an unarticulated position and an articulated position, a sensor configured to detect a position of the end effector and provide a signal indicative of the position of the end effector, and a control circuit coupled to the sensor and the motor. The control circuit is configured to detect a position of the end effector via the signal provided by the sensor and provide a drive signal to the motor to drive the end effector at a velocity corresponding to the signal indicative of the position of the end effector.

10 Claims, 28 Drawing Sheets

(51) Int. Cl.
*A61B 34/20* (2016.01)
*A61B 90/00* (2016.01)

(56) References Cited

U.S. PATENT DOCUMENTS

| | | | |
|---|---|---|---|
| 719,487 | A | 2/1903 | Minor |
| 804,229 | A | 11/1905 | Hutchinson |
| 951,393 | A | 3/1910 | Hahn |
| 1,075,556 | A | 10/1913 | Fenoughty |
| 1,188,721 | A | 6/1916 | Bittner |
| 1,306,107 | A | 6/1919 | Elliott |
| 1,314,601 | A | 9/1919 | McCaskey |
| 1,677,337 | A | 7/1928 | Grove |
| 1,794,907 | A | 3/1931 | Kelly |
| 1,849,427 | A | 3/1932 | Hook |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | Chapelle |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,882 | A | 12/1940 | Peck |
| 2,318,379 | A | 5/1943 | Davis et al. |
| 2,329,440 | A | 9/1943 | Place |
| 2,377,581 | A | 6/1945 | Shaffrey |
| 2,406,389 | A | 8/1946 | Lee |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,060,972 | A | 10/1962 | Sheldon |
| 3,075,062 | A | 1/1963 | Laccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,608,549 | A | 9/1971 | Merrill |
| 3,618,842 | A | 11/1971 | Bryan |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,688,966 | A | 9/1972 | Perkins et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,154,122 | A | 5/1979 | Severin |
| 4,160,857 | A | 7/1979 | Nardella et al. |

(56) References Cited

U.S. PATENT DOCUMENTS

| | | | |
|---|---|---|---|
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,198,734 | A | 4/1980 | Brumlik |
| 4,198,982 | A | 4/1980 | Fortner et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,389,963 | A | 6/1983 | Pearson |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |
| 4,402,445 | A | 9/1983 | Green |
| 4,406,621 | A | 9/1983 | Bailey |
| 4,408,692 | A | 10/1983 | Sigel et al. |
| 4,409,057 | A | 10/1983 | Molenda et al. |
| 4,415,112 | A | 11/1983 | Green |
| 4,416,276 | A | 11/1983 | Newton et al. |
| 4,417,890 | A | 11/1983 | Dennehey et al. |
| 4,421,264 | A | 12/1983 | Arter et al. |
| 4,423,456 | A | 12/1983 | Zaidenweber |
| 4,425,915 | A | 1/1984 | Ivanov |
| 4,428,376 | A | 1/1984 | Mericle |
| 4,429,695 | A | 2/1984 | Green |
| 4,430,997 | A | 2/1984 | DiGiovanni et al. |
| 4,434,796 | A | 3/1984 | Karapetian et al. |
| 4,438,659 | A | 3/1984 | Desplats |
| 4,442,964 | A | 4/1984 | Becht |
| 4,448,194 | A | 5/1984 | DiGiovanni et al. |
| 4,451,743 | A | 5/1984 | Suzuki et al. |
| 4,452,376 | A | 6/1984 | Klieman et al. |
| 4,454,887 | A | 6/1984 | Kruger |
| 4,459,519 | A | 7/1984 | Erdman |
| 4,461,305 | A | 7/1984 | Cibley |
| 4,467,805 | A | 8/1984 | Fukuda |
| 4,468,597 | A | 8/1984 | Baumard et al. |
| 4,469,481 | A | 9/1984 | Kobayashi |
| 4,470,414 | A | 9/1984 | Imagawa et al. |
| 4,471,780 | A | 9/1984 | Menges et al. |
| 4,471,781 | A | 9/1984 | Di Giovanni et al. |
| 4,473,077 | A | 9/1984 | Noiles et al. |
| 4,475,679 | A | 10/1984 | Fleury, Jr. |
| 4,478,220 | A | 10/1984 | Di Giovanni et al. |
| 4,480,641 | A | 11/1984 | Failla et al. |
| 4,481,458 | A | 11/1984 | Lane |
| 4,483,562 | A | 11/1984 | Schoolman |
| 4,485,816 | A | 12/1984 | Krumme |
| 4,485,817 | A | 12/1984 | Swiggett |
| 4,486,928 | A | 12/1984 | Tucker et al. |
| 4,488,523 | A | 12/1984 | Shichman |
| 4,489,875 | A | 12/1984 | Crawford et al. |
| 4,493,983 | A | 1/1985 | Taggert |
| 4,494,057 | A | 1/1985 | Hotta |
| 4,499,895 | A | 2/1985 | Takayama |
| 4,500,024 | A | 2/1985 | DiGiovanni et al. |
| D278,081 | S | 3/1985 | Green |
| 4,503,842 | A | 3/1985 | Takayama |
| 4,505,272 | A | 3/1985 | Utyamyshev et al. |
| 4,505,273 | A | 3/1985 | Braun et al. |
| 4,505,414 | A | 3/1985 | Filipi |
| 4,506,671 | A | 3/1985 | Green |
| 4,512,038 | A | 4/1985 | Alexander et al. |
| 4,520,817 | A | 6/1985 | Green |
| 4,522,327 | A | 6/1985 | Korthoff et al. |
| 4,526,174 | A | 7/1985 | Froehlich |
| 4,527,724 | A | 7/1985 | Chow et al. |
| 4,530,357 | A | 7/1985 | Pawloski et al. |
| 4,530,453 | A | 7/1985 | Green |
| 4,531,522 | A | 7/1985 | Bedi et al. |
| 4,532,927 | A | 8/1985 | Miksza, Jr. |
| 4,540,202 | A | 9/1985 | Amphoux et al. |
| 4,548,202 | A | 10/1985 | Duncan |
| 4,556,058 | A | 12/1985 | Green |
| 4,560,915 | A | 12/1985 | Soultanian |
| 4,565,109 | A | 1/1986 | Tsay |
| 4,565,189 | A | 1/1986 | Mabuchi |
| 4,566,620 | A | 1/1986 | Green et al. |
| 4,569,346 | A | 2/1986 | Poirier |
| 4,569,469 | A | 2/1986 | Mongeon et al. |
| 4,571,213 | A | 2/1986 | Ishimoto |
| 4,573,468 | A | 3/1986 | Conta et al. |
| 4,573,469 | A | 3/1986 | Golden et al. |
| 4,573,622 | A | 3/1986 | Green et al. |
| 4,576,165 | A | 3/1986 | Green et al. |
| 4,576,167 | A | 3/1986 | Noiles |
| 4,580,712 | A | 4/1986 | Green |
| 4,585,153 | A | 4/1986 | Failla et al. |
| 4,586,501 | A | 5/1986 | Claracq |
| 4,586,502 | A | 5/1986 | Bedi et al. |
| 4,589,416 | A | 5/1986 | Green |
| 4,589,582 | A | 5/1986 | Bilotti |
| 4,589,870 | A | 5/1986 | Citrin et al. |
| 4,591,085 | A | 5/1986 | Di Giovanni |
| RE32,214 | E | 7/1986 | Schramm |
| 4,597,753 | A | 7/1986 | Turley |
| 4,600,037 | A | 7/1986 | Hatten |
| 4,604,786 | A | 8/1986 | Howie, Jr. |
| 4,605,001 | A | 8/1986 | Rothfuss et al. |
| 4,605,004 | A | 8/1986 | Di Giovanni et al. |
| 4,606,343 | A | 8/1986 | Conta et al. |
| 4,607,636 | A | 8/1986 | Kula et al. |
| 4,607,638 | A | 8/1986 | Crainich |
| 4,608,980 | A | 9/1986 | Aihara |
| 4,608,981 | A | 9/1986 | Rothfuss et al. |
| 4,610,250 | A | 9/1986 | Green |
| 4,610,383 | A | 9/1986 | Rothfuss et al. |
| 4,612,933 | A | 9/1986 | Brinkerhoff et al. |

(56) References Cited

U.S. PATENT DOCUMENTS

D286,180 S 10/1986 Korthoff
D286,442 S 10/1986 Korthoff et al.
4,617,893 A 10/1986 Donner et al.
4,617,914 A 10/1986 Ueda
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,869,414 A 9/1989 Green et al.
4,869,415 A 9/1989 Fox
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa

(56) References Cited

U.S. PATENT DOCUMENTS 4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,661 A 4/1991 Michelson
5,012,411 A 4/1991 Policastro et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,129,570 A 7/1992 Schulze et al.
5,137,198 A 8/1992 Nobis et al.
5,139,513 A 8/1992 Segato
5,141,144 A 8/1992 Foslien et al.
5,142,932 A 9/1992 Moya et al.
5,151,102 A 9/1992 Kamiyama et al.
5,155,941 A 10/1992 Takahashi et al.
5,156,315 A 10/1992 Green et al.
5,156,609 A 10/1992 Nakao et al.
5,156,614 A 10/1992 Green et al.
5,158,222 A 10/1992 Green et al.
5,158,567 A 10/1992 Green
D330,699 S 11/1992 Gill
5,163,598 A 11/1992 Peters et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.
5,176,677 A 1/1993 Wuchinich
5,176,688 A 1/1993 Narayan et al.
5,181,514 A 1/1993 Solomon et al.
5,187,422 A 2/1993 Izenbaard et al.
5,188,102 A 2/1993 Idemoto et al.
5,188,111 A 2/1993 Yates et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
D338,729 S 8/1993 Sprecklemeier et al.
5,234,447 A 8/1993 Kaster et al.
5,236,269 A 8/1993 Handy
5,236,424 A 8/1993 Imran
5,236,440 A 8/1993 Hlavacek
5,239,981 A 8/1993 Anapliotis
5,240,163 A 8/1993 Stein et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,253,793 A 10/1993 Green et al.
5,258,007 A 11/1993 Spetzler et al.
5,258,008 A 11/1993 Wilk
5,258,009 A 11/1993 Conners
5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.

(56) References Cited

U.S. PATENT DOCUMENTS 5,263,937 A 11/1993 Shipp
5,263,973 A 11/1993 Cook
5,264,218 A 11/1993 Rogozinski
5,268,622 A 12/1993 Philipp
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,281,400 A 1/1994 Berry, Jr.
5,282,806 A 2/1994 Haber et al.
5,282,826 A 2/1994 Quadri
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,310 A 3/1994 Makower et al.
5,291,133 A 3/1994 Gokhale et al.
5,292,053 A 3/1994 Bilotti et al.
5,293,024 A 3/1994 Sugahara et al.
5,297,714 A 3/1994 Kramer
5,303,606 A 4/1994 Kokinda
5,304,204 A 4/1994 Bregen
D347,474 S 5/1994 Olson
5,307,976 A 5/1994 Olson et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,935 A 5/1994 Kortenbach et al.
5,313,967 A 5/1994 Lieber et al.
5,314,424 A 5/1994 Nicholas
5,314,445 A 5/1994 Heidmueller nee Degwitz et al.
5,314,466 A 5/1994 Stern et al.
5,318,221 A 6/1994 Green et al.
5,320,627 A 6/1994 Sorensen et al.
D348,930 S 7/1994 Olson
5,326,013 A 7/1994 Green et al.
5,329,923 A 7/1994 Lundquist
5,330,486 A 7/1994 Wilk
5,330,487 A 7/1994 Thornton et al.
5,330,502 A 7/1994 Hassler et al.
5,331,971 A 7/1994 Bales et al.
5,332,142 A 7/1994 Robinson et al.
5,333,422 A 8/1994 Warren et al.
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,338,317 A 8/1994 Hasson et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,454 A 9/1994 Clarke et al.
5,346,504 A 9/1994 Ortiz et al.
5,348,259 A 9/1994 Blanco et al.
5,350,104 A 9/1994 Main et al.
5,350,355 A 9/1994 Sklar
5,350,388 A 9/1994 Epstein
5,350,391 A 9/1994 Lacovelli
5,350,400 A 9/1994 Esposito et al.
5,352,229 A 10/1994 Goble et al.
5,352,235 A 10/1994 Koros et al.
5,352,238 A 10/1994 Green et al.
5,353,798 A 10/1994 Sieben
5,354,250 A 10/1994 Christensen
5,354,303 A 10/1994 Spaeth et al.
5,356,006 A 10/1994 Alpern et al.
5,356,064 A 10/1994 Green et al.
5,358,506 A 10/1994 Green et al.
5,358,510 A 10/1994 Luscombe et al.
5,359,231 A 10/1994 Flowers et al.
D352,780 S 11/1994 Glaeser et al.
5,359,993 A 11/1994 Slater et al.
5,360,305 A 11/1994 Kerrigan
5,360,428 A 11/1994 Hutchinson, Jr.
5,361,902 A 11/1994 Abidin et al.
5,364,001 A 11/1994 Bryan
5,364,002 A 11/1994 Green et al.
5,364,003 A 11/1994 Williamson, IV
5,366,133 A 11/1994 Geiste
5,366,134 A 11/1994 Green et al.
5,366,479 A 11/1994 McGarry et al.
5,368,015 A 11/1994 Wilk
5,368,592 A 11/1994 Stern et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.

(56) References Cited

U.S. PATENT DOCUMENTS 5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,654 A 7/1995 Nic
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.
5,507,425 A 4/1996 Ziglioli
5,507,426 A 4/1996 Young et al.
5,507,773 A 4/1996 Huitema et al.
5,509,596 A 4/1996 Green et al.
5,509,916 A 4/1996 Taylor
5,509,918 A 4/1996 Romano
5,511,564 A 4/1996 Wilk
5,514,129 A 5/1996 Smith
5,514,149 A 5/1996 Green et al.
5,514,157 A 5/1996 Nicholas et al.
5,518,163 A 5/1996 Hooven
5,518,164 A 5/1996 Hooven
5,520,609 A 5/1996 Moll et al.
5,520,634 A 5/1996 Fox et al.
5,520,678 A 5/1996 Heckele et al.
5,520,700 A 5/1996 Beyar et al.
5,522,817 A 6/1996 Sander et al.
5,522,831 A 6/1996 Sleister et al.
5,527,264 A 6/1996 Moll et al.
5,527,320 A 6/1996 Carruthers et al.
5,529,235 A 6/1996 Boiarski et al.
D372,086 S 7/1996 Grasso et al.
5,531,305 A 7/1996 Roberts et al.
5,531,744 A 7/1996 Nardella et al.
5,531,856 A 7/1996 Moll et al.
5,533,521 A 7/1996 Granger
5,533,581 A 7/1996 Barth et al.
5,533,661 A 7/1996 Main et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,540,705 A 7/1996 Meade et al.
5,541,376 A 7/1996 Ladtkow et al.
5,541,489 A 7/1996 Dunstan
5,542,594 A 8/1996 McKean et al.
5,542,945 A 8/1996 Fritzsch
5,542,949 A 8/1996 Yoon
5,543,119 A 8/1996 Sutter et al.

(56) References Cited

U.S. PATENT DOCUMENTS 5,543,695 A 8/1996 Culp et al.
5,544,802 A 8/1996 Crainich
5,547,117 A 8/1996 Hamblin et al.
5,549,583 A 8/1996 Sanford et al.
5,549,621 A 8/1996 Bessler et al.
5,549,627 A 8/1996 Kieturakis
5,549,628 A 8/1996 Cooper et al.
5,549,637 A 8/1996 Crainich
5,551,622 A 9/1996 Yoon
5,553,624 A 9/1996 Francese et al.
5,553,675 A 9/1996 Pitzen et al.
5,553,765 A 9/1996 Knodel et al.
5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis
5,558,671 A 9/1996 Yates
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 Mckeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li
5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
5,607,094 A 3/1997 Clark et al.
5,607,095 A 3/1997 Smith et al.
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.

(56) References Cited

U.S. PATENT DOCUMENTS

| | | | |
|---|---|---|---|
| 5,669,907 | A | 9/1997 | Platt, Jr. et al. |
| 5,669,918 | A | 9/1997 | Balazs et al. |
| 5,672,945 | A | 9/1997 | Krause |
| 5,673,840 | A | 10/1997 | Schulze et al. |
| 5,673,841 | A | 10/1997 | Schulze et al. |
| 5,673,842 | A | 10/1997 | Bittner et al. |
| 5,674,184 | A | 10/1997 | Hassler, Jr. |
| 5,674,286 | A | 10/1997 | D'Alessio et al. |
| 5,678,748 | A | 10/1997 | Plyley et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,681,341 | A | 10/1997 | Lunsford et al. |
| 5,683,349 | A | 11/1997 | Makower et al. |
| 5,685,474 | A | 11/1997 | Seeber |
| 5,686,090 | A | 11/1997 | Schilder et al. |
| 5,688,270 | A | 11/1997 | Yates et al. |
| 5,690,269 | A | 11/1997 | Bolanos et al. |
| 5,690,675 | A | 11/1997 | Sawyer et al. |
| 5,692,668 | A | 12/1997 | Schulze et al. |
| 5,693,020 | A | 12/1997 | Rauh |
| 5,693,042 | A | 12/1997 | Boiarski et al. |
| 5,693,051 | A | 12/1997 | Schulze et al. |
| 5,695,494 | A | 12/1997 | Becker |
| 5,695,502 | A | 12/1997 | Pier et al. |
| 5,695,504 | A | 12/1997 | Gifford, III et al. |
| 5,695,524 | A | 12/1997 | Kelley et al. |
| 5,697,542 | A | 12/1997 | Knodel et al. |
| 5,697,543 | A | 12/1997 | Burdorff |
| 5,697,909 | A | 12/1997 | Eggers et al. |
| 5,697,943 | A | 12/1997 | Sauer et al. |
| 5,700,270 | A | 12/1997 | Peyser et al. |
| 5,700,276 | A | 12/1997 | Benecke |
| 5,702,387 | A | 12/1997 | Arts et al. |
| 5,702,408 | A | 12/1997 | Wales et al. |
| 5,702,409 | A | 12/1997 | Rayburn et al. |
| 5,704,087 | A | 1/1998 | Strub |
| 5,704,534 | A | 1/1998 | Huitema et al. |
| 5,706,997 | A | 1/1998 | Green et al. |
| 5,706,998 | A | 1/1998 | Plyley et al. |
| 5,707,392 | A | 1/1998 | Kortenbach |
| 5,709,334 | A | 1/1998 | Sorrentino et al. |
| 5,709,335 | A | 1/1998 | Heck |
| 5,709,680 | A | 1/1998 | Yates et al. |
| 5,709,706 | A | 1/1998 | Kienzle et al. |
| 5,711,472 | A | 1/1998 | Bryan |
| 5,711,960 | A | 1/1998 | Shikinami |
| 5,712,460 | A | 1/1998 | Carr et al. |
| 5,713,128 | A | 2/1998 | Schrenk et al. |
| 5,713,505 | A | 2/1998 | Huitema |
| 5,713,895 | A | 2/1998 | Lontine et al. |
| 5,713,896 | A | 2/1998 | Nardella |
| 5,713,920 | A | 2/1998 | Bezwada et al. |
| 5,715,604 | A | 2/1998 | Lanzoni |
| 5,715,836 | A | 2/1998 | Kliegis et al. |
| 5,715,987 | A | 2/1998 | Kelley et al. |
| 5,715,988 | A | 2/1998 | Palmer |
| 5,716,352 | A | 2/1998 | Viola et al. |
| 5,716,366 | A | 2/1998 | Yates |
| 5,718,359 | A | 2/1998 | Palmer et al. |
| 5,718,360 | A | 2/1998 | Green et al. |
| 5,718,548 | A | 2/1998 | Cotellessa |
| 5,718,714 | A | 2/1998 | Livneh |
| 5,720,744 | A | 2/1998 | Eggleston et al. |
| D393,067 | S | 3/1998 | Geary et al. |
| 5,724,025 | A | 3/1998 | Tavori |
| 5,725,536 | A | 3/1998 | Oberlin et al. |
| 5,725,554 | A | 3/1998 | Simon et al. |
| 5,728,110 | A | 3/1998 | Vidal et al. |
| 5,728,113 | A | 3/1998 | Sherts |
| 5,728,121 | A | 3/1998 | Bimbo et al. |
| 5,730,758 | A | 3/1998 | Allgeyer |
| 5,732,821 | A | 3/1998 | Stone et al. |
| 5,732,871 | A | 3/1998 | Clark et al. |
| 5,732,872 | A | 3/1998 | Bolduc et al. |
| 5,733,308 | A | 3/1998 | Daugherty et al. |
| 5,735,445 | A | 4/1998 | Vidal et al. |
| 5,735,848 | A | 4/1998 | Yates et al. |
| 5,735,874 | A | 4/1998 | Measamer et al. |
| 5,736,271 | A | 4/1998 | Cisar et al. |
| 5,738,474 | A | 4/1998 | Blewett |
| 5,738,629 | A | 4/1998 | Moll et al. |
| 5,738,648 | A | 4/1998 | Lands et al. |
| 5,741,271 | A | 4/1998 | Nakao et al. |
| 5,743,456 | A | 4/1998 | Jones et al. |
| 5,747,953 | A | 5/1998 | Philipp |
| 5,749,889 | A | 5/1998 | Bacich et al. |
| 5,749,893 | A | 5/1998 | Vidal et al. |
| 5,749,896 | A | 5/1998 | Cook |
| 5,749,968 | A | 5/1998 | Melanson et al. |
| 5,752,644 | A | 5/1998 | Bolanos et al. |
| 5,752,965 | A | 5/1998 | Francis et al. |
| 5,752,970 | A | 5/1998 | Yoon |
| 5,752,973 | A | 5/1998 | Kieturakis |
| 5,755,717 | A | 5/1998 | Yates et al. |
| 5,755,726 | A | 5/1998 | Pratt et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,765,565 | A | 6/1998 | Adair |
| 5,766,188 | A | 6/1998 | Igaki |
| 5,766,205 | A | 6/1998 | Zvenyatsky et al. |
| 5,769,303 | A | 6/1998 | Knodel et al. |
| 5,769,748 | A | 6/1998 | Eyerly et al. |
| 5,769,791 | A | 6/1998 | Benaron et al. |
| 5,769,892 | A | 6/1998 | Kingwell |
| 5,772,099 | A | 6/1998 | Gravener |
| 5,772,379 | A | 6/1998 | Evensen |
| 5,772,578 | A | 6/1998 | Heimberger et al. |
| 5,772,659 | A | 6/1998 | Becker et al. |
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,748 | A | 7/1998 | Palmer et al. |
| 5,782,749 | A | 7/1998 | Riza |
| 5,782,859 | A | 7/1998 | Nicholas et al. |
| 5,784,934 | A | 7/1998 | Izumisawa |
| 5,785,232 | A | 7/1998 | Vidal et al. |
| 5,785,647 | A | 7/1998 | Tompkins et al. |
| 5,787,897 | A | 8/1998 | Kieturakis |
| 5,791,231 | A | 8/1998 | Cohn et al. |
| 5,792,135 | A | 8/1998 | Madhani et al. |
| 5,792,162 | A | 8/1998 | Jolly et al. |
| 5,792,165 | A | 8/1998 | Klieman et al. |
| 5,792,573 | A | 8/1998 | Pitzen et al. |
| 5,794,834 | A | 8/1998 | Hamblin et al. |
| 5,796,188 | A | 8/1998 | Bays |
| 5,797,536 | A | 8/1998 | Smith et al. |
| 5,797,537 | A | 8/1998 | Oberlin et al. |
| 5,797,538 | A | 8/1998 | Heaton et al. |
| 5,797,637 | A | 8/1998 | Ervin |
| 5,797,900 | A | 8/1998 | Madhani et al. |
| 5,797,906 | A | 8/1998 | Rhum et al. |
| 5,797,927 | A | 8/1998 | Yoon |
| 5,797,941 | A | 8/1998 | Schulze et al. |
| 5,797,959 | A | 8/1998 | Castro et al. |
| 5,799,857 | A | 9/1998 | Robertson et al. |
| 5,800,379 | A | 9/1998 | Edwards |
| 5,800,423 | A | 9/1998 | Jensen |
| 5,804,726 | A | 9/1998 | Geib et al. |
| 5,804,936 | A | 9/1998 | Brodsky et al. |
| 5,806,676 | A | 9/1998 | Wasgien |
| 5,807,241 | A | 9/1998 | Heimberger |
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |
| 5,810,721 | A | 9/1998 | Mueller et al. |
| 5,810,811 | A | 9/1998 | Yates et al. |

(56) References Cited

U.S. PATENT DOCUMENTS

| | | | |
|---|---|---|---|
| 5,810,846 | A | 9/1998 | Virnich et al. |
| 5,810,855 | A | 9/1998 | Rayburn et al. |
| 5,812,188 | A | 9/1998 | Adair |
| 5,813,813 | A | 9/1998 | Daum et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,084 | A | 10/1998 | Jensen |
| 5,817,091 | A | 10/1998 | Nardella et al. |
| 5,817,093 | A | 10/1998 | Williamson, IV et al. |
| 5,817,109 | A | 10/1998 | McGarry et al. |
| 5,817,119 | A | 10/1998 | Klieman et al. |
| 5,820,009 | A | 10/1998 | Melling et al. |
| 5,823,066 | A | 10/1998 | Huitema et al. |
| 5,824,333 | A | 10/1998 | Scopelianos et al. |
| 5,826,776 | A | 10/1998 | Schulze et al. |
| 5,827,271 | A | 10/1998 | Buysse et al. |
| 5,827,298 | A | 10/1998 | Hart et al. |
| 5,827,323 | A | 10/1998 | Klieman et al. |
| 5,829,662 | A | 11/1998 | Allen et al. |
| 5,830,598 | A | 11/1998 | Patterson |
| 5,833,690 | A | 11/1998 | Yates et al. |
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |
| 5,843,097 | A | 12/1998 | Mayenberger et al. |
| 5,843,122 | A | 12/1998 | Riza |
| 5,843,132 | A | 12/1998 | Ilvento |
| 5,843,169 | A | 12/1998 | Taheri |
| 5,846,254 | A | 12/1998 | Schulze et al. |
| 5,847,566 | A | 12/1998 | Marritt et al. |
| 5,849,011 | A | 12/1998 | Jones et al. |
| 5,849,020 | A | 12/1998 | Long et al. |
| 5,849,023 | A | 12/1998 | Mericle |
| 5,851,179 | A | 12/1998 | Ritson et al. |
| 5,851,212 | A | 12/1998 | Zirps et al. |
| 5,853,366 | A | 12/1998 | Dowlatshahi |
| 5,855,311 | A | 1/1999 | Hamblin et al. |
| 5,855,583 | A | 1/1999 | Wang et al. |
| 5,860,581 | A | 1/1999 | Robertson et al. |
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,760 | A | 2/1999 | McGuckin, Jr. |
| 5,868,790 | A | 2/1999 | Vincent et al. |
| 5,871,135 | A | 2/1999 | Williamson IV et al. |
| 5,873,885 | A | 2/1999 | Weidenbenner |
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,878 | A | 4/1999 | Pierce |
| 5,894,979 | A | 4/1999 | Powell |
| 5,897,552 | A | 4/1999 | Edwards et al. |
| 5,897,562 | A | 4/1999 | Bolanos et al. |
| 5,899,824 | A | 5/1999 | Kurtz et al. |
| 5,899,914 | A | 5/1999 | Zirps et al. |
| 5,901,895 | A | 5/1999 | Heaton et al. |
| 5,902,312 | A | 5/1999 | Frater et al. |
| 5,903,117 | A | 5/1999 | Gregory |
| 5,904,647 | A | 5/1999 | Ouchi |
| 5,904,693 | A | 5/1999 | Dicesare et al. |
| 5,904,702 | A | 5/1999 | Ek et al. |
| 5,906,577 | A | 5/1999 | Beane et al. |
| 5,906,625 | A | 5/1999 | Bito et al. |
| 5,907,211 | A | 5/1999 | Hall et al. |
| 5,908,402 | A | 6/1999 | Blythe |
| 5,908,427 | A | 6/1999 | Mckean et al. |
| 5,909,062 | A | 6/1999 | Krietzman |
| 5,911,353 | A | 6/1999 | Bolanos et al. |
| 5,915,616 | A | 6/1999 | Viola et al. |
| 5,916,225 | A | 6/1999 | Kugel |
| 5,918,791 | A | 7/1999 | Sorrentino et al. |
| 5,919,198 | A | 7/1999 | Graves, Jr. et al. |
| 5,921,956 | A | 7/1999 | Grinberg et al. |
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,984,949 | A | 11/1999 | Levin |
| 5,988,479 | A | 11/1999 | Palmer |
| 5,990,379 | A | 11/1999 | Gregory |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |
| 6,013,076 | A | 1/2000 | Goble et al. |
| 6,013,991 | A | 1/2000 | Philipp |
| 6,015,406 | A | 1/2000 | Goble et al. |
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,019,780 | A | 2/2000 | Lombardo et al. |
| 6,022,352 | A | 2/2000 | Vandewalle |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |

(56) References Cited

U.S. PATENT DOCUMENTS

| | | | |
|---|---|---|---|
| 6,027,501 | A | 2/2000 | Goble et al. |
| 6,030,384 | A | 2/2000 | Nezhat |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,126 | A | 3/2000 | Hsieh |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |
| 6,045,560 | A | 4/2000 | Mckean et al. |
| 6,047,861 | A | 4/2000 | Vidal et al. |
| 6,049,145 | A | 4/2000 | Austin et al. |
| 6,050,172 | A | 4/2000 | Corves et al. |
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |
| 6,053,390 | A | 4/2000 | Green et al. |
| 6,053,899 | A | 4/2000 | Slanda et al. |
| 6,053,922 | A | 4/2000 | Krause et al. |
| 6,054,142 | A | 4/2000 | Li et al. |
| 6,055,062 | A | 4/2000 | Dina et al. |
| RE36,720 | E | 5/2000 | Green et al. |
| 6,056,735 | A | 5/2000 | Okada et al. |
| 6,056,746 | A | 5/2000 | Goble et al. |
| 6,059,806 | A | 5/2000 | Hoegerle |
| 6,062,360 | A | 5/2000 | Shields |
| 6,063,020 | A | 5/2000 | Jones et al. |
| 6,063,025 | A | 5/2000 | Bridges et al. |
| 6,063,050 | A | 5/2000 | Manna et al. |
| 6,063,095 | A | 5/2000 | Wang et al. |
| 6,063,097 | A | 5/2000 | Oi et al. |
| 6,063,098 | A | 5/2000 | Houser et al. |
| 6,065,679 | A | 5/2000 | Levie et al. |
| 6,065,919 | A | 5/2000 | Peck |
| 6,066,132 | A | 5/2000 | Chen et al. |
| 6,066,151 | A | 5/2000 | Miyawaki et al. |
| 6,068,627 | A | 5/2000 | Orszulak et al. |
| 6,071,233 | A | 6/2000 | Ishikawa et al. |
| 6,072,299 | A | 6/2000 | Kurle et al. |
| 6,074,386 | A | 6/2000 | Goble et al. |
| 6,074,401 | A | 6/2000 | Gardiner et al. |
| 6,075,441 | A | 6/2000 | Maloney |
| 6,077,280 | A | 6/2000 | Fossum |
| 6,077,286 | A | 6/2000 | Cuschieri et al. |
| 6,077,290 | A | 6/2000 | Marini |
| 6,079,606 | A | 6/2000 | Milliman et al. |
| 6,080,181 | A | 6/2000 | Jensen et al. |
| 6,082,577 | A | 7/2000 | Coates et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,600 | A | 7/2000 | Kortenbach |
| 6,090,106 | A | 7/2000 | Goble et al. |
| 6,090,123 | A | 7/2000 | Culp et al. |
| 6,093,186 | A | 7/2000 | Goble |
| D429,252 | S | 8/2000 | Haitani et al. |
| 6,099,537 | A | 8/2000 | Sugai et al. |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,701 | A | 9/2000 | Nezhat |
| H1904 | H | 10/2000 | Yates et al. |
| 6,126,058 | A | 10/2000 | Adams et al. |
| 6,126,359 | A | 10/2000 | Dittrich et al. |
| 6,126,670 | A | 10/2000 | Walker et al. |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,546 | A | 10/2000 | Koenig et al. |
| 6,142,149 | A | 11/2000 | Steen |
| 6,142,933 | A | 11/2000 | Longo et al. |
| 6,147,135 | A | 11/2000 | Yuan et al. |
| 6,149,660 | A | 11/2000 | Laufer et al. |
| 6,151,323 | A | 11/2000 | O'Connell et al. |
| 6,152,935 | A | 11/2000 | Kammerer et al. |
| 6,155,473 | A | 12/2000 | Tompkins et al. |
| 6,156,056 | A | 12/2000 | Kearns et al. |
| 6,157,169 | A | 12/2000 | Lee |
| 6,159,146 | A | 12/2000 | El Gazayerli |
| 6,159,200 | A | 12/2000 | Verdura et al. |
| 6,159,224 | A | 12/2000 | Yoon |
| 6,162,208 | A | 12/2000 | Hipps |
| 6,162,220 | A | 12/2000 | Nezhat |
| 6,162,537 | A | 12/2000 | Martin et al. |
| 6,165,175 | A | 12/2000 | Wampler et al. |
| 6,165,184 | A | 12/2000 | Verdura et al. |
| 6,165,188 | A | 12/2000 | Saadat et al. |
| 6,167,185 | A | 12/2000 | Smiley et al. |
| 6,168,605 | B1 | 1/2001 | Measamer et al. |
| 6,171,305 | B1 | 1/2001 | Sherman |
| 6,171,316 | B1 | 1/2001 | Kovac et al. |
| 6,171,330 | B1 | 1/2001 | Benchetrit |
| 6,173,074 | B1 | 1/2001 | Russo |
| 6,174,308 | B1 | 1/2001 | Goble et al. |
| 6,174,309 | B1 | 1/2001 | Wrublewski et al. |
| 6,174,318 | B1 | 1/2001 | Bates et al. |
| 6,175,290 | B1 | 1/2001 | Forsythe et al. |
| 6,179,195 | B1 | 1/2001 | Adams et al. |
| 6,179,776 | B1 | 1/2001 | Adams et al. |
| 6,181,105 | B1 | 1/2001 | Cutolo et al. |
| 6,182,673 | B1 | 2/2001 | Kindermann et al. |
| 6,185,356 | B1 | 2/2001 | Parker et al. |
| 6,186,142 | B1 | 2/2001 | Schmidt et al. |
| 6,186,957 | B1 | 2/2001 | Milam |
| 6,187,003 | B1 | 2/2001 | Buysse et al. |
| 6,190,386 | B1 | 2/2001 | Rydell |
| 6,193,129 | B1 | 2/2001 | Bittner et al. |
| 6,197,042 | B1 | 3/2001 | Ginn et al. |
| 6,200,311 | B1 | 3/2001 | Danek et al. |
| 6,200,330 | B1 | 3/2001 | Benderev et al. |
| 6,202,914 | B1 | 3/2001 | Geiste et al. |
| 6,206,894 | B1 | 3/2001 | Thompson et al. |
| 6,206,897 | B1 | 3/2001 | Jamiolkowski et al. |
| 6,206,903 | B1 | 3/2001 | Ramans |
| 6,206,904 | B1 | 3/2001 | Ouchi |
| 6,209,414 | B1 | 4/2001 | Uneme |
| 6,210,403 | B1 | 4/2001 | Klicek |
| 6,211,626 | B1 | 4/2001 | Lys et al. |
| 6,213,999 | B1 | 4/2001 | Platt, Jr. et al. |
| 6,214,028 | B1 | 4/2001 | Yoon et al. |
| 6,220,368 | B1 | 4/2001 | Ark et al. |
| 6,221,007 | B1 | 4/2001 | Green |
| 6,221,023 | B1 | 4/2001 | Matsuba et al. |
| 6,223,100 | B1 | 4/2001 | Green |
| 6,223,835 | B1 | 5/2001 | Habedank et al. |
| 6,224,617 | B1 | 5/2001 | Saadat et al. |
| 6,228,080 | B1 | 5/2001 | Gines |
| 6,228,081 | B1 | 5/2001 | Goble |
| 6,228,083 | B1 | 5/2001 | Lands et al. |
| 6,228,084 | B1 | 5/2001 | Kirwan, Jr. |

(56) References Cited

U.S. PATENT DOCUMENTS 6,228,089 B1 5/2001 Wahrburg
6,228,098 B1 5/2001 Kayan et al.
6,231,565 B1 5/2001 Tovey et al.
6,234,178 B1 5/2001 Goble et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman

(56) References Cited

U.S. PATENT DOCUMENTS

| | | | |
|---|---|---|---|
| 6,488,659 | B1 | 12/2002 | Rosenman |
| 6,491,201 | B1 | 12/2002 | Whitman |
| 6,491,690 | B1 | 12/2002 | Goble et al. |
| 6,491,701 | B2 | 12/2002 | Tierney et al. |
| 6,491,702 | B2 | 12/2002 | Heilbrun et al. |
| 6,492,785 | B1 | 12/2002 | Kasten et al. |
| 6,494,882 | B1 | 12/2002 | Lebouitz et al. |
| 6,494,885 | B1 | 12/2002 | Dhindsa |
| 6,494,888 | B1 | 12/2002 | Laufer et al. |
| 6,494,896 | B1 | 12/2002 | D'Alessio et al. |
| 6,498,480 | B1 | 12/2002 | Manara |
| 6,500,176 | B1 | 12/2002 | Truckai et al. |
| 6,500,194 | B2 | 12/2002 | Benderev et al. |
| D468,749 | S | 1/2003 | Friedman |
| 6,503,139 | B2 | 1/2003 | Coral |
| 6,503,257 | B2 | 1/2003 | Grant et al. |
| 6,503,259 | B2 | 1/2003 | Huxel et al. |
| 6,505,768 | B2 | 1/2003 | Whitman |
| 6,506,197 | B1 | 1/2003 | Rollero et al. |
| 6,510,854 | B2 | 1/2003 | Goble |
| 6,511,468 | B1 | 1/2003 | Cragg et al. |
| 6,512,360 | B1 | 1/2003 | Goto et al. |
| 6,514,252 | B2 | 2/2003 | Nezhat et al. |
| 6,516,073 | B1 | 2/2003 | Schulz et al. |
| 6,517,528 | B1 | 2/2003 | Pantages et al. |
| 6,517,535 | B2 | 2/2003 | Edwards |
| 6,517,565 | B1 | 2/2003 | Whitman et al. |
| 6,517,566 | B1 | 2/2003 | Hovland et al. |
| 6,520,971 | B1 | 2/2003 | Perry et al. |
| 6,520,972 | B2 | 2/2003 | Peters |
| 6,522,101 | B2 | 2/2003 | Malackowski |
| 6,524,180 | B1 | 2/2003 | Simms et al. |
| 6,525,499 | B2 | 2/2003 | Naganuma |
| D471,206 | S | 3/2003 | Buzzard et al. |
| 6,527,782 | B2 | 3/2003 | Hogg et al. |
| 6,527,785 | B2 | 3/2003 | Sancoff et al. |
| 6,530,942 | B2 | 3/2003 | Fogarty et al. |
| 6,532,958 | B1 | 3/2003 | Buan et al. |
| 6,533,157 | B1 | 3/2003 | Whitman |
| 6,533,723 | B1 | 3/2003 | Lockery et al. |
| 6,533,784 | B2 | 3/2003 | Truckai et al. |
| 6,535,764 | B2 | 3/2003 | Imran et al. |
| 6,539,297 | B2 | 3/2003 | Weiberle et al. |
| D473,239 | S | 4/2003 | Cockerill |
| 6,539,816 | B2 | 4/2003 | Kogiso et al. |
| 6,540,737 | B2 | 4/2003 | Bacher et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | DeGuillebon et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |
| 6,588,931 | B2 | 7/2003 | Betzner et al. |
| 6,589,118 | B1 | 7/2003 | Soma et al. |
| 6,589,164 | B1 | 7/2003 | Flaherty |
| 6,592,538 | B1 | 7/2003 | Hotchkiss et al. |
| 6,592,572 | B1 | 7/2003 | Suzuta |
| 6,592,597 | B2 | 7/2003 | Grant et al. |
| 6,594,552 | B1 | 7/2003 | Nowlin et al. |
| 6,595,914 | B2 | 7/2003 | Kato |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,611,793 | B1 | 8/2003 | Burnside et al. |
| 6,613,069 | B2 | 9/2003 | Boyd et al. |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,161 | B2 | 9/2003 | Schulze et al. |
| 6,620,166 | B1 | 9/2003 | Wenstrom, Jr. et al. |
| 6,625,517 | B1 | 9/2003 | Bogdanov et al. |
| 6,626,834 | B2 | 9/2003 | Dunne et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,635,838 | B1 | 10/2003 | Kornelson |
| 6,636,412 | B2 | 10/2003 | Smith |
| 6,638,108 | B2 | 10/2003 | Tachi |
| 6,638,285 | B2 | 10/2003 | Gabbay |
| 6,638,297 | B1 | 10/2003 | Huitema |
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,901 | B2 | 11/2003 | Fleischman et al. |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,659,940 | B2 | 12/2003 | Adler |
| 6,660,008 | B1 | 12/2003 | Foerster et al. |
| 6,663,623 | B1 | 12/2003 | Oyama et al. |
| 6,663,641 | B1 | 12/2003 | Kovac et al. |
| 6,666,854 | B1 | 12/2003 | Lange |
| 6,666,860 | B1 | 12/2003 | Takahashi |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,670,806 | B2 | 12/2003 | Wendt et al. |
| 6,671,185 | B2 | 12/2003 | Duval |
| D484,977 | S | 1/2004 | Ryan et al. |
| 6,676,660 | B2 | 1/2004 | Wampler et al. |
| 6,677,687 | B2 | 1/2004 | Ho et al. |
| 6,679,269 | B2 | 1/2004 | Swanson |
| 6,679,410 | B2 | 1/2004 | Wursch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |

(56) References Cited

U.S. PATENT DOCUMENTS

| | | | |
|---|---|---|---|
| 6,695,774 | B2 | 2/2004 | Hale et al. |
| 6,695,849 | B2 | 2/2004 | Michelson |
| 6,696,814 | B2 | 2/2004 | Henderson et al. |
| 6,697,048 | B2 | 2/2004 | Rosenberg et al. |
| 6,698,643 | B2 | 3/2004 | Whitman |
| 6,699,177 | B1 | 3/2004 | Wang et al. |
| 6,699,214 | B2 | 3/2004 | Gellman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,709,445 | B2 | 3/2004 | Boebel et al. |
| 6,712,773 | B1 | 3/2004 | Viola |
| 6,716,215 | B1 | 4/2004 | David et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,720,734 | B2 | 4/2004 | Norris |
| 6,722,550 | B1 | 4/2004 | Ricordi et al. |
| 6,722,552 | B2 | 4/2004 | Fenton, Jr. |
| 6,723,087 | B2 | 4/2004 | O'Neill et al. |
| 6,723,091 | B2 | 4/2004 | Goble et al. |
| 6,723,106 | B1 | 4/2004 | Charles et al. |
| 6,723,109 | B2 | 4/2004 | Solingen |
| 6,726,651 | B1 | 4/2004 | Robinson et al. |
| 6,726,697 | B2 | 4/2004 | Nicholas et al. |
| 6,726,705 | B2 | 4/2004 | Peterson et al. |
| 6,726,706 | B2 | 4/2004 | Dominguez |
| 6,729,119 | B2 | 5/2004 | Schnipke et al. |
| 6,731,976 | B2 | 5/2004 | Penn et al. |
| 6,736,810 | B2 | 5/2004 | Hoey et al. |
| 6,736,825 | B2 | 5/2004 | Blatter et al. |
| 6,736,854 | B2 | 5/2004 | Vadurro et al. |
| 6,740,030 | B2 | 5/2004 | Martone et al. |
| 6,743,230 | B2 | 6/2004 | Lutze et al. |
| 6,744,385 | B2 | 6/2004 | Kazuya et al. |
| 6,747,121 | B2 | 6/2004 | Gogolewski |
| 6,747,300 | B2 | 6/2004 | Nadd et al. |
| 6,749,560 | B1 | 6/2004 | Konstorum et al. |
| 6,749,600 | B1 | 6/2004 | Levy |
| 6,752,768 | B2 | 6/2004 | Burdorff et al. |
| 6,752,816 | B2 | 6/2004 | Culp et al. |
| 6,754,959 | B1 | 6/2004 | Guiette, III et al. |
| 6,755,195 | B1 | 6/2004 | Lemke et al. |
| 6,755,338 | B2 | 6/2004 | Hahnen et al. |
| 6,755,843 | B2 | 6/2004 | Chung et al. |
| 6,756,705 | B2 | 6/2004 | Pulford, Jr. |
| 6,758,846 | B2 | 7/2004 | Goble et al. |
| 6,761,685 | B2 | 7/2004 | Adams et al. |
| 6,762,339 | B1 | 7/2004 | Klun et al. |
| 6,763,307 | B2 | 7/2004 | Berg et al. |
| 6,764,445 | B2 | 7/2004 | Ramans et al. |
| 6,766,957 | B2 | 7/2004 | Matsuura et al. |
| 6,767,352 | B2 | 7/2004 | Field et al. |
| 6,767,356 | B2 | 7/2004 | Kanner et al. |
| 6,769,590 | B2 | 8/2004 | Vresh et al. |
| 6,769,594 | B2 | 8/2004 | Orban, III |
| 6,770,027 | B2 | 8/2004 | Banik et al. |
| 6,770,070 | B1 | 8/2004 | Balbierz |
| 6,770,072 | B1 | 8/2004 | Truckai et al. |
| 6,770,078 | B2 | 8/2004 | Bonutti |
| 6,773,409 | B2 | 8/2004 | Truckai et al. |
| 6,773,437 | B2 | 8/2004 | Ogilvie et al. |
| 6,773,438 | B1 | 8/2004 | Knodel et al. |
| 6,775,575 | B2 | 8/2004 | Bommannan et al. |
| 6,777,838 | B2 | 8/2004 | Miekka et al. |
| 6,778,846 | B1 | 8/2004 | Martinez et al. |
| 6,780,151 | B2 | 8/2004 | Grabover et al. |
| 6,780,180 | B1 | 8/2004 | Goble et al. |
| 6,783,524 | B2 | 8/2004 | Anderson et al. |
| 6,784,775 | B2 | 8/2004 | Mandell et al. |
| 6,786,382 | B1 | 9/2004 | Hoffman |
| 6,786,864 | B2 | 9/2004 | Matsuura et al. |
| 6,786,896 | B1 | 9/2004 | Madhani et al. |
| 6,788,018 | B1 | 9/2004 | Blumenkranz |
| 6,790,173 | B2 | 9/2004 | Saadat et al. |
| 6,793,652 | B1 | 9/2004 | Whitman et al. |
| 6,793,661 | B2 | 9/2004 | Hamilton et al. |
| 6,793,663 | B2 | 9/2004 | Kneifel et al. |
| 6,793,669 | B2 | 9/2004 | Nakamura et al. |
| 6,796,921 | B1 | 9/2004 | Buck et al. |
| 6,799,669 | B2 | 10/2004 | Fukumura et al. |
| 6,802,822 | B1 | 10/2004 | Dodge |
| 6,802,843 | B2 | 10/2004 | Truckai et al. |
| 6,802,844 | B2 | 10/2004 | Ferree |
| 6,805,273 | B2 | 10/2004 | Bilotti et al. |
| 6,806,808 | B1 | 10/2004 | Watters et al. |
| 6,806,867 | B1 | 10/2004 | Arruda et al. |
| 6,808,525 | B2 | 10/2004 | Latterell et al. |
| 6,810,359 | B2 | 10/2004 | Sakaguchi |
| 6,814,154 | B2 | 11/2004 | Chou |
| 6,814,741 | B2 | 11/2004 | Bowman et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,818,018 | B1 | 11/2004 | Sawhney |
| 6,820,791 | B2 | 11/2004 | Adams |
| 6,821,273 | B2 | 11/2004 | Mollenauer |
| 6,821,282 | B2 | 11/2004 | Perry et al. |
| 6,821,284 | B2 | 11/2004 | Sturtz et al. |
| 6,827,246 | B2 | 12/2004 | Sullivan et al. |
| 6,827,712 | B2 | 12/2004 | Tovey et al. |
| 6,827,725 | B2 | 12/2004 | Batchelor et al. |
| 6,828,902 | B2 | 12/2004 | Casden |
| 6,830,174 | B2 | 12/2004 | Hillstead et al. |
| 6,831,629 | B2 | 12/2004 | Nishino et al. |
| 6,832,998 | B2 | 12/2004 | Goble |
| 6,834,001 | B2 | 12/2004 | Myono |
| 6,835,173 | B2 | 12/2004 | Couvillon, Jr. |
| 6,835,199 | B2 | 12/2004 | McGuckin, Jr. et al. |
| 6,835,336 | B2 | 12/2004 | Watt |
| 6,836,611 | B2 | 12/2004 | Popovic et al. |
| 6,837,846 | B2 | 1/2005 | Jaffe et al. |
| 6,837,883 | B2 | 1/2005 | Moll et al. |
| 6,838,493 | B2 | 1/2005 | Williams et al. |
| 6,840,423 | B2 | 1/2005 | Adams et al. |
| 6,840,938 | B1 | 1/2005 | Morley et al. |
| 6,841,967 | B2 | 1/2005 | Kim et al. |
| 6,843,403 | B2 | 1/2005 | Whitmar |
| 6,843,789 | B2 | 1/2005 | Goble |
| 6,843,793 | B2 | 1/2005 | Brock et al. |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,847,190 | B2 | 1/2005 | Schaefer et al. |
| 6,849,071 | B2 | 2/2005 | Whitman et al. |
| 6,850,817 | B1 | 2/2005 | Green |
| 6,852,122 | B2 | 2/2005 | Rush |
| 6,852,330 | B2 | 2/2005 | Bowman et al. |
| 6,853,879 | B2 | 2/2005 | Sunaoshi |
| 6,858,005 | B2 | 2/2005 | Ohline et al. |
| 6,859,882 | B2 | 2/2005 | Fung |
| RE38,708 | E | 3/2005 | Bolanos et al. |
| D502,994 | S | 3/2005 | Blake, III |
| 6,861,142 | B1 | 3/2005 | Wilkie et al. |
| 6,861,954 | B2 | 3/2005 | Levin |
| 6,863,668 | B2 | 3/2005 | Gillespie et al. |
| 6,863,694 | B1 | 3/2005 | Boyce et al. |
| 6,863,924 | B2 | 3/2005 | Ranganathan et al. |
| 6,866,178 | B2 | 3/2005 | Adams et al. |
| 6,866,668 | B2 | 3/2005 | Giannetti et al. |
| 6,866,671 | B2 | 3/2005 | Tierney et al. |
| 6,867,248 | B1 | 3/2005 | Martin et al. |
| 6,869,430 | B2 | 3/2005 | Balbierz et al. |
| 6,869,435 | B2 | 3/2005 | Blake, III |
| 6,872,214 | B2 | 3/2005 | Sonnenschein et al. |
| 6,874,669 | B2 | 4/2005 | Adams et al. |
| 6,876,850 | B2 | 4/2005 | Maeshima et al. |
| 6,877,647 | B2 | 4/2005 | Green et al. |
| 6,878,106 | B1 | 4/2005 | Herrmann |
| 6,882,127 | B2 | 4/2005 | Konigbauer |
| 6,883,199 | B1 | 4/2005 | Lundell et al. |
| 6,884,392 | B2 | 4/2005 | Malkin et al. |
| 6,884,428 | B2 | 4/2005 | Binette et al. |
| 6,886,730 | B2 | 5/2005 | Fujisawa et al. |

(56) References Cited

U.S. PATENT DOCUMENTS 6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.

(56) References Cited

U.S. PATENT DOCUMENTS

| | | | |
|---|---|---|---|
| 7,066,879 | B2 | 6/2006 | Fowler et al. |
| 7,066,944 | B2 | 6/2006 | Laufer et al. |
| 7,067,038 | B2 | 6/2006 | Trokhan et al. |
| 7,070,083 | B2 | 7/2006 | Jankowski |
| 7,070,559 | B2 | 7/2006 | Adams et al. |
| 7,070,597 | B2 | 7/2006 | Truckai et al. |
| 7,071,287 | B2 | 7/2006 | Rhine et al. |
| 7,075,770 | B1 | 7/2006 | Smith |
| 7,077,856 | B2 | 7/2006 | Whitman |
| 7,080,769 | B2 | 7/2006 | Vresh et al. |
| 7,081,114 | B2 | 7/2006 | Rashidi |
| 7,081,318 | B2 | 7/2006 | Lee et al. |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,083,619 | B2 | 8/2006 | Truckai et al. |
| 7,083,620 | B2 | 8/2006 | Jahns et al. |
| 7,083,626 | B2 | 8/2006 | Hart et al. |
| 7,086,267 | B2 | 8/2006 | Dworak et al. |
| 7,087,049 | B2 | 8/2006 | Nowlin et al. |
| 7,087,054 | B2 | 8/2006 | Truckai et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,683 | B2 | 8/2006 | Brock et al. |
| 7,090,684 | B2 | 8/2006 | McGuckin, Jr. et al. |
| 7,091,191 | B2 | 8/2006 | Laredo et al. |
| 7,091,412 | B2 | 8/2006 | Wang et al. |
| 7,093,492 | B2 | 8/2006 | Treiber et al. |
| 7,094,202 | B2 | 8/2006 | Nobis et al. |
| 7,094,247 | B2 | 8/2006 | Monassevitch et al. |
| 7,094,916 | B2 | 8/2006 | DeLuca et al. |
| 7,096,972 | B2 | 8/2006 | Orozco, Jr. |
| 7,097,089 | B2 | 8/2006 | Marczyk |
| 7,097,644 | B2 | 8/2006 | Long |
| 7,097,650 | B2 | 8/2006 | Weller et al. |
| 7,098,794 | B2 | 8/2006 | Lindsay et al. |
| 7,100,949 | B2 | 9/2006 | Williams et al. |
| 7,101,187 | B1 | 9/2006 | Deconinck et al. |
| 7,101,371 | B2 | 9/2006 | Dycus et al. |
| 7,101,394 | B2 | 9/2006 | Hamm et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,768 | B2 | 9/2006 | Cummins et al. |
| 7,111,769 | B2 | 9/2006 | Wales et al. |
| 7,112,214 | B2 | 9/2006 | Peterson et al. |
| RE39,358 | E | 10/2006 | Goble |
| D530,339 | S | 10/2006 | Hernandez et al. |
| 7,114,642 | B2 | 10/2006 | Whitman |
| 7,116,100 | B1 | 10/2006 | Mock et al. |
| 7,118,020 | B2 | 10/2006 | Lee et al. |
| 7,118,528 | B1 | 10/2006 | Piskun |
| 7,118,563 | B2 | 10/2006 | Weckwerth et al. |
| 7,118,582 | B1 | 10/2006 | Wang et al. |
| 7,119,534 | B2 | 10/2006 | Butzmann |
| 7,121,446 | B2 | 10/2006 | Arad et al. |
| 7,121,773 | B2 | 10/2006 | Mikiya et al. |
| 7,122,028 | B2 | 10/2006 | Looper et al. |
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,134,364 | B2 | 11/2006 | Kageler et al. |
| 7,134,587 | B2 | 11/2006 | Schwemberger et al. |
| 7,135,027 | B2 | 11/2006 | Delmotte |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,153,314 | B2 | 12/2006 | Laufer et al. |
| 7,155,316 | B2 | 12/2006 | Sutherland et al. |
| 7,156,863 | B2 | 1/2007 | Sonnenschein et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,190,147 | B2 | 3/2007 | Gileff et al. |
| 7,193,199 | B2 | 3/2007 | Jang |
| 7,195,627 | B2 | 3/2007 | Amoah et al. |
| 7,196,911 | B2 | 3/2007 | Takano et al. |
| D541,418 | S | 4/2007 | Schechter et al. |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,225,959 | B2 | 6/2007 | Patton et al. |
| 7,225,963 | B2 | 6/2007 | Scirica |
| 7,225,964 | B2 | 6/2007 | Mastri et al. |
| 7,226,450 | B2 | 6/2007 | Athanasiou et al. |
| 7,226,467 | B2 | 6/2007 | Lucatero et al. |

(56) References Cited

U.S. PATENT DOCUMENTS 7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,313,430 B2 12/2007 Urquhart et al.
7,314,473 B2 1/2008 Jinno et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.

(56) References Cited

U.S. PATENT DOCUMENTS 7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,500,979 B2 3/2009 Hueil et al.
7,501,198 B2 3/2009 Barlev et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.
7,575,144 B2 8/2009 Ortiz et al.
7,578,825 B2 8/2009 Huebner
D600,712 S 9/2009 LaManna et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Lio et al.
7,604,150 B2 10/2009 Boudreaux
7,604,151 B2 10/2009 Hess et al.
7,604,668 B2 10/2009 Farnsworth et al.
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola

(56) References Cited

U.S. PATENT DOCUMENTS

D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh et al.
7,670,334 B2 3/2010 Hueil et al.
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,758 B2 5/2010 Lee et al.
7,708,768 B2 5/2010 Danek et al.
7,709,136 B2 5/2010 Touchton et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 Mckay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,736,254 B2 6/2010 Schena
7,736,306 B2 6/2010 Brustad et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.

(56) References Cited

U.S. PATENT DOCUMENTS 7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,879,063 B2 2/2011 Khosravi
7,879,070 B2 2/2011 Ortiz et al.
7,883,461 B2 2/2011 Albrecht et al.
7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger

(56) References Cited

U.S. PATENT DOCUMENTS

| | | | |
|---|---|---|---|
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |
| 7,976,563 B2 | 7/2011 | Summerer |
| 7,979,137 B2 | 7/2011 | Tracey et al. |
| 7,980,443 B2 | 7/2011 | Scheib et al. |
| 7,981,102 B2 | 7/2011 | Patel et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |

(56) References Cited

U.S. PATENT DOCUMENTS

| | | | |
|---|---|---|---|
| 8,056,788 | B2 | 11/2011 | Mastri et al. |
| 8,056,789 | B1 | 11/2011 | White et al. |
| 8,057,508 | B2 | 11/2011 | Shelton, IV |
| 8,058,771 | B2 | 11/2011 | Giordano et al. |
| 8,060,250 | B2 | 11/2011 | Reiland et al. |
| 8,061,014 | B2 | 11/2011 | Smith et al. |
| 8,061,576 | B2 | 11/2011 | Cappola |
| 8,062,236 | B2 | 11/2011 | Soltz |
| 8,062,306 | B2 | 11/2011 | Nobis et al. |
| 8,062,330 | B2 | 11/2011 | Prommersberger et al. |
| 8,063,619 | B2 | 11/2011 | Zhu et al. |
| 8,066,158 | B2 | 11/2011 | Vogel et al. |
| 8,066,166 | B2 | 11/2011 | Demmy et al. |
| 8,066,167 | B2 | 11/2011 | Measamer et al. |
| 8,066,168 | B2 | 11/2011 | Vidal et al. |
| 8,066,720 | B2 | 11/2011 | Knodel et al. |
| D650,074 | S | 12/2011 | Hunt et al. |
| D650,789 | S | 12/2011 | Arnold |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,743 | B2 | 12/2011 | Kagan et al. |
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |
| 8,102,138 | B2 | 1/2012 | Sekine et al. |
| 8,102,278 | B2 | 1/2012 | Deck et al. |
| 8,105,320 | B2 | 1/2012 | Manzo |
| 8,105,350 | B2 | 1/2012 | Lee et al. |
| 8,107,925 | B2 | 1/2012 | Natsuno et al. |
| 8,108,033 | B2 | 1/2012 | Drew et al. |
| 8,108,072 | B2 | 1/2012 | Zhao et al. |
| 8,109,426 | B2 | 2/2012 | Milliman et al. |
| 8,110,208 | B1 | 2/2012 | Hen |
| 8,113,405 | B2 | 2/2012 | Milliman |
| 8,113,407 | B2 | 2/2012 | Holsten et al. |
| 8,113,408 | B2 | 2/2012 | Wenchell et al. |
| 8,113,410 | B2 | 2/2012 | Hall et al. |
| 8,114,017 | B2 | 2/2012 | Bacher |
| 8,114,100 | B2 | 2/2012 | Smith et al. |
| 8,118,206 | B2 | 2/2012 | Zand et al. |
| 8,118,207 | B2 | 2/2012 | Racenet et al. |
| 8,120,301 | B2 | 2/2012 | Goldberg et al. |
| 8,122,128 | B2 | 2/2012 | Burke, II et al. |
| 8,123,103 | B2 | 2/2012 | Milliman |
| 8,123,523 | B2 | 2/2012 | Carron et al. |
| 8,123,766 | B2 | 2/2012 | Bauman et al. |
| 8,123,767 | B2 | 2/2012 | Bauman et al. |
| 8,125,168 | B2 | 2/2012 | Johnson et al. |
| 8,127,975 | B2 | 3/2012 | Olson et al. |
| 8,127,976 | B2 | 3/2012 | Scirica et al. |
| 8,128,624 | B2 | 3/2012 | Couture et al. |
| 8,128,643 | B2 | 3/2012 | Aranyi et al. |
| 8,128,645 | B2 | 3/2012 | Sonnenschein et al. |
| 8,128,662 | B2 | 3/2012 | Altarac et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,133,500 | B2 | 3/2012 | Ringeisen et al. |
| 8,134,306 | B2 | 3/2012 | Drader et al. |
| 8,136,711 | B2 | 3/2012 | Beardsley et al. |
| 8,136,712 | B2 | 3/2012 | Zingman |
| 8,136,713 | B2 | 3/2012 | Hathaway et al. |
| 8,137,339 | B2 | 3/2012 | Jinno et al. |
| 8,140,417 | B2 | 3/2012 | Shibata |
| 8,141,762 | B2 | 3/2012 | Bedi et al. |
| 8,141,763 | B2 | 3/2012 | Milliman |
| 8,142,200 | B2 | 3/2012 | Crunkilton et al. |
| 8,142,425 | B2 | 3/2012 | Eggers |
| 8,142,461 | B2 | 3/2012 | Houser et al. |
| 8,142,515 | B2 | 3/2012 | Therin et al. |
| 8,143,520 | B2 | 3/2012 | Cutler |
| 8,146,790 | B2 | 4/2012 | Milliman |
| 8,147,421 | B2 | 4/2012 | Farquhar et al. |
| 8,147,456 | B2 | 4/2012 | Fisher et al. |
| 8,147,485 | B2 | 4/2012 | Wham et al. |
| 8,152,041 | B2 | 4/2012 | Kostrzewski |
| 8,152,756 | B2 | 4/2012 | Webster et al. |
| 8,154,239 | B2 | 4/2012 | Katsuki et al. |
| 8,157,145 | B2 | 4/2012 | Shelton, IV et al. |
| 8,157,148 | B2 | 4/2012 | Scirica |
| 8,157,151 | B2 | 4/2012 | Ingmanson et al. |
| 8,157,152 | B2 | 4/2012 | Holsten et al. |
| 8,157,153 | B2 | 4/2012 | Shelton, IV et al. |
| 8,157,793 | B2 | 4/2012 | Omori et al. |
| 8,161,977 | B2 | 4/2012 | Shelton, IV et al. |
| 8,162,138 | B2 | 4/2012 | Bettenhausen et al. |
| 8,162,197 | B2 | 4/2012 | Mastri et al. |
| 8,162,668 | B2 | 4/2012 | Toly |
| 8,162,933 | B2 | 4/2012 | Francischelli et al. |
| 8,162,965 | B2 | 4/2012 | Reschke et al. |
| 8,167,185 | B2 | 5/2012 | Shelton, IV et al. |
| 8,167,622 | B2 | 5/2012 | Zhou |
| 8,167,895 | B2 | 5/2012 | D'Agostino et al. |
| 8,167,898 | B1 | 5/2012 | Schaller et al. |
| 8,170,241 | B2 | 5/2012 | Roe et al. |
| 8,172,004 | B2 | 5/2012 | Ho |
| 8,172,120 | B2 | 5/2012 | Boyden et al. |
| 8,172,122 | B2 | 5/2012 | Kasvikis et al. |
| 8,172,124 | B2 | 5/2012 | Shelton, IV et al. |
| 8,177,776 | B2 | 5/2012 | Humayun et al. |
| 8,177,797 | B2 | 5/2012 | Shimoji et al. |
| 8,179,705 | B2 | 5/2012 | Chapuis |
| 8,180,458 | B2 | 5/2012 | Kane et al. |
| 8,181,839 | B2 | 5/2012 | Beetel |
| 8,181,840 | B2 | 5/2012 | Milliman |
| 8,182,422 | B2 | 5/2012 | Bayer et al. |
| 8,182,444 | B2 | 5/2012 | Uber, III et al. |
| 8,183,807 | B2 | 5/2012 | Tsai et al. |
| 8,186,555 | B2 | 5/2012 | Shelton, IV et al. |
| 8,186,556 | B2 | 5/2012 | Viola |
| 8,186,558 | B2 | 5/2012 | Sapienza |
| 8,186,560 | B2 | 5/2012 | Hess et al. |
| 8,190,238 | B2 | 5/2012 | Moll et al. |
| 8,191,752 | B2 | 6/2012 | Scirica |
| 8,192,350 | B2 | 6/2012 | Ortiz et al. |
| 8,192,460 | B2 | 6/2012 | Orban et al. |
| 8,192,651 | B2 | 6/2012 | Young et al. |
| 8,193,129 | B2 | 6/2012 | Tagawa et al. |
| 8,196,795 | B2 | 6/2012 | Moore et al. |
| 8,196,796 | B2 | 6/2012 | Shelton, IV et al. |
| 8,197,501 | B2 | 6/2012 | Shadeck et al. |
| 8,197,502 | B2 | 6/2012 | Smith et al. |
| 8,197,837 | B2 | 6/2012 | Jamiolkowski et al. |
| 8,201,720 | B2 | 6/2012 | Hessler |
| 8,201,721 | B2 | 6/2012 | Zemlok et al. |
| 8,202,549 | B2 | 6/2012 | Stucky et al. |
| 8,205,779 | B2 | 6/2012 | Ma et al. |
| 8,205,780 | B2 | 6/2012 | Sorrentino et al. |

(56) References Cited

U.S. PATENT DOCUMENTS 8,205,781 B2 6/2012 Baxter, III et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.

(56) References Cited

U.S. PATENT DOCUMENTS 8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,381,828 B2 2/2013 Whitman et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari

(56) References Cited

U.S. PATENT DOCUMENTS

| | | | |
|---|---|---|---|
| 8,475,474 | B2 | 7/2013 | Bombard et al. |
| 8,479,968 | B2 | 7/2013 | Hodgkinson et al. |
| 8,479,969 | B2 | 7/2013 | Shelton, IV |
| 8,480,703 | B2 | 7/2013 | Nicholas et al. |
| 8,483,509 | B2 | 7/2013 | Matsuzaka |
| 8,485,412 | B2 | 7/2013 | Shelton, IV et al. |
| 8,485,413 | B2 | 7/2013 | Scheib et al. |
| 8,485,970 | B2 | 7/2013 | Widenhouse et al. |
| 8,487,199 | B2 | 7/2013 | Palmer et al. |
| 8,487,487 | B2 | 7/2013 | Dietz et al. |
| 8,490,851 | B2 | 7/2013 | Blier et al. |
| 8,490,852 | B2 | 7/2013 | Viola |
| 8,490,853 | B2 | 7/2013 | Criscuolo et al. |
| 8,491,581 | B2 | 7/2013 | Deville et al. |
| 8,491,603 | B2 | 7/2013 | Yeung et al. |
| 8,496,153 | B2 | 7/2013 | Demmy et al. |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,498,691 | B2 | 7/2013 | Moll et al. |
| 8,499,673 | B2 | 8/2013 | Keller |
| 8,499,966 | B2 | 8/2013 | Palmer et al. |
| 8,499,992 | B2 | 8/2013 | Whitman et al. |
| 8,499,993 | B2 | 8/2013 | Shelton, IV et al. |
| 8,500,721 | B2 | 8/2013 | Jinno |
| 8,500,762 | B2 | 8/2013 | Sholev et al. |
| 8,502,091 | B2 | 8/2013 | Palmer et al. |
| 8,505,799 | B2 | 8/2013 | Viola et al. |
| 8,505,801 | B2 | 8/2013 | Ehrenfels et al. |
| 8,506,555 | B2 | 8/2013 | Ruiz Morales |
| 8,506,557 | B2 | 8/2013 | Zemlok et al. |
| 8,506,580 | B2 | 8/2013 | Zergiebel et al. |
| 8,506,581 | B2 | 8/2013 | Wingardner, III et al. |
| 8,511,308 | B2 | 8/2013 | Hecox et al. |
| 8,512,359 | B2 | 8/2013 | Whitman et al. |
| 8,512,402 | B2 | 8/2013 | Marczyk et al. |
| 8,517,239 | B2 | 8/2013 | Scheib et al. |
| 8,517,241 | B2 | 8/2013 | Nicholas et al. |
| 8,517,243 | B2 | 8/2013 | Giordano et al. |
| 8,517,244 | B2 | 8/2013 | Shelton, IV et al. |
| 8,517,938 | B2 | 8/2013 | Eisenhardt et al. |
| 8,518,024 | B2 | 8/2013 | Williams et al. |
| 8,521,273 | B2 | 8/2013 | Kliman |
| 8,523,042 | B2 | 9/2013 | Masiakos et al. |
| 8,523,043 | B2 | 9/2013 | Ullrich et al. |
| 8,523,787 | B2 | 9/2013 | Ludwin et al. |
| 8,523,881 | B2 | 9/2013 | Cabiri et al. |
| 8,523,900 | B2 | 9/2013 | Jinno et al. |
| 8,529,588 | B2 | 9/2013 | Ahlberg et al. |
| 8,529,599 | B2 | 9/2013 | Holsten |
| 8,529,600 | B2 | 9/2013 | Woodard, Jr. et al. |
| 8,529,819 | B2 | 9/2013 | Ostapoff et al. |
| 8,532,747 | B2 | 9/2013 | Nock et al. |
| 8,534,527 | B2 | 9/2013 | Brendel et al. |
| 8,534,528 | B2 | 9/2013 | Shelton, IV |
| 8,535,304 | B2 | 9/2013 | Sklar et al. |
| 8,535,340 | B2 | 9/2013 | Allen |
| 8,539,866 | B2 | 9/2013 | Nayak et al. |
| 8,540,128 | B2 | 9/2013 | Shelton, IV et al. |
| 8,540,129 | B2 | 9/2013 | Baxter, III et al. |
| 8,540,130 | B2 | 9/2013 | Moore et al. |
| 8,540,131 | B2 | 9/2013 | Swayze |
| 8,540,133 | B2 | 9/2013 | Bedi et al. |
| 8,540,646 | B2 | 9/2013 | Mendez-Coll |
| 8,540,733 | B2 | 9/2013 | Whitman et al. |
| 8,540,735 | B2 | 9/2013 | Mitelberg et al. |
| 8,550,984 | B2 | 10/2013 | Takemoto |
| 8,551,076 | B2 | 10/2013 | Duval et al. |
| 8,555,660 | B2 | 10/2013 | Takenaka et al. |
| 8,556,151 | B2 | 10/2013 | Viola |
| 8,556,918 | B2 | 10/2013 | Bauman et al. |
| 8,556,935 | B1 | 10/2013 | Knodel et al. |
| 8,560,147 | B2 | 10/2013 | Taylor et al. |
| 8,561,617 | B2 | 10/2013 | Lindh et al. |
| 8,561,870 | B2 | 10/2013 | Baxter, III et al. |
| 8,561,871 | B2 | 10/2013 | Rajappa et al. |
| 8,561,873 | B2 | 10/2013 | Ingmanson et al. |
| 8,562,592 | B2 | 10/2013 | Conlon et al. |
| 8,562,598 | B2 | 10/2013 | Falkenstein et al. |
| 8,567,656 | B2 | 10/2013 | Shelton, IV et al. |
| 8,568,416 | B2 | 10/2013 | Schmitz et al. |
| 8,568,425 | B2 | 10/2013 | Ross et al. |
| D692,916 | S | 11/2013 | Granchi et al. |
| 8,573,459 | B2 | 11/2013 | Smith et al. |
| 8,573,461 | B2 | 11/2013 | Shelton, IV et al. |
| 8,573,462 | B2 | 11/2013 | Smith et al. |
| 8,573,465 | B2 | 11/2013 | Shelton, IV |
| 8,574,199 | B2 | 11/2013 | Bulow et al. |
| 8,574,263 | B2 | 11/2013 | Mueller |
| 8,575,880 | B2 | 11/2013 | Grantz |
| 8,575,895 | B2 | 11/2013 | Garrastacho et al. |
| 8,579,176 | B2 | 11/2013 | Smith et al. |
| 8,579,178 | B2 | 11/2013 | Holsten et al. |
| 8,579,897 | B2 | 11/2013 | Vakharia et al. |
| 8,579,937 | B2 | 11/2013 | Gresham |
| 8,584,919 | B2 | 11/2013 | Hueil et al. |
| 8,584,920 | B2 | 11/2013 | Hodgkinson |
| 8,584,921 | B2 | 11/2013 | Scirica |
| 8,585,583 | B2 | 11/2013 | Sakaguchi et al. |
| 8,585,721 | B2 | 11/2013 | Kirsch |
| 8,590,760 | B2 | 11/2013 | Cummins et al. |
| 8,590,762 | B2 | 11/2013 | Hess et al. |
| 8,590,764 | B2 | 11/2013 | Hartwick et al. |
| 8,596,515 | B2 | 12/2013 | Okoniewski |
| 8,597,745 | B2 | 12/2013 | Farnsworth et al. |
| 8,599,450 | B2 | 12/2013 | Kubo et al. |
| 8,602,125 | B2 | 12/2013 | King |
| 8,602,287 | B2 | 12/2013 | Yates et al. |
| 8,602,288 | B2 | 12/2013 | Shelton, IV et al. |
| 8,603,077 | B2 | 12/2013 | Cooper et al. |
| 8,603,089 | B2 | 12/2013 | Viola |
| 8,603,110 | B2 | 12/2013 | Maruyama et al. |
| 8,603,135 | B2 | 12/2013 | Mueller |
| 8,608,043 | B2 | 12/2013 | Scirica |
| 8,608,044 | B2 | 12/2013 | Hueil et al. |
| 8,608,045 | B2 | 12/2013 | Smith et al. |
| 8,608,046 | B2 | 12/2013 | Laurent et al. |
| 8,608,745 | B2 | 12/2013 | Guzman et al. |
| 8,613,383 | B2 | 12/2013 | Beckman et al. |
| 8,616,427 | B2 | 12/2013 | Viola |
| 8,616,431 | B2 | 12/2013 | Timm et al. |
| 8,620,473 | B2 | 12/2013 | Diolaiti et al. |
| 8,622,274 | B2 | 1/2014 | Yates et al. |
| 8,622,275 | B2 | 1/2014 | Baxter, III et al. |
| 8,627,993 | B2 | 1/2014 | Smith et al. |
| 8,627,994 | B2 | 1/2014 | Zemlok et al. |
| 8,627,995 | B2 | 1/2014 | Smith et al. |
| 8,628,467 | B2 | 1/2014 | Whitman et al. |
| 8,628,518 | B2 | 1/2014 | Blumenkranz et al. |
| 8,628,544 | B2 | 1/2014 | Farascioni |
| 8,628,545 | B2 | 1/2014 | Cabrera et al. |
| 8,631,987 | B2 | 1/2014 | Shelton, IV et al. |
| 8,631,992 | B1 | 1/2014 | Hausen et al. |
| 8,631,993 | B2 | 1/2014 | Kostrzewski |
| 8,632,462 | B2 | 1/2014 | Yoo et al. |
| 8,632,525 | B2 | 1/2014 | Kerr et al. |
| 8,632,535 | B2 | 1/2014 | Shelton, IV et al. |
| 8,632,539 | B2 | 1/2014 | Twomey et al. |
| 8,632,563 | B2 | 1/2014 | Nagase et al. |
| 8,636,187 | B2 | 1/2014 | Hueil et al. |
| 8,636,190 | B2 | 1/2014 | Zemlok et al. |
| 8,636,191 | B2 | 1/2014 | Meagher |
| 8,636,193 | B2 | 1/2014 | Whitman et al. |
| 8,636,736 | B2 | 1/2014 | Yates et al. |
| 8,636,766 | B2 | 1/2014 | Milliman et al. |
| 8,639,936 | B2 | 1/2014 | Hu et al. |
| 8,640,788 | B2 | 2/2014 | Dachs et al. |
| 8,646,674 | B2 | 2/2014 | Schulte et al. |
| 8,647,258 | B2 | 2/2014 | Aranyi et al. |
| 8,652,120 | B2 | 2/2014 | Giordano et al. |
| 8,652,151 | B2 | 2/2014 | Lehman et al. |
| 8,652,155 | B2 | 2/2014 | Houser et al. |
| 8,656,929 | B2 | 2/2014 | Miller et al. |
| 8,657,174 | B2 | 2/2014 | Yates et al. |

(56) References Cited

U.S. PATENT DOCUMENTS 8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.

(56) References Cited

U.S. PATENT DOCUMENTS

| | | | |
|---|---|---|---|
| 8,810,197 | B2 | 8/2014 | Juergens |
| 8,811,017 | B2 | 8/2014 | Fujii et al. |
| 8,813,866 | B2 | 8/2014 | Suzuki |
| 8,814,024 | B2 | 8/2014 | Woodard, Jr. et al. |
| 8,814,025 | B2 | 8/2014 | Miller et al. |
| 8,814,836 | B2 | 8/2014 | Ignon et al. |
| 8,815,594 | B2 | 8/2014 | Harris et al. |
| 8,818,523 | B2 | 8/2014 | Olson et al. |
| 8,820,603 | B2 | 9/2014 | Shelton, IV et al. |
| 8,820,605 | B2 | 9/2014 | Shelton, IV |
| 8,820,606 | B2 | 9/2014 | Hodgkinson |
| 8,820,607 | B2 | 9/2014 | Marczyk |
| 8,820,608 | B2 | 9/2014 | Miyamoto |
| 8,821,514 | B2 | 9/2014 | Aranyi |
| 8,822,934 | B2 | 9/2014 | Sayeh et al. |
| 8,825,164 | B2 | 9/2014 | Tweden et al. |
| 8,827,133 | B2 | 9/2014 | Shelton, IV et al. |
| 8,827,134 | B2 | 9/2014 | Viola et al. |
| 8,827,903 | B2 | 9/2014 | Shelton, IV et al. |
| 8,828,046 | B2 | 9/2014 | Stefanchik et al. |
| 8,831,779 | B2 | 9/2014 | Ortmaier et al. |
| 8,833,219 | B2 | 9/2014 | Pierce |
| 8,833,630 | B2 | 9/2014 | Milliman |
| 8,833,632 | B2 | 9/2014 | Swensgard |
| 8,834,353 | B2 | 9/2014 | Dejima et al. |
| 8,834,465 | B2 | 9/2014 | Ramstein et al. |
| 8,834,498 | B2 | 9/2014 | Byrum et al. |
| 8,834,518 | B2 | 9/2014 | Faller et al. |
| 8,840,003 | B2 | 9/2014 | Morgan et al. |
| 8,840,603 | B2 | 9/2014 | Shelton, IV et al. |
| 8,840,609 | B2 | 9/2014 | Stuebe |
| 8,840,876 | B2 | 9/2014 | Eemeta et al. |
| 8,844,789 | B2 | 9/2014 | Shelton, IV et al. |
| 8,844,790 | B2 | 9/2014 | Demmy et al. |
| 8,851,215 | B2 | 10/2014 | Goto |
| 8,851,354 | B2 | 10/2014 | Swensgard et al. |
| 8,851,355 | B2 | 10/2014 | Aranyi et al. |
| 8,852,174 | B2 | 10/2014 | Burbank |
| 8,852,185 | B2 | 10/2014 | Twomey |
| 8,852,199 | B2 | 10/2014 | Deslauriers et al. |
| 8,852,218 | B2 | 10/2014 | Hughett, Sr. et al. |
| 8,857,693 | B2 | 10/2014 | Schuckmann et al. |
| 8,857,694 | B2 | 10/2014 | Shelton, IV et al. |
| 8,858,538 | B2 | 10/2014 | Belson et al. |
| 8,858,547 | B2 | 10/2014 | Brogna |
| 8,858,571 | B2 | 10/2014 | Shelton, IV et al. |
| 8,858,590 | B2 | 10/2014 | Shelton, IV et al. |
| 8,864,007 | B2 | 10/2014 | Widenhouse et al. |
| 8,864,009 | B2 | 10/2014 | Shelton, IV et al. |
| 8,864,010 | B2 | 10/2014 | Williams |
| 8,864,750 | B2 | 10/2014 | Ross et al. |
| 8,869,912 | B2 | 10/2014 | Roßkamp et al. |
| 8,869,913 | B2 | 10/2014 | Matthias et al. |
| 8,870,050 | B2 | 10/2014 | Hodgkinson |
| 8,870,867 | B2 | 10/2014 | Walberg et al. |
| 8,870,912 | B2 | 10/2014 | Brisson et al. |
| 8,875,971 | B2 | 11/2014 | Hall et al. |
| 8,875,972 | B2 | 11/2014 | Weisenburgh, II et al. |
| 8,876,857 | B2 | 11/2014 | Burbank |
| 8,876,858 | B2 | 11/2014 | Braun |
| 8,887,979 | B2 | 11/2014 | Mastri et al. |
| 8,888,688 | B2 | 11/2014 | Julian et al. |
| 8,888,695 | B2 | 11/2014 | Piskun et al. |
| 8,888,792 | B2 | 11/2014 | Harris et al. |
| 8,888,809 | B2 | 11/2014 | Davison et al. |
| 8,893,946 | B2 | 11/2014 | Boudreaux et al. |
| 8,893,949 | B2 | 11/2014 | Shelton, IV et al. |
| 8,894,647 | B2 | 11/2014 | Beardsley et al. |
| 8,894,654 | B2 | 11/2014 | Anderson |
| 8,899,460 | B2 | 12/2014 | Wojcicki |
| 8,899,461 | B2 | 12/2014 | Farascioni |
| 8,899,462 | B2 | 12/2014 | Kostrzewski et al. |
| 8,899,463 | B2 | 12/2014 | Schall et al. |
| 8,899,464 | B2 | 12/2014 | Hueil et al. |
| 8,899,465 | B2 | 12/2014 | Shelton, IV et al. |
| 8,899,466 | B2 | 12/2014 | Baxter, III et al. |
| 8,900,267 | B2 | 12/2014 | Woolfson et al. |
| 8,905,287 | B2 | 12/2014 | Racenet et al. |
| 8,905,977 | B2 | 12/2014 | Shelton et al. |
| 8,910,846 | B2 | 12/2014 | Viola |
| 8,910,847 | B2 | 12/2014 | Nalagatla et al. |
| 8,911,426 | B2 | 12/2014 | Coppeta et al. |
| 8,911,448 | B2 | 12/2014 | Stein |
| 8,911,460 | B2 | 12/2014 | Neurohr et al. |
| 8,911,471 | B2 | 12/2014 | Spivey et al. |
| 8,912,746 | B2 | 12/2014 | Reid et al. |
| 8,920,368 | B2 | 12/2014 | Sandhu et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,936,614 | B2 | 1/2015 | Allen, IV |
| 8,939,343 | B2 | 1/2015 | Milliman et al. |
| 8,939,344 | B2 | 1/2015 | Olson et al. |
| 8,939,898 | B2 | 1/2015 | Omoto |
| 8,944,069 | B2 | 2/2015 | Miller et al. |
| 8,945,095 | B2 | 2/2015 | Blumenkranz et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |

(56) References Cited

U.S. PATENT DOCUMENTS

| | | | |
|---|---|---|---|
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,849 | B2 | 4/2015 | Stulen et al. |
| 9,017,851 | B2 | 4/2015 | Felder et al. |
| D729,274 | S | 5/2015 | Clement et al. |
| 9,021,684 | B2 | 5/2015 | Lenker et al. |
| 9,023,014 | B2 | 5/2015 | Chowaniec et al. |
| 9,023,069 | B2 | 5/2015 | Kasvikis et al. |
| 9,023,071 | B2 | 5/2015 | Miller et al. |
| 9,026,347 | B2 | 5/2015 | Gadh et al. |
| 9,027,817 | B2 | 5/2015 | Milliman et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,030,166 | B2 | 5/2015 | Kano |
| 9,030,169 | B2 | 5/2015 | Christensen et al. |
| 9,033,203 | B2 | 5/2015 | Woodard, Jr. et al. |
| 9,033,204 | B2 | 5/2015 | Shelton, IV et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,720 | B2 | 5/2015 | Madan |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,261 | B2 | 6/2015 | Houser |
| 9,044,281 | B2 | 6/2015 | Pool et al. |
| 9,050,083 | B2 | 6/2015 | Yates et al. |
| 9,050,084 | B2 | 6/2015 | Schmid et al. |
| 9,050,089 | B2 | 6/2015 | Orszulak |
| 9,050,100 | B2 | 6/2015 | Yates et al. |
| 9,050,120 | B2 | 6/2015 | Swarup et al. |
| 9,050,123 | B2 | 6/2015 | Krause et al. |
| 9,050,176 | B2 | 6/2015 | Datta et al. |
| 9,050,192 | B2 | 6/2015 | Mansmann |
| 9,055,941 | B2 | 6/2015 | Schmid et al. |
| 9,055,942 | B2 | 6/2015 | Balbierz et al. |
| 9,055,943 | B2 | 6/2015 | Zemlok et al. |
| 9,055,944 | B2 | 6/2015 | Hodgkinson et al. |
| 9,055,961 | B2 | 6/2015 | Manzo et al. |
| 9,060,770 | B2 | 6/2015 | Shelton, IV et al. |
| 9,060,776 | B2 | 6/2015 | Yates et al. |
| 9,060,794 | B2 | 6/2015 | Kang et al. |
| 9,060,894 | B2 | 6/2015 | Wubbeling |
| 9,061,392 | B2 | 6/2015 | Forgues et al. |
| 9,072,515 | B2 | 7/2015 | Hall et al. |
| 9,072,523 | B2 | 7/2015 | Houser et al. |
| 9,072,535 | B2 | 7/2015 | Shelton, IV et al. |
| 9,072,536 | B2 | 7/2015 | Shelton, IV et al. |
| 9,078,653 | B2 | 7/2015 | Leimbach et al. |
| 9,078,654 | B2 | 7/2015 | Whitman et al. |
| 9,084,601 | B2 | 7/2015 | Moore et al. |
| 9,084,602 | B2 | 7/2015 | Gleiman |
| 9,086,875 | B2 | 7/2015 | Harrat et al. |
| 9,089,326 | B2 | 7/2015 | Krumanaker et al. |
| 9,089,330 | B2 | 7/2015 | Widenhouse et al. |
| 9,089,338 | B2 | 7/2015 | Smith et al. |
| 9,089,352 | B2 | 7/2015 | Jeong |
| 9,089,360 | B2 | 7/2015 | Messerly et al. |
| 9,091,588 | B2 | 7/2015 | Lefler |
| D736,792 | S | 8/2015 | Brinda et al. |
| 9,095,339 | B2 | 8/2015 | Moore et al. |
| 9,095,346 | B2 | 8/2015 | Houser et al. |
| 9,095,362 | B2 | 8/2015 | Dachs, II et al. |
| 9,095,367 | B2 | 8/2015 | Olson et al. |
| 9,096,033 | B2 | 8/2015 | Holop et al. |
| 9,098,153 | B2 | 8/2015 | Shen et al. |
| 9,099,863 | B2 | 8/2015 | Smith et al. |
| 9,099,877 | B2 | 8/2015 | Banos et al. |
| 9,099,922 | B2 | 8/2015 | Toosky et al. |
| 9,101,358 | B2 | 8/2015 | Kerr et al. |
| 9,101,385 | B2 | 8/2015 | Shelton, IV et al. |
| 9,101,475 | B2 | 8/2015 | Wei et al. |
| 9,101,621 | B2 | 8/2015 | Zeldis |
| 9,107,663 | B2 | 8/2015 | Swensgard |
| 9,107,667 | B2 | 8/2015 | Hodgkinson |
| 9,107,690 | B2 | 8/2015 | Bales, Jr. et al. |
| 9,110,587 | B2 | 8/2015 | Kim et al. |
| 9,113,862 | B2 | 8/2015 | Morgan et al. |
| 9,113,864 | B2 | 8/2015 | Morgan et al. |
| 9,113,865 | B2 | 8/2015 | Shelton, IV et al. |
| 9,113,868 | B2 | 8/2015 | Felder et al. |
| 9,113,873 | B2 | 8/2015 | Marczyk et al. |
| 9,113,874 | B2 | 8/2015 | Shelton, IV et al. |
| 9,113,876 | B2 | 8/2015 | Zemlok et al. |
| 9,113,879 | B2 | 8/2015 | Felder et al. |
| 9,113,880 | B2 | 8/2015 | Zemlok et al. |
| 9,113,881 | B2 | 8/2015 | Scirica |
| 9,113,883 | B2 | 8/2015 | Aronhalt et al. |
| 9,113,884 | B2 | 8/2015 | Shelton, IV et al. |
| 9,113,887 | B2 | 8/2015 | Behnke, II et al. |
| 9,119,615 | B2 | 9/2015 | Felder et al. |
| 9,119,657 | B2 | 9/2015 | Shelton, IV et al. |
| 9,119,898 | B2 | 9/2015 | Bayon et al. |
| 9,119,957 | B2 | 9/2015 | Gantz et al. |
| 9,123,286 | B2 | 9/2015 | Park |
| 9,124,097 | B2 | 9/2015 | Cruz |
| 9,125,651 | B2 | 9/2015 | Mandakolathur Vasudevan et al. |
| 9,125,654 | B2 | 9/2015 | Aronhalt et al. |
| 9,125,662 | B2 | 9/2015 | Shelton, IV |
| 9,126,317 | B2 | 9/2015 | Lawton et al. |
| 9,131,835 | B2 | 9/2015 | Widenhouse et al. |
| 9,131,940 | B2 | 9/2015 | Huitema et al. |
| 9,131,950 | B2 | 9/2015 | Matthew |
| 9,131,957 | B2 | 9/2015 | Skarbnik et al. |
| 9,138,225 | B2 | 9/2015 | Huang et al. |
| 9,138,226 | B2 | 9/2015 | Racenet et al. |
| 9,144,455 | B2 | 9/2015 | Kennedy et al. |
| D740,414 | S | 10/2015 | Katsura |
| D741,882 | S | 10/2015 | Shmilov et al. |
| 9,149,274 | B2 | 10/2015 | Spivey et al. |
| 9,149,324 | B2 | 10/2015 | Huang et al. |
| 9,149,325 | B2 | 10/2015 | Worrell et al. |
| 9,153,994 | B2 | 10/2015 | Wood et al. |
| 9,161,753 | B2 | 10/2015 | Prior |
| 9,161,769 | B2 | 10/2015 | Stoddard et al. |
| 9,161,803 | B2 | 10/2015 | Yates et al. |
| 9,161,807 | B2 | 10/2015 | Garrison |
| 9,161,855 | B2 | 10/2015 | Rousseau et al. |
| 9,164,271 | B2 | 10/2015 | Ebata et al. |

(56) References Cited

U.S. PATENT DOCUMENTS 9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,750 B2 1/2016 Weir et al.
9,226,751 B2 1/2016 Shelton, IV et al.
9,226,754 B2 1/2016 D'Agostino et al.
9,226,761 B2 1/2016 Burbank
9,226,767 B2 1/2016 Stulen et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.

(56) References Cited

U.S. PATENT DOCUMENTS 9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,345,477 B2 5/2016 Anim et al.
9,345,479 B2 5/2016 Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,226 B2 6/2016 Zemlok et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,669 B2 7/2016 Karkanias et al.
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
D767,624 S 9/2016 Lee et al.
9,433,411 B2 9/2016 Racenet et al.
9,433,414 B2 9/2016 Chen et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,523 B2 10/2016 Meade et al.
9,474,540 B2 10/2016 Stokes et al.
9,475,180 B2 10/2016 Eshleman et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.

(56) References Cited

U.S. PATENT DOCUMENTS

| | | | |
|---|---|---|---|
| 9,498,231 | B2 | 11/2016 | Haider et al. |
| 9,504,455 | B2 | 11/2016 | Whitman et al. |
| 9,504,483 | B2 | 11/2016 | Houser et al. |
| 9,504,520 | B2 | 11/2016 | Worrell et al. |
| 9,504,521 | B2 | 11/2016 | Deutmeyer et al. |
| 9,504,528 | B2 | 11/2016 | Ivinson et al. |
| 9,507,399 | B2 | 11/2016 | Chien |
| D774,547 | S | 12/2016 | Capela et al. |
| D775,336 | S | 12/2016 | Shelton, IV et al. |
| 9,510,827 | B2 | 12/2016 | Kostrzewski |
| 9,510,828 | B2 | 12/2016 | Yates et al. |
| 9,510,830 | B2 | 12/2016 | Shelton, IV et al. |
| 9,510,846 | B2 | 12/2016 | Sholev et al. |
| 9,510,895 | B2 | 12/2016 | Houser et al. |
| 9,510,925 | B2 | 12/2016 | Hotter et al. |
| 9,517,063 | B2 | 12/2016 | Swayze et al. |
| 9,517,065 | B2 | 12/2016 | Simms et al. |
| 9,517,068 | B2 | 12/2016 | Shelton, IV et al. |
| 9,517,326 | B2 | 12/2016 | Hinman et al. |
| 9,521,996 | B2 | 12/2016 | Armstrong |
| 9,522,003 | B2 | 12/2016 | Weir et al. |
| 9,522,014 | B2 | 12/2016 | Nishizawa et al. |
| 9,522,029 | B2 | 12/2016 | Yates et al. |
| 9,526,481 | B2 | 12/2016 | Storz et al. |
| 9,526,499 | B2 | 12/2016 | Kostrzewski et al. |
| 9,526,563 | B2 | 12/2016 | Twomey |
| 9,526,564 | B2 | 12/2016 | Rusin |
| D776,683 | S | 1/2017 | Gobinski et al. |
| D777,773 | S | 1/2017 | Shi |
| 9,532,783 | B2 | 1/2017 | Swayze et al. |
| 9,539,060 | B2 | 1/2017 | Lightcap et al. |
| 9,539,726 | B2 | 1/2017 | Simaan et al. |
| 9,545,253 | B2 | 1/2017 | Worrell et al. |
| 9,545,258 | B2 | 1/2017 | Smith et al. |
| 9,549,732 | B2 | 1/2017 | Yates et al. |
| 9,549,733 | B2 | 1/2017 | Knodel |
| 9,549,735 | B2 | 1/2017 | Shelton, IV et al. |
| 9,554,794 | B2 | 1/2017 | Baber et al. |
| 9,554,796 | B2 | 1/2017 | Kostrzewski |
| 9,554,803 | B2 | 1/2017 | Smith et al. |
| 9,554,812 | B2 | 1/2017 | Inkpen et al. |
| 9,559,624 | B2 | 1/2017 | Philipp |
| 9,561,013 | B2 | 2/2017 | Tsuchiya |
| 9,561,029 | B2 | 2/2017 | Scheib et al. |
| 9,561,030 | B2 | 2/2017 | Zhang et al. |
| 9,561,031 | B2 | 2/2017 | Heinrich et al. |
| 9,561,032 | B2 | 2/2017 | Shelton, IV et al. |
| 9,561,038 | B2 | 2/2017 | Shelton, IV et al. |
| 9,561,045 | B2 | 2/2017 | Hinman et al. |
| 9,566,061 | B2 | 2/2017 | Aronhalt et al. |
| 9,566,062 | B2 | 2/2017 | Boudreaux |
| 9,566,065 | B2 | 2/2017 | Knodel |
| 9,566,067 | B2 | 2/2017 | Milliman et al. |
| 9,572,574 | B2 | 2/2017 | Shelton, IV et al. |
| 9,572,576 | B2 | 2/2017 | Hodgkinson et al. |
| 9,572,577 | B2 | 2/2017 | Lloyd et al. |
| 9,572,592 | B2 | 2/2017 | Price et al. |
| 9,574,644 | B2 | 2/2017 | Parihar |
| 9,579,088 | B2 | 2/2017 | Farritor et al. |
| 9,579,143 | B2 | 2/2017 | Ullrich et al. |
| 9,579,158 | B2 | 2/2017 | Brianza et al. |
| D780,803 | S | 3/2017 | Gill et al. |
| D781,879 | S | 3/2017 | Butcher et al. |
| D782,530 | S | 3/2017 | Paek et al. |
| 9,585,550 | B2 | 3/2017 | Abel et al. |
| 9,585,657 | B2 | 3/2017 | Shelton, IV et al. |
| 9,585,658 | B2 | 3/2017 | Shelton, IV |
| 9,585,659 | B2 | 3/2017 | Viola et al. |
| 9,585,660 | B2 | 3/2017 | Laurent et al. |
| 9,585,662 | B2 | 3/2017 | Shelton, IV et al. |
| 9,585,663 | B2 | 3/2017 | Shelton, IV et al. |
| 9,585,672 | B2 | 3/2017 | Bastia |
| 9,590,433 | B2 | 3/2017 | Li |
| 9,592,050 | B2 | 3/2017 | Schmid et al. |
| 9,592,052 | B2 | 3/2017 | Shelton, IV |
| 9,592,053 | B2 | 3/2017 | Shelton, IV et al. |
| 9,592,054 | B2 | 3/2017 | Schmid et al. |
| 9,597,073 | B2 | 3/2017 | Sorrentino et al. |
| 9,597,075 | B2 | 3/2017 | Shelton, IV et al. |
| 9,597,078 | B2 | 3/2017 | Scirica et al. |
| 9,597,080 | B2 | 3/2017 | Milliman et al. |
| 9,597,104 | B2 | 3/2017 | Nicholas et al. |
| 9,597,143 | B2 | 3/2017 | Madan et al. |
| 9,603,595 | B2 | 3/2017 | Shelton, IV et al. |
| 9,603,598 | B2 | 3/2017 | Shelton, IV et al. |
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,632 | B2 | 4/2017 | Linder et al. |
| 9,629,652 | B2 | 4/2017 | Mumaw et al. |
| 9,629,814 | B2 | 4/2017 | Widenhouse et al. |
| D785,794 | S | 5/2017 | Magno, Jr. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,091 | B2 | 5/2017 | Beardsley et al. |
| 9,636,111 | B2 | 5/2017 | Wenchell |
| 9,636,112 | B2 | 5/2017 | Penna et al. |
| 9,636,113 | B2 | 5/2017 | Wenchell |
| 9,636,850 | B2 | 5/2017 | Stopek et al. |
| 9,641,122 | B2 | 5/2017 | Romanowich et al. |
| 9,642,620 | B2 | 5/2017 | Baxter, III et al. |
| 9,642,642 | B2 | 5/2017 | Lim |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,649,190 | B2 | 5/2017 | Mathies |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,661,991 | B2 | 5/2017 | Glossop |
| 9,662,108 | B2 | 5/2017 | Williams |
| 9,662,110 | B2 | 5/2017 | Huang et al. |
| 9,662,116 | B2 | 5/2017 | Smith et al. |
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,668,735 | B2 | 6/2017 | Beetel |
| 9,675,344 | B2 | 6/2017 | Combrowski et al. |
| 9,675,348 | B2 | 6/2017 | Smith et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,368 | B2 | 6/2017 | Guo et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter et al. |
| 9,681,873 | B2 | 6/2017 | Smith et al. |
| 9,681,884 | B2 | 6/2017 | Clem et al. |

(56) References Cited

U.S. PATENT DOCUMENTS 9,687,230 B2 6/2017 Leimbach et al.
9,687,231 B2 6/2017 Baxter, III et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,731,410 B2 8/2017 Hirabayashi et al.
9,733,663 B2 8/2017 Leimbach et al.
9,737,297 B2 8/2017 Racenet et al.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.

(56) References Cited

U.S. PATENT DOCUMENTS

| | | | |
|---|---|---|---|
| 9,839,428 | B2 | 12/2017 | Baxter, III et al. |
| 9,839,429 | B2 | 12/2017 | Weisenburgh et al. |
| 9,839,480 | B2 | 12/2017 | Pribanic et al. |
| 9,844,368 | B2 | 12/2017 | Boudreaux et al. |
| 9,844,369 | B2 | 12/2017 | Huitema et al. |
| 9,844,372 | B2 | 12/2017 | Shelton, IV et al. |
| 9,844,373 | B2 | 12/2017 | Swayze et al. |
| 9,844,374 | B2 | 12/2017 | Lytle, IV et al. |
| 9,844,375 | B2 | 12/2017 | Overmyer et al. |
| 9,844,376 | B2 | 12/2017 | Baxter et al. |
| 9,844,379 | B2 | 12/2017 | Shelton, IV et al. |
| 9,848,871 | B2 | 12/2017 | Harris et al. |
| 9,848,873 | B2 | 12/2017 | Shelton, IV |
| 9,848,875 | B2 | 12/2017 | Aronhalt et al. |
| 9,848,877 | B2 | 12/2017 | Shelton, IV et al. |
| 9,850,994 | B2 | 12/2017 | Schena |
| D808,989 | S | 1/2018 | Ayvazian et al. |
| 9,855,039 | B2 | 1/2018 | Racenet et al. |
| 9,855,040 | B2 | 1/2018 | Kostrzewski |
| 9,855,662 | B2 | 1/2018 | Ruiz Morales et al. |
| 9,861,261 | B2 | 1/2018 | Shahinian |
| 9,861,359 | B2 | 1/2018 | Shelton, IV et al. |
| 9,861,361 | B2 | 1/2018 | Aronhalt et al. |
| 9,861,362 | B2 | 1/2018 | Whitman et al. |
| 9,861,366 | B2 | 1/2018 | Aranyi |
| 9,861,382 | B2 | 1/2018 | Smith et al. |
| 9,861,446 | B2 | 1/2018 | Lang |
| 9,867,612 | B2 | 1/2018 | Parihar et al. |
| 9,867,613 | B2 | 1/2018 | Marczyk et al. |
| 9,867,615 | B2 | 1/2018 | Fanelli et al. |
| 9,867,618 | B2 | 1/2018 | Hall et al. |
| 9,867,620 | B2 | 1/2018 | Fischvogt et al. |
| 9,868,198 | B2 | 1/2018 | Nicholas et al. |
| 9,872,682 | B2 | 1/2018 | Hess et al. |
| 9,872,683 | B2 | 1/2018 | Hopkins et al. |
| 9,872,684 | B2 | 1/2018 | Hall et al. |
| 9,872,722 | B2 | 1/2018 | Lech |
| 9,877,721 | B2 | 1/2018 | Schellin et al. |
| 9,877,722 | B2 | 1/2018 | Schellin et al. |
| 9,877,723 | B2 | 1/2018 | Hall et al. |
| 9,877,776 | B2 | 1/2018 | Boudreaux |
| D810,099 | S | 2/2018 | Riedel |
| 9,883,843 | B2 | 2/2018 | Garlow |
| 9,883,860 | B2 | 2/2018 | Leimbach et al. |
| 9,883,861 | B2 | 2/2018 | Shelton, IV et al. |
| 9,884,456 | B2 | 2/2018 | Schellin et al. |
| 9,888,919 | B2 | 2/2018 | Leimbach et al. |
| 9,888,921 | B2 | 2/2018 | Williams et al. |
| 9,888,924 | B2 | 2/2018 | Ebersole et al. |
| 9,889,230 | B2 | 2/2018 | Bennett et al. |
| 9,895,147 | B2 | 2/2018 | Shelton, IV |
| 9,895,148 | B2 | 2/2018 | Shelton, IV et al. |
| 9,895,813 | B2 | 2/2018 | Blumenkranz et al. |
| 9,901,339 | B2 | 2/2018 | Farascioni |
| 9,901,341 | B2 | 2/2018 | Kostrzewski |
| 9,901,342 | B2 | 2/2018 | Shelton, IV et al. |
| 9,901,344 | B2 | 2/2018 | Moore et al. |
| 9,901,345 | B2 | 2/2018 | Moore et al. |
| 9,901,346 | B2 | 2/2018 | Moore et al. |
| 9,901,406 | B2 | 2/2018 | State et al. |
| 9,901,412 | B2 | 2/2018 | Lathrop et al. |
| D813,899 | S | 3/2018 | Erant et al. |
| 9,907,456 | B2 | 3/2018 | Miyoshi |
| 9,907,553 | B2 | 3/2018 | Cole et al. |
| 9,907,600 | B2 | 3/2018 | Stulen et al. |
| 9,907,620 | B2 | 3/2018 | Shelton, IV et al. |
| 9,913,641 | B2 | 3/2018 | Takemoto et al. |
| 9,913,642 | B2 | 3/2018 | Leimbach et al. |
| 9,913,644 | B2 | 3/2018 | McCuen |
| 9,913,646 | B2 | 3/2018 | Shelton, IV |
| 9,913,647 | B2 | 3/2018 | Weisenburgh, II et al. |
| 9,913,648 | B2 | 3/2018 | Shelton, IV et al. |
| 9,913,694 | B2 | 3/2018 | Brisson |
| 9,913,733 | B2 | 3/2018 | Piron et al. |
| 9,918,704 | B2 | 3/2018 | Shelton, IV et al. |
| 9,918,714 | B2 | 3/2018 | Gibbons, Jr. |
| 9,918,715 | B2 | 3/2018 | Menn |
| 9,918,716 | B2 | 3/2018 | Baxter, III et al. |
| 9,918,717 | B2 | 3/2018 | Czernik |
| 9,918,730 | B2 | 3/2018 | Trees et al. |
| 9,924,941 | B2 | 3/2018 | Burbank |
| 9,924,942 | B2 | 3/2018 | Swayze et al. |
| 9,924,943 | B2 | 3/2018 | Mohan Pinjala et al. |
| 9,924,944 | B2 | 3/2018 | Shelton, IV et al. |
| 9,924,945 | B2 | 3/2018 | Zheng et al. |
| 9,924,946 | B2 | 3/2018 | Vendely et al. |
| 9,924,947 | B2 | 3/2018 | Shelton, IV et al. |
| 9,924,961 | B2 | 3/2018 | Shelton, IV et al. |
| 9,931,106 | B2 | 4/2018 | Au et al. |
| 9,931,116 | B2 | 4/2018 | Racenet et al. |
| 9,931,118 | B2 | 4/2018 | Shelton, IV et al. |
| 9,931,120 | B2 | 4/2018 | Chen et al. |
| 9,936,949 | B2 | 4/2018 | Measamer et al. |
| 9,936,950 | B2 | 4/2018 | Shelton, IV et al. |
| 9,936,951 | B2 | 4/2018 | Hufnagel et al. |
| 9,936,952 | B2 | 4/2018 | Demmy |
| 9,936,954 | B2 | 4/2018 | Shelton, IV et al. |
| 9,937,626 | B2 | 4/2018 | Rockrohr |
| 9,943,309 | B2 | 4/2018 | Shelton, IV et al. |
| 9,943,310 | B2 | 4/2018 | Harris et al. |
| 9,943,312 | B2 | 4/2018 | Posada et al. |
| 9,949,754 | B2 | 4/2018 | Newhauser et al. |
| 9,953,193 | B2 | 4/2018 | Butler et al. |
| D819,072 | S | 5/2018 | Clediere |
| 9,955,954 | B2 | 5/2018 | Destoumieux et al. |
| 9,955,965 | B2 | 5/2018 | Chen et al. |
| 9,955,966 | B2 | 5/2018 | Zergiebel |
| 9,956,677 | B2 | 5/2018 | Baskar et al. |
| 9,962,129 | B2 | 5/2018 | Jerebko et al. |
| 9,962,157 | B2 | 5/2018 | Sapre |
| 9,962,158 | B2 | 5/2018 | Hall et al. |
| 9,962,159 | B2 | 5/2018 | Heinrich et al. |
| 9,962,161 | B2 | 5/2018 | Scheib et al. |
| 9,968,354 | B2 | 5/2018 | Shelton, IV et al. |
| 9,968,355 | B2 | 5/2018 | Shelton, IV et al. |
| 9,968,356 | B2 | 5/2018 | Shelton, IV et al. |
| 9,968,397 | B2 | 5/2018 | Taylor et al. |
| 9,974,529 | B2 | 5/2018 | Shelton, IV et al. |
| 9,974,538 | B2 | 5/2018 | Baxter, III et al. |
| 9,974,539 | B2 | 5/2018 | Yates et al. |
| 9,974,541 | B2 | 5/2018 | Calderoni |
| 9,974,542 | B2 | 5/2018 | Hodgkinson |
| 9,980,713 | B2 | 5/2018 | Aronhalt et al. |
| 9,980,724 | B2 | 5/2018 | Farascioni et al. |
| 9,980,729 | B2 | 5/2018 | Moore et al. |
| 9,980,769 | B2 | 5/2018 | Trees et al. |
| D819,680 | S | 6/2018 | Nguyen |
| D819,682 | S | 6/2018 | Howard et al. |
| D819,684 | S | 6/2018 | Dart |
| D820,307 | S | 6/2018 | Jian et al. |
| D820,867 | S | 6/2018 | Dickens et al. |
| 9,987,000 | B2 | 6/2018 | Shelton, IV et al. |
| 9,987,003 | B2 | 6/2018 | Timm et al. |
| 9,987,006 | B2 | 6/2018 | Morgan et al. |
| 9,987,095 | B2 | 6/2018 | Chowaniec et al. |
| 9,987,097 | B2 | 6/2018 | van der Weide et al. |
| 9,987,099 | B2 | 6/2018 | Chen et al. |
| 9,993,248 | B2 | 6/2018 | Shelton, IV et al. |
| 9,993,258 | B2 | 6/2018 | Shelton, IV et al. |
| 9,993,284 | B2 | 6/2018 | Boudreaux |
| 9,999,408 | B2 | 6/2018 | Boudreaux et al. |
| 9,999,423 | B2 | 6/2018 | Schuckmann et al. |
| 9,999,426 | B2 | 6/2018 | Moore et al. |
| 9,999,431 | B2 | 6/2018 | Shelton, IV et al. |
| 9,999,472 | B2 | 6/2018 | Weir et al. |
| 10,004,497 | B2 | 6/2018 | Overmyer et al. |
| 10,004,498 | B2 | 6/2018 | Morgan et al. |
| 10,004,500 | B2 | 6/2018 | Shelton, IV et al. |
| 10,004,501 | B2 | 6/2018 | Shelton, IV et al. |
| 10,004,505 | B2 | 6/2018 | Moore et al. |
| 10,004,506 | B2 | 6/2018 | Shelton, IV et al. |
| D822,206 | S | 7/2018 | Shelton, IV et al. |
| 10,010,322 | B2 | 7/2018 | Shelton, IV et al. |
| 10,010,324 | B2 | 7/2018 | Huitema et al. |

(56) References Cited

U.S. PATENT DOCUMENTS 10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,123 B2 7/2018 Williams et al.
10,022,125 B2 7/2018 Stopek
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,624 B2 9/2018 Shelton, IV et al.
10,064,639 B2 9/2018 Ishida et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,679 B2 10/2018 Baber et al.
10,111,698 B2 10/2018 Scheib et al.
10,111,702 B2 10/2018 Kostrzewski
10,117,649 B2 11/2018 Baxter, III et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.
10,123,798 B2 11/2018 Baxter, III et al.
10,124,493 B2 11/2018 Rothfuss et al.
10,130,352 B2 11/2018 Widenhouse et al.
10,130,359 B2 11/2018 Hess et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
D835,659 S 12/2018 Anzures et al.
D836,124 S 12/2018 Fan
10,143,474 B2 12/2018 Bucciaglia et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,163,065 B1 12/2018 Koski et al.
10,163,589 B2 12/2018 Zergiebel et al.
D837,244 S 1/2019 Kuo et al.
D837,245 S 1/2019 Kuo et al.
10,166,023 B2 1/2019 Vendely et al.
10,166,025 B2 1/2019 Leimbach et al.
10,166,026 B2 1/2019 Shelton, IV et al.
10,172,611 B2 1/2019 Shelton, IV et al.
10,172,615 B2 1/2019 Marczyk et al.
10,172,616 B2 1/2019 Murray et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,180,463 B2 1/2019 Beckman et al.
10,182,813 B2 1/2019 Leimbach et al.
10,182,815 B2 1/2019 Williams et al.
10,182,816 B2 1/2019 Shelton, IV et al.
10,182,818 B2 1/2019 Hensel et al.
10,182,819 B2 1/2019 Shelton, IV
10,182,868 B2 1/2019 Meier et al.
10,188,385 B2 1/2019 Kerr et al.
10,188,393 B2 1/2019 Smith et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.

(56) References Cited

U.S. PATENT DOCUMENTS 10,194,908 B2 2/2019 Duque et al.
10,194,910 B2 2/2019 Shelton, IV et al.
10,194,913 B2 2/2019 Nalagatla et al.
10,194,976 B2 2/2019 Boudreaux
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,364 B2 2/2019 Leimbach et al.
10,201,365 B2 2/2019 Boudreaux et al.
10,201,381 B2 2/2019 Zergiebel et al.
10,206,605 B2 2/2019 Shelton, IV et al.
10,206,676 B2 2/2019 Shelton, IV
10,206,677 B2 2/2019 Harris et al.
10,206,678 B2 2/2019 Shelton, IV et al.
10,206,748 B2 2/2019 Burbank
10,210,244 B1 2/2019 Branavan et al.
10,211,586 B2 2/2019 Adams et al.
10,213,198 B2 2/2019 Aronhalt et al.
10,213,201 B2 2/2019 Shelton, IV et al.
10,213,202 B2 2/2019 Flanagan et al.
10,213,203 B2 2/2019 Swayze et al.
10,213,262 B2 2/2019 Shelton, IV et al.
D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.
10,238,389 B2 3/2019 Yates et al.
10,238,390 B2 3/2019 Harris et al.
10,238,391 B2 3/2019 Leimbach et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,032 B2 4/2019 Shelton, IV
10,245,033 B2 4/2019 Overmyer et al.
10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,697 B2 5/2019 Shelton, IV et al.
10,278,702 B2 5/2019 Shelton, IV et al.
10,278,703 B2 5/2019 Nativ et al.
10,278,707 B2 5/2019 Thompson et al.
10,278,722 B2 5/2019 Shelton, IV et al.
10,278,780 B2 5/2019 Shelton, IV
10,285,694 B2 5/2019 Viola et al.
10,285,695 B2 5/2019 Jaworek et al.
10,285,699 B2 5/2019 Vendely et al.
10,285,705 B2 5/2019 Shelton, IV et al.
10,292,701 B2 5/2019 Scheib et al.
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,792 B2 5/2019 Huitema et al.
10,299,817 B2 5/2019 Shelton, IV et al.
10,299,818 B2 5/2019 Riva
10,299,878 B2 5/2019 Shelton, IV et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,589 B2 6/2019 Shelton, IV et al.
10,314,590 B2 6/2019 Shelton, IV et al.
10,315,566 B2 6/2019 Choi et al.
10,321,907 B2 6/2019 Shelton, IV et al.
10,321,909 B2 6/2019 Shelton, IV et al.
10,321,927 B2 6/2019 Hinman
10,327,743 B2 6/2019 St. Goar et al.
10,327,764 B2 6/2019 Harris et al.
10,327,765 B2 6/2019 Timm et al.
10,327,767 B2 6/2019 Shelton, IV et al.
10,327,769 B2 6/2019 Overmyer et al.
10,327,776 B2 6/2019 Harris et al.
10,327,777 B2 6/2019 Harris et al.
D854,032 S 7/2019 Jones et al.
D854,151 S 7/2019 Shelton, IV et al.
10,335,144 B2 7/2019 Shelton, IV et al.
10,335,145 B2 7/2019 Harris et al.
10,335,147 B2 7/2019 Rector et al.
10,335,148 B2 7/2019 Shelton, IV et al.
10,335,149 B2 7/2019 Baxter, III et al.
10,335,150 B2 7/2019 Shelton, IV
10,335,151 B2 7/2019 Shelton, IV et al.
10,337,148 B2 7/2019 Rouse et al.
10,342,533 B2 7/2019 Shelton, IV et al.
10,342,535 B2 7/2019 Scheib et al.
10,342,541 B2 7/2019 Shelton, IV et al.
10,342,543 B2 7/2019 Shelton, IV et al.
10,342,623 B2 7/2019 Huelman et al.
10,349,937 B2 7/2019 Williams
10,349,939 B2 7/2019 Shelton, IV et al.

(56) References Cited

U.S. PATENT DOCUMENTS 10,349,941 B2 7/2019 Marczyk et al.
10,349,963 B2 7/2019 Fiksen et al.
10,350,016 B2 7/2019 Burbank et al.
D855,634 S 8/2019 Kim
D856,359 S 8/2019 Huang et al.
10,390,830 B2 8/2019 Schulz
10,390,897 B2 8/2019 Kostrzewski
D860,219 S 9/2019 Rasmussen et al.
D861,035 S 9/2019 Park et al.
10,398,460 B2 9/2019 Overmyer
10,404,136 B2 9/2019 Oktavec et al.
10,405,932 B2 9/2019 Overmyer
10,405,937 B2 9/2019 Black et al.
10,413,370 B2 9/2019 Yates et al.
10,413,373 B2 9/2019 Yates et al.
10,420,548 B2 9/2019 Whitman et al.
10,420,554 B2 9/2019 Collings et al.
10,420,559 B2 9/2019 Marczyk et al.
D861,707 S 10/2019 Yang
D862,518 S 10/2019 Niven et al.
D863,343 S 10/2019 Mazlish et al.
D864,388 S 10/2019 Barber
10,426,466 B2 10/2019 Contini et al.
10,426,468 B2 10/2019 Contini et al.
10,426,555 B2 10/2019 Crowley et al.
D865,796 S 11/2019 Xu et al.
10,463,371 B2 11/2019 Kostrzewski
10,470,767 B2 11/2019 Gleiman et al.
10,471,282 B2 11/2019 Kirk et al.
10,471,576 B2 11/2019 Totsu
10,478,185 B2 11/2019 Nicholas
10,478,187 B2 11/2019 Shelton, IV et al.
10,478,207 B2 11/2019 Lathrop
D869,655 S 12/2019 Shelton, IV et al.
D870,742 S 12/2019 Cornell
10,492,851 B2 12/2019 Hughett, Sr. et al.
10,498,269 B2 12/2019 Zemlok et al.
10,499,917 B2 12/2019 Scheib et al.
10,508,720 B2 12/2019 Nicholas
10,512,461 B2 12/2019 Gupta et al.
10,517,592 B2 12/2019 Shelton, IV et al.
10,537,351 B2 1/2020 Shelton, IV et al.
10,542,908 B2 1/2020 Mei et al.
10,542,985 B2 1/2020 Zhan et al.
10,548,593 B2 2/2020 Shelton, IV et al.
10,548,673 B2 2/2020 Harris et al.
10,561,419 B2 2/2020 Beardsley
10,561,432 B2 2/2020 Estrella et al.
10,561,474 B2 2/2020 Adams et al.
D879,808 S 3/2020 Harris et al.
D879,809 S 3/2020 Harris et al.
10,595,887 B2 3/2020 Shelton, IV et al.
10,595,929 B2 3/2020 Boudreaux et al.
10,603,117 B2 3/2020 Schings et al.
10,610,236 B2 4/2020 Baril
10,617,411 B2 4/2020 Williams
10,624,709 B2 4/2020 Remm
10,625,062 B2 4/2020 Matlock et al.
10,631,857 B2 4/2020 Kostrzewski
10,631,858 B2 4/2020 Burbank
10,631,860 B2 4/2020 Bakos et al.
10,677,035 B2 6/2020 Balan et al.
10,695,074 B2 6/2020 Carusillo
10,695,081 B2 6/2020 Shelton, IV et al.
D890,784 S 7/2020 Shelton, IV et al.
10,702,266 B2 7/2020 Parihar et al.
10,705,660 B2 7/2020 Xiao
10,722,233 B2 7/2020 Wellman
10,722,317 B2 7/2020 Ward et al.
10,729,443 B2 8/2020 Cabrera et al.
10,736,616 B2 8/2020 Scheib et al.
10,736,644 B2 8/2020 Windolf et al.
10,743,930 B2 8/2020 Nagtegaal
10,751,048 B2 8/2020 Whitman et al.
10,772,628 B2 9/2020 Chen et al.
10,772,651 B2 9/2020 Shelton, IV et al.
10,806,451 B2 10/2020 Harris et al.
10,813,683 B2 10/2020 Baxter, III et al.
10,842,473 B2 11/2020 Scheib et al.
D906,355 S 12/2020 Messerly et al.
10,849,621 B2 12/2020 Whitfield et al.
10,849,697 B2 12/2020 Yates et al.
10,856,870 B2 * 12/2020 Harris .............. A61B 17/00234
10,874,393 B2 12/2020 Satti, III et al.
D907,647 S 1/2021 Siebel et al.
D907,648 S 1/2021 Siebel et al.
10,892,899 B2 1/2021 Shelton, IV et al.
D910,847 S 2/2021 Shelton, IV et al.
10,905,415 B2 2/2021 DiNardo et al.
10,912,562 B2 2/2021 Dunki-Jacobs et al.
10,932,804 B2 3/2021 Scheib et al.
10,932,806 B2 3/2021 Shelton, IV et al.
10,932,872 B2 3/2021 Shelton, IV et al.
10,944,728 B2 3/2021 Wiener et al.
10,952,708 B2 3/2021 Scheib et al.
10,952,728 B2 3/2021 Shelton, IV et al.
10,959,744 B2 3/2021 Shelton, IV et al.
2001/0000531 A1 4/2001 Casscells et al.
2001/0025183 A1 9/2001 Shahidi
2001/0025184 A1 9/2001 Messerly
2001/0034530 A1 10/2001 Malackowski et al.
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0029032 A1 3/2002 Arkin
2002/0029036 A1 3/2002 Goble et al.
2002/0042620 A1 4/2002 Julian et al.
2002/0087048 A1 7/2002 Brock et al.
2002/0091374 A1 7/2002 Cooper
2002/0095175 A1 7/2002 Brock et al.
2002/0103494 A1 8/2002 Pacey
2002/0111624 A1 8/2002 Witt et al.
2002/0116063 A1 8/2002 Giannetti et al.
2002/0117534 A1 8/2002 Green et al.
2002/0127265 A1 9/2002 Bowman et al.
2002/0128633 A1 9/2002 Brock et al.
2002/0134811 A1 9/2002 Napier et al.
2002/0135474 A1 9/2002 Sylliassen
2002/0143340 A1 10/2002 Kaneko
2002/0151770 A1 10/2002 Noll et al.
2002/0158593 A1 10/2002 Henderson et al.
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2003/0009193 A1 1/2003 Corsaro
2003/0011245 A1 1/2003 Fiebig
2003/0012805 A1 1/2003 Chen et al.
2003/0040670 A1 2/2003 Govari
2003/0045835 A1 3/2003 Anderson et al.
2003/0066858 A1 4/2003 Holgersson
2003/0078647 A1 4/2003 Vallana et al.
2003/0083648 A1 5/2003 Wang et al.
2003/0084983 A1 5/2003 Rangachari et al.
2003/0093103 A1 5/2003 Malackowski et al.
2003/0094356 A1 5/2003 Waldron
2003/0096158 A1 5/2003 Takano et al.
2003/0114851 A1 6/2003 Truckai et al.
2003/0121586 A1 7/2003 Mitra et al.
2003/0139741 A1 7/2003 Goble et al.
2003/0149406 A1 8/2003 Martineau et al.
2003/0153908 A1 8/2003 Goble et al.
2003/0153968 A1 8/2003 Geis et al.
2003/0163085 A1 8/2003 Tanner et al.
2003/0164172 A1 9/2003 Chumas et al.
2003/0181900 A1 9/2003 Long
2003/0190584 A1 10/2003 Heasley
2003/0195387 A1 10/2003 Kortenbach et al.
2003/0205029 A1 11/2003 Chapolini et al.
2003/0212005 A1 11/2003 Petito et al.
2003/0216732 A1 11/2003 Truckai et al.
2003/0236505 A1 12/2003 Bonadio et al.
2004/0006335 A1 1/2004 Garrison

(56) References Cited

U.S. PATENT DOCUMENTS

| | | | |
|---|---|---|---|
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092992 | A1 | 5/2004 | Adams et al. |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0232201 | A1 | 11/2004 | Wenchell et al. |
| 2004/0236352 | A1 | 11/2004 | Wang et al. |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0260315 | A1 | 12/2004 | Dell et al. |
| 2004/0267310 | A1 | 12/2004 | Racenet et al. |
| 2005/0010158 | A1 | 1/2005 | Brugger et al. |
| 2005/0010213 | A1 | 1/2005 | Stad et al. |
| 2005/0021078 | A1 | 1/2005 | Vleugels et al. |
| 2005/0032511 | A1 | 2/2005 | Malone et al. |
| 2005/0033352 | A1 | 2/2005 | Zepf et al. |
| 2005/0051163 | A1 | 3/2005 | Deem et al. |
| 2005/0054946 | A1 | 3/2005 | Krzyzanowski |
| 2005/0057225 | A1 | 3/2005 | Marquet |
| 2005/0058890 | A1 | 3/2005 | Brazell et al. |
| 2005/0059997 | A1 | 3/2005 | Bauman et al. |
| 2005/0070929 | A1 | 3/2005 | Dalessandro et al. |
| 2005/0075561 | A1 | 4/2005 | Golden |
| 2005/0080342 | A1 | 4/2005 | Gilreath et al. |
| 2005/0085693 | A1 | 4/2005 | Belson et al. |
| 2005/0090817 | A1 | 4/2005 | Phan |
| 2005/0096683 | A1 | 5/2005 | Ellins et al. |
| 2005/0116673 | A1 | 6/2005 | Carl et al. |
| 2005/0124855 | A1 | 6/2005 | Jaffe et al. |
| 2005/0125897 | A1 | 6/2005 | Wyslucha et al. |
| 2005/0129735 | A1 | 6/2005 | Cook et al. |
| 2005/0130682 | A1 | 6/2005 | Takara et al. |
| 2005/0131173 | A1 | 6/2005 | McDaniel et al. |
| 2005/0131211 | A1 | 6/2005 | Bayley et al. |
| 2005/0131390 | A1 | 6/2005 | Heinrich et al. |
| 2005/0131436 | A1 | 6/2005 | Johnston et al. |
| 2005/0131457 | A1 | 6/2005 | Douglas et al. |
| 2005/0137454 | A1 | 6/2005 | Saadat et al. |
| 2005/0137455 | A1 | 6/2005 | Ewers et al. |
| 2005/0139636 | A1 | 6/2005 | Schwemberger et al. |
| 2005/0143759 | A1 | 6/2005 | Kelly |
| 2005/0143769 | A1 | 6/2005 | White et al. |
| 2005/0145671 | A1 | 7/2005 | Viola |
| 2005/0150928 | A1 | 7/2005 | Kameyama et al. |
| 2005/0154258 | A1 | 7/2005 | Tartaglia et al. |
| 2005/0154406 | A1 | 7/2005 | Bombard et al. |
| 2005/0159778 | A1 | 7/2005 | Heinrich et al. |
| 2005/0165419 | A1 | 7/2005 | Sauer et al. |
| 2005/0169974 | A1 | 8/2005 | Tenerz et al. |
| 2005/0171522 | A1 | 8/2005 | Christopherson |
| 2005/0177176 | A1 | 8/2005 | Gerbi et al. |
| 2005/0177181 | A1 | 8/2005 | Kagan et al. |
| 2005/0177249 | A1 | 8/2005 | Kladakis et al. |
| 2005/0182298 | A1 | 8/2005 | Ikeda et al. |
| 2005/0182443 | A1 | 8/2005 | Jonn et al. |
| 2005/0184121 | A1 | 8/2005 | Heinrich |
| 2005/0186240 | A1 | 8/2005 | Ringeisen et al. |
| 2005/0187545 | A1 | 8/2005 | Hooven et al. |
| 2005/0203550 | A1 | 9/2005 | Laufer et al. |
| 2005/0209614 | A1 | 9/2005 | Fenter et al. |
| 2005/0216055 | A1 | 9/2005 | Scirica et al. |
| 2005/0222587 | A1 | 10/2005 | Jinno et al. |
| 2005/0222611 | A1 | 10/2005 | Weitkamp |
| 2005/0222616 | A1 | 10/2005 | Rethy et al. |
| 2005/0222665 | A1 | 10/2005 | Aranyi |
| 2005/0228224 | A1 | 10/2005 | Okada et al. |
| 2005/0228446 | A1 | 10/2005 | Mooradian et al. |
| 2005/0230453 | A1 | 10/2005 | Viola |
| 2005/0240178 | A1 | 10/2005 | Morley et al. |
| 2005/0245965 | A1 | 11/2005 | Orban, III et al. |
| 2005/0246881 | A1 | 11/2005 | Kelly et al. |
| 2005/0251063 | A1 | 11/2005 | Basude |
| 2005/0256452 | A1 | 11/2005 | DeMarchi et al. |
| 2005/0261676 | A1 | 11/2005 | Hall et al. |
| 2005/0263563 | A1 | 12/2005 | Racenet et al. |
| 2005/0267455 | A1 | 12/2005 | Eggers et al. |
| 2005/0274034 | A1 | 12/2005 | Hayashida et al. |
| 2005/0283188 | A1 | 12/2005 | Loshakove et al. |
| 2005/0283226 | A1 | 12/2005 | Haverkost |
| 2006/0008787 | A1 | 1/2006 | Hayman et al. |
| 2006/0015009 | A1 | 1/2006 | Jaffe et al. |
| 2006/0020258 | A1 | 1/2006 | Strauss et al. |
| 2006/0020336 | A1 | 1/2006 | Liddicoat |
| 2006/0025812 | A1 | 2/2006 | Shelton |
| 2006/0041188 | A1 | 2/2006 | Dirusso et al. |
| 2006/0047275 | A1 | 3/2006 | Goble |
| 2006/0049229 | A1 | 3/2006 | Milliman et al. |
| 2006/0052824 | A1 | 3/2006 | Ransick et al. |
| 2006/0052825 | A1 | 3/2006 | Ransick et al. |
| 2006/0064086 | A1 | 3/2006 | Odom |
| 2006/0079735 | A1 | 4/2006 | Martone et al. |
| 2006/0079874 | A1 | 4/2006 | Faller et al. |
| 2006/0079879 | A1 | 4/2006 | Faller et al. |
| 2006/0086032 | A1 | 4/2006 | Valencic et al. |
| 2006/0087746 | A1 | 4/2006 | Lipow |
| 2006/0089535 | A1 | 4/2006 | Raz et al. |
| 2006/0097699 | A1 | 5/2006 | Kamenoff |
| 2006/0100643 | A1 | 5/2006 | Laufer et al. |
| 2006/0100649 | A1 | 5/2006 | Hart |
| 2006/0106369 | A1 | 5/2006 | Desai et al. |
| 2006/0111711 | A1 | 5/2006 | Goble |
| 2006/0111723 | A1 | 5/2006 | Chapolini et al. |
| 2006/0116634 | A1 | 6/2006 | Shachar |
| 2006/0142772 | A1 | 6/2006 | Ralph et al. |
| 2006/0144898 | A1 | 7/2006 | Bilotti et al. |

(56) References Cited

U.S. PATENT DOCUMENTS

2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0235368 A1 10/2006 Oz
2006/0241666 A1 10/2006 Briggs et al.
2006/0244460 A1 11/2006 Weaver
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289602 A1 12/2006 Wales et al.
2006/0291981 A1 12/2006 Viola et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0018958 A1 1/2007 Tavakoli et al.
2007/0026039 A1 2/2007 Drumheller et al.
2007/0026040 A1 2/2007 Crawley et al.
2007/0027468 A1 2/2007 Wales et al.
2007/0027551 A1 2/2007 Farnsworth et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0155010 A1 7/2007 Farnsworth et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175949 A1* 8/2007 Shelton ............ A61B 17/07207
227/176.1
2007/0175950 A1 8/2007 Shelton et al.
2007/0175951 A1 8/2007 Shelton et al.
2007/0175955 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0194079 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0208359 A1 9/2007 Hoffman
2007/0208375 A1 9/2007 Nishizawa et al.
2007/0213750 A1 9/2007 Weadock
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0260132 A1 11/2007 Sterling
2007/0262592 A1 11/2007 Hwang et al.
2007/0270660 A1 11/2007 Caylor et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0003196 A1 1/2008 Jonn et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0071328 A1 3/2008 Haubrich et al.
2008/0077158 A1 3/2008 Haider et al.
2008/0078802 A1 4/2008 Hess et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0085296 A1 4/2008 Powell et al.
2008/0086078 A1 4/2008 Powell et al.
2008/0091072 A1 4/2008 Omori et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long

(56) References Cited

U.S. PATENT DOCUMENTS

2008/0200933 A1 8/2008 Bakos et al.
2008/0200934 A1 8/2008 Fox
2008/0206186 A1 8/2008 Butler et al.
2008/0234709 A1 9/2008 Houser
2008/0242939 A1 10/2008 Johnston
2008/0249536 A1 10/2008 Stahler et al.
2008/0249608 A1 10/2008 Dave
2008/0255413 A1 10/2008 Zemlok et al.
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296346 A1 12/2008 Shelton, IV et al.
2008/0297287 A1 12/2008 Shachar et al.
2008/0298784 A1 12/2008 Kastner
2008/0308602 A1 12/2008 Timm et al.
2008/0308603 A1 12/2008 Shelton et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0012534 A1 1/2009 Madhani et al.
2009/0015195 A1 1/2009 Loth-Krausser
2009/0020958 A1 1/2009 Soul
2009/0048583 A1 2/2009 Williams et al.
2009/0048589 A1 2/2009 Takashino et al.
2009/0076506 A1 3/2009 Baker
2009/0078736 A1 3/2009 Van Lue
2009/0081313 A1 3/2009 Aghion et al.
2009/0088659 A1 4/2009 Graham et al.
2009/0090763 A1 4/2009 Zemlok et al.
2009/0092651 A1 4/2009 Shah et al.
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0118762 A1 5/2009 Crainch et al.
2009/0119011 A1 5/2009 Kondo et al.
2009/0131819 A1 5/2009 Ritchie et al.
2009/0132400 A1 5/2009 Conway
2009/0143855 A1 6/2009 Weber et al.
2009/0149871 A9 6/2009 Kagan et al.
2009/0171147 A1 7/2009 Lee et al.
2009/0177218 A1 7/2009 Young et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.
2009/0206125 A1 8/2009 Huitema et al.
2009/0206126 A1 8/2009 Huitema et al.
2009/0206131 A1 8/2009 Weisenburgh et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0221993 A1 9/2009 Sohi et al.
2009/0227834 A1 9/2009 Nakamoto et al.
2009/0234273 A1 9/2009 Intoccia et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248041 A1 10/2009 Williams et al.
2009/0248100 A1 10/2009 Vaisnys et al.
2009/0253959 A1 10/2009 Yoshie et al.
2009/0255974 A1 10/2009 Viola
2009/0261141 A1 10/2009 Stratton et al.
2009/0262078 A1 10/2009 Pizzi
2009/0270895 A1 10/2009 Churchill et al.
2009/0278406 A1 11/2009 Hoffman
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0325859 A1 12/2009 Ameer et al.
2010/0005035 A1 1/2010 Carpenter et al.
2010/0012703 A1 1/2010 Calabrese et al.
2010/0015104 A1 1/2010 Fraser et al.
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0032179 A1 2/2010 Hanspers et al.
2010/0036370 A1 2/2010 Mirel et al.
2010/0051668 A1 3/2010 Milliman et al.
2010/0057118 A1 3/2010 Dietz et al.
2010/0065604 A1 3/2010 Weng
2010/0069942 A1 3/2010 Shelton, IV
2010/0076483 A1 3/2010 Imuta
2010/0076489 A1 3/2010 Stopek et al.
2010/0081883 A1 4/2010 Murray et al.
2010/0094340 A1 4/2010 Stopek et al.
2010/0100123 A1 4/2010 Bennett
2010/0100124 A1 4/2010 Calabrese et al.
2010/0116519 A1 5/2010 Gareis
2010/0122339 A1 5/2010 Boccacci
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0159435 A1 6/2010 Mueller et al.
2010/0179022 A1 7/2010 Shirokoshi
2010/0180711 A1 7/2010 Kilibarda et al.
2010/0191262 A1 7/2010 Harris et al.
2010/0191292 A1 7/2010 DeMeo et al.
2010/0193566 A1 8/2010 Scheib et al.
2010/0204717 A1 8/2010 Knodel
2010/0204721 A1 8/2010 Young et al.
2010/0217281 A1 8/2010 Matsuoka et al.
2010/0222901 A1 9/2010 Swayze et al.
2010/0228250 A1 9/2010 Brogna
2010/0241137 A1 9/2010 Doyle et al.
2010/0245102 A1 9/2010 Yokoi
2010/0249497 A1 9/2010 Peine et al.
2010/0249947 A1 9/2010 Lesh et al.
2010/0256675 A1 10/2010 Romans
2010/0258327 A1 10/2010 Esenwein et al.
2010/0267662 A1 10/2010 Fielder et al.
2010/0274160 A1 10/2010 Yachi et al.
2010/0292540 A1 11/2010 Hess et al.
2010/0298636 A1 11/2010 Castro et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0331856 A1 12/2010 Carlson et al.
2011/0006101 A1 1/2011 Hall et al.
2011/0009694 A1 1/2011 Schultz et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0029270 A1 2/2011 Mueglitz
2011/0034910 A1 2/2011 Ross et al.
2011/0036891 A1 2/2011 Zemlok et al.
2011/0046667 A1 2/2011 Culligan et al.
2011/0052660 A1 3/2011 Yang et al.

(56) References Cited

U.S. PATENT DOCUMENTS

2011/0056717 A1 3/2011 Herisse
2011/0060363 A1 3/2011 Hess et al.
2011/0066156 A1 3/2011 McGahan et al.
2011/0082538 A1 4/2011 Dahlgren et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0101069 A1 5/2011 Bombard et al.
2011/0101794 A1 5/2011 Schroeder et al.
2011/0112517 A1 5/2011 Peine et al.
2011/0112530 A1 5/2011 Keller
2011/0114697 A1 5/2011 Baxter, III et al.
2011/0121049 A1 5/2011 Malinouskas et al.
2011/0125149 A1 5/2011 El-Galley et al.
2011/0125176 A1 5/2011 Yates et al.
2011/0127945 A1 6/2011 Yoneda
2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0192882 A1 8/2011 Hess et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0225105 A1 9/2011 Scholer et al.
2011/0230713 A1 9/2011 Kleemann et al.
2011/0238044 A1 9/2011 Main et al.
2011/0241597 A1 10/2011 Zhu et al.
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278343 A1 11/2011 Knodel et al.
2011/0279268 A1 11/2011 Konishi et al.
2011/0290856 A1 12/2011 Shelton, IV et al.
2011/0290858 A1 12/2011 Whitman et al.
2011/0293690 A1 12/2011 Griffin et al.
2011/0295295 A1 12/2011 Shelton, IV et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0016239 A1 1/2012 Barthe et al.
2012/0016413 A1 1/2012 Timm et al.
2012/0016467 A1 1/2012 Chen et al.
2012/0029272 A1 2/2012 Shelton, IV et al.
2012/0033360 A1 2/2012 Hsu
2012/0059286 A1 3/2012 Hastings et al.
2012/0064483 A1 3/2012 Lint et al.
2012/0074200 A1 3/2012 Schmid et al.
2012/0078139 A1 3/2012 Aldridge et al.
2012/0078244 A1 3/2012 Worrell et al.
2012/0080336 A1 4/2012 Shelton, IV et al.
2012/0080344 A1 4/2012 Shelton, IV
2012/0080478 A1 4/2012 Morgan et al.
2012/0080498 A1 4/2012 Shelton, IV et al.
2012/0086276 A1 4/2012 Sawyers
2012/0095458 A1 4/2012 Cybulski et al.
2012/0109186 A1 5/2012 Parrott et al.
2012/0116261 A1 5/2012 Mumaw et al.
2012/0116262 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0171539 A1 7/2012 Rejman et al.
2012/0175398 A1 7/2012 Sandborn et al.
2012/0197272 A1 8/2012 Oray et al.
2012/0211542 A1 8/2012 Racenet
2012/0220990 A1 8/2012 Mckenzie et al.
2012/0234895 A1 9/2012 O'Connor et al.
2012/0234897 A1 9/2012 Shelton, IV et al.
2012/0239068 A1 9/2012 Morris et al.
2012/0248169 A1 10/2012 Widenhouse et al.
2012/0251861 A1 10/2012 Liang et al.
2012/0253328 A1 10/2012 Cunningham et al.
2012/0271327 A1 10/2012 West et al.
2012/0283707 A1 11/2012 Giordano et al.
2012/0289811 A1 11/2012 Viola et al.
2012/0289979 A1 11/2012 Eskaros et al.
2012/0292367 A1 11/2012 Morgan et al.
2012/0296342 A1 11/2012 Haglund Wendelschafer
2012/0298722 A1 11/2012 Hess et al.
2012/0301498 A1 11/2012 Altreuter et al.
2012/0303002 A1 11/2012 Chowaniec et al.
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0057162 A1 3/2013 Pollischansky
2013/0068816 A1 3/2013 Mandakolathur Vasudevan et al.
2013/0087597 A1 4/2013 Shelton, IV et al.
2013/0090534 A1 4/2013 Burns et al.
2013/0096568 A1 4/2013 Justis
2013/0098970 A1 4/2013 Racenet et al.
2013/0105552 A1 5/2013 Weir et al.
2013/0106352 A1 5/2013 Nagamine
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153636 A1 6/2013 Shelton, IV et al.
2013/0153641 A1 6/2013 Shelton, IV et al.
2013/0158390 A1 6/2013 Tan et al.
2013/0162198 A1 6/2013 Yokota et al.
2013/0169217 A1 7/2013 Watanabe et al.
2013/0172878 A1 7/2013 Smith
2013/0175317 A1 7/2013 Yates et al.
2013/0211244 A1 8/2013 Nathaniel
2013/0214025 A1 8/2013 Zemlok et al.
2013/0215449 A1 8/2013 Yamasaki
2013/0233906 A1 9/2013 Hess et al.
2013/0238021 A1 9/2013 Gross et al.
2013/0245704 A1 9/2013 Koltz et al.
2013/0248578 A1 9/2013 Arteaga Gonzalez
2013/0253480 A1 9/2013 Kimball et al.
2013/0256373 A1 10/2013 Schmid et al.
2013/0256379 A1 10/2013 Schmid et al.
2013/0256380 A1 10/2013 Schmid et al.
2013/0267978 A1 10/2013 Trissel
2013/0270322 A1 10/2013 Scheib et al.
2013/0277410 A1 10/2013 Fernandez et al.
2013/0306704 A1 11/2013 Balbierz et al.
2013/0317753 A1 11/2013 Kamen et al.
2013/0324982 A1 12/2013 Smith et al.
2013/0327552 A1 12/2013 Lovelass et al.
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0005640 A1 1/2014 Shelton, IV et al.

(56) References Cited

U.S. PATENT DOCUMENTS

| | | | |
|---|---|---|---|
| 2014/0005678 | A1 | 1/2014 | Shelton, IV et al. |
| 2014/0005702 | A1 | 1/2014 | Timm et al. |
| 2014/0005718 | A1 | 1/2014 | Shelton, IV et al. |
| 2014/0012289 | A1 | 1/2014 | Snow et al. |
| 2014/0012299 | A1 | 1/2014 | Stoddard et al. |
| 2014/0014704 | A1 | 1/2014 | Onukuri et al. |
| 2014/0014705 | A1 | 1/2014 | Baxter, III |
| 2014/0014707 | A1 | 1/2014 | Onukuri et al. |
| 2014/0018832 | A1 | 1/2014 | Shelton, IV |
| 2014/0022283 | A1 | 1/2014 | Chan et al. |
| 2014/0039549 | A1 | 2/2014 | Belsky et al. |
| 2014/0048580 | A1 | 2/2014 | Merchant et al. |
| 2014/0081176 | A1 | 3/2014 | Hassan |
| 2014/0094681 | A1 | 4/2014 | Valentine et al. |
| 2014/0100558 | A1 | 4/2014 | Schmitz et al. |
| 2014/0107640 | A1 | 4/2014 | Yates et al. |
| 2014/0110456 | A1 | 4/2014 | Taylor |
| 2014/0115229 | A1 | 4/2014 | Kothamasu et al. |
| 2014/0131418 | A1 | 5/2014 | Kostrzewski |
| 2014/0135832 | A1 | 5/2014 | Park et al. |
| 2014/0151433 | A1 | 6/2014 | Shelton, IV et al. |
| 2014/0158747 | A1 | 6/2014 | Measamer et al. |
| 2014/0166723 | A1 | 6/2014 | Beardsley et al. |
| 2014/0166724 | A1 | 6/2014 | Schellin et al. |
| 2014/0166725 | A1 | 6/2014 | Schellin et al. |
| 2014/0166726 | A1 | 6/2014 | Schellin et al. |
| 2014/0171966 | A1 | 6/2014 | Giordano et al. |
| 2014/0175147 | A1 | 6/2014 | Manoux et al. |
| 2014/0175150 | A1 | 6/2014 | Shelton, IV et al. |
| 2014/0175152 | A1 | 6/2014 | Hess et al. |
| 2014/0181710 | A1 | 6/2014 | Baalu et al. |
| 2014/0188091 | A1 | 7/2014 | Vidal et al. |
| 2014/0188159 | A1 | 7/2014 | Steege |
| 2014/0207124 | A1 | 7/2014 | Aldridge et al. |
| 2014/0207125 | A1 | 7/2014 | Applegate et al. |
| 2014/0209658 | A1 | 7/2014 | Skalla et al. |
| 2014/0213848 | A1 | 7/2014 | Moskowitz et al. |
| 2014/0224857 | A1 | 8/2014 | Schmid |
| 2014/0228632 | A1 | 8/2014 | Sholev et al. |
| 2014/0228867 | A1 | 8/2014 | Thomas et al. |
| 2014/0230595 | A1 | 8/2014 | Butt et al. |
| 2014/0239047 | A1 | 8/2014 | Hodgkinson et al. |
| 2014/0243865 | A1 | 8/2014 | Swayze et al. |
| 2014/0246475 | A1 | 9/2014 | Hall et al. |
| 2014/0248167 | A1 | 9/2014 | Sugimoto et al. |
| 2014/0249557 | A1 | 9/2014 | Koch, Jr. et al. |
| 2014/0249573 | A1 | 9/2014 | Arav |
| 2014/0263541 | A1 | 9/2014 | Leimbach et al. |
| 2014/0263552 | A1 | 9/2014 | Hall et al. |
| 2014/0263554 | A1 | 9/2014 | Leimbach et al. |
| 2014/0263558 | A1 | 9/2014 | Hausen et al. |
| 2014/0276730 | A1 | 9/2014 | Boudreaux et al. |
| 2014/0284371 | A1 | 9/2014 | Morgan et al. |
| 2014/0288460 | A1 | 9/2014 | Ouyang et al. |
| 2014/0291378 | A1 | 10/2014 | Shelton, IV et al. |
| 2014/0291379 | A1 | 10/2014 | Schellin et al. |
| 2014/0291383 | A1 | 10/2014 | Spivey et al. |
| 2014/0299648 | A1 | 10/2014 | Shelton, IV et al. |
| 2014/0303645 | A1 | 10/2014 | Morgan et al. |
| 2014/0303660 | A1 | 10/2014 | Boyden et al. |
| 2014/0309666 | A1 | 10/2014 | Shelton, IV et al. |
| 2014/0330161 | A1 | 11/2014 | Swayze et al. |
| 2014/0330298 | A1 | 11/2014 | Arshonsky et al. |
| 2014/0330579 | A1 | 11/2014 | Cashman et al. |
| 2014/0367445 | A1 | 12/2014 | Ingmanson et al. |
| 2014/0374130 | A1 | 12/2014 | Nakamura et al. |
| 2014/0378950 | A1 | 12/2014 | Chiu |
| 2015/0002089 | A1 | 1/2015 | Rejman et al. |
| 2015/0008248 | A1 | 1/2015 | Giordano et al. |
| 2015/0025549 | A1 | 1/2015 | Kilroy et al. |
| 2015/0038961 | A1 | 2/2015 | Clark et al. |
| 2015/0053737 | A1 | 2/2015 | Leimbach et al. |
| 2015/0053742 | A1 | 2/2015 | Shelton, IV et al. |
| 2015/0053743 | A1 | 2/2015 | Yates et al. |
| 2015/0053746 | A1 | 2/2015 | Shelton, IV et al. |
| 2015/0053748 | A1 | 2/2015 | Yates et al. |
| 2015/0060518 | A1 | 3/2015 | Shelton, IV et al. |
| 2015/0060519 | A1 | 3/2015 | Shelton, IV et al. |
| 2015/0060520 | A1 | 3/2015 | Shelton, IV et al. |
| 2015/0060521 | A1 | 3/2015 | Weisenburgh, II et al. |
| 2015/0066000 | A1 | 3/2015 | An et al. |
| 2015/0076207 | A1 | 3/2015 | Boudreaux et al. |
| 2015/0076208 | A1 | 3/2015 | Shelton, IV |
| 2015/0076209 | A1 | 3/2015 | Shelton, IV et al. |
| 2015/0076210 | A1 | 3/2015 | Shelton, IV et al. |
| 2015/0076211 | A1 | 3/2015 | Irka et al. |
| 2015/0076212 | A1 | 3/2015 | Shelton, IV |
| 2015/0080868 | A1 | 3/2015 | Kerr |
| 2015/0082624 | A1 | 3/2015 | Craig et al. |
| 2015/0083781 | A1 | 3/2015 | Giordano et al. |
| 2015/0083782 | A1 | 3/2015 | Scheib et al. |
| 2015/0087952 | A1 | 3/2015 | Albert et al. |
| 2015/0088127 | A1 | 3/2015 | Craig et al. |
| 2015/0088547 | A1 | 3/2015 | Balram et al. |
| 2015/0090760 | A1 | 4/2015 | Giordano et al. |
| 2015/0090761 | A1 | 4/2015 | Giordano et al. |
| 2015/0090762 | A1 | 4/2015 | Giordano et al. |
| 2015/0108199 | A1 | 4/2015 | Shelton, IV et al. |
| 2015/0122870 | A1 | 5/2015 | Zemlok et al. |
| 2015/0127021 | A1 | 5/2015 | Harris et al. |
| 2015/0134077 | A1 | 5/2015 | Shelton, IV et al. |
| 2015/0148830 | A1 | 5/2015 | Stulen et al. |
| 2015/0150554 | A1 | 6/2015 | Soltz |
| 2015/0150620 | A1 | 6/2015 | Miyamoto et al. |
| 2015/0173749 | A1 | 6/2015 | Shelton, IV et al. |
| 2015/0173756 | A1 | 6/2015 | Baxter, III et al. |
| 2015/0173789 | A1 | 6/2015 | Baxter, III et al. |
| 2015/0182220 | A1 | 7/2015 | Yates et al. |
| 2015/0196295 | A1 | 7/2015 | Shelton, IV et al. |
| 2015/0196296 | A1 | 7/2015 | Swayze et al. |
| 2015/0196299 | A1 | 7/2015 | Swayze et al. |
| 2015/0196348 | A1 | 7/2015 | Yates et al. |
| 2015/0201918 | A1 | 7/2015 | Kumar et al. |
| 2015/0201932 | A1 | 7/2015 | Swayze et al. |
| 2015/0201936 | A1 | 7/2015 | Swayze et al. |
| 2015/0201937 | A1 | 7/2015 | Swayze et al. |
| 2015/0201938 | A1 | 7/2015 | Swayze et al. |
| 2015/0201939 | A1 | 7/2015 | Swayze et al. |
| 2015/0201940 | A1 | 7/2015 | Swayze et al. |
| 2015/0201941 | A1 | 7/2015 | Swayze et al. |
| 2015/0209045 | A1 | 7/2015 | Hodgkinson et al. |
| 2015/0222212 | A1 | 8/2015 | Iwata |
| 2015/0223868 | A1 | 8/2015 | Brandt et al. |
| 2015/0230697 | A1 | 8/2015 | Phee et al. |
| 2015/0231409 | A1 | 8/2015 | Racenet et al. |
| 2015/0238118 | A1 | 8/2015 | Legassey et al. |
| 2015/0272557 | A1 | 10/2015 | Overmyer et al. |
| 2015/0272571 | A1 | 10/2015 | Leimbach et al. |
| 2015/0272580 | A1 | 10/2015 | Leimbach et al. |
| 2015/0272582 | A1 | 10/2015 | Leimbach et al. |
| 2015/0272604 | A1 | 10/2015 | Chowaniec et al. |
| 2015/0297200 | A1 | 10/2015 | Fitzsimmons et al. |
| 2015/0297222 | A1 | 10/2015 | Huitema et al. |
| 2015/0297223 | A1 | 10/2015 | Huitema et al. |
| 2015/0297225 | A1 | 10/2015 | Huitema et al. |
| 2015/0297228 | A1 | 10/2015 | Huitema et al. |
| 2015/0297229 | A1 | 10/2015 | Schellin et al. |
| 2015/0297233 | A1 | 10/2015 | Huitema et al. |
| 2015/0297234 | A1 | 10/2015 | Schellin et al. |
| 2015/0297235 | A1 | 10/2015 | Harris et al. |
| 2015/0302539 | A1 | 10/2015 | Mazar et al. |
| 2015/0303417 | A1 | 10/2015 | Koeder et al. |
| 2015/0313594 | A1 | 11/2015 | Shelton, IV et al. |
| 2015/0324317 | A1 | 11/2015 | Collins et al. |
| 2015/0327864 | A1 | 11/2015 | Hodgkinson et al. |
| 2015/0336249 | A1 | 11/2015 | Iwata et al. |
| 2015/0351762 | A1 | 12/2015 | Vendely et al. |
| 2015/0352699 | A1 | 12/2015 | Sakai et al. |
| 2015/0366585 | A1 | 12/2015 | Lemay et al. |
| 2015/0367497 | A1 | 12/2015 | Ito et al. |
| 2015/0372265 | A1 | 12/2015 | Morisaku et al. |
| 2015/0374361 | A1 | 12/2015 | Gettinger et al. |
| 2015/0374369 | A1 | 12/2015 | Yates et al. |
| 2015/0374371 | A1 | 12/2015 | Richard et al. |

(56) References Cited

U.S. PATENT DOCUMENTS

2015/0374372 A1 12/2015 Zergiebel et al.
2015/0374375 A1 12/2015 Shelton, IV et al.
2015/0374378 A1 12/2015 Giordano et al.
2016/0000430 A1 1/2016 Ming et al.
2016/0000431 A1 1/2016 Giordano et al.
2016/0000437 A1 1/2016 Giordano et al.
2016/0000438 A1 1/2016 Swayze et al.
2016/0000442 A1 1/2016 Shelton, IV
2016/0000452 A1 1/2016 Yates et al.
2016/0000453 A1 1/2016 Yates et al.
2016/0023342 A1 1/2016 Koenig et al.
2016/0030042 A1 2/2016 Heinrich et al.
2016/0051257 A1 2/2016 Shelton, IV et al.
2016/0051316 A1 2/2016 Boudreaux
2016/0058443 A1 3/2016 Yates et al.
2016/0066913 A1 3/2016 Swayze et al.
2016/0069449 A1 3/2016 Kanai et al.
2016/0074040 A1 3/2016 Widenhouse et al.
2016/0074103 A1 3/2016 Sartor
2016/0082161 A1 3/2016 Zilberman et al.
2016/0089137 A1 3/2016 Hess et al.
2016/0089146 A1 3/2016 Harris et al.
2016/0089149 A1 3/2016 Harris et al.
2016/0089198 A1 3/2016 Arya et al.
2016/0095585 A1 4/2016 Zergiebel et al.
2016/0106431 A1 4/2016 Shelton, IV et al.
2016/0113653 A1 4/2016 Zingman
2016/0120544 A1 5/2016 Shelton, IV et al.
2016/0120545 A1 5/2016 Shelton, IV et al.
2016/0135835 A1 5/2016 Onuma
2016/0135895 A1 5/2016 Faasse et al.
2016/0166248 A1 6/2016 Deville et al.
2016/0166256 A1 6/2016 Baxter et al.
2016/0166308 A1 6/2016 Manwaring et al.
2016/0174974 A1 6/2016 Schmid et al.
2016/0183939 A1 6/2016 Shelton, IV et al.
2016/0183943 A1 6/2016 Shelton, IV
2016/0183944 A1 6/2016 Swensgard et al.
2016/0192916 A1 7/2016 Shelton, IV et al.
2016/0192917 A1 7/2016 Shelton, IV et al.
2016/0192918 A1 7/2016 Shelton, IV et al.
2016/0192960 A1 7/2016 Bueno et al.
2016/0192977 A1 7/2016 Manwaring et al.
2016/0199059 A1 7/2016 Shelton, IV et al.
2016/0199061 A1 7/2016 Shelton, IV et al.
2016/0199063 A1 7/2016 Mandakolathur Vasudevan et al.
2016/0199089 A1 7/2016 Hess et al.
2016/0199956 A1 7/2016 Shelton, IV et al.
2016/0206310 A1 7/2016 Shelton, IV
2016/0206314 A1 7/2016 Scheib et al.
2016/0220248 A1 8/2016 Timm et al.
2016/0220266 A1 8/2016 Shelton, IV et al.
2016/0235403 A1 8/2016 Shelton, IV et al.
2016/0235404 A1 8/2016 Shelton, IV
2016/0235405 A1 8/2016 Shelton, IV et al.
2016/0235409 A1 8/2016 Shelton, IV et al.
2016/0235467 A1 8/2016 Godara et al.
2016/0235494 A1 8/2016 Shelton, IV et al.
2016/0242777 A1 8/2016 Shelton, IV et al.
2016/0242781 A1 8/2016 Shelton, IV et al.
2016/0242782 A1 8/2016 Shelton, IV et al.
2016/0242783 A1 8/2016 Shelton, IV et al.
2016/0249910 A1 9/2016 Shelton, IV et al.
2016/0249922 A1 9/2016 Morgan et al.
2016/0256071 A1 9/2016 Shelton, IV et al.
2016/0256154 A1 9/2016 Shelton, IV et al.
2016/0256159 A1 9/2016 Pinjala et al.
2016/0256160 A1 9/2016 Shelton, IV et al.
2016/0256185 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262746 A1 9/2016 Shelton, IV et al.
2016/0262921 A1 9/2016 Balbierz et al.
2016/0270780 A1 9/2016 Hall et al.
2016/0278765 A1 9/2016 Shelton, IV et al.
2016/0278771 A1 9/2016 Shelton, IV et al.
2016/0287249 A1 10/2016 Alexander, III et al.
2016/0287250 A1 10/2016 Shelton, IV et al.
2016/0287253 A1 10/2016 Shelton, IV et al.
2016/0287265 A1 10/2016 Macdonald et al.
2016/0287279 A1 10/2016 Bovay et al.
2016/0310143 A1 10/2016 Bettuchi
2016/0314716 A1 10/2016 Grubbs
2016/0331375 A1 11/2016 Shelton, IV et al.
2016/0345976 A1 12/2016 Gonzalez et al.
2016/0346034 A1 12/2016 Arya et al.
2016/0354085 A1 12/2016 Shelton, IV et al.
2016/0367122 A1 12/2016 Ichimura et al.
2016/0367246 A1 12/2016 Baxter, III et al.
2016/0367255 A1 12/2016 Wise et al.
2016/0374672 A1 12/2016 Bear et al.
2016/0374675 A1 12/2016 Shelton, IV et al.
2016/0374678 A1 12/2016 Becerra et al.
2017/0000485 A1 1/2017 Shelton, IV et al.
2017/0000553 A1 1/2017 Wiener et al.
2017/0007236 A1 1/2017 Shelton, IV et al.
2017/0007237 A1 1/2017 Yates et al.
2017/0007238 A1 1/2017 Yates et al.
2017/0007239 A1 1/2017 Shelton, IV
2017/0007241 A1 1/2017 Shelton, IV et al.
2017/0007243 A1 1/2017 Shelton, IV et al.
2017/0007244 A1 1/2017 Shelton, IV et al.
2017/0007245 A1 1/2017 Shelton, IV et al.
2017/0007246 A1 1/2017 Shelton, IV et al.
2017/0007247 A1 1/2017 Shelton, IV et al.
2017/0007248 A1 1/2017 Shelton, IV et al.
2017/0007249 A1 1/2017 Shelton, IV et al.
2017/0007250 A1 1/2017 Shelton, IV et al.
2017/0007251 A1 1/2017 Yates et al.
2017/0007347 A1 1/2017 Jaworek et al.
2017/0014125 A1 1/2017 Shelton, IV et al.
2017/0027572 A1 2/2017 Nalagatla et al.
2017/0027573 A1 2/2017 Nalagatla et al.
2017/0027574 A1 2/2017 Nalagatla et al.
2017/0049444 A1 2/2017 Schellin et al.
2017/0049447 A1 2/2017 Barton et al.
2017/0049448 A1 2/2017 Widenhouse et al.
2017/0055819 A1 3/2017 Hansen et al.
2017/0055986 A1 3/2017 Harris et al.
2017/0055991 A1 3/2017 Kang
2017/0055998 A1 3/2017 Baxter, III et al.
2017/0055999 A1 3/2017 Baxter, III et al.
2017/0056000 A1 3/2017 Nalagatla et al.
2017/0056002 A1 3/2017 Nalagatla et al.
2017/0056005 A1 3/2017 Shelton, IV et al.
2017/0056006 A1 3/2017 Shelton, IV et al.
2017/0056007 A1 3/2017 Eckert et al.
2017/0056014 A1 3/2017 Harris et al.
2017/0066054 A1 3/2017 Birky
2017/0079642 A1 3/2017 Overmyer et al.
2017/0079643 A1 3/2017 Yates et al.
2017/0086827 A1 3/2017 Vendely et al.
2017/0086829 A1 3/2017 Vendely et al.
2017/0086830 A1 3/2017 Yates et al.
2017/0086831 A1 3/2017 Shelton, IV et al.
2017/0086832 A1 3/2017 Harris et al.
2017/0086836 A1 3/2017 Harris et al.
2017/0086837 A1 3/2017 Vendely et al.
2017/0086838 A1 3/2017 Harris et al.
2017/0086842 A1 3/2017 Shelton, IV et al.
2017/0086843 A1 3/2017 Vendely et al.
2017/0086844 A1 3/2017 Vendely et al.
2017/0086930 A1 3/2017 Thompson et al.
2017/0095250 A1 4/2017 Kostrzewski et al.
2017/0105733 A1 4/2017 Scheib et al.
2017/0119386 A1 5/2017 Scheib et al.
2017/0119387 A1 5/2017 Dalessandro et al.
2017/0119388 A1 5/2017 Kostrzewski
2017/0119390 A1 5/2017 Schellin et al.
2017/0119392 A1 5/2017 Shelton, IV et al.
2017/0119397 A1 5/2017 Harris et al.
2017/0135695 A1 5/2017 Shelton, IV et al.
2017/0135697 A1 5/2017 Mozdzierz et al.

(56) References Cited

U.S. PATENT DOCUMENTS

2017/0150983 A1 6/2017 Ingmanson et al.
2017/0172382 A1 6/2017 Nir et al.
2017/0172550 A1 6/2017 Mukherjee et al.
2017/0172662 A1 6/2017 Panescu et al.
2017/0172672 A1 6/2017 Bailey et al.
2017/0182195 A1 6/2017 Wagner
2017/0182211 A1 6/2017 Raxworthy et al.
2017/0189019 A1 7/2017 Harris et al.
2017/0196554 A1 7/2017 Rousseau et al.
2017/0196556 A1 7/2017 Shah et al.
2017/0196558 A1 7/2017 Morgan et al.
2017/0196561 A1 7/2017 Shelton, IV et al.
2017/0196562 A1 7/2017 Shelton, IV et al.
2017/0196637 A1 7/2017 Shelton, IV et al.
2017/0196649 A1 7/2017 Yates et al.
2017/0202571 A1 7/2017 Shelton, IV et al.
2017/0202592 A1* 7/2017 Shelton, IV ... A61B 17/320092
2017/0202596 A1 7/2017 Shelton, IV et al.
2017/0202770 A1 7/2017 Friedrich et al.
2017/0209145 A1 7/2017 Swayze et al.
2017/0209146 A1 7/2017 Yates et al.
2017/0209226 A1 7/2017 Overmyer et al.
2017/0215881 A1 8/2017 Shelton, IV et al.
2017/0215943 A1 8/2017 Allen, IV
2017/0224330 A1 8/2017 Worthington et al.
2017/0224331 A1 8/2017 Worthington et al.
2017/0224332 A1 8/2017 Hunter et al.
2017/0224334 A1 8/2017 Worthington et al.
2017/0224335 A1 8/2017 Weaner et al.
2017/0224339 A1 8/2017 Huang et al.
2017/0224342 A1 8/2017 Worthington et al.
2017/0224343 A1 8/2017 Baxter, III et al.
2017/0231626 A1 8/2017 Shelton, IV et al.
2017/0231627 A1 8/2017 Shelton, IV et al.
2017/0231628 A1 8/2017 Shelton, IV et al.
2017/0238928 A1 8/2017 Morgan et al.
2017/0238929 A1 8/2017 Yates et al.
2017/0238962 A1 8/2017 Hansen et al.
2017/0245952 A1 8/2017 Shelton, IV et al.
2017/0249431 A1 8/2017 Shelton, IV et al.
2017/0258469 A1 9/2017 Shelton, IV et al.
2017/0262110 A1 9/2017 Polishchuk et al.
2017/0265774 A1 9/2017 Johnson et al.
2017/0265856 A1 9/2017 Shelton, IV et al.
2017/0281155 A1 10/2017 Shelton, IV et al.
2017/0281161 A1 10/2017 Shelton, IV et al.
2017/0281162 A1 10/2017 Shelton, IV et al.
2017/0281164 A1 10/2017 Harris et al.
2017/0281166 A1 10/2017 Morgan et al.
2017/0281167 A1 10/2017 Shelton, IV et al.
2017/0281168 A1 10/2017 Shelton, IV et al.
2017/0281169 A1 10/2017 Harris et al.
2017/0281171 A1 10/2017 Shelton, IV et al.
2017/0281172 A1 10/2017 Shelton, IV et al.
2017/0281173 A1 10/2017 Shelton, IV et al.
2017/0281174 A1 10/2017 Harris et al.
2017/0281177 A1 10/2017 Harris et al.
2017/0281179 A1 10/2017 Shelton, IV et al.
2017/0281180 A1 10/2017 Morgan et al.
2017/0281183 A1 10/2017 Miller et al.
2017/0281184 A1 10/2017 Shelton, IV et al.
2017/0281185 A1 10/2017 Miller et al.
2017/0281186 A1 10/2017 Shelton, IV et al.
2017/0281187 A1 10/2017 Shelton, IV et al.
2017/0281189 A1 10/2017 Nalagatla et al.
2017/0290584 A1 10/2017 Jasemian et al.
2017/0290585 A1 10/2017 Shelton, IV et al.
2017/0296169 A1 10/2017 Yates et al.
2017/0296170 A1 10/2017 Shelton, IV et al.
2017/0296171 A1 10/2017 Shelton, IV et al.
2017/0296172 A1 10/2017 Harris et al.
2017/0296173 A1 10/2017 Shelton, IV et al.
2017/0296177 A1 10/2017 Harris et al.
2017/0296178 A1 10/2017 Miller et al.
2017/0296179 A1 10/2017 Shelton, IV et al.
2017/0296180 A1 10/2017 Harris et al.
2017/0296183 A1 10/2017 Shelton, IV et al.
2017/0296185 A1 10/2017 Swensgard et al.
2017/0296189 A1 10/2017 Vendely et al.
2017/0296190 A1 10/2017 Aronhalt et al.
2017/0296191 A1 10/2017 Shelton, IV et al.
2017/0296213 A1 10/2017 Swensgard et al.
2017/0311944 A1 11/2017 Morgan et al.
2017/0311949 A1 11/2017 Shelton, IV
2017/0311950 A1 11/2017 Shelton, IV et al.
2017/0312041 A1 11/2017 Giordano et al.
2017/0312042 A1 11/2017 Giordano et al.
2017/0319201 A1 11/2017 Morgan et al.
2017/0319207 A1 11/2017 Shelton, IV et al.
2017/0319209 A1 11/2017 Morgan et al.
2017/0325813 A1 11/2017 Aranyi et al.
2017/0333034 A1 11/2017 Morgan et al.
2017/0333035 A1 11/2017 Morgan et al.
2017/0333070 A1 11/2017 Laurent et al.
2017/0348010 A1 12/2017 Chiang
2017/0348043 A1 12/2017 Wang et al.
2017/0354413 A1 12/2017 Chen et al.
2017/0354415 A1 12/2017 Casasanta, Jr. et al.
2017/0358052 A1 12/2017 Yuan
2017/0360439 A1 12/2017 Chen et al.
2017/0360441 A1 12/2017 Sgroi
2017/0360442 A1 12/2017 Shelton, IV et al.
2017/0367695 A1 12/2017 Shelton, IV et al.
2017/0367696 A1 12/2017 Shelton, IV et al.
2017/0367697 A1 12/2017 Shelton, IV et al.
2017/0367698 A1 12/2017 Shelton, IV et al.
2017/0367699 A1 12/2017 Shelton, IV et al.
2017/0367700 A1 12/2017 Leimbach et al.
2017/0367991 A1 12/2017 Widenhouse et al.
2018/0000483 A1 1/2018 Leimbach et al.
2018/0000545 A1 1/2018 Giordano et al.
2018/0008270 A1 1/2018 Moore et al.
2018/0008271 A1 1/2018 Moore et al.
2018/0008356 A1 1/2018 Giordano et al.
2018/0008357 A1 1/2018 Giordano et al.
2018/0028184 A1 2/2018 Shelton, IV et al.
2018/0028185 A1 2/2018 Shelton, IV et al.
2018/0042611 A1 2/2018 Swayze et al.
2018/0049824 A1 2/2018 Harris et al.
2018/0049883 A1 2/2018 Moskowitz et al.
2018/0055513 A1 3/2018 Shelton, IV et al.
2018/0055524 A1 3/2018 Shelton, IV et al.
2018/0055525 A1 3/2018 Shelton, IV et al.
2018/0055526 A1 3/2018 Shelton, IV et al.
2018/0064437 A1 3/2018 Yates et al.
2018/0064440 A1 3/2018 Shelton, IV et al.
2018/0064441 A1 3/2018 Shelton, IV et al.
2018/0064442 A1 3/2018 Shelton, IV et al.
2018/0064443 A1 3/2018 Shelton, IV et al.
2018/0070939 A1 3/2018 Giordano et al.
2018/0070942 A1 3/2018 Shelton, IV et al.
2018/0078248 A1 3/2018 Swayze et al.
2018/0078268 A1 3/2018 Messerly et al.
2018/0085116 A1 3/2018 Yates et al.
2018/0085117 A1 3/2018 Shelton, IV et al.
2018/0092710 A1 4/2018 Bosisio et al.
2018/0103952 A1 4/2018 Aronhalt et al.
2018/0103953 A1 4/2018 Shelton, IV et al.
2018/0103955 A1 4/2018 Shelton, IV et al.
2018/0110516 A1 4/2018 Baxter et al.
2018/0110518 A1 4/2018 Overmyer et al.
2018/0110519 A1 4/2018 Lytle, IV et al.
2018/0110520 A1 4/2018 Shelton, IV et al.
2018/0110521 A1 4/2018 Shelton, IV et al.
2018/0110522 A1 4/2018 Shelton, IV et al.
2018/0110523 A1 4/2018 Shelton, IV
2018/0110574 A1 4/2018 Shelton, IV et al.
2018/0110575 A1 4/2018 Shelton, IV et al.
2018/0114591 A1 4/2018 Pribanic et al.
2018/0116658 A1 5/2018 Aronhalt, IV et al.
2018/0116662 A1 5/2018 Shelton, IV et al.
2018/0116665 A1 5/2018 Hall et al.
2018/0125481 A1 5/2018 Yates et al.
2018/0125487 A1 5/2018 Beardsley

(56) References Cited

U.S. PATENT DOCUMENTS

| | | | |
|---|---|---|---|
| 2018/0125488 | A1 | 5/2018 | Morgan et al. |
| 2018/0125489 | A1 | 5/2018 | Leimbach et al. |
| 2018/0125590 | A1 | 5/2018 | Giordano et al. |
| 2018/0125594 | A1 | 5/2018 | Beardsley |
| 2018/0126504 | A1 | 5/2018 | Shelton, IV et al. |
| 2018/0132845 | A1 | 5/2018 | Schmid et al. |
| 2018/0132849 | A1 | 5/2018 | Miller et al. |
| 2018/0132850 | A1 | 5/2018 | Leimbach et al. |
| 2018/0132851 | A1 | 5/2018 | Hall et al. |
| 2018/0132926 | A1 | 5/2018 | Asher et al. |
| 2018/0132952 | A1 | 5/2018 | Spivey et al. |
| 2018/0133856 | A1 | 5/2018 | Shelton, IV et al. |
| 2018/0140299 | A1 | 5/2018 | Weaner et al. |
| 2018/0140368 | A1 | 5/2018 | Shelton, IV et al. |
| 2018/0146960 | A1 | 5/2018 | Shelton, IV et al. |
| 2018/0150153 | A1 | 5/2018 | Yoon et al. |
| 2018/0153542 | A1 | 6/2018 | Shelton, IV et al. |
| 2018/0161034 | A1 | 6/2018 | Scheib et al. |
| 2018/0168575 | A1 | 6/2018 | Simms et al. |
| 2018/0168576 | A1 | 6/2018 | Hunter et al. |
| 2018/0168577 | A1 | 6/2018 | Aronhalt et al. |
| 2018/0168578 | A1 | 6/2018 | Aronhalt et al. |
| 2018/0168579 | A1 | 6/2018 | Aronhalt et al. |
| 2018/0168580 | A1 | 6/2018 | Hunter et al. |
| 2018/0168581 | A1 | 6/2018 | Hunter et al. |
| 2018/0168582 | A1 | 6/2018 | Swayze et al. |
| 2018/0168583 | A1 | 6/2018 | Hunter et al. |
| 2018/0168584 | A1 | 6/2018 | Harris et al. |
| 2018/0168585 | A1 | 6/2018 | Shelton, IV et al. |
| 2018/0168586 | A1 | 6/2018 | Shelton, IV et al. |
| 2018/0168589 | A1 | 6/2018 | Swayze et al. |
| 2018/0168590 | A1 | 6/2018 | Overmyer et al. |
| 2018/0168591 | A1 | 6/2018 | Swayze et al. |
| 2018/0168592 | A1 | 6/2018 | Overmyer et al. |
| 2018/0168593 | A1 | 6/2018 | Overmyer et al. |
| 2018/0168594 | A1 | 6/2018 | Shelton, IV et al. |
| 2018/0168595 | A1 | 6/2018 | Overmyer et al. |
| 2018/0168596 | A1 | 6/2018 | Beckman et al. |
| 2018/0168597 | A1 | 6/2018 | Fanelli et al. |
| 2018/0168598 | A1 | 6/2018 | Shelton, IV et al. |
| 2018/0168599 | A1 | 6/2018 | Bakos et al. |
| 2018/0168600 | A1 | 6/2018 | Shelton, IV et al. |
| 2018/0168601 | A1 | 6/2018 | Bakos et al. |
| 2018/0168602 | A1 | 6/2018 | Bakos et al. |
| 2018/0168603 | A1 | 6/2018 | Morgan et al. |
| 2018/0168604 | A1 | 6/2018 | Shelton, IV et al. |
| 2018/0168605 | A1 | 6/2018 | Baber et al. |
| 2018/0168606 | A1 | 6/2018 | Shelton, IV et al. |
| 2018/0168607 | A1 | 6/2018 | Shelton, IV et al. |
| 2018/0168608 | A1 | 6/2018 | Shelton, IV et al. |
| 2018/0168609 | A1 | 6/2018 | Fanelli et al. |
| 2018/0168610 | A1 | 6/2018 | Shelton, IV et al. |
| 2018/0168611 | A1 | 6/2018 | Shelton, IV et al. |
| 2018/0168612 | A1 | 6/2018 | Shelton, IV et al. |
| 2018/0168613 | A1 | 6/2018 | Shelton, IV et al. |
| 2018/0168614 | A1 | 6/2018 | Shelton, IV et al. |
| 2018/0168615 | A1 | 6/2018 | Shelton, IV et al. |
| 2018/0168616 | A1 | 6/2018 | Shelton, IV et al. |
| 2018/0168617 | A1 | 6/2018 | Shelton, IV et al. |
| 2018/0168618 | A1 | 6/2018 | Scott et al. |
| 2018/0168619 | A1 | 6/2018 | Scott et al. |
| 2018/0168620 | A1 | 6/2018 | Huang et al. |
| 2018/0168621 | A1 | 6/2018 | Shelton, IV et al. |
| 2018/0168622 | A1 | 6/2018 | Shelton, IV et al. |
| 2018/0168623 | A1 | 6/2018 | Simms et al. |
| 2018/0168624 | A1 | 6/2018 | Shelton, IV et al. |
| 2018/0168625 | A1 | 6/2018 | Posada et al. |
| 2018/0168626 | A1 | 6/2018 | Shelton, IV et al. |
| 2018/0168627 | A1 | 6/2018 | Weaner et al. |
| 2018/0168628 | A1 | 6/2018 | Hunter et al. |
| 2018/0168629 | A1 | 6/2018 | Shelton, IV et al. |
| 2018/0168630 | A1 | 6/2018 | Shelton, IV et al. |
| 2018/0168631 | A1 | 6/2018 | Harris et al. |
| 2018/0168632 | A1 | 6/2018 | Harris et al. |
| 2018/0168633 | A1 | 6/2018 | Shelton, IV et al. |
| 2018/0168634 | A1 | 6/2018 | Harris et al. |
| 2018/0168635 | A1 | 6/2018 | Shelton, IV et al. |
| 2018/0168636 | A1 | 6/2018 | Shelton, IV et al. |
| 2018/0168637 | A1 | 6/2018 | Harris et al. |
| 2018/0168638 | A1 | 6/2018 | Harris et al. |
| 2018/0168639 | A1 | 6/2018 | Shelton, IV et al. |
| 2018/0168640 | A1 | 6/2018 | Shelton, IV et al. |
| 2018/0168641 | A1 | 6/2018 | Harris et al. |
| 2018/0168642 | A1 | 6/2018 | Shelton, IV et al. |
| 2018/0168643 | A1 | 6/2018 | Shelton, IV et al. |
| 2018/0168644 | A1 | 6/2018 | Shelton, IV et al. |
| 2018/0168645 | A1 | 6/2018 | Shelton, IV et al. |
| 2018/0168646 | A1 | 6/2018 | Shelton, IV et al. |
| 2018/0168647 | A1 | 6/2018 | Shelton, IV et al. |
| 2018/0168648 | A1 | 6/2018 | Shelton, IV et al. |
| 2018/0168649 | A1 | 6/2018 | Shelton, IV et al. |
| 2018/0168650 | A1 | 6/2018 | Shelton, IV et al. |
| 2018/0168651 | A1 | 6/2018 | Shelton, IV et al. |
| 2018/0168715 | A1 | 6/2018 | Strobl |
| 2018/0199940 | A1 | 7/2018 | Zergiebel et al. |
| 2018/0206843 | A1 | 7/2018 | Yates et al. |
| 2018/0206906 | A1 | 7/2018 | Moua et al. |
| 2018/0214147 | A1 | 8/2018 | Merchant et al. |
| 2018/0221046 | A1 | 8/2018 | Demmy et al. |
| 2018/0221050 | A1 | 8/2018 | Kostrzewski et al. |
| 2018/0228490 | A1 | 8/2018 | Richard et al. |
| 2018/0242962 | A1 | 8/2018 | Walen et al. |
| 2018/0250001 | A1 | 9/2018 | Aronhalt et al. |
| 2018/0250086 | A1 | 9/2018 | Grubbs |
| 2018/0256184 | A1 | 9/2018 | Shelton, IV et al. |
| 2018/0271520 | A1 | 9/2018 | Shelton, IV et al. |
| 2018/0271604 | A1 | 9/2018 | Grout et al. |
| 2018/0273597 | A1 | 9/2018 | Stimson |
| 2018/0280020 | A1 | 10/2018 | Hess et al. |
| 2018/0280021 | A1 | 10/2018 | Timm et al. |
| 2018/0280023 | A1 | 10/2018 | Timm et al. |
| 2018/0286274 | A1 | 10/2018 | Kamiguchi et al. |
| 2018/0289369 | A1 | 10/2018 | Shelton, IV et al. |
| 2018/0289371 | A1 | 10/2018 | Wang et al. |
| 2018/0296211 | A1 | 10/2018 | Timm et al. |
| 2018/0296213 | A1 | 10/2018 | Strobl |
| 2018/0296215 | A1 | 10/2018 | Baxter, III et al. |
| 2018/0296216 | A1 | 10/2018 | Shelton, IV et al. |
| 2018/0296217 | A1 | 10/2018 | Moore et al. |
| 2018/0303481 | A1 | 10/2018 | Shelton, IV et al. |
| 2018/0303482 | A1 | 10/2018 | Shelton, IV et al. |
| 2018/0310931 | A1 | 11/2018 | Hall et al. |
| 2018/0310935 | A1 | 11/2018 | Wixey |
| 2018/0311002 | A1 | 11/2018 | Giordano et al. |
| 2018/0317907 | A1 | 11/2018 | Kostrzewski |
| 2018/0317916 | A1 | 11/2018 | Wixey |
| 2018/0317917 | A1 | 11/2018 | Huang et al. |
| 2018/0317918 | A1 | 11/2018 | Shelton, IV |
| 2018/0317919 | A1 | 11/2018 | Shelton, IV et al. |
| 2018/0325611 | A1 | 11/2018 | Robinson et al. |
| 2018/0333155 | A1 | 11/2018 | Hall et al. |
| 2018/0333169 | A1 | 11/2018 | Leimbach et al. |
| 2018/0344319 | A1 | 12/2018 | Shelton, IV et al. |
| 2018/0353170 | A1 | 12/2018 | Overmyer et al. |
| 2018/0353176 | A1 | 12/2018 | Shelton, IV et al. |
| 2018/0353177 | A1 | 12/2018 | Shelton, IV et al. |
| 2018/0353178 | A1 | 12/2018 | Shelton, IV et al. |
| 2018/0353179 | A1 | 12/2018 | Shelton, IV et al. |
| 2018/0360443 | A1 | 12/2018 | Shelton, IV et al. |
| 2018/0360444 | A1 | 12/2018 | Harris et al. |
| 2018/0360445 | A1 | 12/2018 | Shelton, IV et al. |
| 2018/0360446 | A1 | 12/2018 | Shelton, IV et al. |
| 2018/0360447 | A1 | 12/2018 | Shelton, IV et al. |
| 2018/0360448 | A1 | 12/2018 | Harris et al. |
| 2018/0360449 | A1 | 12/2018 | Shelton, IV et al. |
| 2018/0360450 | A1 | 12/2018 | Shelton, IV et al. |
| 2018/0360452 | A1 | 12/2018 | Shelton, IV et al. |
| 2018/0360454 | A1 | 12/2018 | Shelton, IV et al. |
| 2018/0360455 | A1 | 12/2018 | Shelton, IV et al. |
| 2018/0360469 | A1 | 12/2018 | Shelton, IV et al. |
| 2018/0360471 | A1 | 12/2018 | Parfett et al. |
| 2018/0360472 | A1 | 12/2018 | Harris et al. |
| 2018/0360473 | A1 | 12/2018 | Shelton, IV et al. |
| 2018/0360549 | A1 | 12/2018 | Hares et al. |

(56) References Cited

U.S. PATENT DOCUMENTS

| | | | |
|---|---|---|---|
| 2018/0368822 | A1 | 12/2018 | Shelton, IV et al. |
| 2018/0368833 | A1 | 12/2018 | Shelton, IV et al. |
| 2018/0368837 | A1 | 12/2018 | Morgan et al. |
| 2018/0368838 | A1 | 12/2018 | Shelton, IV et al. |
| 2018/0368839 | A1 | 12/2018 | Shelton, IV et al. |
| 2018/0368840 | A1 | 12/2018 | Shelton, IV et al. |
| 2018/0368841 | A1 | 12/2018 | Shelton, IV et al. |
| 2018/0368842 | A1 | 12/2018 | Shelton, IV et al. |
| 2018/0368843 | A1 | 12/2018 | Shelton, IV et al. |
| 2018/0368844 | A1 | 12/2018 | Bakos et al. |
| 2018/0368845 | A1 | 12/2018 | Bakos et al. |
| 2018/0368846 | A1 | 12/2018 | Shelton, IV et al. |
| 2018/0368847 | A1 | 12/2018 | Shelton, IV et al. |
| 2019/0000446 | A1 | 1/2019 | Shelton, IV et al. |
| 2019/0000447 | A1 | 1/2019 | Shelton, IV et al. |
| 2019/0000448 | A1 | 1/2019 | Shelton, IV et al. |
| 2019/0000450 | A1 | 1/2019 | Shelton, IV et al. |
| 2019/0000454 | A1 | 1/2019 | Swayze et al. |
| 2019/0000456 | A1 | 1/2019 | Shelton, IV et al. |
| 2019/0000457 | A1 | 1/2019 | Shelton, IV et al. |
| 2019/0000458 | A1 | 1/2019 | Shelton, IV et al. |
| 2019/0000459 | A1 | 1/2019 | Shelton, IV et al. |
| 2019/0000460 | A1 | 1/2019 | Shelton, IV et al. |
| 2019/0000461 | A1 | 1/2019 | Shelton, IV et al. |
| 2019/0000462 | A1 | 1/2019 | Shelton, IV et al. |
| 2019/0000463 | A1 | 1/2019 | Shelton, IV et al. |
| 2019/0000464 | A1 | 1/2019 | Shelton, IV et al. |
| 2019/0000465 | A1 | 1/2019 | Shelton, IV et al. |
| 2019/0000466 | A1 | 1/2019 | Shelton, IV et al. |
| 2019/0000467 | A1 | 1/2019 | Shelton, IV et al. |
| 2019/0000468 | A1 | 1/2019 | Adams et al. |
| 2019/0000469 | A1 | 1/2019 | Shelton, IV et al. |
| 2019/0000470 | A1 | 1/2019 | Yates et al. |
| 2019/0000471 | A1 | 1/2019 | Shelton, IV et al. |
| 2019/0000472 | A1 | 1/2019 | Shelton, IV et al. |
| 2019/0000473 | A1 | 1/2019 | Shelton, IV et al. |
| 2019/0000474 | A1 | 1/2019 | Shelton, IV et al. |
| 2019/0000475 | A1 | 1/2019 | Shelton, IV et al. |
| 2019/0000476 | A1 | 1/2019 | Shelton, IV et al. |
| 2019/0000477 | A1 | 1/2019 | Shelton, IV et al. |
| 2019/0000478 | A1 | 1/2019 | Messerly et al. |
| 2019/0000479 | A1 | 1/2019 | Harris et al. |
| 2019/0000481 | A1 | 1/2019 | Harris et al. |
| 2019/0000525 | A1 | 1/2019 | Messerly et al. |
| 2019/0000528 | A1 | 1/2019 | Yates et al. |
| 2019/0000530 | A1 | 1/2019 | Yates et al. |
| 2019/0000531 | A1 | 1/2019 | Messerly et al. |
| 2019/0000534 | A1 | 1/2019 | Messerly et al. |
| 2019/0000538 | A1 | 1/2019 | Widenhouse et al. |
| 2019/0000565 | A1 | 1/2019 | Shelton, IV et al. |
| 2019/0008509 | A1 | 1/2019 | Shelton, IV et al. |
| 2019/0008511 | A1 | 1/2019 | Kerr et al. |
| 2019/0015096 | A1 | 1/2019 | Shelton, IV et al. |
| 2019/0015102 | A1 | 1/2019 | Baber et al. |
| 2019/0015165 | A1 | 1/2019 | Giordano et al. |
| 2019/0029675 | A1 | 1/2019 | Yates et al. |
| 2019/0029676 | A1 | 1/2019 | Yates et al. |
| 2019/0029677 | A1 | 1/2019 | Yates et al. |
| 2019/0029678 | A1 | 1/2019 | Shelton, IV et al. |
| 2019/0029681 | A1 | 1/2019 | Swayze et al. |
| 2019/0029682 | A1 | 1/2019 | Huitema et al. |
| 2019/0029701 | A1 | 1/2019 | Shelton, IV et al. |
| 2019/0033955 | A1 | 1/2019 | Leimbach et al. |
| 2019/0038279 | A1 | 2/2019 | Shelton, IV et al. |
| 2019/0038281 | A1 | 2/2019 | Shelton, IV et al. |
| 2019/0038282 | A1 | 2/2019 | Shelton, IV et al. |
| 2019/0038283 | A1 | 2/2019 | Shelton, IV et al. |
| 2019/0038292 | A1 | 2/2019 | Zhang |
| 2019/0038371 | A1 | 2/2019 | Wixey et al. |
| 2019/0046181 | A1 | 2/2019 | McCuen |
| 2019/0046187 | A1 | 2/2019 | Yates et al. |
| 2019/0059886 | A1 | 2/2019 | Shelton, IV et al. |
| 2019/0076142 | A1 | 3/2019 | Wixey |
| 2019/0076143 | A1 | 3/2019 | Smith |
| 2019/0090870 | A1 | 3/2019 | Shelton, IV et al. |
| 2019/0090871 | A1 | 3/2019 | Shelton, IV et al. |
| 2019/0091183 | A1 | 3/2019 | Tomat et al. |
| 2019/0099177 | A1 | 4/2019 | Yates et al. |
| 2019/0099178 | A1 | 4/2019 | Leimbach et al. |
| 2019/0099179 | A1 | 4/2019 | Leimbach et al. |
| 2019/0099180 | A1 | 4/2019 | Leimbach et al. |
| 2019/0099181 | A1 | 4/2019 | Shelton, IV et al. |
| 2019/0099182 | A1 | 4/2019 | Bakos et al. |
| 2019/0099183 | A1 | 4/2019 | Leimbach et al. |
| 2019/0099184 | A1 | 4/2019 | Setser et al. |
| 2019/0099224 | A1 | 4/2019 | Leimbach et al. |
| 2019/0099229 | A1 | 4/2019 | Spivey et al. |
| 2019/0102930 | A1 | 4/2019 | Leimbach et al. |
| 2019/0104919 | A1 | 4/2019 | Shelton, IV et al. |
| 2019/0105035 | A1 | 4/2019 | Shelton, IV et al. |
| 2019/0105036 | A1 | 4/2019 | Morgan et al. |
| 2019/0105037 | A1 | 4/2019 | Morgan et al. |
| 2019/0105038 | A1 | 4/2019 | Schmid et al. |
| 2019/0105039 | A1 | 4/2019 | Morgan et al. |
| 2019/0105043 | A1 | 4/2019 | Jaworek et al. |
| 2019/0105044 | A1 | 4/2019 | Shelton, IV et al. |
| 2019/0105049 | A1 | 4/2019 | Moore et al. |
| 2019/0110791 | A1 | 4/2019 | Shelton, IV et al. |
| 2019/0110792 | A1 | 4/2019 | Shelton, IV et al. |
| 2019/0110793 | A1 | 4/2019 | Parihar et al. |
| 2019/0117216 | A1 | 4/2019 | Overmyer et al. |
| 2019/0117217 | A1 | 4/2019 | Overmyer et al. |
| 2019/0117222 | A1 | 4/2019 | Shelton, IV et al. |
| 2019/0117224 | A1 | 4/2019 | Setser et al. |
| 2019/0117225 | A1 | 4/2019 | Moore et al. |
| 2019/0125320 | A1 | 5/2019 | Shelton, IV et al. |
| 2019/0125321 | A1 | 5/2019 | Shelton, IV et al. |
| 2019/0125324 | A1 | 5/2019 | Scheib et al. |
| 2019/0125335 | A1 | 5/2019 | Shelton, IV et al. |
| 2019/0125336 | A1 | 5/2019 | Deck et al. |
| 2019/0125338 | A1 | 5/2019 | Shelton, IV et al. |
| 2019/0125339 | A1 | 5/2019 | Shelton, IV et al. |
| 2019/0125343 | A1 | 5/2019 | Wise et al. |
| 2019/0125344 | A1 | 5/2019 | DiNardo et al. |
| 2019/0125345 | A1 | 5/2019 | Baber et al. |
| 2019/0125347 | A1 | 5/2019 | Stokes et al. |
| 2019/0125348 | A1 | 5/2019 | Shelton, IV et al. |
| 2019/0125352 | A1 | 5/2019 | Shelton, IV et al. |
| 2019/0125353 | A1 | 5/2019 | Shelton, IV et al. |
| 2019/0125354 | A1 | 5/2019 | Deck et al. |
| 2019/0125355 | A1 | 5/2019 | Shelton, IV et al. |
| 2019/0125356 | A1 | 5/2019 | Shelton, IV et al. |
| 2019/0125357 | A1 | 5/2019 | Shelton, IV et al. |
| 2019/0125358 | A1 | 5/2019 | Shelton, IV et al. |
| 2019/0125359 | A1 | 5/2019 | Shelton, IV et al. |
| 2019/0125360 | A1 | 5/2019 | Shelton, IV et al. |
| 2019/0125361 | A1 | 5/2019 | Shelton, IV et al. |
| 2019/0125365 | A1 | 5/2019 | Parfett et al. |
| 2019/0125377 | A1 | 5/2019 | Shelton, IV |
| 2019/0125378 | A1 | 5/2019 | Shelton, IV et al. |
| 2019/0125379 | A1 | 5/2019 | Shelton, IV et al. |
| 2019/0125380 | A1 | 5/2019 | Hunter et al. |
| 2019/0125384 | A1 | 5/2019 | Scheib et al. |
| 2019/0125387 | A1 | 5/2019 | Parihar et al. |
| 2019/0125388 | A1 | 5/2019 | Shelton, IV et al. |
| 2019/0125389 | A1 | 5/2019 | Shelton, IV et al. |
| 2019/0125430 | A1 | 5/2019 | Shelton, IV et al. |
| 2019/0125431 | A1 | 5/2019 | Shelton, IV et al. |
| 2019/0125432 | A1 | 5/2019 | Shelton, IV et al. |
| 2019/0125454 | A1 | 5/2019 | Stokes et al. |
| 2019/0125455 | A1 | 5/2019 | Shelton, IV et al. |
| 2019/0125456 | A1 | 5/2019 | Shelton, IV et al. |
| 2019/0125457 | A1 | 5/2019 | Parihar et al. |
| 2019/0125458 | A1 | 5/2019 | Shelton, IV et al. |
| 2019/0125459 | A1 | 5/2019 | Shelton, IV et al. |
| 2019/0125475 | A1 | 5/2019 | Wise et al. |
| 2019/0125476 | A1 | 5/2019 | Shelton, IV et al. |
| 2019/0133422 | A1 | 5/2019 | Nakamura |
| 2019/0133585 | A1 | 5/2019 | Smith et al. |
| 2019/0142421 | A1 | 5/2019 | Shelton, IV |
| 2019/0142449 | A1 | 5/2019 | Shelton, IV et al. |
| 2019/0150925 | A1 | 5/2019 | Marczyk et al. |
| 2019/0159778 | A1 | 5/2019 | Shelton, IV et al. |
| 2019/0183490 | A1 | 6/2019 | Shelton, IV et al. |

(56) References Cited

U.S. PATENT DOCUMENTS

| | | | |
|---|---|---|---|
| 2019/0183491 | A1 | 6/2019 | Shelton, IV et al. |
| 2019/0183492 | A1 | 6/2019 | Shelton, IV et al. |
| 2019/0183493 | A1 | 6/2019 | Shelton, IV et al. |
| 2019/0183494 | A1 | 6/2019 | Shelton, IV et al. |
| 2019/0183495 | A1 | 6/2019 | Shelton, IV et al. |
| 2019/0183496 | A1 | 6/2019 | Shelton, IV et al. |
| 2019/0183497 | A1 | 6/2019 | Shelton, IV et al. |
| 2019/0183498 | A1 | 6/2019 | Shelton, IV et al. |
| 2019/0183499 | A1 | 6/2019 | Shelton, IV et al. |
| 2019/0183500 | A1 | 6/2019 | Shelton, IV et al. |
| 2019/0183501 | A1 | 6/2019 | Shelton, IV et al. |
| 2019/0183502 | A1 | 6/2019 | Shelton, IV et al. |
| 2019/0183503 | A1 | 6/2019 | Shelton, IV et al. |
| 2019/0183504 | A1 | 6/2019 | Shelton, IV et al. |
| 2019/0183505 | A1 | 6/2019 | Vendely et al. |
| 2019/0183592 | A1 | 6/2019 | Shelton, IV et al. |
| 2019/0183594 | A1 | 6/2019 | Shelton, IV et al. |
| 2019/0183597 | A1 | 6/2019 | Shelton, IV et al. |
| 2019/0192137 | A1 | 6/2019 | Shelton, IV et al. |
| 2019/0192138 | A1 | 6/2019 | Shelton, IV et al. |
| 2019/0192141 | A1 | 6/2019 | Shelton, IV et al. |
| 2019/0192144 | A1 | 6/2019 | Parfett et al. |
| 2019/0192145 | A1 | 6/2019 | Shelton, IV et al. |
| 2019/0192146 | A1 | 6/2019 | Widenhouse et al. |
| 2019/0192147 | A1 | 6/2019 | Shelton, IV et al. |
| 2019/0192148 | A1 | 6/2019 | Shelton, IV et al. |
| 2019/0192149 | A1 | 6/2019 | Shelton, IV et al. |
| 2019/0192150 | A1 | 6/2019 | Widenhouse et al. |
| 2019/0192151 | A1 | 6/2019 | Shelton, IV et al. |
| 2019/0192152 | A1 | 6/2019 | Morgan et al. |
| 2019/0192153 | A1 | 6/2019 | Shelton, IV et al. |
| 2019/0192154 | A1 | 6/2019 | Shelton, IV et al. |
| 2019/0192155 | A1 | 6/2019 | Shelton, IV et al. |
| 2019/0192156 | A1 | 6/2019 | Simms et al. |
| 2019/0192157 | A1 | 6/2019 | Scott et al. |
| 2019/0192158 | A1 | 6/2019 | Scott et al. |
| 2019/0192159 | A1 | 6/2019 | Simms et al. |
| 2019/0192227 | A1 | 6/2019 | Shelton, IV et al. |
| 2019/0192235 | A1 | 6/2019 | Harris et al. |
| 2019/0192236 | A1 | 6/2019 | Shelton, IV et al. |
| 2019/0200844 | A1 | 7/2019 | Shelton, IV et al. |
| 2019/0200863 | A1 | 7/2019 | Shelton, IV et al. |
| 2019/0200895 | A1 | 7/2019 | Shelton, IV et al. |
| 2019/0200905 | A1 | 7/2019 | Shelton, IV et al. |
| 2019/0200906 | A1 | 7/2019 | Shelton, IV et al. |
| 2019/0200977 | A1 | 7/2019 | Shelton, IV et al. |
| 2019/0200981 | A1 | 7/2019 | Harris et al. |
| 2019/0200991 | A1 | 7/2019 | Moore et al. |
| 2019/0200992 | A1 | 7/2019 | Moore et al. |
| 2019/0200993 | A1 | 7/2019 | Moore et al. |
| 2019/0200994 | A1 | 7/2019 | Moore et al. |
| 2019/0200998 | A1 | 7/2019 | Shelton, IV et al. |
| 2019/0201023 | A1 | 7/2019 | Shelton, IV et al. |
| 2019/0201024 | A1 | 7/2019 | Shelton, IV et al. |
| 2019/0201025 | A1 | 7/2019 | Shelton, IV et al. |
| 2019/0201026 | A1 | 7/2019 | Shelton, IV et al. |
| 2019/0201027 | A1 | 7/2019 | Shelton, IV et al. |
| 2019/0201028 | A1 | 7/2019 | Shelton, IV et al. |
| 2019/0201029 | A1 | 7/2019 | Shelton, IV et al. |
| 2019/0201030 | A1 | 7/2019 | Shelton, IV et al. |
| 2019/0201033 | A1 | 7/2019 | Yates et al. |
| 2019/0201034 | A1 | 7/2019 | Shelton, IV et al. |
| 2019/0201045 | A1 | 7/2019 | Yates et al. |
| 2019/0201046 | A1 | 7/2019 | Shelton, IV et al. |
| 2019/0201047 | A1 | 7/2019 | Yates et al. |
| 2019/0201104 | A1 | 7/2019 | Shelton, IV et al. |
| 2019/0201105 | A1 | 7/2019 | Shelton, IV et al. |
| 2019/0201111 | A1 | 7/2019 | Shelton, IV et al. |
| 2019/0201112 | A1 | 7/2019 | Wiener et al. |
| 2019/0201113 | A1 | 7/2019 | Shelton, IV et al. |
| 2019/0201114 | A1 | 7/2019 | Shelton, IV et al. |
| 2019/0201115 | A1 | 7/2019 | Shelton, IV et al. |
| 2019/0201116 | A1 | 7/2019 | Shelton, IV et al. |
| 2019/0201118 | A1 | 7/2019 | Shelton, IV et al. |
| 2019/0201119 | A1 | 7/2019 | Harris et al. |
| 2019/0201120 | A1 | 7/2019 | Shelton, IV et al. |
| 2019/0201135 | A1 | 7/2019 | Shelton, IV et al. |
| 2019/0201136 | A1 | 7/2019 | Shelton, IV et al. |
| 2019/0201137 | A1 | 7/2019 | Shelton, IV et al. |
| 2019/0201138 | A1 | 7/2019 | Yates et al. |
| 2019/0201139 | A1 | 7/2019 | Shelton, IV et al. |
| 2019/0201140 | A1 | 7/2019 | Yates et al. |
| 2019/0201141 | A1 | 7/2019 | Shelton, IV et al. |
| 2019/0201142 | A1 | 7/2019 | Shelton, IV et al. |
| 2019/0201143 | A1 | 7/2019 | Shelton, IV et al. |
| 2019/0201145 | A1 | 7/2019 | Shelton, IV et al. |
| 2019/0201594 | A1 | 7/2019 | Shelton, IV et al. |
| 2019/0205001 | A1 | 7/2019 | Messerly et al. |
| 2019/0205566 | A1 | 7/2019 | Shelton, IV et al. |
| 2019/0205567 | A1 | 7/2019 | Shelton, IV et al. |
| 2019/0206003 | A1 | 7/2019 | Harris et al. |
| 2019/0206004 | A1 | 7/2019 | Shelton, IV et al. |
| 2019/0206050 | A1 | 7/2019 | Yates et al. |
| 2019/0206551 | A1 | 7/2019 | Yates et al. |
| 2019/0206555 | A1 | 7/2019 | Morgan et al. |
| 2019/0206561 | A1 | 7/2019 | Shelton, IV et al. |
| 2019/0206562 | A1 | 7/2019 | Shelton, IV et al. |
| 2019/0206563 | A1 | 7/2019 | Shelton, IV et al. |
| 2019/0206564 | A1 | 7/2019 | Shelton, IV et al. |
| 2019/0206565 | A1 | 7/2019 | Shelton, IV |
| 2019/0206569 | A1 | 7/2019 | Shelton, IV et al. |
| 2019/0208641 | A1 | 7/2019 | Yates et al. |
| 2019/0209164 | A1 | 7/2019 | Timm et al. |
| 2019/0209165 | A1 | 7/2019 | Timm et al. |
| 2019/0209171 | A1 | 7/2019 | Shelton, IV et al. |
| 2019/0209172 | A1 | 7/2019 | Shelton, IV et al. |
| 2019/0209247 | A1 | 7/2019 | Giordano et al. |
| 2019/0209248 | A1 | 7/2019 | Giordano et al. |
| 2019/0209249 | A1 | 7/2019 | Giordano et al. |
| 2019/0209250 | A1 | 7/2019 | Giordano et al. |
| 2019/0216558 | A1 | 7/2019 | Giordano et al. |
| 2019/0223865 | A1 | 7/2019 | Shelton, IV et al. |
| 2019/0223871 | A1 | 7/2019 | Moore et al. |
| 2019/0261984 | A1 | 8/2019 | Nelson et al. |
| 2019/0261991 | A1 | 8/2019 | Beckman et al. |
| 2019/0267403 | A1 | 8/2019 | Li et al. |
| 2019/0269400 | A1 | 9/2019 | Mandakolathur Vasudevan et al. |
| 2019/0269402 | A1 | 9/2019 | Murray et al. |
| 2019/0269403 | A1 | 9/2019 | Baxter, III et al. |
| 2019/0269407 | A1 | 9/2019 | Swensgard et al. |
| 2019/0269428 | A1 | 9/2019 | Allen et al. |
| 2019/0274677 | A1 | 9/2019 | Shelton, IV |
| 2019/0274678 | A1 | 9/2019 | Shelton, IV |
| 2019/0274679 | A1 | 9/2019 | Shelton, IV |
| 2019/0274680 | A1 | 9/2019 | Shelton, IV |
| 2019/0274685 | A1 | 9/2019 | Olson et al. |
| 2019/0290263 | A1 | 9/2019 | Morgan et al. |
| 2019/0290264 | A1 | 9/2019 | Morgan et al. |
| 2019/0290265 | A1 | 9/2019 | Shelton, IV et al. |
| 2019/0290267 | A1 | 9/2019 | Baxter, III et al. |
| 2019/0290274 | A1 | 9/2019 | Shelton, IV |
| 2019/0290281 | A1 | 9/2019 | Aronhalt et al. |
| 2019/0290297 | A1 | 9/2019 | Haider et al. |
| 2019/0298340 | A1 | 10/2019 | Shelton, IV et al. |
| 2019/0298341 | A1 | 10/2019 | Shelton, IV et al. |
| 2019/0298342 | A1 | 10/2019 | Shelton, IV et al. |
| 2019/0298343 | A1 | 10/2019 | Shelton, IV et al. |
| 2019/0298346 | A1 | 10/2019 | Shelton, IV et al. |
| 2019/0298347 | A1 | 10/2019 | Shelton, IV et al. |
| 2019/0298348 | A1 | 10/2019 | Harris et al. |
| 2019/0298350 | A1 | 10/2019 | Shelton, IV et al. |
| 2019/0298351 | A1 | 10/2019 | Shelton, IV et al. |
| 2019/0298352 | A1 | 10/2019 | Shelton, IV et al. |
| 2019/0298353 | A1 | 10/2019 | Shelton, IV et al. |
| 2019/0298354 | A1 | 10/2019 | Shelton, IV et al. |
| 2019/0298355 | A1 | 10/2019 | Shelton, IV et al. |
| 2019/0298356 | A1 | 10/2019 | Shelton, IV et al. |
| 2019/0298357 | A1 | 10/2019 | Shelton, IV et al. |
| 2019/0298360 | A1 | 10/2019 | Shelton, IV et al. |
| 2019/0298361 | A1 | 10/2019 | Shelton, IV et al. |
| 2019/0298362 | A1 | 10/2019 | Shelton, IV et al. |
| 2019/0307452 | A1 | 10/2019 | Shelton, IV et al. |
| 2019/0307453 | A1 | 10/2019 | Shelton, IV et al. |
| 2019/0307454 | A1 | 10/2019 | Shelton, IV et al. |

(56) References Cited

U.S. PATENT DOCUMENTS

| | | | |
|---|---|---|---|
| 2019/0307455 | A1 | 10/2019 | Shelton, IV et al. |
| 2019/0307456 | A1 | 10/2019 | Shelton, IV et al. |
| 2019/0307476 | A1 | 10/2019 | Shelton, IV et al. |
| 2019/0307477 | A1 | 10/2019 | Shelton, IV et al. |
| 2019/0307478 | A1 | 10/2019 | Shelton, IV et al. |
| 2019/0307479 | A1 | 10/2019 | Shelton, IV et al. |
| 2019/0314016 | A1 | 10/2019 | Huitema et al. |
| 2019/0314017 | A1 | 10/2019 | Huitema et al. |
| 2019/0314018 | A1 | 10/2019 | Huitema et al. |
| 2019/0321039 | A1 | 10/2019 | Harris et al. |
| 2019/0321040 | A1 | 10/2019 | Shelton, IV |
| 2019/0321041 | A1 | 10/2019 | Shelton, IV |
| 2019/0328386 | A1 | 10/2019 | Harris et al. |
| 2019/0328387 | A1 | 10/2019 | Overmyer et al. |
| 2019/0328390 | A1 | 10/2019 | Harris et al. |
| 2019/0336128 | A1 | 11/2019 | Harris et al. |
| 2019/0343514 | A1 | 11/2019 | Shelton, IV et al. |
| 2019/0343515 | A1 | 11/2019 | Morgan et al. |
| 2019/0343518 | A1 | 11/2019 | Shelton, IV |
| 2019/0343525 | A1 | 11/2019 | Shelton, IV et al. |
| 2019/0350582 | A1 | 11/2019 | Shelton, IV et al. |
| 2019/0357909 | A1 | 11/2019 | Huitema et al. |
| 2019/0365384 | A1 | 12/2019 | Baxter, III et al. |
| 2019/0374224 | A1 | 12/2019 | Huitema et al. |
| 2020/0000461 | A1 | 1/2020 | Yates et al. |
| 2020/0000468 | A1 | 1/2020 | Shelton, IV et al. |
| 2020/0000469 | A1 | 1/2020 | Shelton, IV et al. |
| 2020/0000471 | A1 | 1/2020 | Shelton, IV et al. |
| 2020/0000531 | A1 | 1/2020 | Giordano et al. |
| 2020/0008800 | A1 | 1/2020 | Shelton, IV et al. |
| 2020/0008802 | A1 | 1/2020 | Aronhalt et al. |
| 2020/0008809 | A1 | 1/2020 | Shelton, IV et al. |
| 2020/0015815 | A1 | 1/2020 | Harris et al. |
| 2020/0015819 | A1 | 1/2020 | Shelton, IV et al. |
| 2020/0022702 | A1 | 1/2020 | Shelton, IV et al. |
| 2020/0029964 | A1 | 1/2020 | Overmyer et al. |
| 2020/0030050 | A1 | 1/2020 | Shelton, IV et al. |
| 2020/0038016 | A1 | 2/2020 | Shelton, IV et al. |
| 2020/0038018 | A1 | 2/2020 | Shelton, IV et al. |
| 2020/0038020 | A1 | 2/2020 | Yates et al. |
| 2020/0046348 | A1 | 2/2020 | Shelton, IV et al. |
| 2020/0046893 | A1 | 2/2020 | Shelton, IV et al. |
| 2020/0054320 | A1 | 2/2020 | Harris et al. |
| 2020/0054321 | A1 | 2/2020 | Harris et al. |
| 2020/0054322 | A1 | 2/2020 | Harris et al. |
| 2020/0054323 | A1 | 2/2020 | Harris et al. |
| 2020/0054324 | A1 | 2/2020 | Shelton, IV et al. |
| 2020/0054325 | A1 | 2/2020 | Harris et al. |
| 2020/0054326 | A1 | 2/2020 | Harris et al. |
| 2020/0054327 | A1 | 2/2020 | Harris et al. |
| 2020/0054328 | A1 | 2/2020 | Harris et al. |
| 2020/0054329 | A1 | 2/2020 | Shelton, IV et al. |
| 2020/0054330 | A1 | 2/2020 | Harris et al. |
| 2020/0054331 | A1 | 2/2020 | Harris et al. |
| 2020/0054332 | A1 | 2/2020 | Shelton, IV et al. |
| 2020/0054333 | A1 | 2/2020 | Shelton, IV et al. |
| 2020/0054334 | A1 | 2/2020 | Shelton, IV et al. |
| 2020/0054355 | A1 | 2/2020 | Laurent et al. |
| 2020/0060680 | A1 | 2/2020 | Shelton, IV et al. |
| 2020/0060681 | A1 | 2/2020 | Shelton, IV et al. |
| 2020/0060713 | A1 | 2/2020 | Leimbach et al. |
| 2020/0077994 | A1 | 3/2020 | Shelton, IV et al. |
| 2020/0078015 | A1 | 3/2020 | Miller et al. |
| 2020/0078016 | A1 | 3/2020 | Swayze et al. |
| 2020/0085427 | A1 | 3/2020 | Giordano et al. |
| 2020/0085431 | A1 | 3/2020 | Swayze et al. |
| 2020/0085435 | A1 | 3/2020 | Shelton, IV et al. |
| 2020/0085436 | A1 | 3/2020 | Beckman et al. |
| 2020/0085518 | A1 | 3/2020 | Giordano et al. |
| 2020/0093484 | A1 | 3/2020 | Shelton, IV et al. |
| 2020/0093485 | A1 | 3/2020 | Shelton, IV et al. |
| 2020/0093487 | A1 | 3/2020 | Baber et al. |
| 2020/0093488 | A1 | 3/2020 | Baber et al. |
| 2020/0093506 | A1 | 3/2020 | Leimbach et al. |
| 2020/0093550 | A1 | 3/2020 | Spivey et al. |
| 2020/0100699 | A1 | 4/2020 | Shelton, IV et al. |
| 2020/0100783 | A1 | 4/2020 | Yates et al. |
| 2020/0100787 | A1 | 4/2020 | Shelton, IV et al. |
| 2020/0107829 | A1 | 4/2020 | Shelton, IV et al. |
| 2020/0138434 | A1 | 5/2020 | Miller et al. |
| 2020/0138435 | A1 | 5/2020 | Shelton, IV et al. |
| 2020/0138436 | A1 | 5/2020 | Yates et al. |
| 2020/0138437 | A1 | 5/2020 | Vendely et al. |
| 2020/0146678 | A1 | 5/2020 | Leimbach et al. |
| 2020/0146741 | A1 | 5/2020 | Long et al. |
| 2020/0155151 | A1 | 5/2020 | Overmyer et al. |
| 2020/0155155 | A1 | 5/2020 | Shelton, IV et al. |
| 2020/0178958 | A1 | 6/2020 | Overmyer et al. |
| 2020/0178960 | A1 | 6/2020 | Overmyer et al. |
| 2020/0187943 | A1 | 6/2020 | Shelton, IV et al. |
| 2020/0214706 | A1 | 7/2020 | Vendely et al. |
| 2020/0214731 | A1 | 7/2020 | Shelton, IV et al. |
| 2020/0222047 | A1 | 7/2020 | Shelton, IV et al. |
| 2020/0229812 | A1 | 7/2020 | Parihar et al. |
| 2020/0229816 | A1 | 7/2020 | Bakos et al. |
| 2020/0237371 | A1 | 7/2020 | Huitema et al. |
| 2020/0246001 | A1 | 8/2020 | Ming et al. |
| 2020/0253605 | A1 | 8/2020 | Swayze et al. |
| 2020/0261106 | A1 | 8/2020 | Hess et al. |
| 2020/0268377 | A1 | 8/2020 | Schmid et al. |
| 2020/0268394 | A1 | 8/2020 | Parfett et al. |
| 2020/0275926 | A1 | 9/2020 | Shelton, IV et al. |
| 2020/0275927 | A1 | 9/2020 | Shelton, IV et al. |
| 2020/0275928 | A1 | 9/2020 | Shelton, IV et al. |
| 2020/0275930 | A1 | 9/2020 | Harris et al. |
| 2020/0281585 | A1 | 9/2020 | Timm et al. |
| 2020/0281587 | A1 | 9/2020 | Schmid et al. |
| 2020/0281590 | A1 | 9/2020 | Shelton, IV et al. |
| 2020/0289112 | A1 | 9/2020 | Whitfield et al. |
| 2020/0297340 | A1 | 9/2020 | Hess et al. |
| 2020/0297341 | A1 | 9/2020 | Yates et al. |
| 2020/0297346 | A1 | 9/2020 | Shelton, IV et al. |
| 2020/0297438 | A1 | 9/2020 | Shelton, IV et al. |
| 2020/0305862 | A1 | 10/2020 | Yates et al. |
| 2020/0305863 | A1 | 10/2020 | Yates et al. |
| 2020/0305864 | A1 | 10/2020 | Yates et al. |
| 2020/0305865 | A1 | 10/2020 | Shelton, IV |
| 2020/0305868 | A1 | 10/2020 | Shelton, IV |
| 2020/0305869 | A1 | 10/2020 | Shelton, IV |
| 2020/0305870 | A1 | 10/2020 | Shelton, IV |
| 2020/0305871 | A1 | 10/2020 | Shelton, IV et al. |
| 2020/0305874 | A1 | 10/2020 | Huitema et al. |
| 2020/0315612 | A1 | 10/2020 | Shelton, IV et al. |
| 2020/0315615 | A1 | 10/2020 | Yates et al. |
| 2020/0315616 | A1 | 10/2020 | Yates et al. |
| 2020/0315625 | A1 | 10/2020 | Hall et al. |
| 2020/0315983 | A1 | 10/2020 | Widenhouse et al. |
| 2020/0323526 | A1 | 10/2020 | Huang et al. |
| 2020/0330092 | A1 | 10/2020 | Shelton, IV et al. |
| 2020/0330093 | A1 | 10/2020 | Shelton, IV et al. |
| 2020/0330094 | A1 | 10/2020 | Baxter, III et al. |
| 2020/0330096 | A1 | 10/2020 | Shelton, IV et al. |
| 2020/0337693 | A1 | 10/2020 | Shelton, IV et al. |
| 2020/0337702 | A1 | 10/2020 | Shelton, IV et al. |
| 2020/0337703 | A1 | 10/2020 | Shelton, IV et al. |
| 2020/0337791 | A1 | 10/2020 | Shelton, IV et al. |
| 2020/0345346 | A1 | 11/2020 | Shelton, IV et al. |
| 2020/0345349 | A1 | 11/2020 | Kimball et al. |
| 2020/0345352 | A1 | 11/2020 | Shelton, IV et al. |
| 2020/0345353 | A1 | 11/2020 | Leimbach et al. |
| 2020/0345354 | A1 | 11/2020 | Leimbach et al. |
| 2020/0345355 | A1 | 11/2020 | Baxter, III et al. |
| 2020/0345356 | A1 | 11/2020 | Leimbach et al. |
| 2020/0345357 | A1 | 11/2020 | Leimbach et al. |
| 2020/0345358 | A1 | 11/2020 | Jenkins |
| 2020/0345359 | A1 | 11/2020 | Baxter, III et al. |
| 2020/0345360 | A1 | 11/2020 | Leimbach et al. |
| 2020/0345446 | A1 | 11/2020 | Kimball et al. |
| 2020/0352562 | A1 | 11/2020 | Timm et al. |
| 2020/0367885 | A1 | 11/2020 | Yates et al. |
| 2020/0367886 | A1 | 11/2020 | Shelton, IV et al. |
| 2020/0375585 | A1 | 12/2020 | Swayze et al. |
| 2020/0375592 | A1 | 12/2020 | Hall et al. |
| 2020/0375593 | A1 | 12/2020 | Hunter et al. |

(56) References Cited

U.S. PATENT DOCUMENTS

| | | | |
|---|---|---|---|
| 2020/0375597 | A1 | 12/2020 | Shelton, IV et al. |
| 2020/0390444 | A1 | 12/2020 | Harris et al. |
| 2020/0397433 | A1 | 12/2020 | Lytle, IV et al. |
| 2020/0397434 | A1 | 12/2020 | Overmyer et al. |
| 2020/0405290 | A1 | 12/2020 | Shelton, IV et al. |
| 2020/0405291 | A1 | 12/2020 | Shelton, IV et al. |
| 2020/0405292 | A1 | 12/2020 | Shelton, IV et al. |
| 2020/0405293 | A1 | 12/2020 | Shelton, IV et al. |
| 2020/0405294 | A1 | 12/2020 | Shelton, IV |
| 2020/0405295 | A1 | 12/2020 | Shelton, IV et al. |
| 2020/0405296 | A1 | 12/2020 | Shelton, IV et al. |
| 2020/0405297 | A1 | 12/2020 | Shelton, IV et al. |
| 2020/0405301 | A1 | 12/2020 | Shelton, IV et al. |
| 2020/0405302 | A1 | 12/2020 | Shelton, IV et al. |
| 2020/0405303 | A1 | 12/2020 | Shelton, IV |
| 2020/0405305 | A1 | 12/2020 | Shelton, IV et al. |
| 2020/0405306 | A1 | 12/2020 | Shelton, IV et al. |
| 2020/0405307 | A1 | 12/2020 | Shelton, IV et al. |
| 2020/0405308 | A1 | 12/2020 | Shelton, IV |
| 2020/0405309 | A1 | 12/2020 | Shelton, IV et al. |
| 2020/0405311 | A1 | 12/2020 | Shelton, IV et al. |
| 2020/0405312 | A1 | 12/2020 | Shelton, IV et al. |
| 2020/0405313 | A1 | 12/2020 | Shelton, IV |
| 2020/0405314 | A1 | 12/2020 | Shelton, IV et al. |
| 2020/0405316 | A1 | 12/2020 | Shelton, IV et al. |
| 2020/0405341 | A1 | 12/2020 | Hess et al. |
| 2020/0405409 | A1 | 12/2020 | Shelton, IV et al. |
| 2020/0405410 | A1 | 12/2020 | Shelton, IV |
| 2020/0405436 | A1 | 12/2020 | Shelton, IV et al. |
| 2020/0405437 | A1 | 12/2020 | Shelton, IV et al. |
| 2020/0405438 | A1 | 12/2020 | Shelton, IV et al. |
| 2020/0405439 | A1 | 12/2020 | Shelton, IV et al. |
| 2020/0405440 | A1 | 12/2020 | Shelton, IV et al. |
| 2020/0405441 | A1 | 12/2020 | Shelton, IV et al. |
| 2020/0410177 | A1 | 12/2020 | Shelton, IV |
| 2020/0410180 | A1 | 12/2020 | Shelton, IV et al. |
| 2021/0000466 | A1 | 1/2021 | Leimbach et al. |
| 2021/0000467 | A1 | 1/2021 | Shelton, IV et al. |
| 2021/0000470 | A1 | 1/2021 | Leimbach et al. |
| 2021/0015480 | A1 | 1/2021 | Shelton, IV et al. |
| 2021/0022741 | A1 | 1/2021 | Baxter, III et al. |
| 2021/0030416 | A1 | 2/2021 | Shelton, IV et al. |
| 2021/0045742 | A1 | 2/2021 | Shelton, IV et al. |
| 2021/0052271 | A1 | 2/2021 | Harris et al. |
| 2021/0059661 | A1 | 3/2021 | Schmid et al. |
| 2021/0059662 | A1 | 3/2021 | Shelton, IV |
| 2021/0059666 | A1 | 3/2021 | Schmid et al. |
| 2021/0059669 | A1 | 3/2021 | Yates et al. |
| 2021/0059670 | A1 | 3/2021 | Overmyer et al. |
| 2021/0059671 | A1 | 3/2021 | Shelton, IV et al. |
| 2021/0059672 | A1 | 3/2021 | Giordano et al. |
| 2021/0059673 | A1 | 3/2021 | Shelton, IV et al. |
| 2021/0068817 | A1 | 3/2021 | Shelton, IV et al. |
| 2021/0068818 | A1 | 3/2021 | Overmyer et al. |
| 2021/0068820 | A1 | 3/2021 | Parihar et al. |
| 2021/0068830 | A1 | 3/2021 | Baber et al. |
| 2021/0068831 | A1 | 3/2021 | Baber et al. |
| 2021/0068832 | A1 | 3/2021 | Yates et al. |
| 2021/0068835 | A1 | 3/2021 | Shelton, IV et al. |
| 2021/0077092 | A1 | 3/2021 | Parihar et al. |
| 2021/0077099 | A1 | 3/2021 | Shelton, IV et al. |
| 2021/0077100 | A1 | 3/2021 | Shelton, IV et al. |
| 2021/0085313 | A1 | 3/2021 | Morgan et al. |
| 2021/0085314 | A1 | 3/2021 | Schmid et al. |
| 2021/0085315 | A1 | 3/2021 | Aronhalt et al. |
| 2021/0085316 | A1 | 3/2021 | Harris et al. |
| 2021/0085317 | A1 | 3/2021 | Miller et al. |
| 2021/0085318 | A1 | 3/2021 | Swayze et al. |
| 2021/0085319 | A1 | 3/2021 | Swayze et al. |
| 2021/0085320 | A1 | 3/2021 | Leimbach et al. |
| 2021/0085321 | A1 | 3/2021 | Shelton, IV et al. |
| 2021/0085325 | A1 | 3/2021 | Shelton, IV et al. |
| 2021/0085326 | A1 | 3/2021 | Vendely et al. |

FOREIGN PATENT DOCUMENTS

| | | | |
|---|---|---|---|
| AU | 2011218702 | B2 | 6/2013 |
| AU | 2012200178 | B2 | 7/2013 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101721236 | A | 6/2010 |
| CN | 101828940 | A | 9/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247183 | A | 11/2011 |
| CN | 101779977 | B | 12/2011 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103690212 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |

(56) References Cited

FOREIGN PATENT DOCUMENTS

| | | | |
|---|---|---|---|
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 103648410 | B | 10/2016 |
| CN | 106344091 | A | 1/2017 |
| CN | 104349800 | B | 11/2017 |
| CN | 107635483 | A | 1/2018 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2842500 | A1 | 3/2015 |
| EP | 2853220 | A1 | 4/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3326548 | A1 | 5/2018 |
| EP | 3363378 | A1 | 8/2018 |
| EP | 3275378 | B1 | 7/2019 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H04215747 | A | 8/1992 |
| JP | H04131860 | U | 12/1992 |
| JP | H0584252 | A | 4/1993 |
| JP | H05123325 | A | 5/1993 |
| JP | H 05226945 | A | 9/1993 |
| JP | H0630945 | A | 2/1994 |

(56) References Cited

FOREIGN PATENT DOCUMENTS

| | | | |
|---|---|---|---|
| JP | H06237937 | A | 8/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H09-323068 | A | 12/1997 |
| JP | H10118090 | A | 5/1998 |
| JP | H10-200699 | A | 7/1998 |
| JP | H 10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001087272 | A | 4/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007289715 | A | 11/2007 |
| JP | 2007306710 | A | 11/2007 |
| JP | D1322057 | | 2/2008 |
| JP | 2008-220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | D1432094 | | 12/2011 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541983 | A | 11/2013 |
| JP | 2013541997 | A | 11/2013 |
| JP | D1492363 | | 2/2014 |
| JP | 2014121599 | A | 7/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015521525 | A | 7/2015 |
| JP | 2016-512057 | A | 4/2016 |
| JP | 2016530949 | A | 10/2016 |
| JP | 1601498 | S | 4/2018 |
| KR | 20100110134 | A | 10/2010 |
| KR | 20110003229 | A | 1/2011 |
| KR | 300631507 | | 3/2012 |
| KR | 300747646 | | 6/2014 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |

(56) References Cited

FOREIGN PATENT DOCUMENTS

| | | | |
|---|---|---|---|
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006/073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008/061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012/013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014/113438 | A1 | 7/2014 |
| WO | WO-2014175894 | A1 | 10/2014 |
| WO | WO-2015/032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |

OTHER PUBLICATIONS

Author: disclosed anonymously. Motor-Driven surgical stapler improvements, Published in Feb. 2008, Kenneth Mason Publications Ltd, Research Disclosure Journal, ISSN 0374-4353 (Year: 2008).*

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Young, "Microcellular foams via phase separation," Journal of Vacuum Science & Technology A 4(3), (May/Jun. 1986).

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Solorio et al., "Gelatin Microspheres Crosslinked with Genipin for Local Delivery of Growth Factors," J. Tissue Eng. Regen. Med. (2010), 4(7): pp. 514-523.

Pitt et al., "Attachment of Hyaluronan to Metallic Surfaces," J. Biomed. Mater. Res. 68A: pp. 95-106, 2004.

Covidien iDrive ™ Ultra in Service Reference Card, "iDrive™ Ultra Powered Stapling Device," (4 pages).

Covidien iDrive ™ Ultra Powered Stapling System ibrochure, "The Power of iDrive ™ Ultra Powered Stapling System and Tri-Staple™ Technology," (23 pages).

Covidien "iDrive™ Ultra Powered Stapling System, A Guide for Surgeons," (6 pages).

Covidien "iDrive™ Ultra Powered Stapling System, Cleaning and Sterilization Guide," (2 pages).

"Indian Standard: Automotive Vehicles—Brakes and Braking Systems (IS 11852-1:2001)", Mar. 1, 2001.

Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.

Covidien Brochure "iDrive™ Ultra Powered Stapling System," (6 pages).

Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

Data Sheet of LM4F230H5QR, 2007.

(56) References Cited

OTHER PUBLICATIONS

Covidien Brochure, "Endo GIA™ Reloads with Tri-Staple ™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
http://ninpgan.net/publications/51-100/89.pdf; 2004, Ning Pan, On Uniqueness of Fibrous Materials, Design & Nature II. Eds: Colins, M. and Brebbia, C. Wit Press, Boston, 493-504.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
"Biomedical Coatings," Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileld=db3a304332d040720132d9395 03e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg-Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
"Foot and Ankle: Core Knowledge in Orthopaedics"; by DiGiovanni MD, Elsevier; (p. 27, left column heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016 [retrieved on Jun. 4, 2019], retrieved from the Internet [URL: https://www.iconfinder.com/iconsets/elite] (Year: 2016).
"Tutorial overview of inductively coupled RFID Systems," UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "*An Inductive Link-Based Wireless Power Transfer System for Biomedical Applications*," Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.

(56) References Cited

OTHER PUBLICATIONS

NF Monographs: Sodium Stearate, U.S. Pharmacopeia, http://www.pharmacopeia.cn/v29240/usp29nf24s0_m77360.html, accessed May 23, 2016.

Fischer, Martin H, "Colloid-Chemical Studies on Soaps", The Chemical Engineer, pp. 184-193, Aug. 1919.

V.K. Ahluwalia and Madhuri Goyal, A Textbook of Organic Chemistry, Section 19.11.3, p. 356, 2000.

A.V. Kasture and S.G. Wadodkar, Pharmaceutical Chemistry-II: Second Year Diploma in Pharmacy, Nirali Prakashan, p. 339, 2007.

Forum discussion regarding "Speed is Faster", published on Oct. 1, 2014 and retrieved on Nov. 8, 2019 from URL https://english.stackexchange.com/questions/199018/how-is-that-correct- speed-is-faster-or-prices-are-cheaper (Year: 2014).

"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).

Jauchem, J.R., "Effects of low-level radio-frequency (3 kHz to 300 GHZ) enery on human cardiovascular, reproductive, immune, and other systems: A review of the recent literatured," Int. J. Hyg. Environ. Health 211 (2008) 1-29.

Sandvik, "Welding Handbook," https://www.meting.rs/wp-content/uploads/2018/05/welding-handbook.pdf, retrieved on Jun. 22, 2020. pp. 5-6.

Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.

Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

* cited by examiner

SURGICAL INSTRUMENT HAVING CONTROLLABLE ARTICULATION VELOCITY

TECHNICAL FIELD

The present disclosure relates to surgical instruments and, in various circumstances, surgical stapling and cutting instruments and staple cartridges therefor that are designed to staple and cut tissue.

BACKGROUND

In a motorized surgical stapling and cutting instrument it may be useful to control the velocity of a cutting member or to control the articulation velocity of an end effector. Velocity of a displacement member may be determined by measuring elapsed time at predetermined position intervals of the displacement member or measuring the position of the displacement member at predetermined time intervals. The control may be open loop or closed loop. Such measurements may be useful to evaluate tissue conditions such as tissue thickness and adjust the velocity of the cutting member during a firing stroke to account for the tissue conditions. Tissue thickness may be determined by comparing expected velocity of the cutting member to the actual velocity of the cutting member. In some situations, it may be useful to articulate the end effector at a constant articulation velocity. In other situations, it may be useful to drive the end effector at a different articulation velocity than a default articulation velocity at one or more regions within a sweep range of the end effector.

During use of a motorized surgical stapling and cutting instrument it is possible that the end effector sweep rate may vary undesirably in areas of interest such as near the end of stroke or near the home position for removal from a trocar. Therefore, it may be desirable to provide articulation velocity control to improve user control. It may be desirable to vary the end effector articulation by varying the duty cycle of the motor drive signal to vary the articulation head angle rate as a function of the end effector articulation angle.

SUMMARY

In one aspect, the present disclosure provides a surgical instrument comprising a motor configured to drive an end effector between an unarticulated position and an articulated position; a sensor configured to detect an articulation position of the end effector and provide a signal indicative of the articulation position of the end effector; and a control circuit coupled to the sensor and the motor, the control circuit configured to: determine the articulation position of the end effector via the signal provided by the sensor; and provide a drive signal to the motor to articulate the end effector at a velocity corresponding to the signal indicative of the articulation position of the end effector.

In another aspect, the surgical instrument comprises an articulation driver configured to drive an end effector that is articulatable between a first position and a second position, the articulation driver configured to drive the end effector from the first position to the second position; a motor coupled to the articulation driver, the motor configured to drive the articulation driver; a sensor configured to detect a position of the articulation driver and provide a signal indicative of the position of the articulation driver; and a control circuit coupled to the motor and the sensor, the control circuit configured to: detect a position of the articulation driver via the signal provided by the sensor; determine an angular position of the end effector according to the signal indicative of the position of the articulation driver; and provide a drive signal to the motor to drive the motor at a velocity corresponding to the angular position of the end effector.

In another aspect, a method of controlling a motor in a surgical instrument is provided. The surgical instrument comprising a motor configured to drive an end effector between an unarticulated position and an articulated position, a sensor configured to detect an articulation position of the end effector and provide a signal indicative of the articulation position of the end effector, and a control circuit coupled to the sensor and the motor, the method comprising: determining, by the control circuit, the articulation position of the end effector via the signal provided by the sensor; and providing, by the control circuit, a drive signal to the motor to articulate the end effector at a velocity corresponding to the signal indicative of the articulation position of the end effector.

FIGURES

The novel features of the aspects described herein are set forth with particularity in the appended claims. These aspects, however, both as to organization and methods of operation may be better understood by reference to the following description, taken in conjunction with the accompanying drawings.

FIG. 29 depicts a control algorithm for controlling an articulation velocity of an end effector utilizing variable voltage and no pulse width modulation.

FIG. 30 depicts a control algorithm for controlling an articulation velocity of an end effector utilizing constant voltage and pulse width modulation.

FIG. 31 depicts a control algorithm for controlling an articulation velocity of an end effector utilizing variable voltage and pulse width modulation.

FIG. 32 depicts a control algorithm for controlling an articulation velocity of an end effector utilizing constant voltage and no pulse width modulation.

DESCRIPTION

Figure 1:
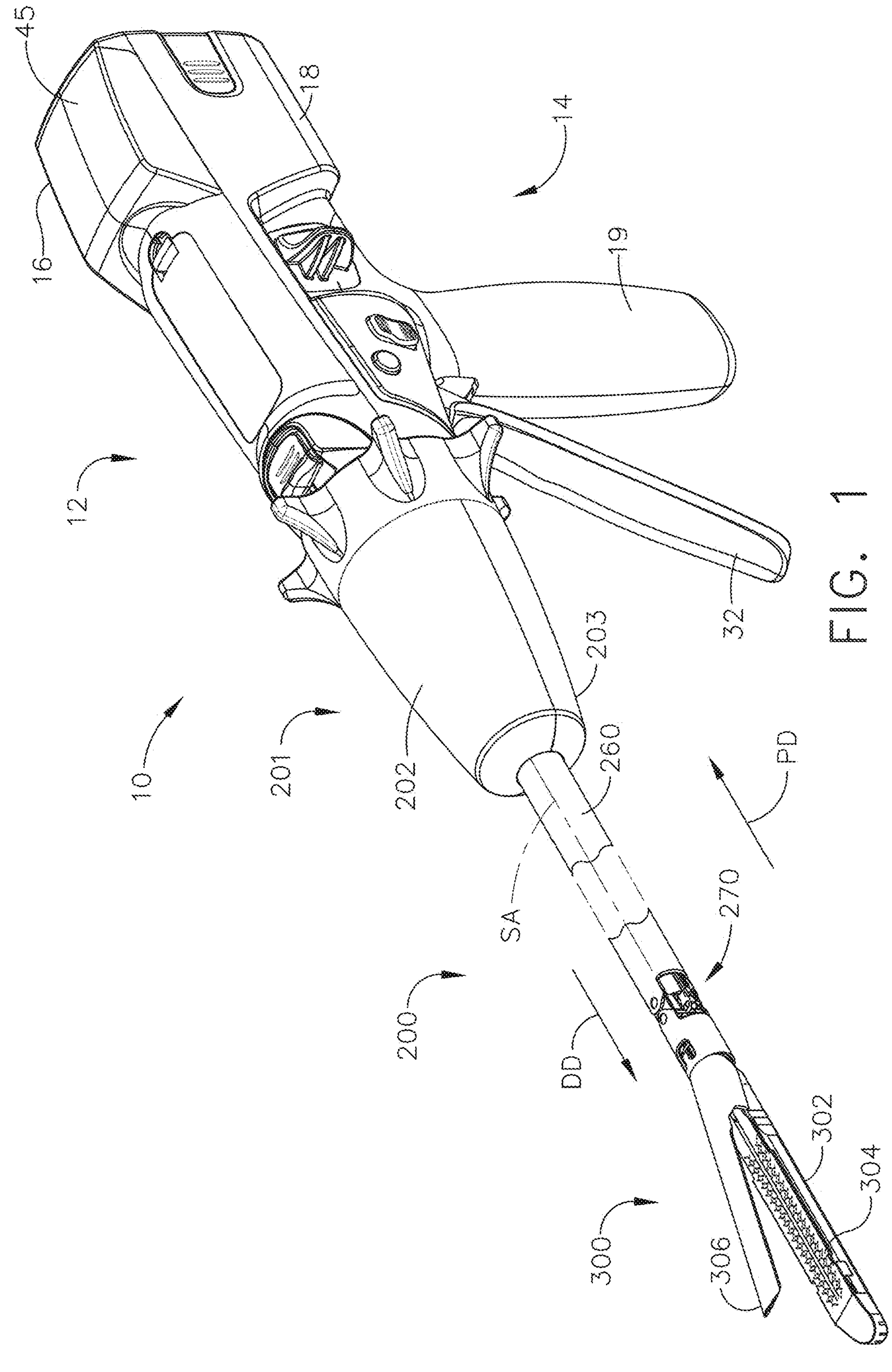
FIG. 1 is a perspective view of a surgical instrument that has an interchangeable shaft assembly operably coupled thereto according to one aspect of this disclosure.

Applicant of the present application owns the following patent applications filed Jun. 20, 2017, and which are each herein incorporated by reference in their respective entireties:

- U.S. patent application Ser. No. 15/627,998, titled CONTROL OF MOTOR VELOCITY OF A SURGICAL STAPLING AND CUTTING INSTRUMENT BASED ON ANGLE OF ARTICULATION, by inventors Frederick E. Shelton, IV et al., filed Jun. 20, 2017.
- U.S. patent application Ser. No. 15/628,019, titled SURGICAL INSTRUMENT WITH VARIABLE DURATION TRIGGER ARRANGEMENT, by inventors Frederick E. Shelton, IV et al., filed Jun. 20, 2017.
- U.S. patent application Ser. No. 15/628,036, titled SYSTEMS AND METHODS FOR CONTROLLING DISPLACEMENT MEMBER MOTION OF A SURGICAL STAPLING AND CUTTING INSTRUMENT, by inventors Frederick E. Shelton, IV et al., filed Jun. 20, 2017.
- U.S. patent application Ser. No. 15/628,050, titled SYSTEMS AND METHODS FOR CONTROLLING MOTOR VELOCITY OF A SURGICAL STAPLING AND CUTTING INSTRUMENT ACCORDING TO ARTICULATION ANGLE OF END EFFECTOR, by inventors Frederick E. Shelton, IV et al., filed Jun. 20, 2017.
- U.S. patent application Ser. No. 15/628,075, titled SYSTEMS AND METHODS FOR CONTROLLING MOTOR VELOCITY OF A SURGICAL STAPLING AND CUTTING INSTRUMENT, by inventors Frederick E. Shelton, IV et al., filed Jun. 20, 2017.
- U.S. patent application Ser. No. 15/628,158, titled SYSTEMS AND METHODS FOR CONTROLLING VELOCITY OF A DISPLACEMENT MEMBER OF A SURGICAL STAPLING AND CUTTING INSTRUMENT, by inventors Frederick E. Shelton, IV et al., filed Jun. 20, 2017.
- U.S. Patent Application Ser. No. 15/628,162, titled SYSTEMS AND METHODS FOR CONTROLLING DISPLACEMENT MEMBER VELOCITY FOR A SURGICAL INSTRUMENT, by inventors Frederick E. Shelton, IV et al., filed Jun. 20, 2017.
- U.S. patent application Ser. No. 15/628,168, titled CONTROL OF MOTOR VELOCITY OF A SURGICAL STAPLING AND CUTTING INSTRUMENT BASED ON ANGLE OF ARTICULATION, by inventors Frederick E. Shelton, IV et al., filed Jun. 20, 2017.

U.S. patent application Ser. No. 15/628,175, titled TECHNIQUES FOR ADAPTIVE CONTROL OF MOTOR VELOCITY OF A SURGICAL STAPLING AND CUTTING INSTRUMENT, by inventors Frederick E. Shelton, IV et al., filed Jun. 20, 2017.

U.S. patent application Ser. No. 15/628,045, titled TECHNIQUES FOR CLOSED LOOP CONTROL OF MOTOR VELOCITY OF A SURGICAL STAPLING AND CUTTING INSTRUMENT, by inventors Raymond E. Parfett et al., filed Jun. 20, 2017.

U.S. patent application Ser. No. 15/628,053, titled CLOSED LOOP FEEDBACK CONTROL OF MOTOR VELOCITY OF A SURGICAL STAPLING AND CUTTING INSTRUMENT BASED ON MAGNITUDE OF VELOCITY ERROR MEASUREMENTS, by inventors Raymond E. Parfett et al., filed Jun. 20, 2017.

U.S. patent application Ser. No. 15/628,060, titled CLOSED LOOP FEEDBACK CONTROL OF MOTOR VELOCITY OF A SURGICAL STAPLING AND CUTTING INSTRUMENT BASED ON MEASURED TIME OVER A SPECIFIED DISPLACEMENT DISTANCE, by inventors Jason L. Harris et al., filed Jun. 20, 2017.

U.S. patent application Ser. No. 15/628,067, titled CLOSED LOOP FEEDBACK CONTROL OF MOTOR VELOCITY OF A SURGICAL STAPLING AND CUTTING INSTRUMENT BASED ON MEASURED DISPLACEMENT DISTANCE TRAVELED OVER A SPECIFIED TIME INTERVAL, by inventors Frederick E. Shelton, IV et al., filed Jun. 20, 2017.

U.S. patent application Ser. No. 15/628,072, titled CLOSED LOOP FEEDBACK CONTROL OF MOTOR VELOCITY OF A SURGICAL STAPLING AND CUTTING INSTRUMENT BASED ON MEASURED TIME OVER A SPECIFIED NUMBER OF SHAFT ROTATIONS, by inventors Frederick E. Shelton, IV et al., filed Jun. 20, 2017.

U.S. patent application Ser. No. 15/628,029, titled SYSTEMS AND METHODS FOR CONTROLLING DISPLAYING MOTOR VELOCITY FOR A SURGICAL INSTRUMENT, by inventors Jason L. Harris et al., filed Jun. 20, 2017.

U.S. patent application Ser. No. 15/628,077, titled SYSTEMS AND METHODS FOR CONTROLLING MOTOR SPEED ACCORDING TO USER INPUT FOR A SURGICAL INSTRUMENT, by inventors Jason L. Harris et al., filed Jun. 20, 2017.

U.S. patent application Ser. No. 15/628,115, titled CLOSED LOOP FEEDBACK CONTROL OF MOTOR VELOCITY OF A SURGICAL STAPLING AND CUTTING INSTRUMENT BASED ON SYSTEM CONDITIONS, by inventors Frederick E. Shelton, IV et al., filed Jun. 20, 2017.

U.S. patent application Ser. No. 29/608,238, titled GRAPHICAL USER INTERFACE FOR A DISPLAY OR PORTION THEREOF, by inventors Jason L. Harris et al., filed Jun. 20, 2017.

U.S. patent application Ser. No. 29/608,231, titled GRAPHICAL USER INTERFACE FOR A DISPLAY OR PORTION THEREOF, by inventors Jason L. Harris et al., filed Jun. 20, 2017.

U.S. patent application Ser. No. 29/608,246, titled GRAPHICAL USER INTERFACE FOR A DISPLAY OR PORTION THEREOF, by inventors Frederick E. Shelton, IV et al., filed Jun. 20, 2017.

Certain aspects are shown and described to provide an understanding of the structure, function, manufacture, and use of the disclosed devices and methods. Features shown or described in one example may be combined with features of other examples and modifications and variations are within the scope of this disclosure.

The terms "proximal" and "distal" are relative to a clinician manipulating the handle of the surgical instrument where "proximal" refers to the portion closer to the clinician and "distal" refers to the portion located further from the clinician. For expediency, spatial terms "vertical," "horizontal," "up," and "down" used with respect to the drawings are not intended to be limiting and/or absolute, because surgical instruments can used in many orientations and positions.

Example devices and methods are provided for performing laparascopic and minimally invasive surgical procedures. Such devices and methods, however, can be used in other surgical procedures and applications including open surgical procedures, for example. The surgical instruments can be inserted into a through a natural orifice or through an incision or puncture hole formed in tissue. The working portions or end effector portions of the instruments can be inserted directly into the body or through an access device that has a working channel through which the end effector and elongated shaft of the surgical instrument can be advanced.

FIGS. 1-4 depict a motor-driven surgical instrument 10 for cutting and fastening that may or may not be reused. In the illustrated examples, the surgical instrument 10 includes a housing 12 that comprises a handle assembly 14 that is configured to be grasped, manipulated, and actuated by the clinician. The housing 12 is configured for operable attachment to an interchangeable shaft assembly 200 that has an end effector 300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, entitled SURGICAL STAPLING INSTRUMENTS WITH ROTATABLE STAPLE DEPLOYMENT ARRANGEMENTS, which is herein incorporated by reference in its entirety.

FIG. 1 is a perspective view of a surgical instrument 10 that has an interchangeable shaft assembly 200 operably coupled thereto according to one aspect of this disclosure. The housing 12 includes an end effector 300 that comprises a surgical cutting and fastening device configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types. The housing 12 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 14 may comprise a pair of interconnectable handle housing segments 16, 18 interconnected by screws, snap features, adhesive, etc. The handle housing segments 16, 18 cooperate to form a pistol grip portion 19 that can be gripped and manipulated by the clinician. The handle assembly 14 operably supports a plurality of drive systems configured to generate and apply control motions to corresponding portions of the interchangeable shaft assembly that is operably attached thereto. A display may be provided below a cover 45.

Figure 2:
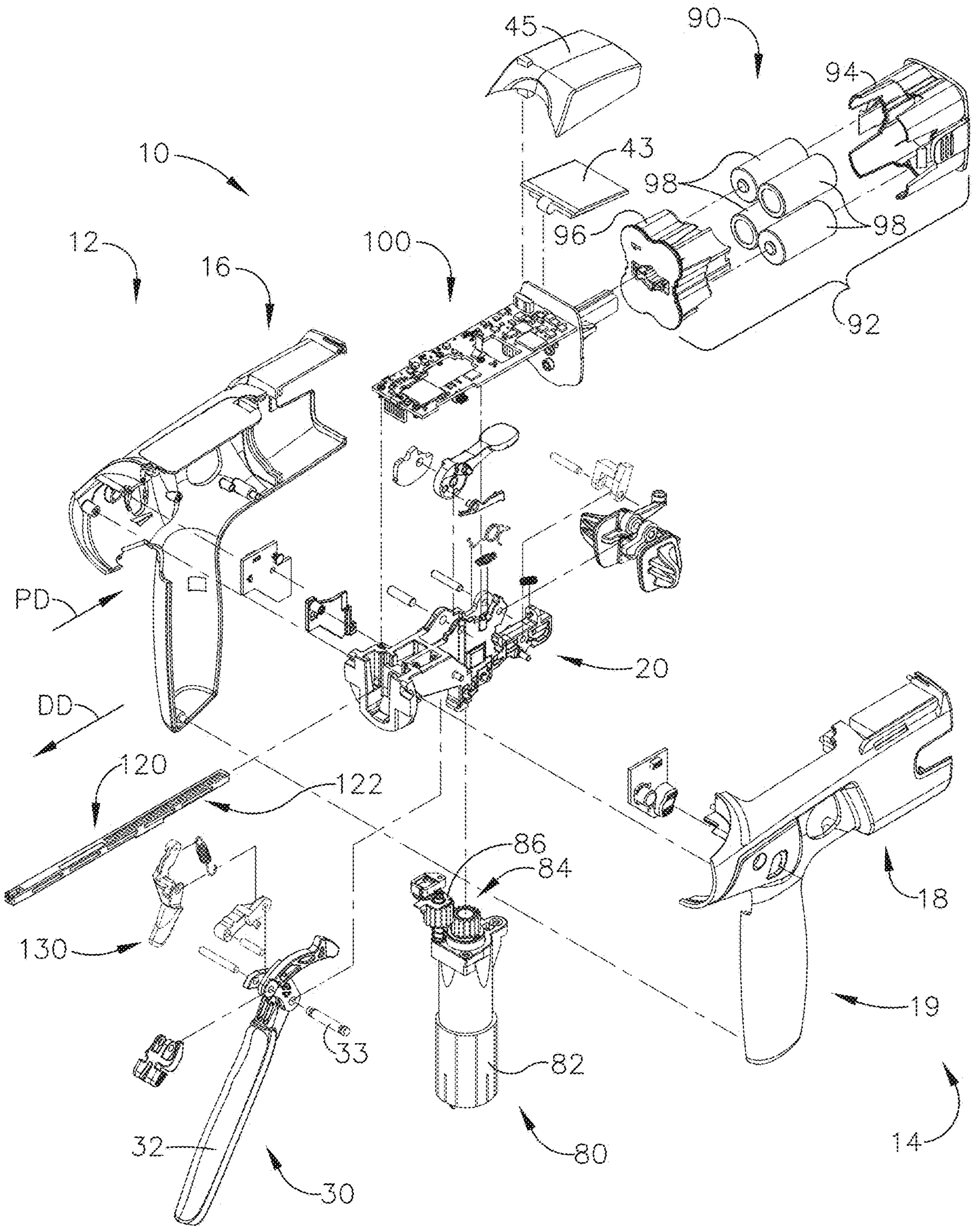
FIG. 2 is an exploded assembly view of a portion of the surgical instrument of FIG. 1 according to one aspect of this disclosure.

FIG. 2 is an exploded assembly view of a portion of the surgical instrument 10 of FIG. 1 according to one aspect of this disclosure. The handle assembly 14 may include a frame 20 that operably supports a plurality of drive systems. The frame 20 can operably support a "first" or closure drive system 30, which can apply closing and opening motions to the interchangeable shaft assembly 200. The closure drive system 30 may include an actuator such as a closure trigger 32 pivotally supported by the frame 20. The closure trigger 32 is pivotally coupled to the handle assembly 14 by a pivot pin 33 to enable the closure trigger 32 to be manipulated by a clinician. When the clinician grips the pistol grip portion 19 of the handle assembly 14, the closure trigger 32 can pivot from a starting or "unactuated" position to an "actuated" position and more particularly to a fully compressed or fully actuated position.

The handle assembly 14 and the frame 20 may operably support a firing drive system 80 configured to apply firing motions to corresponding portions of the interchangeable shaft assembly attached thereto. The firing drive system 80 may employ an electric motor 82 located in the pistol grip portion 19 of the handle assembly 14. The electric motor 82 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 82 may be powered by a power source 90 that may comprise a removable power pack 92. The removable power pack 92 may comprise a proximal housing portion 94 configured to attach to a distal housing portion 96. The proximal housing portion 94 and the distal housing portion 96 are configured to operably support a plurality of batteries 98 therein. Batteries 98 may each comprise, for example, a Lithium Ion (LI) or other suitable battery. The distal housing portion 96 is configured for removable operable attachment to a control circuit board 100, which is operably coupled to the electric motor 82. Several batteries 98 connected in series may power the surgical instrument 10. The power source 90 may be replaceable and/or rechargeable. A display 43, which is located below the cover 45, is electrically coupled to the control circuit board 100. The cover 45 may be removed to expose the display 43.

The electric motor 82 can include a rotatable shaft (not shown) that operably interfaces with a gear reducer assembly 84 mounted in meshing engagement with a with a set, or rack, of drive teeth 122 on a longitudinally movable drive member 120. The longitudinally movable drive member 120 has a rack of drive teeth 122 formed thereon for meshing engagement with a corresponding drive gear 86 of the gear reducer assembly 84.

In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the longitudinally movable drive member 120 will be axially driven in the distal direction "DD." When the electric motor 82 is driven in the opposite rotary direction, the longitudinally movable drive member 120 will be axially driven in a proximal direction "PD." The handle assembly 14 can include a switch that can be configured to reverse the polarity applied to the electric motor 82 by the power source 90. The handle assembly 14 may include a sensor configured to detect the position of the longitudinally movable drive member 120 and/or the direction in which the longitudinally movable drive member 120 is being moved.

Actuation of the electric motor 82 can be controlled by a firing trigger 130 that is pivotally supported on the handle assembly 14. The firing trigger 130 may be pivoted between an unactuated position and an actuated position.

Turning back to FIG. 1, the interchangeable shaft assembly 200 includes an end effector 300 comprising an elongated channel 302 configured to operably support a surgical staple cartridge 304 therein. The end effector 300 may include an anvil 306 that is pivotally supported relative to the elongated channel 302. The interchangeable shaft assembly 200 may include an articulation joint 270. Construction and operation of the end effector 300 and the articulation joint 270 are set forth in U.S. Patent Application Publication No. 2014/0263541, entitled ARTICULATABLE SURGICAL INSTRUMENT COMPRISING AN ARTICULATION LOCK, which is herein incorporated by reference in its entirety. The interchangeable shaft assembly 200 may include a proximal housing or nozzle 201 comprised of nozzle portions 202, 203. The interchangeable shaft assembly 200 may include a closure tube 260 extending along a shaft axis SA that can be utilized to close and/or open the anvil 306 of the end effector 300.

Turning back to FIG. 1, the closure tube 260 is translated distally (direction "DD") to close the anvil 306, for example, in response to the actuation of the closure trigger 32 in the manner described in the aforementioned reference U.S. Patent Application Publication No. 2014/0263541. The anvil 306 is opened by proximally translating the closure tube 260. In the anvil-open position, the closure tube 260 is moved to its proximal position.

Figure 3:
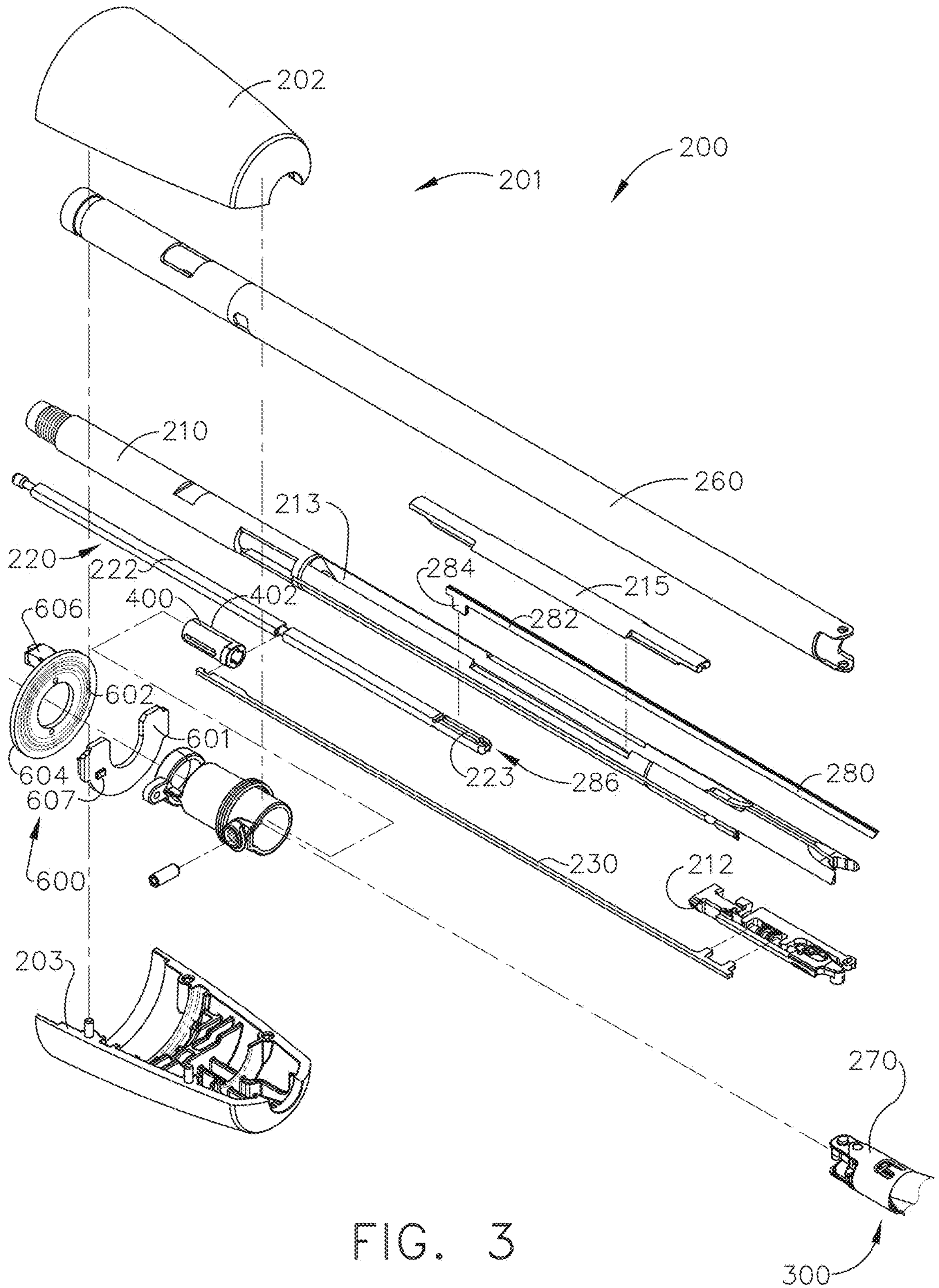
FIG. 3 is an exploded assembly view of portions of the interchangeable shaft assembly according to one aspect of this disclosure.

FIG. 3 is another exploded assembly view of portions of the interchangeable shaft assembly 200 according to one aspect of this disclosure. The interchangeable shaft assembly 200 may include a firing member 220 supported for axial travel within the spine 210. The firing member 220 includes an intermediate firing shaft 222 configured to attach to a distal cutting portion or knife bar 280. The firing member 220 may be referred to as a "second shaft" or a "second shaft assembly". The intermediate firing shaft 222 may include a longitudinal slot 223 in a distal end configured to receive a tab 284 on the proximal end 282 of the knife bar 280. The longitudinal slot 223 and the proximal end 282 may be configured to permit relative movement there between and can comprise a slip joint 286. The slip joint 286 can permit the intermediate firing shaft 222 of the firing member 220 to articulate the end effector 300 about the articulation joint 270 without moving, or at least substantially moving, the knife bar 280. Once the end effector 300 has been suitably oriented, the intermediate firing shaft 222 can be advanced distally until a proximal sidewall of the longitudinal slot 223 contacts the tab 284 to advance the knife bar 280 and fire the staple cartridge positioned within the channel 302. The spine 210 has an elongated opening or window 213 therein to facilitate assembly and insertion of the intermediate firing shaft 222 into the spine 210. Once the intermediate firing shaft 222 has been inserted therein, a top frame segment 215 may be engaged with the shaft frame 212 to enclose the intermediate firing shaft 222 and knife bar 280 therein. Operation of the firing member 220 may be found in U.S. Patent Application Publication No. 2014/0263541. A spine 210 can be configured to slidably support a firing member 220 and the closure tube 260 that extends around the spine 210. The spine 210 may slidably support an articulation driver 230.

The interchangeable shaft assembly 200 can include a clutch assembly 400 configured to selectively and releasably couple the articulation driver 230 to the firing member 220. The clutch assembly 400 includes a lock collar, or lock sleeve 402, positioned around the firing member 220 wherein the lock sleeve 402 can be rotated between an engaged position in which the lock sleeve 402 couples the articulation driver 230 to the firing member 220 and a disengaged position in which the articulation driver 230 is not operably coupled to the firing member 220. When the lock sleeve 402 is in the engaged position, distal movement of the firing member 220 can move the articulation driver 230 distally and, correspondingly, proximal movement of the firing member 220 can move the articulation driver 230 proximally. When the lock sleeve 402 is in the disengaged position, movement of the firing member 220 is not transmitted to the articulation driver 230 and, as a result, the firing member 220 can move independently of the articulation driver 230. The nozzle 201 may be employed to operably engage and disengage the articulation drive system with the firing drive system in the various manners described in U.S. Patent Application Publication No. 2014/0263541.

The interchangeable shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 and a distal connector flange 601 positioned within a slot defined in the nozzle portions 202, 203. The proximal connector flange 604 can comprise a first face and the distal connector flange 601 can comprise a second face positioned adjacent to and movable relative to the first face. The distal connector flange 601 can rotate relative to the proximal connector flange 604 about the shaft axis SA-SA (FIG. 1). The proximal connector flange 604 can comprise a plurality of concentric, or at least substantially concentric, conductors 602 defined in the first face thereof. A connector 607 can be mounted on the proximal side of the distal connector flange 601 and may have a plurality of contacts wherein each contact corresponds to and is in electrical contact with one of the conductors 602. Such an arrangement permits relative rotation between the proximal connector flange 604 and the distal connector flange 601 while maintaining electrical contact there between. The proximal connector flange 604 can include an electrical connector 606 that can place the conductors 602 in signal communication with a shaft circuit board, for example. In at least one instance, a wiring harness comprising a plurality of conductors can extend between the electrical connector 606 and the shaft circuit board. The electrical connector 606 may extend proximally through a connector opening defined in the chassis mounting flange. U.S. Patent Application Publication No. 2014/0263551, entitled STAPLE CARTRIDGE TISSUE THICKNESS SENSOR SYSTEM, is incorporated herein by reference in its entirety. U.S. Patent Application Publication No. 2014/0263552, entitled STAPLE CARTRIDGE TISSUE THICKNESS SENSOR SYSTEM, is incorporated by reference in its entirety. Further details regarding slip ring assembly 600 may be found in U.S. Patent Application Publication No. 2014/0263541.

The interchangeable shaft assembly 200 can include a proximal portion fixably mounted to the handle assembly 14 and a distal portion that is rotatable about a longitudinal axis. The rotatable distal shaft portion can be rotated relative to the proximal portion about the slip ring assembly 600. The distal connector flange 601 of the slip ring assembly 600 can be positioned within the rotatable distal shaft portion.

Figure 4:
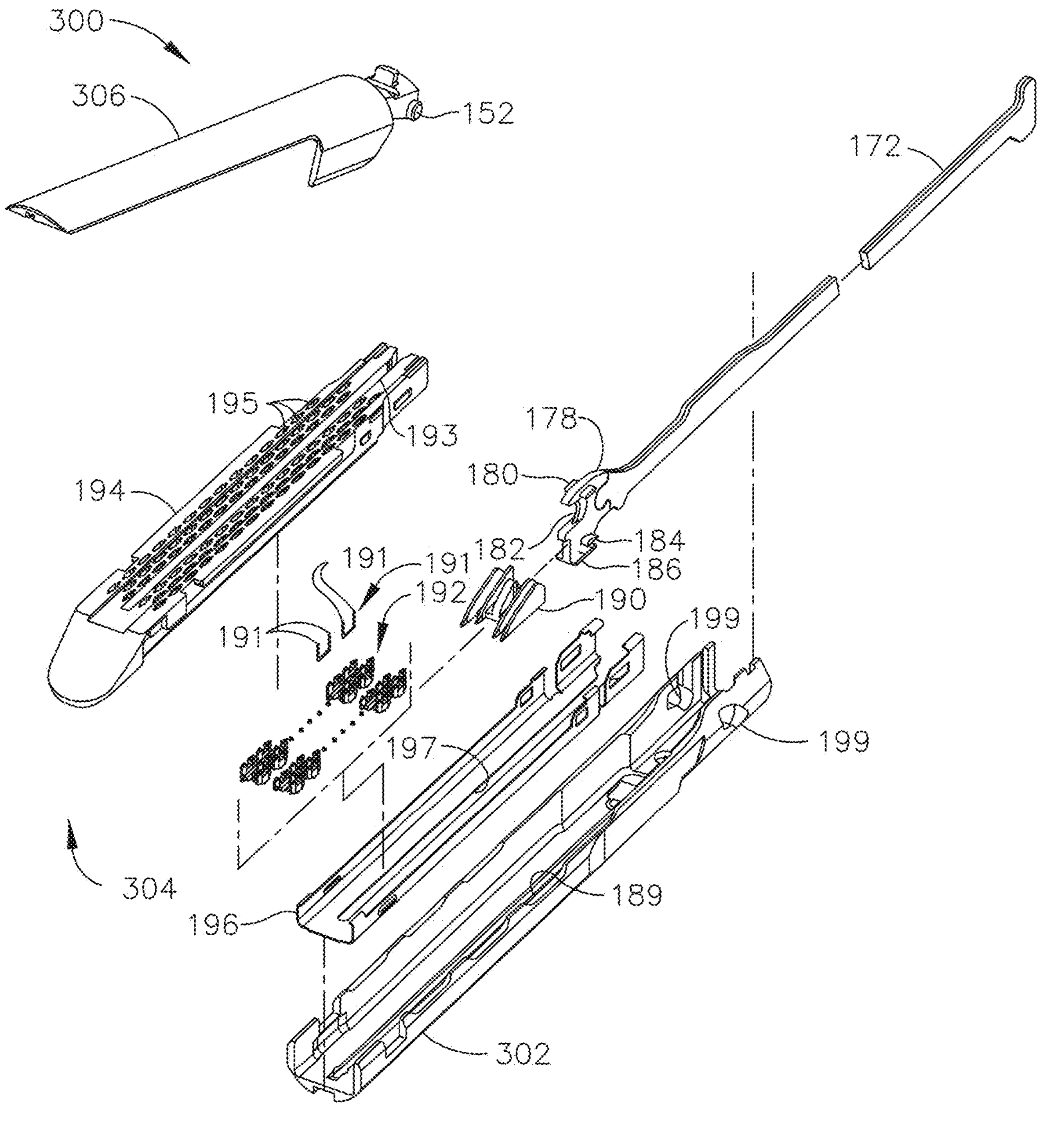
FIG. 4 is an exploded view of an end effector of the surgical instrument of FIG. 1 according to one aspect of this disclosure.

FIG. 4 is an exploded view of one aspect of an end effector 300 of the surgical instrument 10 of FIG. 1 according to one aspect of this disclosure. The end effector 300 may include the anvil 306 and the surgical staple cartridge 304. The anvil 306 may be coupled to an elongated channel 302. Apertures 199 can be defined in the elongated channel 302 to receive pins 152 extending from the anvil 306 to allow the anvil 306 to pivot from an open position to a closed position relative to the elongated channel 302 and surgical staple cartridge 304. A firing bar 172 is configured to longitudinally translate into the end effector 300. The firing bar 172 may be constructed from one solid section, or may include a laminate material comprising a stack of steel plates. The firing bar 172 comprises an I-beam 178 and a cutting edge 182 at a distal end thereof. A distally projecting end of the firing bar 172 can be attached to the I-beam 178 to assist in spacing the anvil 306 from a surgical staple cartridge 304 positioned in the elongated channel 302 when the anvil 306 is in a closed position. The I-beam 178 may include a sharpened cutting edge 182 to sever tissue as the I-beam 178 is advanced distally by the firing bar 172. In operation, the I-beam 178 may, or fire, the surgical staple cartridge 304. The surgical staple cartridge 304 can include a molded cartridge body 194 that holds a plurality of staples 191 resting upon staple drivers 192 within respective upwardly open staple cavities 195. A wedge sled 190 is driven distally by the I-beam 178, sliding upon a cartridge tray 196 of the surgical staple cartridge 304. The wedge sled 190 upwardly cams the staple drivers 192 to force out the staples 191 into deforming contact with the anvil 306 while the cutting edge 182 of the I-beam 178 severs clamped tissue.

The I-beam 178 can include upper pins 180 that engage the anvil 306 during firing. The I-beam 178 may include middle pins 184 and a bottom foot 186 to engage portions of the cartridge body 194, cartridge tray 196, and elongated channel 302. When a surgical staple cartridge 304 is positioned within the elongated channel 302, a slot 193 defined in the cartridge body 194 can be aligned with a longitudinal slot 197 defined in the cartridge tray 196 and a slot 189 defined in the elongated channel 302. In use, the I-beam 178 can slide through the aligned longitudinal slots 193, 197, and 189 wherein, as indicated in FIG. 4, the bottom foot 186 of the I-beam 178 can engage a groove running along the bottom surface of elongated channel 302 along the length of slot 189, the middle pins 184 can engage the top surfaces of cartridge tray 196 along the length of longitudinal slot 197, and the upper pins 180 can engage the anvil 306. The I-beam 178 can space, or limit the relative movement between, the anvil 306 and the surgical staple cartridge 304 as the firing bar 172 is advanced distally to fire the staples from the surgical staple cartridge 304 and/or incise the tissue captured between the anvil 306 and the surgical staple cartridge 304. The firing bar 172 and the I-beam 178 can be retracted proximally allowing the anvil 306 to be opened to release the two stapled and severed tissue portions.

Figure 5A:
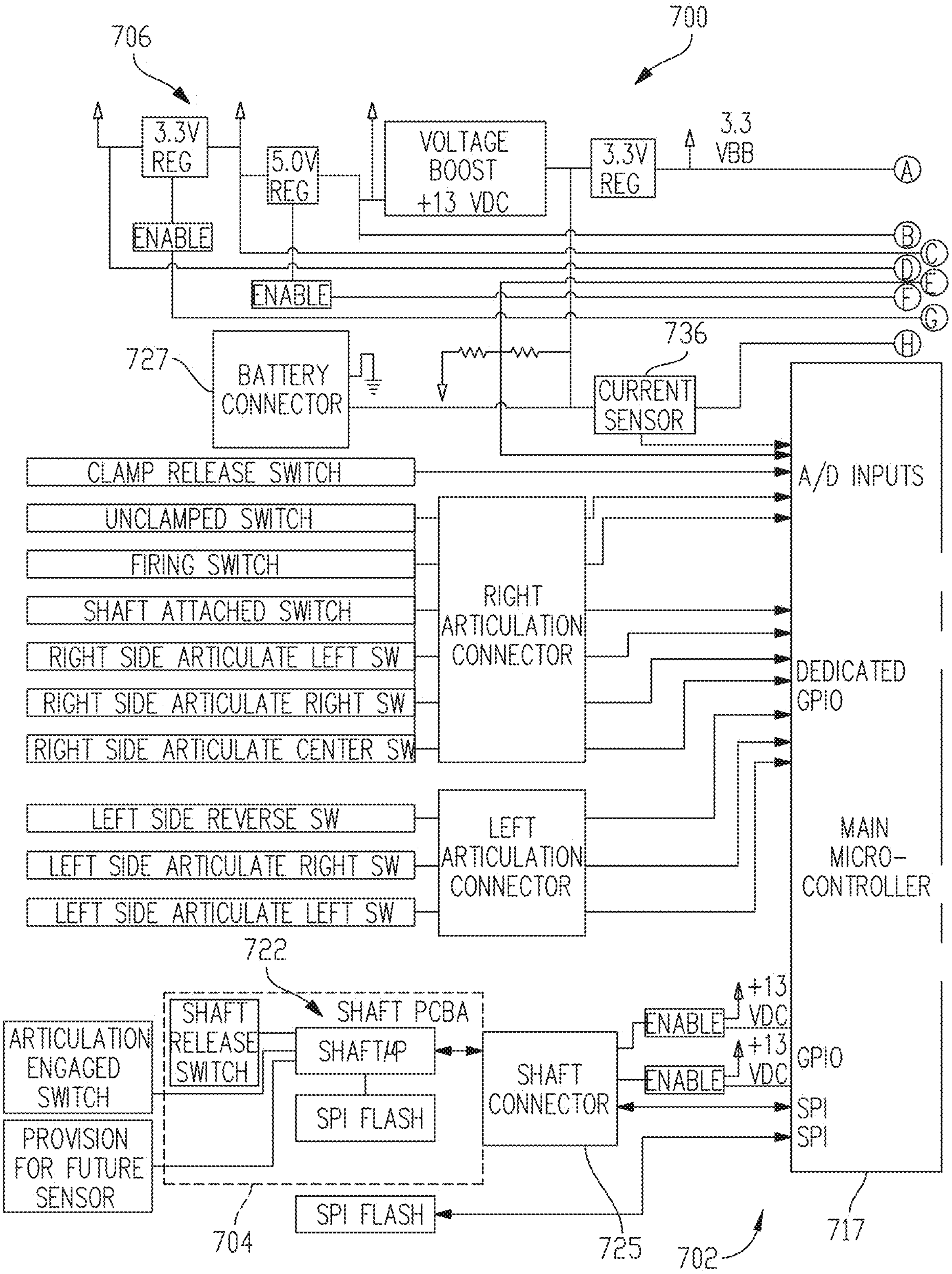
FIGS. 5A-5B is a block diagram of a control circuit of the surgical instrument of FIG. 1 spanning two drawing sheets according to one aspect of this disclosure.
Figure 5B:
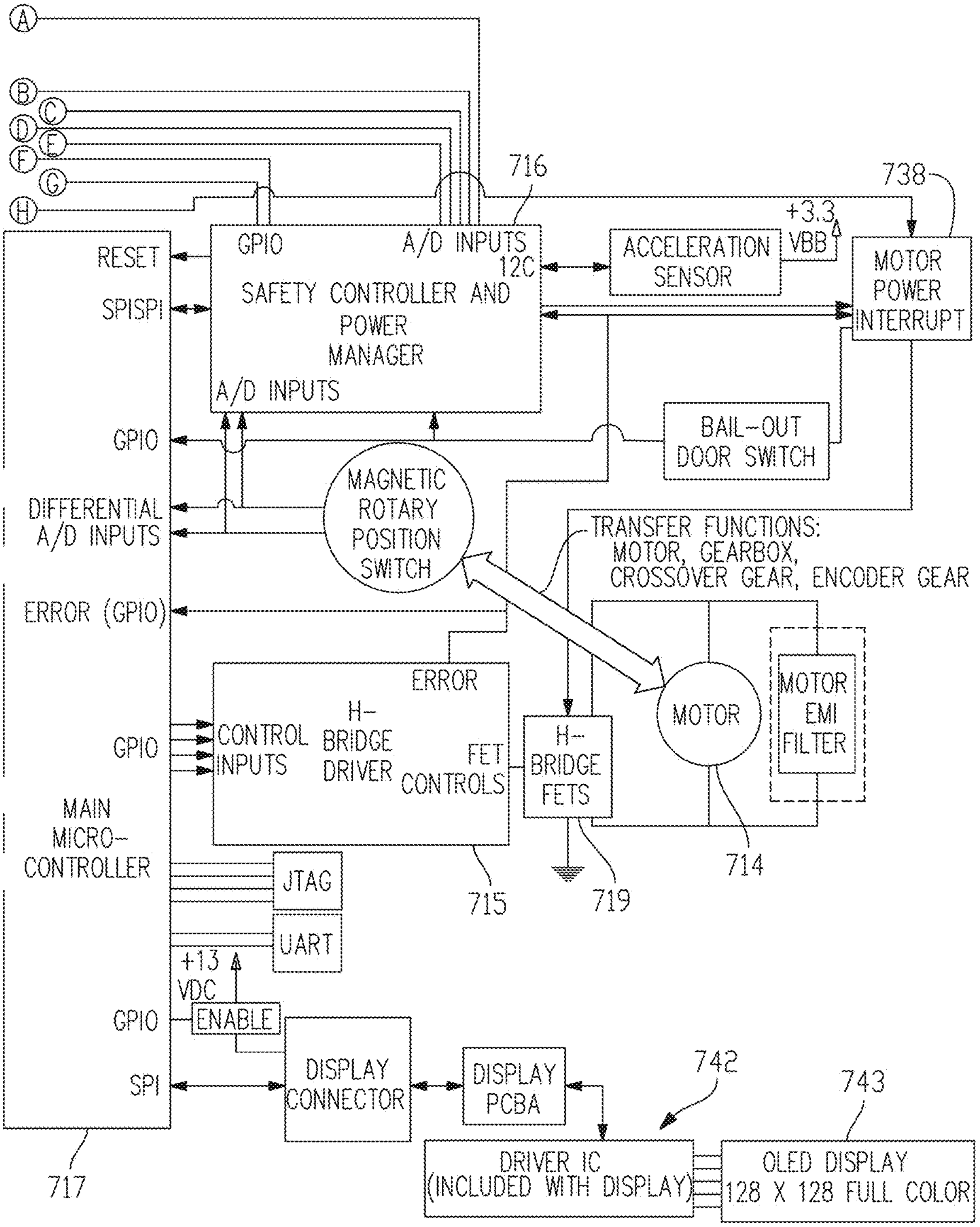

FIGS. 5A-5B is a block diagram of a control circuit 700 of the surgical instrument 10 of FIG. 1 spanning two drawing sheets according to one aspect of this disclosure. Referring primarily to FIGS. 5A-5B, a handle assembly 702 may include a motor 714 which can be controlled by a motor driver 715 and can be employed by the firing system of the surgical instrument 10. In various forms, the motor 714 may be a DC brushed driving motor having a maximum rotational speed of approximately 25,000 RPM. In other arrangements, the motor 714 may include a brushless motor, a cordless motor, a synchronous motor, a stepper motor, or any other suitable electric motor. The motor driver 715 may comprise an H-Bridge driver comprising field-effect transistors (FETs) 719, for example. The motor 714 can be powered by the power assembly 706 releasably mounted to the handle assembly 200 for supplying control power to the surgical instrument 10. The power assembly 706 may comprise a battery which may include a number of battery cells connected in series that can be used as the power source to power the surgical instrument 10. In certain circumstances, the battery cells of the power assembly 706 may be replaceable and/or rechargeable. In at least one example, the battery cells can be Lithium-Ion batteries which can be separably couplable to the power assembly 706.

The shaft assembly 704 may include a shaft assembly controller 722 which can communicate with a safety controller and power management controller 716 through an interface while the shaft assembly 704 and the power assembly 706 are coupled to the handle assembly 702. For example, the interface may comprise a first interface portion 725 which may include one or more electric connectors for coupling engagement with corresponding shaft assembly electric connectors and a second interface portion 727 which may include one or more electric connectors for coupling engagement with corresponding power assembly electric connectors to permit electrical communication between the shaft assembly controller 722 and the power management controller 716 while the shaft assembly 704 and the power assembly 706 are coupled to the handle assembly 702. One or more communication signals can be transmitted through the interface to communicate one or more of the power requirements of the attached interchangeable shaft assembly 704 to the power management controller 716. In response, the power management controller may modulate the power output of the battery of the power assembly 706, as described below in greater detail, in accordance with the power requirements of the attached shaft assembly 704. The connectors may comprise switches which can be activated after mechanical coupling engagement of the handle assembly 702 to the shaft assembly 704 and/or to the power assembly 706 to allow electrical communication between the shaft assembly controller 722 and the power management controller 716.

The interface can facilitate transmission of the one or more communication signals between the power management controller 716 and the shaft assembly controller 722 by routing such communication signals through a main controller 717 residing in the handle assembly 702, for example. In other circumstances, the interface can facilitate a direct line of communication between the power management controller 716 and the shaft assembly controller 722 through the handle assembly 702 while the shaft assembly 704 and the power assembly 706 are coupled to the handle assembly 702.

The main controller 717 may be any single core or multicore processor such as those known under the trade name ARM Cortex by Texas Instruments. In one aspect, the main controller 717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 706 may include a power management circuit which may comprise the power management controller 716, a power modulator 738, and a current sense circuit 736. The power management circuit can be configured to modulate power output of the battery based on the power requirements of the shaft assembly 704 while the shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery so that the power management controller 716 may adjust the power output of the power assembly 706 to maintain a desired output. The power management controller 716 and/or the shaft assembly controller 722 each may comprise one or more processors and/or memory units which may store a number of software modules.

The surgical instrument 10 (FIGS. 1-4) may comprise an output device 742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 742 may comprise a display 743 which may be included in the handle assembly 702. The shaft assembly controller 722 and/or the power management controller 716 can provide feedback to a user of the surgical instrument 10 through the output device 742. The interface can be configured to connect the shaft assembly controller 722 and/or the power management controller 716 to the output device 742. The output device 742 can instead be integrated with the power assembly 706. In such circumstances, communication between the output device 742 and the shaft assembly controller 722 may be accomplished through the interface while the shaft assembly 704 is coupled to the handle assembly 702.

The control circuit 700 comprises circuit segments configured to control operations of the powered surgical instrument 10. A safety controller segment (Segment 1) comprises a safety controller and the main controller 717 segment (Segment 2). The safety controller and/or the main controller 717 are configured to interact with one or more additional circuit segments such as an acceleration segment, a display segment, a shaft segment, an encoder segment, a motor segment, and a power segment. Each of the circuit segments may be coupled to the safety controller and/or the main controller 717. The main controller 717 is also coupled to a flash memory. The main controller 717 also comprises a serial communication interface. The main controller 717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The main controller 717 is a multipurpose, programmable device that accepts digital data as input, processes it according to instructions stored in its memory, and provides results as output. It is an example of sequential digital logic, as it has internal memory. The control circuit 700 can be configured to implement one or more of the processes described herein.

The acceleration segment (Segment 3) comprises an accelerometer. The accelerometer is configured to detect movement or acceleration of the powered surgical instrument 10. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 717.

The display segment (Segment 4) comprises a display connector coupled to the main controller 717. The display connector couples the main controller 717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 200 (FIGS. 1 and 3) coupled to the surgical instrument 10 (FIGS. 1-4) and/or one or more controls for an end effector 300 coupled to the interchangeable shaft assembly 200. The shaft segment comprises a shaft connector configured to couple the main controller 717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 200 and/or the shaft PCBA. The shaft PCBA may be coupled to the interchangeable shaft assembly 200 and/or integral with the surgical instrument 10. In some examples, the shaft segment comprises a second shaft EEPROM. The second shaft EEPROM comprises a plurality of algorithms, routines, parameters, and/or other data corresponding to one or more shaft assemblies 200 and/or end effectors 300 that may be interfaced with the powered surgical instrument 10.

The position encoder segment (Segment 6) comprises one or more magnetic angle rotary position encoders. The one or more magnetic angle rotary position encoders are configured to identify the rotational position of the motor 714, an interchangeable shaft assembly 200 (FIGS. 1 and 3), and/or an end effector 300 of the surgical instrument 10 (FIGS. 1-4). In some examples, the magnetic angle rotary position encoders may be coupled to the safety controller and/or the main controller 717.

The motor circuit segment (Segment 7) comprises a motor 714 configured to control movements of the powered surgical instrument 10 (FIGS. 1-4). The motor 714 is coupled to the main microcontroller processor 717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 717 and/or the safety controller. In some examples, the motor 714 is coupled to a motor electromagnetic interference (EMI) filter.

The motor controller controls a first motor flag and a second motor flag to indicate the status and position of the motor 714 to the main controller 717. The main controller 717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 717. The switches may be configured to control operations of the surgical instrument 10 (FIGS. 1-4), of the segmented circuit, and/or indicate a status of the surgical instrument 10. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 200 (FIGS. 1 and 3) and/or the end effector 300 (FIGS. 1 and 4). A left side reverse switch and a right side reverse switch are coupled to the main controller 717. The left side switches comprising the left side articulation left switch, the left side articulation right switch, the left side articulation center switch, and the left side reverse switch are coupled to the main controller 717 by a left flex connector. The right side switches comprising the right side articulation left switch, the right side articulation right switch, the right side articulation center switch, and the right side reverse switch are coupled to the main controller 717 by a right flex connector. A firing switch, a clamp release switch, and a shaft engaged switch are coupled to the main controller 717.

Any suitable mechanical, electromechanical, or solid state switches may be employed to implement the plurality of switches, in any combination. For example, the switches may be limit switches operated by the motion of components associated with the surgical instrument 10 (FIGS. 1-4) or the presence of an object. Such switches may be employed to control various functions associated with the surgical instrument 10. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Figure 6:
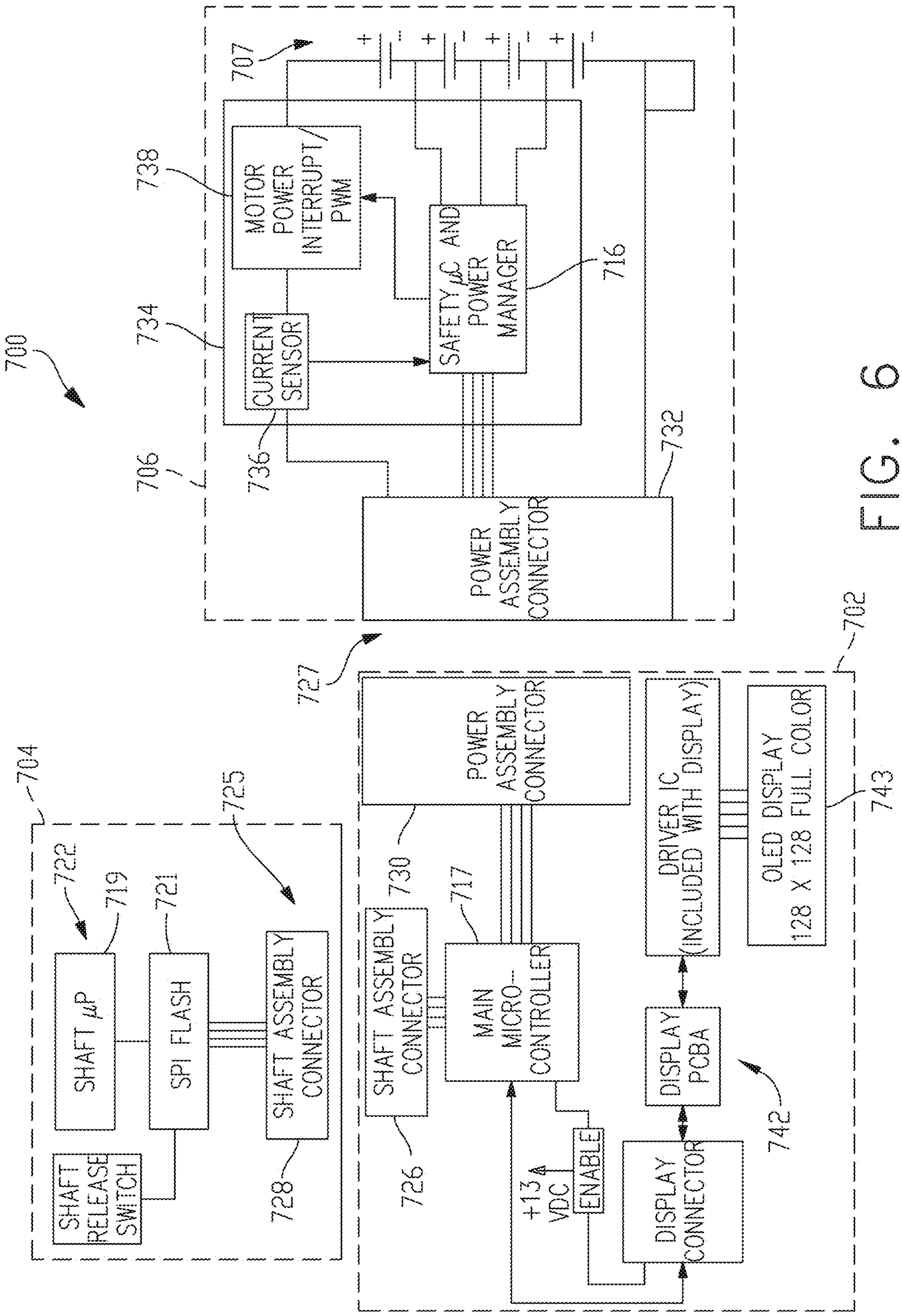
FIG. 6 is a block diagram of the control circuit of the surgical instrument of FIG. 1 illustrating interfaces between the handle assembly, the power assembly, and the handle assembly and the interchangeable shaft assembly according to one aspect of this disclosure.

FIG. 6 is another block diagram of the control circuit 700 of the surgical instrument of FIG. 1 illustrating interfaces between the handle assembly 702 and the power assembly 706 and between the handle assembly 702 and the interchangeable shaft assembly 704 according to one aspect of this disclosure. The handle assembly 702 may comprise a main controller 717, a shaft assembly connector 726 and a power assembly connector 730. The power assembly 706 may include a power assembly connector 732, a power management circuit 734 that may comprise the power management controller 716, a power modulator 738, and a current sense circuit 736. The shaft assembly connectors 730, 732 form an interface 727. The power management circuit 734 can be configured to modulate power output of the battery 707 based on the power requirements of the interchangeable shaft assembly 704 while the interchangeable shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery 707 so that the power management controller 716 may adjust the power output of the power assembly 706 to maintain a desired output. The shaft assembly 704 comprises a shaft processor 719 coupled to a non-volatile memory 721 and shaft assembly connector 728 to electrically couple the shaft assembly 704 to the handle assembly 702. The shaft assembly connectors 726, 728 form interface 725. The main controller 717, the shaft processor 719, and/or the power management controller 716 can be configured to implement one or more of the processes described herein.

The surgical instrument 10 (FIGS. 1-4) may comprise an output device 742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 742 may comprise a display 743 that may be included in the handle assembly 702. The shaft assembly controller 722 and/or the power management controller 716 can provide feedback to a user of the surgical instrument 10 through the output device 742. The interface 727 can be configured to connect the shaft assembly controller 722 and/or the power management controller 716 to the output device 742. The output device 742 can be integrated with the power assembly 706. Communication between the output device 742 and the shaft assembly controller 722 may be accomplished through the interface 725 while the interchangeable shaft assembly 704 is coupled to the handle assembly 702. Having described a control circuit 700 (FIGS. 5A-5B and 6) for controlling the operation of the surgical instrument 10 (FIGS. 1-4), the disclosure now turns to various configurations of the surgical instrument 10 (FIGS. 1-4) and control circuit 700.

Figure 7:
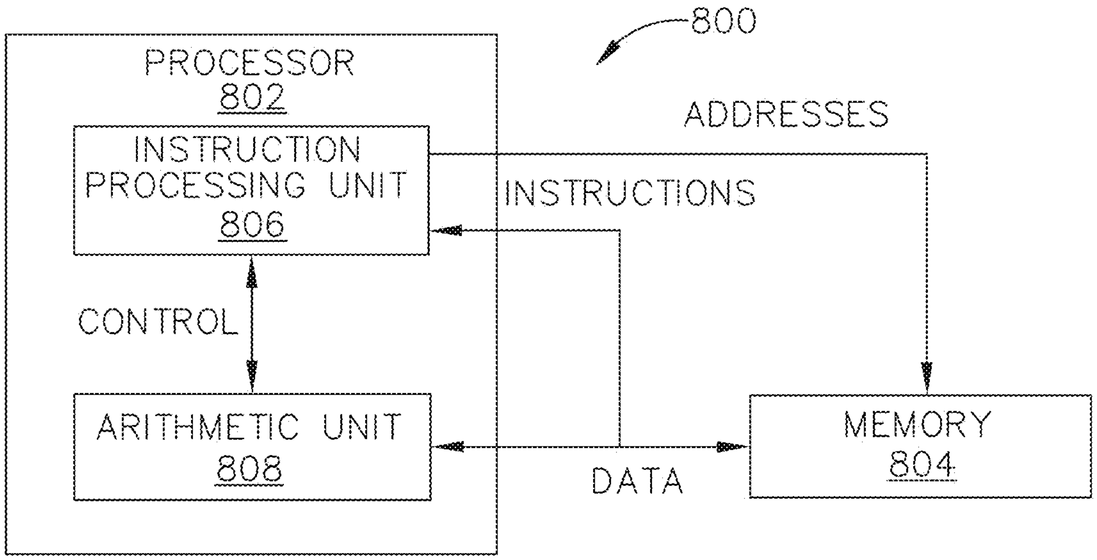
FIG. 7 illustrates a control circuit configured to control aspects of the surgical instrument of FIG. 1 according to one aspect of this disclosure.

FIG. 7 illustrates a control circuit 800 configured to control aspects of the surgical instrument 10 (FIGS. 1-4) according to one aspect of this disclosure. The control circuit 800 can be configured to implement various processes described herein. The control circuit 800 may comprise a controller comprising one or more processors 802 (e.g., microprocessor, microcontroller) coupled to at least one memory circuit 804. The memory circuit 804 stores machine executable instructions that when executed by the processor 802, cause the processor 802 to execute machine instructions to implement various processes described herein. The processor 802 may be any one of a number of single or multi-core processors known in the art. The memory circuit 804 may comprise volatile and non-volatile storage media. The processor 802 may include an instruction processing unit 806 and an arithmetic unit 808. The instruction processing unit may be configured to receive instructions from the memory circuit 804.

Figure 8:
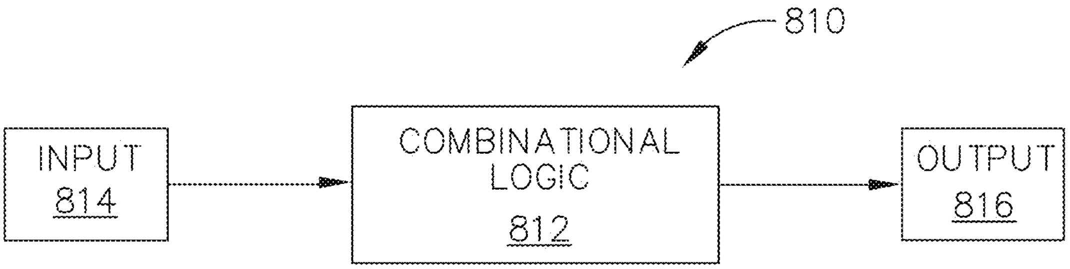
FIG. 8 illustrates a combinational logic circuit configured to control aspects of the surgical instrument of FIG. 1 according to one aspect of this disclosure.

FIG. 8 illustrates a combinational logic circuit 810 configured to control aspects of the surgical instrument 10 (FIGS. 1-4) according to one aspect of this disclosure. The combinational logic circuit 810 can be configured to implement various processes described herein. The circuit 810 may comprise a finite state machine comprising a combinational logic circuit 812 configured to receive data associated with the surgical instrument 10 at an input 814, process the data by the combinational logic 812, and provide an output 816.

Figure 9:
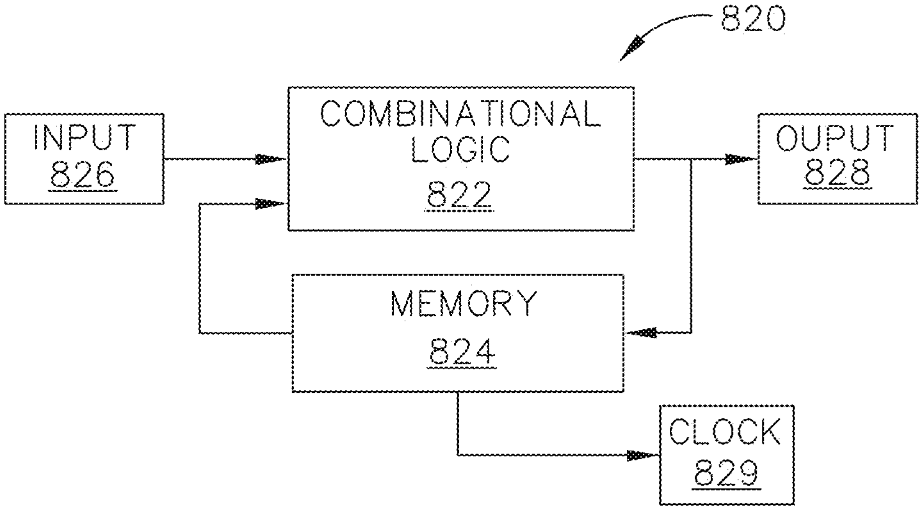
FIG. 9 illustrates a sequential logic circuit configured to control aspects of the surgical instrument of FIG. 1 according to one aspect of this disclosure.

FIG. 9 illustrates a sequential logic circuit 820 configured to control aspects of the surgical instrument 10 (FIGS. 1-4) according to one aspect of this disclosure. The sequential logic circuit 820 or the combinational logic circuit 822 can be configured to implement various processes described herein. The circuit 820 may comprise a finite state machine. The sequential logic circuit 820 may comprise a combinational logic circuit 822, at least one memory circuit 824, and a clock 829, for example. The at least one memory circuit 820 can store a current state of the finite state machine. In certain instances, the sequential logic circuit 820 may be synchronous or asynchronous. The combinational logic circuit 822 is configured to receive data associated with the surgical instrument 10 an input 826, process the data by the combinational logic circuit 822, and provide an output 828. In other aspects, the circuit may comprise a combination of the processor 802 and the finite state machine to implement various processes herein. In other aspects, the finite state machine may comprise a combination of the combinational logic circuit 810 and the sequential logic circuit 820.

Aspects may be implemented as an article of manufacture. The article of manufacture may include a computer readable storage medium arranged to store logic, instructions, and/or data for performing various operations of one or more aspects. For example, the article of manufacture may comprise a magnetic disk, optical disk, flash memory, or firmware containing computer program instructions suitable for execution by a general purpose processor or application specific processor.

Figure 10:
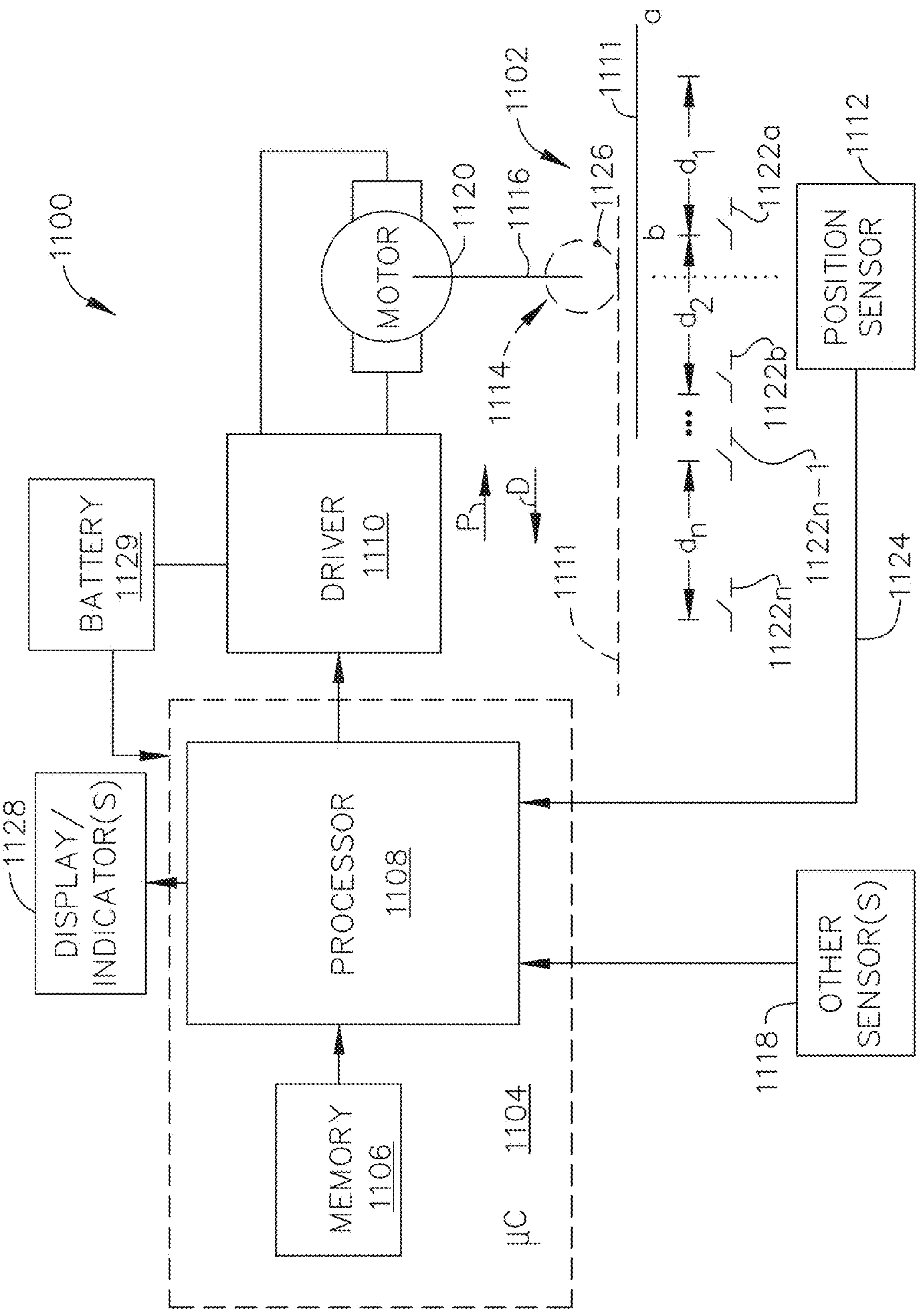
FIG. 10 is a diagram of an absolute positioning system of the surgical instrument of FIG. 1 where the absolute positioning system comprises a controlled motor drive circuit arrangement comprising a sensor arrangement according to one aspect of this disclosure.

FIG. 10 is a diagram of an absolute positioning system 1100 of the surgical instrument 10 (FIGS. 1-4) where the absolute positioning system 1100 comprises a controlled motor drive circuit arrangement comprising a sensor arrangement 1102 according to one aspect of this disclosure. The sensor arrangement 1102 for an absolute positioning system 1100 provides a unique position signal corresponding to the location of a displacement member 1111. Turning briefly to FIGS. 2-4, in one aspect the displacement member 1111 represents the longitudinally movable drive member 120 (FIG. 2) comprising a rack of drive teeth 122 for meshing engagement with a corresponding drive gear 86 of the gear reducer assembly 84. In other aspects, the displacement member 1111 represents the firing member 220 (FIG. 3), which could be adapted and configured to include a rack of drive teeth. In yet another aspect, the displacement member 1111 represents the firing bar 172 (FIG. 4) or the I-beam 178 (FIG. 4), each of which can be adapted and configured to include a rack of drive teeth. Accordingly, as used herein, the term displacement member is used generically to refer to any movable member of the surgical instrument 10 such as the drive member 120, the firing member 220, the firing bar 172, the I-beam 178, or any element that can be displaced. In one aspect, the longitudinally movable drive member 120 is coupled to the firing member 220, the firing bar 172, and the I-beam 178. Accordingly, the absolute positioning system 1100 can, in effect, track the linear displacement of the I-beam 178 by tracking the linear displacement of the longitudinally movable drive member 120. In various other aspects, the displacement member 1111 may be coupled to any sensor suitable for measuring linear displacement. Thus, the longitudinally movable drive member 120, the firing member 220, the firing bar 172, or the I-beam 178, or combinations, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable linearly arranged Hall effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

An electric motor 1120 can include a rotatable shaft 1116 that operably interfaces with a gear assembly 1114 that is mounted in meshing engagement with a set, or rack, of drive teeth on the displacement member 1111. A sensor element 1126 may be operably coupled to a gear assembly 1114 such that a single revolution of the sensor element 1126 corresponds to some linear longitudinal translation of the displacement member 1111. An arrangement of gearing and sensors 1118 can be connected to the linear actuator via a rack and pinion arrangement or a rotary actuator via a spur gear or other connection. A power source 1129 supplies power to the absolute positioning system 1100 and an output indicator 1128 may display the output of the absolute positioning system 1100. In FIG. 2, the displacement member 1111 represents the longitudinally movable drive member 120 comprising a rack of drive teeth 122 formed thereon for meshing engagement with a corresponding drive gear 86 of the gear reducer assembly 84. The displacement member 1111 represents the longitudinally movable firing member 220, firing bar 172, I-beam 178, or combinations thereof.

A single revolution of the sensor element 1126 associated with the position sensor 1112 is equivalent to a longitudinal linear displacement d1 of the of the displacement member 1111, where d1 is the longitudinal linear distance that the displacement member 1111 moves from point "a" to point "b" after a single revolution of the sensor element 1126 coupled to the displacement member 1111. The sensor arrangement 1102 may be connected via a gear reduction that results in the position sensor 1112 completing one or more revolutions for the full stroke of the displacement member 1111. The position sensor 1112 may complete multiple revolutions for the full stroke of the displacement member 1111.

A series of switches 1122*a*-1122*n*, where n is an integer greater than one, may be employed alone or in combination with gear reduction to provide a unique position signal for more than one revolution of the position sensor 1112. The state of the switches 1122*a*-1122*n* are fed back to a controller 1104 that applies logic to determine a unique position signal corresponding to the longitudinal linear displacement d1+d2+ . . . dn of the displacement member 1111. The output 1124 of the position sensor 1112 is provided to the controller 1104. The position sensor 1112 of the sensor arrangement 1102 may comprise a magnetic sensor, an analog rotary sensor like a potentiometer, an array of analog Hall-effect elements, which output a unique combination of position signals or values.

The absolute positioning system 1100 provides an absolute position of the displacement member 1111 upon power up of the instrument without retracting or advancing the displacement member 1111 to a reset (zero or home) position as may be required with conventional rotary encoders that merely count the number of steps forwards or backwards that the motor 1120 has taken to infer the position of a device actuator, drive bar, knife, and the like.

The controller 1104 may be programmed to perform various functions such as precise control over the speed and position of the knife and articulation systems. In one aspect, the controller 1104 includes a processor 1108 and a memory 1106. The electric motor 1120 may be a brushed DC motor with a gearbox and mechanical links to an articulation or knife system. In one aspect, a motor driver 1110 may be an A3941 available from Allegro Microsystems, Inc. Other motor drivers may be readily substituted for use in the absolute positioning system 1100. A more detailed description of the absolute positioning system 1100 is described in U.S. patent application Ser. No. 15/130,590, entitled SYS- TEMS AND METHODS FOR CONTROLLING A SURGICAL STAPLING AND CUTTING INSTRUMENT, filed on Apr. 15, 2016, the entire disclosure of which is herein incorporated by reference.

The controller 1104 may be programmed to provide precise control over the speed and position of the displacement member 1111 and articulation systems. The controller 1104 may be configured to compute a response in the software of the controller 1104. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The absolute positioning system 1100 may comprise and/or be programmed to implement a feedback controller, such as a PID, state feedback, and adaptive controller. A power source 1129 converts the signal from the feedback controller into a physical input to the system, in this case voltage. Other examples include pulse width modulation (PWM) of the voltage, current, and force. Other sensor(s) 1118 may be provided to measure physical parameters of the physical system in addition to position measured by the position sensor 1112. In a digital signal processing system, absolute positioning system 1100 is coupled to a digital data acquisition system where the output of the absolute positioning system 1100 will have finite resolution and sampling frequency. The absolute positioning system 1100 may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input. The controller 1104 may be a control circuit 700 (FIGS. 5A-5B).

The motor driver 1110 may be an A3941 available from Allegro Microsystems, Inc. The A3941 driver 1110 is a full-bridge controller for use with external N-channel power metal oxide semiconductor field effect transistors (MOSFETs) specifically designed for inductive loads, such as brush DC motors. The driver 1110 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 1100.

Figure 11:
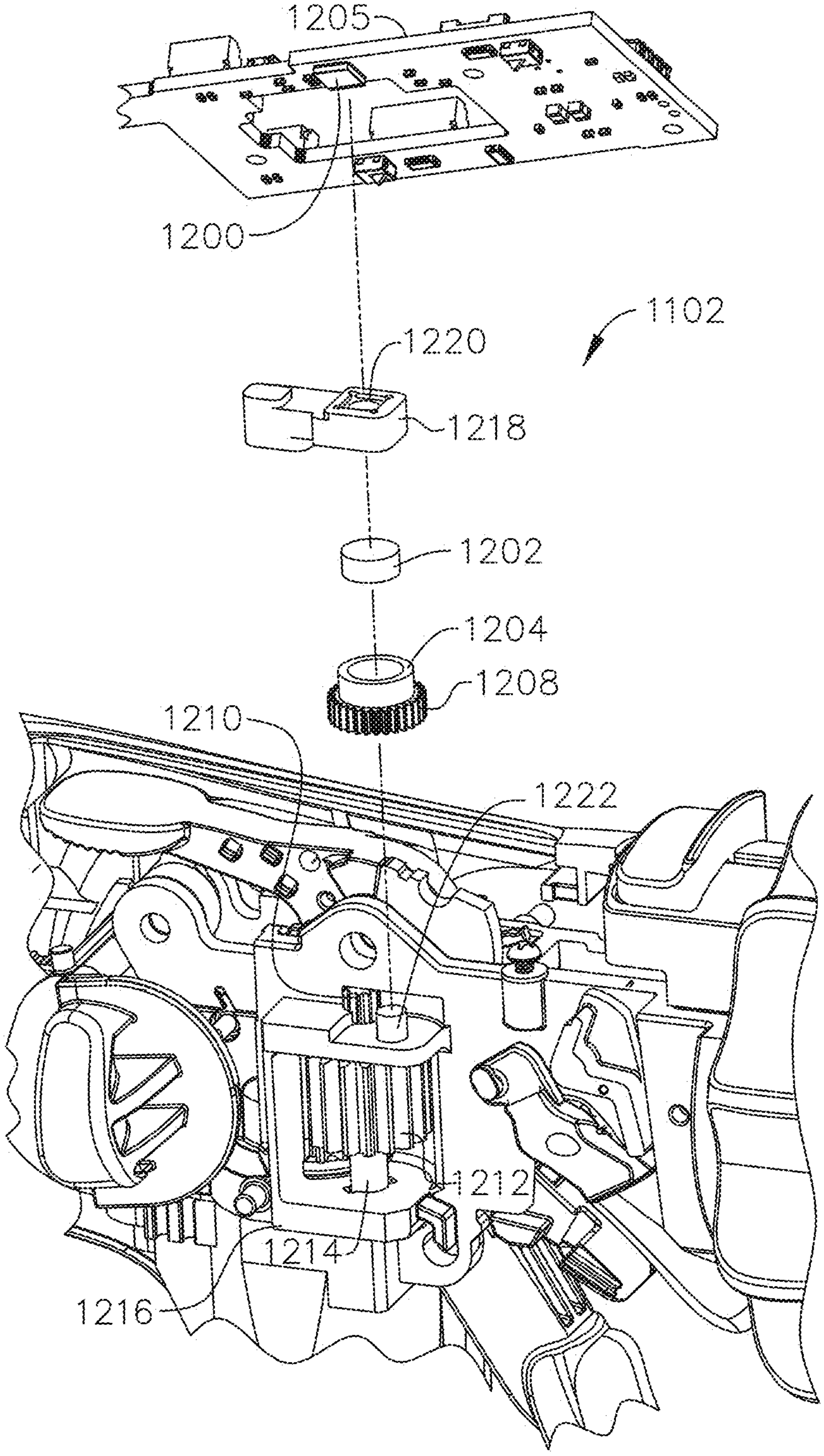
FIG. 11 is an exploded perspective view of the sensor arrangement for an absolute positioning system showing a control circuit board assembly and the relative alignment of the elements of the sensor arrangement according to one aspect of this disclosure.
Figure 12:
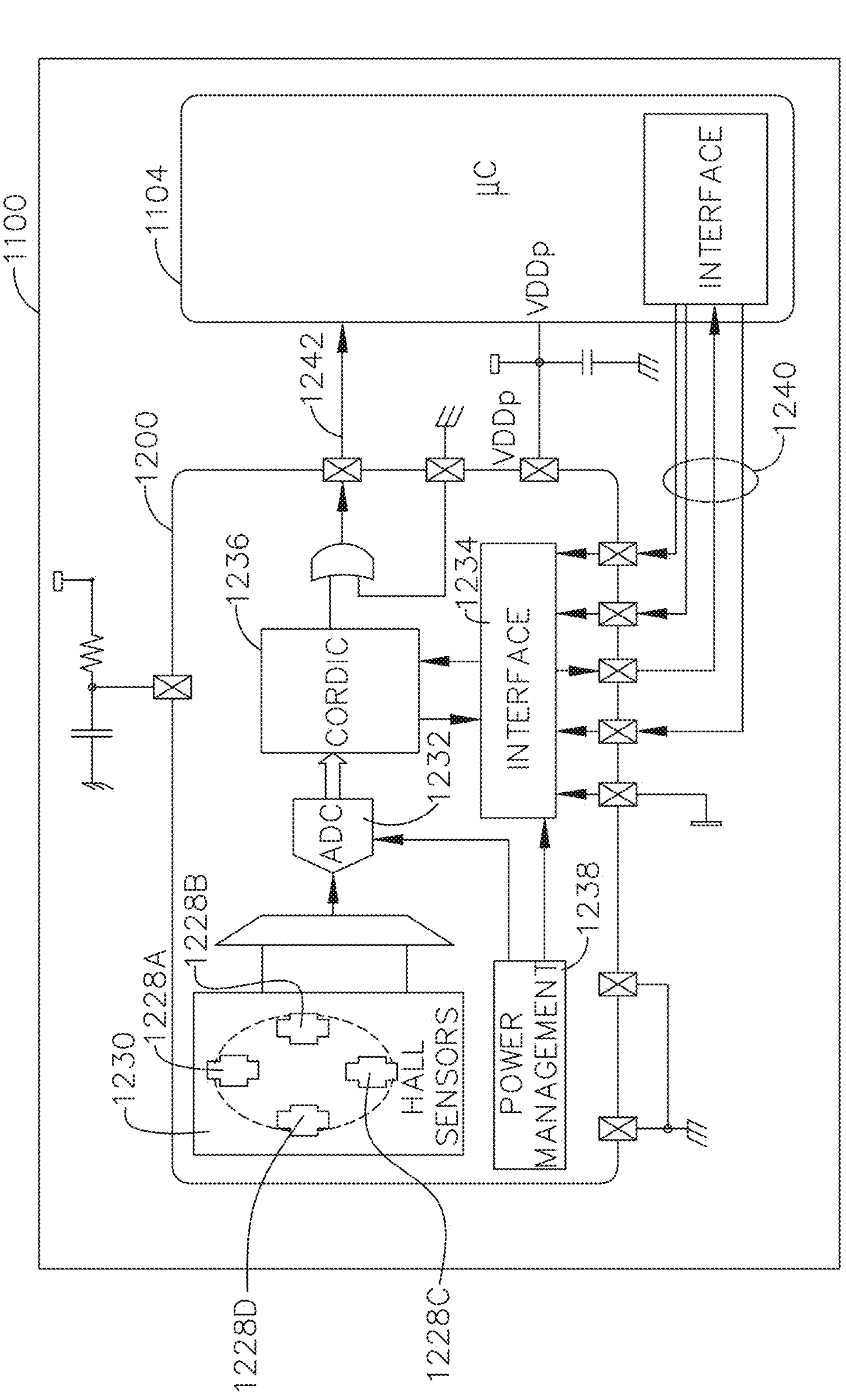
FIG. 12 is a diagram of a position sensor comprising a magnetic rotary absolute positioning system according to one aspect of this disclosure.

Having described a general architecture for implementing aspects of an absolute positioning system 1100 for a sensor arrangement 1102, the disclosure now turns to FIGS. 11 and 12 for a description of one aspect of a sensor arrangement 1102 for the absolute positioning system 1100. FIG. 11 is an exploded perspective view of the sensor arrangement 1102 for the absolute positioning system 1100 showing a circuit 1205 and the relative alignment of the elements of the sensor arrangement 1102, according to one aspect. The sensor arrangement 1102 for an absolute positioning system 1100 comprises a position sensor 1200, a magnet 1202 sensor element, a magnet holder 1204 that turns once every full stroke of the displacement member 1111, and a gear assembly 1206 to provide a gear reduction. With reference briefly to FIG. 2, the displacement member 1111 may represent the longitudinally movable drive member 120 comprising a rack of drive teeth 122 for meshing engagement with a corresponding drive gear 86 of the gear reducer assembly 84. Returning to FIG. 11, a structural element such as bracket 1216 is provided to support the gear assembly 1206, the magnet holder 1204, and the magnet 1202. The position sensor 1200 comprises magnetic sensing elements such as Hall elements and is placed in proximity to the magnet 1202. As the magnet 1202 rotates, the magnetic sensing elements of the position sensor 1200 determine the absolute angular position of the magnet 1202 over one revolution.

The sensor arrangement 1102 may comprises any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

A gear assembly comprises a first gear 1208 and a second gear 1210 in meshing engagement to provide a 3:1 gear ratio connection. A third gear 1212 rotates about a shaft 1214. The third gear 1212 is in meshing engagement with the displacement member 1111 (or 120 as shown in FIG. 2) and rotates in a first direction as the displacement member 1111 advances in a distal direction D and rotates in a second direction as the displacement member 1111 retracts in a proximal direction P. The second gear 1210 also rotates about the shaft 1214 and, therefore, rotation of the second gear 1210 about the shaft 1214 corresponds to the longitudinal translation of the displacement member 1111. Thus, one full stroke of the displacement member 1111 in either the distal or proximal directions D, P corresponds to three rotations of the second gear 1210 and a single rotation of the first gear 1208. Since the magnet holder 1204 is coupled to the first gear 1208, the magnet holder 1204 makes one full rotation with each full stroke of the displacement member 1111.

The position sensor 1200 is supported by a position sensor holder 1218 defining an aperture 1220 suitable to contain the position sensor 1200 in precise alignment with a magnet 1202 rotating below within the magnet holder 1204. The fixture is coupled to the bracket 1216 and to the circuit 1205 and remains stationary while the magnet 1202 rotates with the magnet holder 1204. A hub 1222 is provided to mate with the first gear 1208 and the magnet holder 1204. The second gear 1210 and third gear 1212 coupled to shaft 1214 also are shown.

Figure 15:
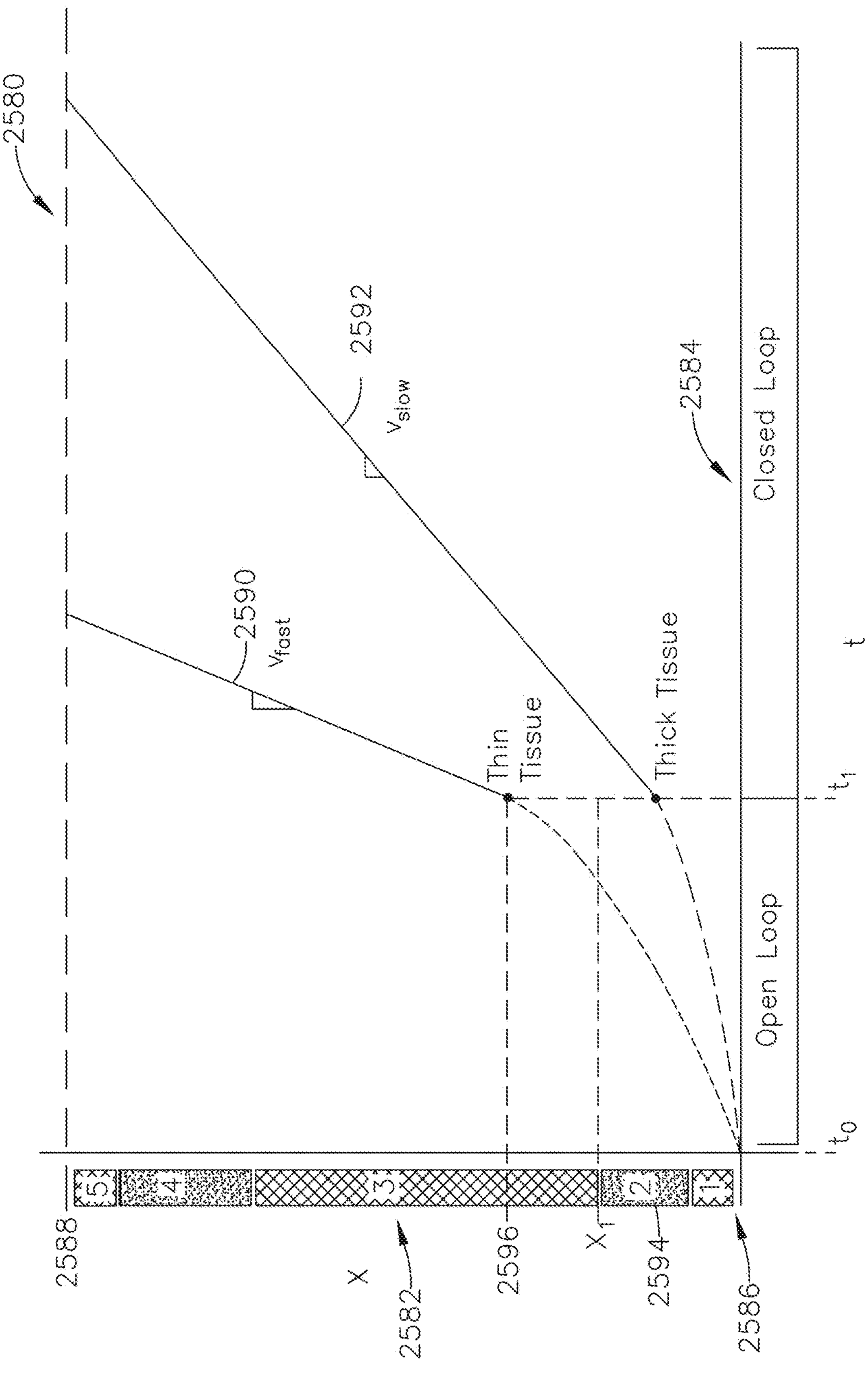
FIG. 15 illustrates a diagram plotting two example displacement member strokes executed according to one aspect of this disclosure.
Figure 16:
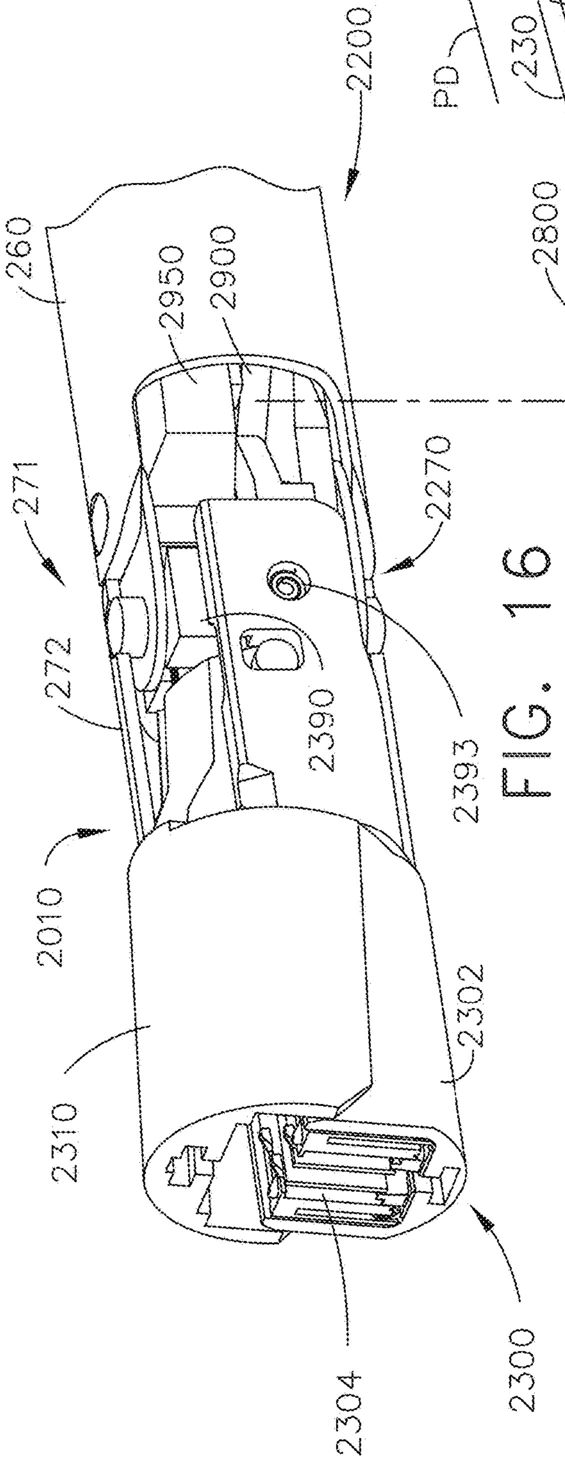
FIG. 16 is a partial perspective view of a portion of an end effector of a surgical instrument showing an elongate shaft assembly in an unarticulated orientation with portions thereof omitted for clarity, according to one aspect of this disclosure.

FIG. 12 is a diagram of a position sensor 1200 for an absolute positioning system 1100 comprising a magnetic rotary absolute positioning system according to one aspect of this disclosure. The position sensor 1200 may be implemented as an AS5055EQFT single-chip magnetic rotary position sensor available from Austria Microsystems, AG. The position sensor 1200 is interfaced with the controller 1104 to provide an absolute positioning system 1100. The position sensor 1200 is a low-voltage and low-power component and includes four Hall-effect elements 1228A, 1228B, 1228C, 1228D in an area 1230 of the position sensor 1200 that is located above the magnet 1202 (FIGS. 15 and 16). A high-resolution ADC 1232 and a smart power management controller 1238 are also provided on the chip. A CORDIC processor 1236 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface 1234 to the controller 1104. The position sensor 1200 provides 12 or 14 bits of resolution. The position sensor 1200 may be an AS5055 chip provided in a small QFN 16-pin 4×4×0.85 mm package.

The Hall-effect elements 1228A, 1228B, 1228C, 1228D are located directly above the rotating magnet 1202 (FIG. 11). The Hall-effect is a well-known effect and for expediency will not be described in detail herein, however, generally, the Hall-effect produces a voltage difference (the Hall voltage) across an electrical conductor transverse to an electric current in the conductor and a magnetic field perpendicular to the current. A Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 1200, the Hall-effect elements 1228A, 1228B, 1228C, 1228D are capable producing a voltage signal that is indicative of the absolute position of the magnet 1202 in terms of the angle over a single revolution of the magnet 1202. This value of the angle, which is unique position signal, is calculated by the CORDIC processor 1236 is stored onboard the AS5055 position sensor 1200 in a register or memory. The value of the angle that is indicative of the position of the magnet 1202 over one revolution is provided to the controller 1104 in a variety of techniques, e.g., upon power up or upon request by the controller 1104.

The AS5055 position sensor 1200 requires only a few external components to operate when connected to the controller 1104. Six wires are needed for a simple application using a single power supply: two wires for power and four wires 1240 for the SPI interface 1234 with the controller 1104. A seventh connection can be added in order to send an interrupt to the controller 1104 to inform that a new valid angle can be read. Upon power-up, the AS5055 position sensor 1200 performs a full power-up sequence including one angle measurement. The completion of this cycle is indicated as an INT output 1242, and the angle value is stored in an internal register. Once this output is set, the AS5055 position sensor 1200 suspends to sleep mode. The controller 1104 can respond to the INT request at the INT output 1242 by reading the angle value from the AS5055 position sensor 1200 over the SPI interface 1234. Once the angle value is read by the controller 1104, the INT output 1242 is cleared again. Sending a "read angle" command by the SPI interface 1234 by the controller 1104 to the position sensor 1200 also automatically powers up the chip and starts another angle measurement. As soon as the controller 1104 has completed reading of the angle value, the INT output 1242 is cleared and a new result is stored in the angle register. The completion of the angle measurement is again indicated by setting the INT output 1242 and a corresponding flag in the status register.

Due to the measurement principle of the AS5055 position sensor 1200, only a single angle measurement is performed in very short time (~600 μs) after each power-up sequence. As soon as the measurement of one angle is completed, the AS5055 position sensor 1200 suspends to power-down state. An on-chip filtering of the angle value by digital averaging is not implemented, as this would require more than one angle measurement and, consequently, a longer power-up time that is not desired in low-power applications. The angle jitter can be reduced by averaging of several angle samples in the controller 1104. For example, an averaging of four samples reduces the jitter by 6 dB (50%).

Figure 13:
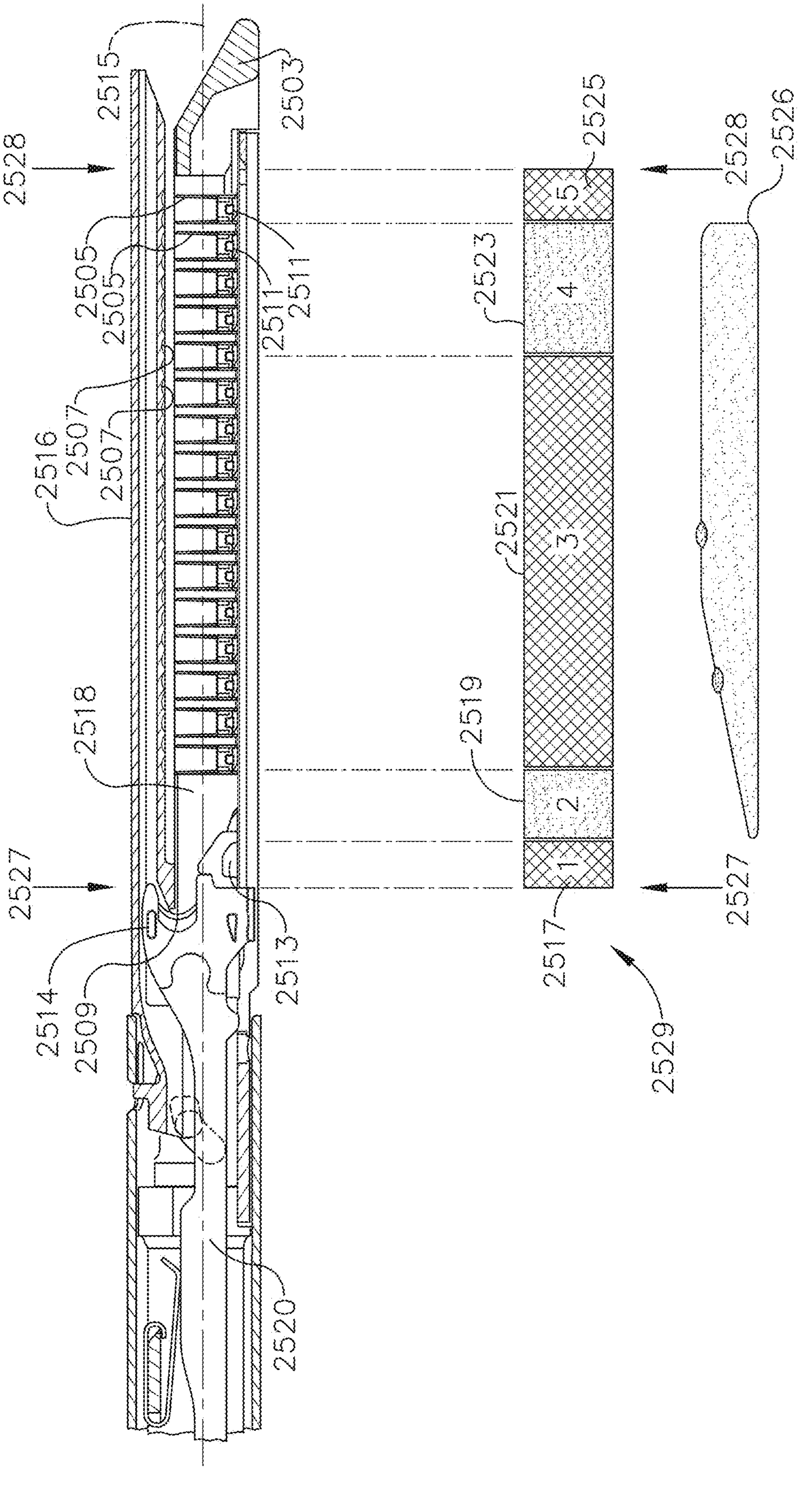
FIG. 13 is a section view of an end effector of the surgical instrument of FIG. 1 showing a firing member stroke relative to tissue grasped within the end effector according to one aspect of this disclosure.

FIG. 13 is a section view of an end effector 2502 of the surgical instrument 10 (FIGS. 1-4) showing an I-beam 2514 firing stroke relative to tissue 2526 grasped within the end effector 2502 according to one aspect of this disclosure. The end effector 2502 is configured to operate with the surgical instrument 10 shown in FIGS. 1-4. The end effector 2502 comprises an anvil 2516 and an elongated channel 2503 with a staple cartridge 2518 positioned in the elongated channel 2503. A firing bar 2520 is translatable distally and proximally along a longitudinal axis 2515 of the end effector 2502. When the end effector 2502 is not articulated, the end effector 2502 is in line with the shaft of the instrument. An I-beam 2514 comprising a cutting edge 2509 is illustrated at a distal portion of the firing bar 2520. A wedge sled 2513 is positioned in the staple cartridge 2518. As the I-beam 2514 translates distally, the cutting edge 2509 contacts and may cut tissue 2526 positioned between the anvil 2516 and the staple cartridge 2518. Also, the I-beam 2514 contacts the wedge sled 2513 and pushes it distally, causing the wedge sled 2513 to contact staple drivers 2511. The staple drivers 2511 may be driven up into staples 2505, causing the staples 2505 to advance through tissue and into pockets 2507 defined in the anvil 2516, which shape the staples 2505.

An example I-beam 2514 firing stroke is illustrated by a chart 2529 aligned with the end effector 2502. Example tissue 2526 is also shown aligned with the end effector 2502. The firing member stroke may comprise a stroke begin position 2527 and a stroke end position 2528. During an I-beam 2514 firing stroke, the I-beam 2514 may be advanced distally from the stroke begin position 2527 to the stroke end position 2528. The I-beam 2514 is shown at one example location of a stroke begin position 2527. The I-beam 2514 firing member stroke chart 2529 illustrates five firing member stroke regions 2517, 2519, 2521, 2523, 2525. In a first firing stroke region 2517, the I-beam 2514 may begin to advance distally. In the first firing stroke region 2517, the I-beam 2514 may contact the wedge sled 2513 and begin to move it distally. While in the first region, however, the cutting edge 2509 may not contact tissue and the wedge sled 2513 may not contact a staple driver 2511. After static friction is overcome, the force to drive the I-beam 2514 in the first region 2517 may be substantially constant.

Figure 18:
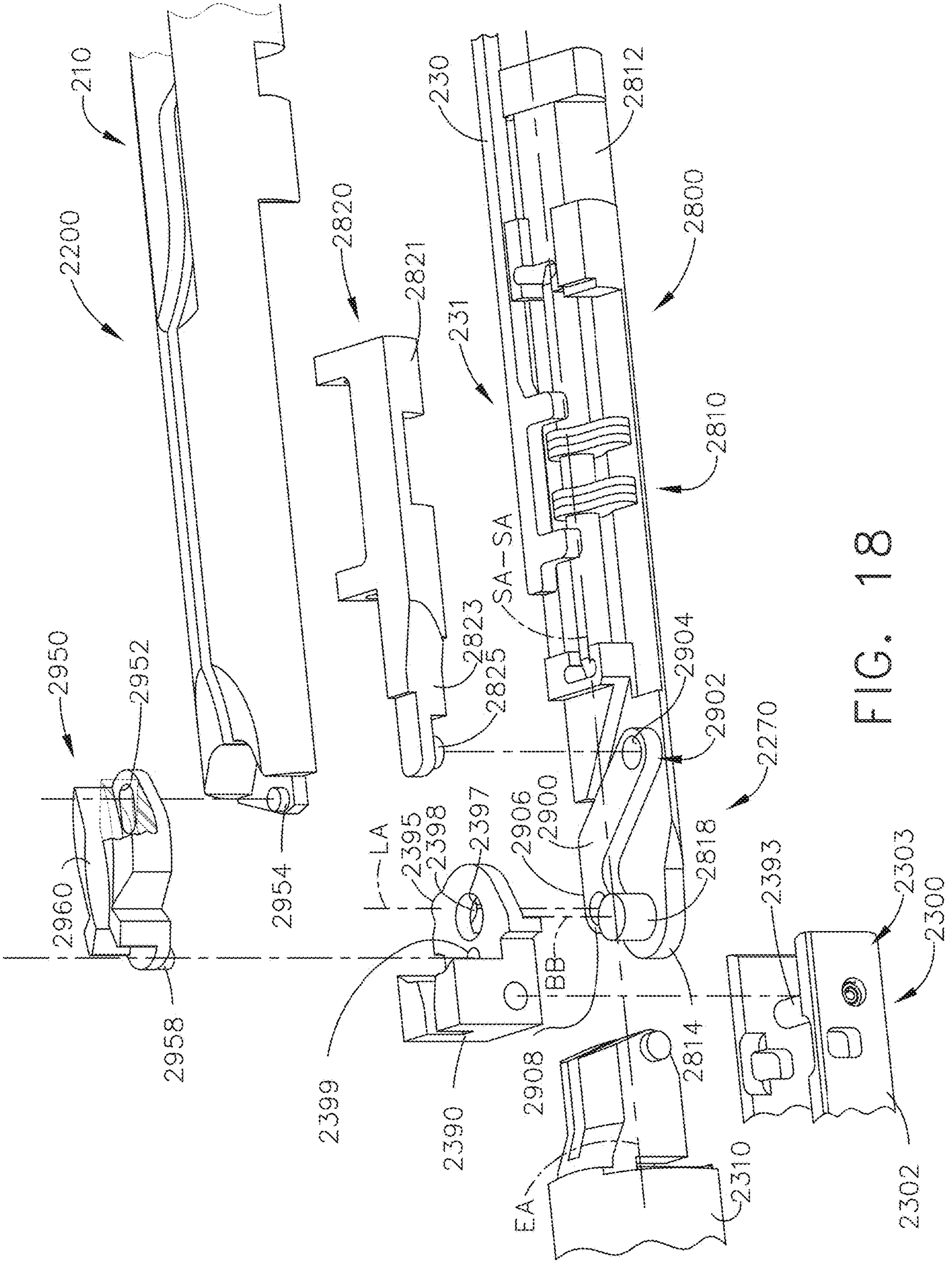
FIG. 18 is an exploded assembly perspective view of the end effector of FIG. 16 showing the elongate shaft assembly aspect, according to one aspect of this disclosure.

In the second firing member stroke region 2519, the cutting edge 2509 may begin to contact and cut tissue 2526. Also, the wedge sled 2513 may begin to contact staple drivers 2511 to drive staples 2505. Force to drive the I-beam 2514 may begin to ramp up. As shown, tissue encountered initially may be compressed and/or thinner because of the way that the anvil 2516 pivots relative to the staple cartridge 2518. In the third firing member stroke region 2521, the cutting edge 2509 may continuously contact and cut tissue 2526 and the wedge sled 2513 may repeatedly contact staple drivers 2511. Force to drive the I-beam 2514 may plateau in the third region 2521. By the fourth firing stroke region 2523, force to drive the I-beam 2514 may begin to decline. For example, tissue in the portion of the end effector 2502 corresponding to the fourth firing region 2523 may be less compressed than tissue closer to the pivot point of the anvil 2516, requiring less force to cut. Also, the cutting edge 2509 and wedge sled 2513 may reach the end of the tissue 2526 while in the fourth region 2523. When the I-beam 2514 reaches the fifth region 2525, the tissue 2526 may be completely severed. The wedge sled 2513 may contact one or more staple drivers 2511 at or near the end of the tissue. Force to advance the I-beam 2514 through the fifth region 2525 may be reduced and, in some examples, may be similar to the force to drive the I-beam 2514 in the first region 2517. At the conclusion of the firing member stroke, the I-beam 2514 may reach the stroke end position 2528. The positioning of firing member stroke regions 2517, 2519, 2521, 2523, 2525 in FIG. 18 is just one example. In some examples, different regions may begin at different positions along the end effector longitudinal axis 2515, for example, based on the positioning of tissue between the anvil 2516 and the staple cartridge 2518.

As discussed above and with reference now to FIGS. 10-13, the electric motor 1122 positioned within the handle assembly of the surgical instrument 10 (FIGS. 1-4) can be utilized to advance and/or retract the firing system of the shaft assembly, including the I-beam 2514, relative to the end effector 2502 of the shaft assembly in order to staple and/or incise tissue captured within the end effector 2502. The I-beam 2514 may be advanced or retracted at a desired speed, or within a range of desired speeds. The controller 1104 may be configured to control the speed of the I-beam 2514. The controller 1104 may be configured to predict the speed of the I-beam 2514 based on various parameters of the power supplied to the electric motor 1122, such as voltage and/or current, for example, and/or other operating parameters of the electric motor 1122 or external influences. The controller 1104 may be configured to predict the current speed of the I-beam 2514 based on the previous values of the current and/or voltage supplied to the electric motor 1122, and/or previous states of the system like velocity, acceleration, and/or position. The controller 1104 may be configured to sense the speed of the I-beam 2514 utilizing the absolute positioning sensor system described herein. The controller can be configured to compare the predicted speed of the I-beam 2514 and the sensed speed of the I-beam 2514 to determine whether the power to the electric motor 1122 should be increased in order to increase the speed of the I-beam 2514 and/or decreased in order to decrease the speed of the I-beam 2514. U.S. Pat. No. 8,210,411, entitled MOTOR-DRIVEN SURGICAL CUTTING INSTRUMENT, which is incorporated herein by reference in its entirety. U.S. Pat. No. 7,845,537, entitled SURGICAL INSTRUMENT HAVING RECORDING CAPABILITIES, which is incorporated herein by reference in its entirety.

Force acting on the I-beam 2514 may be determined using various techniques. The I-beam 2514 force may be determined by measuring the motor 2504 current, where the motor 2504 current is based on the load experienced by the I-beam 2514 as it advances distally. The I-beam 2514 force may be determined by positioning a strain gauge on the drive member 120 (FIG. 2), the firing member 220 (FIG. 2), I-beam 2514 (I-beam 178, FIG. 20), the firing bar 172 (FIG. 2), and/or on a proximal end of the cutting edge 2509. The I-beam 2514 force may be determined by monitoring the actual position of the I-beam 2514 moving at an expected velocity based on the current set velocity of the motor 2504 after a predetermined elapsed period $T_1$ and comparing the actual position of the I-beam 2514 relative to the expected position of the I-beam 2514 based on the current set velocity of the motor 2504 at the end of the period $T_1$. Thus, if the actual position of the I-beam 2514 is less than the expected position of the I-beam 2514, the force on the I-beam 2514 is greater than a nominal force. Conversely, if the actual position of the I-beam 2514 is greater than the expected position of the I-beam 2514, the force on the I-beam 2514 is less than the nominal force. The difference between the actual and expected positions of the I-beam 2514 is proportional to the deviation of the force on the I-beam 2514 from the nominal force. Such techniques are described in U.S. patent application Ser. No. 15/628,075, entitled SYSTEMS AND METHODS FOR CONTROLLING MOTOR VELOCITY OF A SURGICAL STAPLING AND CUTTING INSTRUMENT, filed Jun. 20, 2017, which is incorporated herein by reference in its entirety.

Figure 14:
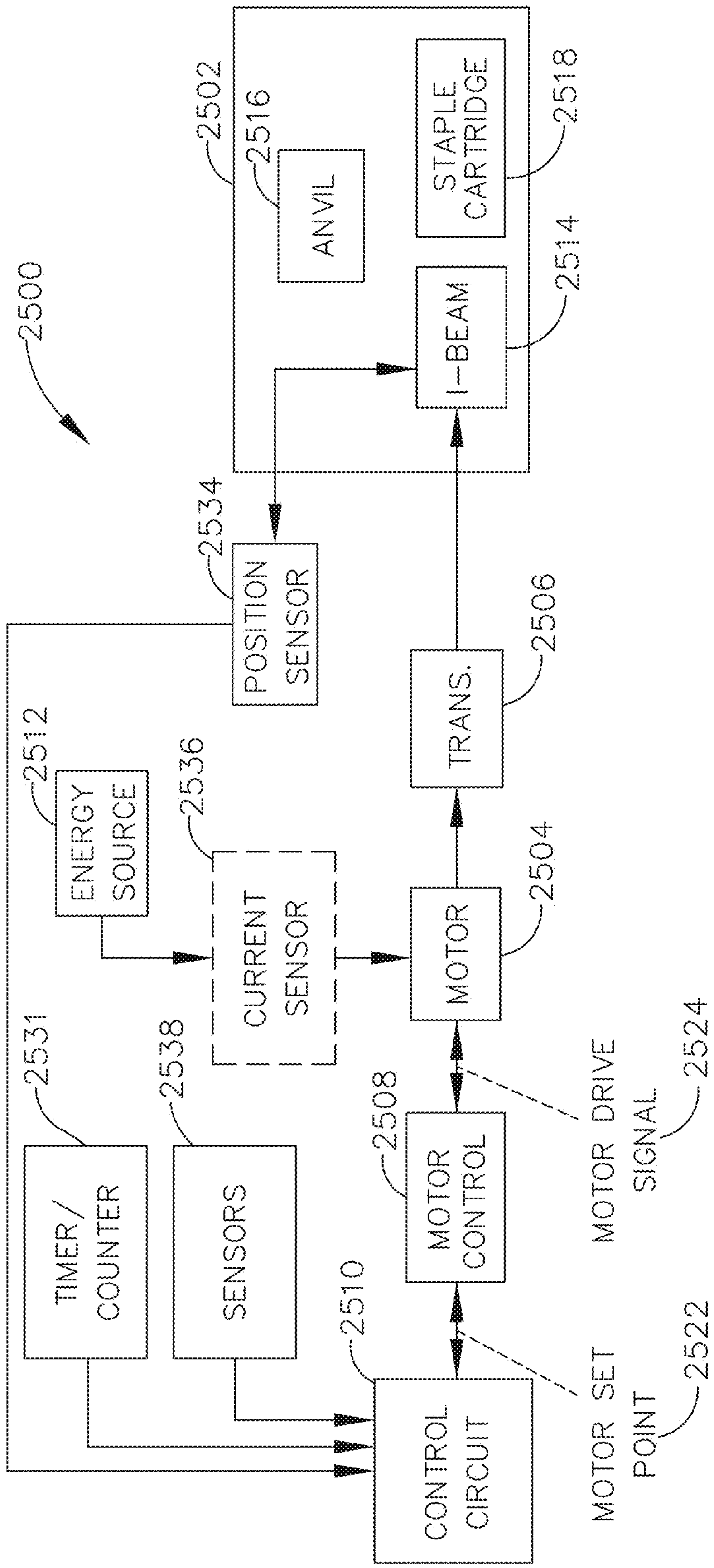
FIG. 14 illustrates a block diagram of a surgical instrument programmed to control distal translation of a displacement member according to one aspect of this disclosure.

FIG. 14 illustrates a block diagram of a surgical instrument 2500 programmed to control distal translation of a displacement member according to one aspect of this disclosure. In one aspect, the surgical instrument 2500 is programmed to control distal translation of a displacement member 1111 such as the I-beam 2514. The surgical instrument 2500 comprises an end effector 2502 that may comprise an anvil 2516, an I-beam 2514 (including a sharp cutting edge 2509), and a removable staple cartridge 2518. The end effector 2502, anvil 2516, I-beam 2514, and staple cartridge 2518 may be configured as described herein, for example, with respect to FIGS. 1-13.

The position, movement, displacement, and/or translation of a liner displacement member 1111, such as the I-beam 2514, can be measured by the absolute positioning system 1100, sensor arrangement 1102, and position sensor 1200 as shown in FIGS. 10-12 and represented as position sensor 2534 in FIG. 14. Because the I-beam 2514 is coupled to the longitudinally movable drive member 120, the position of the I-beam 2514 can be determined by measuring the position of the longitudinally movable drive member 120 employing the position sensor 2534. Accordingly, in the following description, the position, displacement, and/or translation of the I-beam 2514 can be achieved by the position sensor 2534 as described herein. A control circuit 2510, such as the control circuit 700 described in FIGS. 5A and 5B, may be programmed to control the translation of the displacement member 1111, such as the I-beam 2514, as described in connection with FIGS. 10-12. The control circuit 2510, in some examples, may comprise one or more microcontrollers, microprocessors, or other suitable processors for executing instructions that cause the processor or processors to control the displacement member, e.g., the I-beam 2514, in the manner described. In one aspect, a timer/counter circuit 2531 provides an output signal, such as elapsed time or a digital count, to the control circuit 2510 to correlate the position of the I-beam 2514 as determined by the position sensor 2534 with the output of the timer/counter circuit 2531 such that the control circuit 2510 can determine the position of the I-beam 2514 at a specific time (t) relative to a starting position. The timer/counter circuit 2531 may be configured to measure elapsed time, count external evens, or time external events.

The control circuit 2510 may generate a motor set point signal 2522. The motor set point signal 2522 may be provided to a motor controller 2508. The motor controller 2508 may comprise one or more circuits configured to provide a motor drive signal 2524 to the motor 2504 to drive the motor 2504 as described herein. In some examples, the motor 2504 may be a brushed DC electric motor, such as the motor 82, 714, 1120 shown in FIGS. 1, 5B, 10. For example, the velocity of the motor 2504 may be proportional to the motor drive signal 2524. In some examples, the motor 2504 may be a brushless direct current (DC) electric motor and the motor drive signal 2524 may comprise a pulse-width-modulated (PWM) signal provided to one or more stator windings of the motor 2504. Also, in some examples, the motor controller 2508 may be omitted and the control circuit 2510 may generate the motor drive signal 2524 directly.

The motor 2504 may receive power from an energy source 2512. The energy source 2512 may be or include a battery, a super capacitor, or any other suitable energy source 2512. The motor 2504 may be mechanically coupled to the I-beam 2514 via a transmission 2506. The transmission 2506 may include one or more gears or other linkage components to couple the motor 2504 to the I-beam 2514. A position sensor 2534 may sense a position of the I-beam 2514. The position sensor 2534 may be or include any type of sensor that is capable of generating position data that indicates a position of the I-beam 2514. In some examples, the position sensor 2534 may include an encoder configured to provide a series of pulses to the control circuit 2510 as the I-beam 2514 translates distally and proximally. The control circuit 2510 may track the pulses to determine the position of the I-beam 2514. Other suitable position sensor may be used, including, for example, a proximity sensor. Other types of position sensors may provide other signals indicating motion of the I-beam 2514. Also, in some examples, the position sensor 2534 may be omitted. Where the motor 2504 is a stepper motor, the control circuit 2510 may track the position of the I-beam 2514 by aggregating the number and direction of steps that the motor 2504 has been instructed to execute. The position sensor 2534 may be located in the end effector 2502 or at any other portion of the instrument.

The control circuit 2510 may be in communication with one or more sensors 2538. The sensors 2538 may be positioned on the end effector 2502 and adapted to operate with the surgical instrument 2500 to measure the various derived parameters such as gap distance versus time, tissue compression versus time, and anvil strain versus time. The sensors 2538 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 2502. The sensors 2538 may include one or more sensors.

The one or more sensors 2538 may comprise a strain gauge, such as a micro-strain gauge, configured to measure the magnitude of the strain in the anvil 2516 during a clamped condition. The strain gauge provides an electrical signal whose amplitude varies with the magnitude of the strain. The sensors 2538 may comprise a pressure sensor configured to detect a pressure generated by the presence of compressed tissue between the anvil 2516 and the staple cartridge 2518. The sensors 2538 may be configured to detect impedance of a tissue section located between the anvil 2516 and the staple cartridge 2518 that is indicative of the thickness and/or fullness of tissue located therebetween.

The sensors 2538 may be is configured to measure forces exerted on the anvil 2516 by the closure drive system 30. For example, one or more sensors 2538 can be at an interaction point between the closure tube 260 (FIG. 3) and the anvil 2516 to detect the closure forces applied by the closure tube 260 to the anvil 2516. The forces exerted on the anvil 2516 can be representative of the tissue compression experienced by the tissue section captured between the anvil 2516 and the staple cartridge 2518. The one or more sensors 2538 can be positioned at various interaction points along the closure drive system 30 (FIG. 2) to detect the closure forces applied to the anvil 2516 by the closure drive system 30. The one or more sensors 2538 may be sampled in real time during a clamping operation by a processor as described in FIGS. 5A-5B. The control circuit 2510 receives real-time sample measurements to provide analyze time based information and assess, in real time, closure forces applied to the anvil 2516.

A current sensor 2536 can be employed to measure the current drawn by the motor 2504. The force required to advance the I-beam 2514 corresponds to the current drawn by the motor 2504. The force is converted to a digital signal and provided to the control circuit 2510.

Using the physical properties of the instruments disclosed herein in connection with FIGS. 1-14, and with reference to FIG. 14, the control circuit 2510 can be configured to simulate the response of the actual system of the instrument in the software of the controller. A displacement member can be actuated to move an I-beam 2514 in the end effector 2502 at or near a target velocity. The surgical instrument 2500 can include a feedback controller, which can be one of any feedback controllers, including, but not limited to a PID, a State Feedback, LQR, and/or an Adaptive controller, for example. The surgical instrument 2500 can include a power source to convert the signal from the feedback controller into a physical input such as case voltage, pulse width modulated (PWM) voltage, frequency modulated voltage, current, torque, and/or force, for example.

The actual drive system of the surgical instrument 2500 is configured to drive the displacement member, cutting member, or I-beam 2514, by a brushed DC motor with gearbox and mechanical links to an articulation and/or knife system. Another example is the electric motor 2504 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 2504. The outside influence, such as drag, may cause the operation of the physical system to deviate from a desired operation of the physical system.

Before explaining aspects of the surgical instrument 2500 in detail, it should be noted that the example aspects are not limited in application or use to the details of construction and arrangement of parts illustrated in the accompanying drawings and description. The example aspects may be implemented or incorporated in other aspects, variations and modifications, and may be practiced or carried out in various ways. Further, unless otherwise indicated, the terms and expressions employed herein have been chosen for the purpose of describing the example aspects for the convenience of the reader and are not for the purpose of limitation thereof. Also, it will be appreciated that one or more of the following-described aspects, expressions of aspects and/or examples, can be combined with any one or more of the other following-described aspects, expressions of aspects and/or examples.

Various example aspects are directed to a surgical instrument 2500 comprising an end effector 2502 with motor-driven surgical stapling and cutting implements. For example, a motor 2504 may drive a displacement member distally and proximally along a longitudinal axis of the end effector 2502. The end effector 2502 may comprise a pivotable anvil 2516 and, when configured for use, a staple cartridge 2518 positioned opposite the anvil 2516. A clinician may grasp tissue between the anvil 2516 and the staple cartridge 2518, as described herein. When ready to use the instrument 2500, the clinician may provide a firing signal, for example by depressing a trigger of the instrument 2500. In response to the firing signal, the motor 2504 may drive the displacement member distally along the longitudinal axis of the end effector 2502 from a proximal stroke begin position to a stroke end position distal of the stroke begin position. As the displacement member translates distally, an I-beam 2514 with a cutting element positioned at a distal end, may cut the tissue between the staple cartridge 2518 and the anvil 2516.

In various examples, the surgical instrument 2500 may comprise a control circuit 2510 programmed to control the distal translation of the displacement member, such as the I-beam 2514, for example, based on one or more tissue conditions. The control circuit 2510 may be programmed to sense tissue conditions, such as thickness, either directly or indirectly, as described herein. The control circuit 2510 may be programmed to select a firing control program based on tissue conditions. A firing control program may describe the distal motion of the displacement member. Different firing control programs may be selected to better treat different tissue conditions. For example, when thicker tissue is present, the control circuit 2510 may be programmed to translate the displacement member at a lower velocity and/or with lower power. When thinner tissue is present, the control circuit 2510 may be programmed to translate the displacement member at a higher velocity and/or with higher power.

In some examples, the control circuit 2510 may initially operate the motor 2504 in an open-loop configuration for a first open-loop portion of a stroke of the displacement member. Based on a response of the instrument 2500 during the open-loop portion of the stroke, the control circuit 2510 may select a firing control program. The response of the instrument may include, a translation distance of the displacement member during the open-loop portion, a time elapsed during the open-loop portion, energy provided to the motor 2504 during the open-loop portion, a sum of pulse widths of a motor drive signal, etc. After the open-loop portion, the control circuit 2510 may implement the selected firing control program for a second portion of the displacement member stroke. For example, during the closed loop portion of the stroke, the control circuit 2510 may modulate the motor 2504 based on translation data describing a position of the displacement member in a closed-loop manner to translate the displacement member at a constant velocity.

FIG. 15 illustrates a diagram 2580 plotting two example displacement member strokes executed according to one aspect of this disclosure. The diagram 2580 comprises two axes. A horizontal axis 2584 indicates elapsed time. A vertical axis 2582 indicates the position of the I-beam 2514 between a stroke begin position 2586 and a stroke end position 2588. On the horizontal axis 2584, the control circuit 2510 may receive the firing signal and begin providing the initial motor setting at $t_0$. The open-loop portion of the displacement member stroke is an initial time period that may elapse between $t_0$ and $t_1$.

A first example 2592 shows a response of the surgical instrument 2500 when thick tissue is positioned between the anvil 2516 and the staple cartridge 2518. During the open-loop portion of the displacement member stroke, e.g., the initial time period between $t_0$ and $t_1$, the I-beam 2514 may traverse from the stroke begin position 2586 to position 2594. The control circuit 2510 may determine that position 2594 corresponds to a firing control program that advances the I-beam 2514 at a selected constant velocity (Vslow), indicated by the slope of the example 2592 after $t_1$ (e.g., in the closed loop portion). The control circuit 2510 may drive I-beam 2514 to the velocity Vslow by monitoring the position of I-beam 2514 and modulating the motor set point 2522 and/or motor drive signal 2524 to maintain Vslow. A second example 2590 shows a response of the surgical instrument 2500 when thin tissue is positioned between the anvil 2516 and the staple cartridge 2518.

During the initial time period (e.g., the open-loop period) between $t_0$ and $t_1$, the I-beam 2514 may traverse from the stroke begin position 2586 to position 2596. The control circuit may determine that position 2596 corresponds to a firing control program that advances the displacement member at a selected constant velocity (Vfast). Because the tissue in example 2590 is thinner than the tissue in example 2592, it may provide less resistance to the motion of the I-beam 2514. As a result, the I-beam 2514 may traverse a larger portion of the stroke during the initial time period. Also, in some examples, thinner tissue (e.g., a larger portion of the displacement member stroke traversed during the initial time period) may correspond to higher displacement member velocities after the initial time period.

Figure 17:
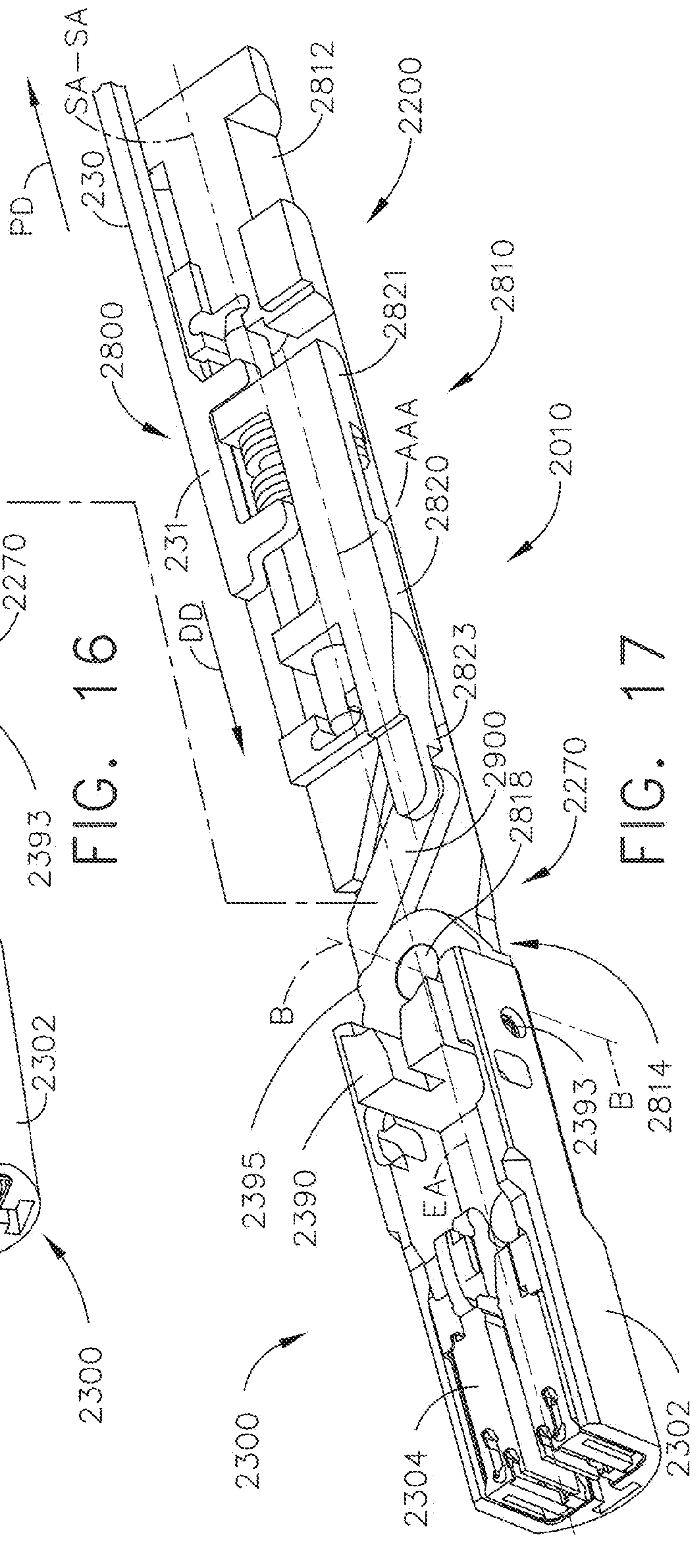
FIG. 17 is another perspective view of the end effector of FIG. 16 showing the elongate shaft assembly an unarticulated orientation, according to one aspect of this disclosure.
Figure 19:
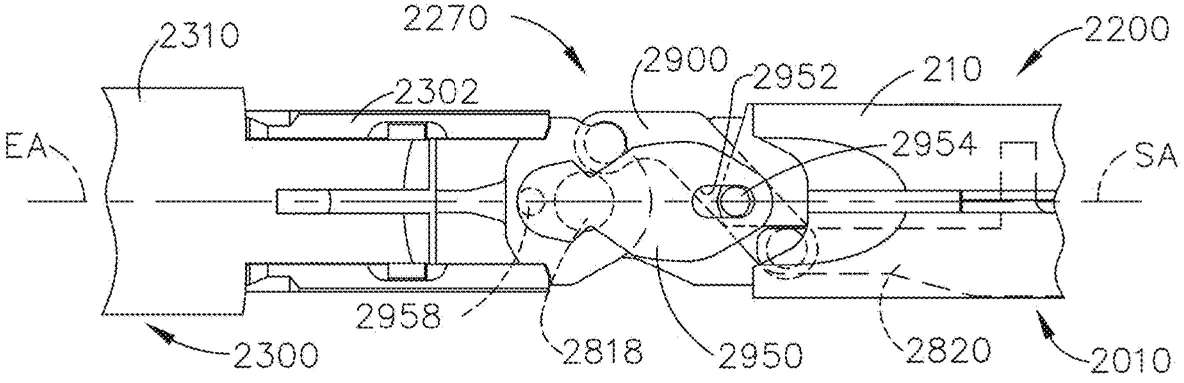
FIG. 19 is a top view of the end effector of FIG. 16 showing the elongate shaft assembly in an unarticulated orientation, according to one aspect of this disclosure.
Figure 20:
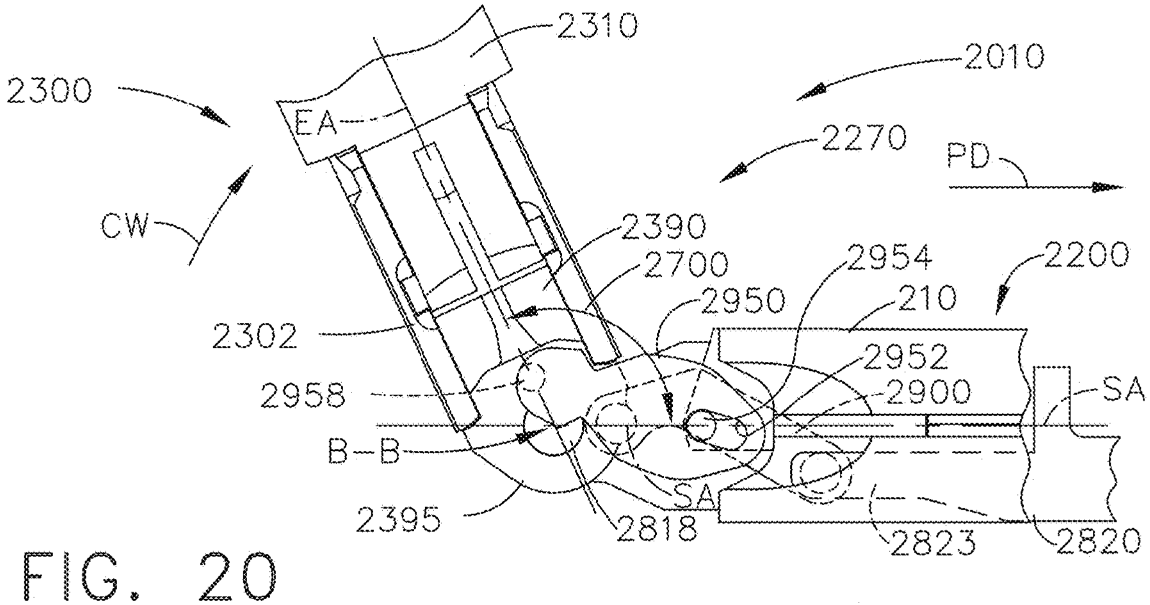
FIG. 20 is another top view of the end effector of FIG. 16 showing the elongate shaft assembly in a first articulated orientation, according to one aspect of this disclosure.
Figure 21:
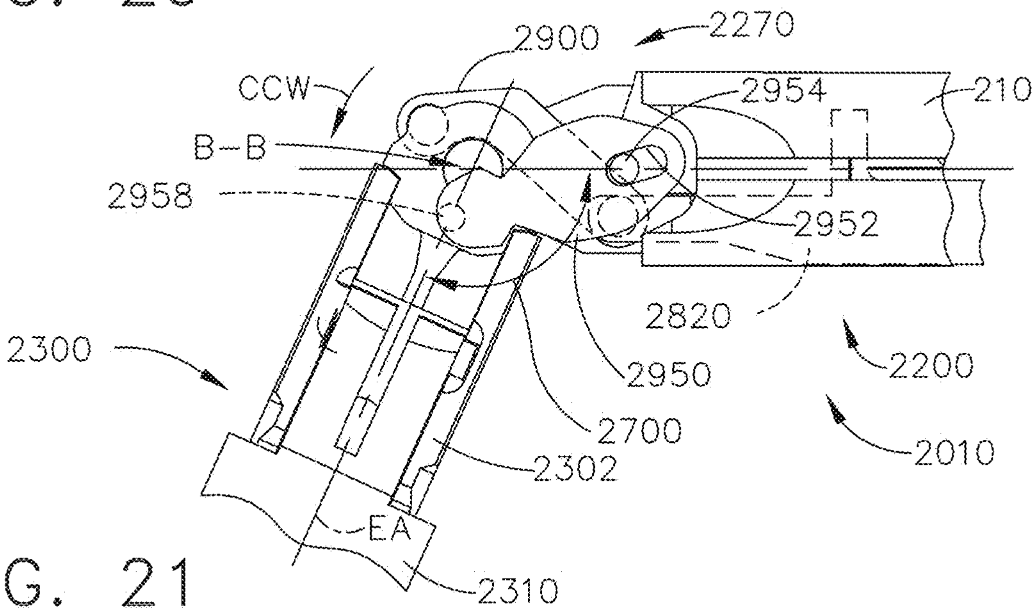
FIG. 21 is another top view of the end effector of FIG. 16 showing the elongate shaft assembly in a second articulated orientation, according to one aspect of this disclosure.

FIGS. 16-21 illustrate an end effector 2300 of a surgical instrument 2010 showing how the end effector 2300 may be articulated relative to the elongate shaft assembly 2200 about an articulation joint 2270 according to one aspect of this disclosure. FIG. 16 is a partial perspective view of a portion of the end effector 2300 showing an elongate shaft assembly 2200 in an unarticulated orientation with portions thereof omitted for clarity. FIG. 17 is a perspective view of the end effector 2300 of FIG. 16 showing the elongate shaft assembly 2200 in an unarticulated orientation. FIG. 18 is an exploded assembly perspective view of the end effector 2300 of FIG. 16 showing the elongate shaft assembly 2200. FIG. 19 is a top view of the end effector 2300 of FIG. 16 showing the elongate shaft assembly 2200 in an unarticulated orientation. FIG. 20 is a top view of the end effector 2300 of FIG. 16 showing the elongate shaft assembly 2200 in a first articulated orientation. FIG. 21 is a top view of the end effector 2300 of FIG. 16 showing the elongate shaft assembly 2200 in a second articulated orientation.

With reference now to FIGS. 16-21, the end effector 2300 is adapted to cut and staple tissue and includes a first jaw in the form of an elongate channel 2302 that is configured to operably support a surgical staple cartridge 2304 therein. The end effector 2300 further includes a second jaw in the form of an anvil 2310 that is supported on the elongate channel 2302 for movement relative thereto. The elongate shaft assembly 2200 includes an articulation system 2800 that employs an articulation lock 2810. The articulation lock 2810 can be configured and operated to selectively lock the surgical end effector 2300 in various articulated positions. Such arrangement enables the surgical end effector 2300 to be rotated, or articulated, relative to the shaft closure sleeve 260 when the articulation lock 2810 is in its unlocked state. Referring specifically to FIG. 18, the elongate shaft assembly 2200 includes a spine 210 that is configured to (1) slidably support a firing member 220 therein and, (2) slidably support the closure sleeve 260 (FIG. 16), which extends around the spine 210. The shaft closure sleeve 260 is attached to an end effector closure sleeve 272 that is pivotally attached to the closure sleeve 260 by a double pivot closure sleeve assembly 271.

The spine 210 also slidably supports a proximal articulation driver 230. The proximal articulation driver 230 has a distal end 231 that is configured to operably engage the articulation lock 2810. The articulation lock 2810 further comprises a shaft frame 2812 that is attached to the spine 210 in the various manners disclosed herein. The shaft frame 2812 is configured to movably support a proximal portion 2821 of a distal articulation driver 2820 therein. The distal articulation driver 2820 is movably supported within the elongate shaft assembly 2200 for selective longitudinal travel in a distal direction DD and a proximal direction PD along an articulation actuation axis AAA that is laterally offset and parallel to the shaft axis SA-SA in response to articulation control motions applied thereto.

In FIGS. 17 and 18, the shaft frame 2812 includes a distal end portion 2814 that has a pivot pin 2818 formed thereon. The pivot pin 2818 is adapted to be pivotally received within a pivot hole 2397 formed in pivot base portion 2395 of an end effector mounting assembly 2390. The end effector mounting assembly 2390 is attached to the proximal end 2303 of the elongate channel 2302 by a spring pin 2393 or equivalent. The pivot pin 2818 defines an articulation axis B-B transverse to the shaft axis SA-SA to facilitate pivotal travel (i.e., articulation) of the end effector 2300 about the articulation axis B-B relative to the shaft frame 2812.

As shown in FIG. 18, a link pin 2825 is formed on a distal end 2823 of the distal articulation link 2820 and is configured to be received within a hole 2904 in a proximal end 2902 of a cross link 2900. The cross link 2900 extends transversely across the shaft axis SA-SA and includes a distal end portion 2906. A distal link hole 2908 is provided through the distal end portion 2906 of the cross link 2900 and is configured to pivotally receive therein a base pin 2398 extending from the bottom of the pivot base portion 2395 of the end effector mounting assembly 2390. The base pin 2395 defines a link axis LA that is parallel to the articulation axis B-B. FIGS. 17 and 20 illustrate the surgical end effector 2300 in an unarticulated position. The end effector axis EA is defined by the elongate channel 2302 is aligned with the shaft axis SA-SA. The term "aligned with" may mean "coaxially aligned" with the shaft axis SA-SA or parallel with the shaft axis SA-SA. Movement of the distal articulation driver 2820 in the proximal direction PD will cause the cross link 2900 to draw the surgical end effector 2300 in a clockwise CW direction about the articulation axis B-B as shown in FIG. 19. Movement of the distal articulation driver 2820 in the distal direction DD will cause the cross link 2900 to move the surgical end effector 2300 in the counterclockwise CCW direction about the articulation axis B-B as shown in FIG. 21. As shown in FIG. 21, the cross link 2900 has a curved shape that permits the cross-link 2900 to curve around the articulation pin 2818 when the surgical end effector 2300 is articulated in that direction. When the surgical end effector 2300 is in a fully articulated position on either side of the shaft axis SA-SA, the articulation angle 2700 between the end effector axis EA and the shaft axis SA-SA is approximately sixty-five degrees (65°). Thus, the range of articulation on either said of the shaft axis is from one degree (1°) to sixty-five degrees (65°).

FIG. 19 shows the articulation joint 2270 in a straight position, i.e., at a zero angle $\theta_0$ relative to the longitudinal direction depicted as shaft axis SA, according to one aspect. FIG. 20 shows the articulation joint 2270 of FIG. 19 articulated in one direction at a first angle $\theta_1$ defined between the shaft axis SA and the end effector axis EA, according to one aspect. FIG. 21 illustrates the articulation joint 2270 of FIG. 19 articulated in another direction at a second angle $\theta_2$ defined between the shaft axis SA and the end effector axis EA.

The surgical end effector 2300 in FIGS. 16-21 comprises a surgical cutting and stapling device that employs a firing member 220 of the various types and configurations described herein. However, the surgical end effector 2300 may comprise other forms of surgical end effectors that do not cut and/or staple tissue. A middle support member 2950 is pivotally and slidably supported relative to the spine 210. In FIG. 18, the middle support member 2950 includes a slot 2952 that is adapted to receive therein a pin 2954 that protrudes from the spine 210. This enables the middle support member 2950 to pivot and translate relative to the pin 2954 when the surgical end effector 2300 is articulated. A pivot pin 2958 protrudes from the underside of the middle support member 2950 to be pivotally received within a corresponding pivot hole 2399 provided in the base portion 2395 of the end effector mounting assembly 2390. The middle support member 2950 further includes a slot 2960 for receiving a firing member 220 there through. The middle support member 2950 serves to provide lateral support to the firing member 220 as it flexes to accommodate articulation of the surgical end effector 2300.

The surgical instrument can additionally be configured to determine the angle at which the end effector 2300 is oriented. In various aspects, the position sensor 1112 of the sensor arrangement 1102 may comprise one or more magnetic sensors, analog rotary sensors (such as potentiometers), arrays of analog Hall effect sensors, which output a unique combination of position signals or values, among others, for example. In one aspect, the articulation joint 2270 of the aspect illustrated in FIGS. 16-21 can additionally comprise an articulation sensor arrangement that is configured to determine the angular position, i.e., articulation angle, of the end effector 2300 and provide a unique position signal corresponding thereto.

The articulation sensor arrangement can be similar to the sensor arrangement 1102 described above and illustrated in FIGS. 10-12. In this aspect, the articulation sensor arrangement can comprise a position sensor and a magnet that is operatively coupled to the articulation joint 2270 such that it rotates in a manner consistent with the rotation of the articulation joint 2270. The magnet can, for example, be coupled to the pivot pin 2818. The position sensor comprises one or more magnetic sensing elements, such as Hall effect sensors, and is placed in proximity to the magnet, either within or adjacent to the articulation joint 2270. Accordingly, as the magnet rotates, the magnetic sensing elements of the position sensor determine the magnet's absolute angular position. As the magnet is coupled to the articulation joint 2270, the angular position of the magnet with respect to the position sensor corresponds to the angular position of the end effector 2300. Therefore, the articulation sensor arrangement is able to determine the angular position of the end effector as the end effector articulates.

In another aspect, the surgical instrument is configured to determine the angle at which the end effector 2300 is positioned in an indirect manner by monitoring the absolute position of the articulation driver 230 (FIG. 3). As the position of the articulation driver 230 corresponds to the angle at which the end effector 2300 is oriented in a known manner, the absolute position of the articulation driver 230 can be tracked and then translated to the angular position of the end effector 2300. In this aspect, the surgical instrument comprises an articulation sensor arrangement that is configured to determine the absolute linear position of the articulation driver 230 and provide a unique position signal corresponding thereto. In some aspects, the articulation sensor arrangement or the controller operably coupled to the articulation sensor arrangement is configured additionally to translate or calculate the angular position of the end effector 2300 from the unique position signal.

The articulation sensor arrangement in this aspect can likewise be similar to the sensor arrangement 1102 described above and illustrated in FIGS. 10-12. In one aspect similar to the aspect illustrated in FIG. 10 with respect to the displacement member 1111, the articulation sensor arrangement comprises a position sensor and a magnet that turns once every full stroke of the longitudinally-movable articulation driver 230. The position sensor comprises one or more magnetic sensing elements, such as Hall effect sensors, and is placed in proximity to the magnet. Accordingly, as the magnet rotates, the magnetic sensing elements of the position sensor determine the absolute angular position of the magnet over one revolution.

In one aspect, a single revolution of a sensor element associated with the position sensor is equivalent to a longitudinal linear displacement d1 of the of the longitudinally-movable articulation driver 230. In other words, d1 is the longitudinal linear distance that the longitudinally-movable articulation driver 230 moves from point "a" to point "b" after a single revolution of a sensor element coupled to the longitudinally-movable articulation driver 230. The articulation sensor arrangement may be connected via a gear reduction that results in the position sensor completing only one revolution for the full stroke of the longitudinally-movable articulation driver 230. In other words, d1 can be equal to the full stroke of the articulation driver 230. The position sensor is configured to then transmit a unique position signal corresponding to the absolute position of the articulation driver 230 to the controller 1104, such as in those aspects depicted in FIG. 10 Upon receiving the unique position signal, the controller 1104 is then configured execute a logic to determine the angular position of the end effector corresponding to the linear position of the articulation driver 230 by, for example, querying a lookup table that returns the value of the pre-calculated angular position of the end effector 2300, calculating via an algorithm the angular position of the end effector 2300 utilizing the linear position of the articulation driver 230 as the input, or performing any other such method as is known in the field.

In various aspects, any number of magnetic sensing elements may be employed on the articulation sensor arrangement, such as, for example, magnetic sensors classified according to whether they measure the total magnetic field or the vector components of the magnetic field. The number of magnetic sensing elements utilized corresponds to the desired resolution to be sensed by the articulation sensor arrangement. In other words, the larger number of magnetic sensing elements used, the finer degree of articulation that can be sensed by the articulation sensor arrangement. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In one aspect, the position sensor of the various aspects of the articulation sensor arrangement may be implemented in a manner similar to the positioning system illustrated in FIG. 12 for tracking the position of the displacement member 1111. In one such aspect, the articulation sensor arrangement may be implemented as an AS5055EQFT single-chip magnetic rotary position sensor available from Austria Microsystems, AG. The position sensor is interfaced with the controller to provide an absolute positioning system for determining the absolute angular position of the end effector 2300, either directly or indirectly. The position sensor is a low voltage and low power component and includes four Hall-effect elements 1228A, 1228B, 1228C, 1228D in an area 1230 of the position sensor 1200 that is located above the magnet 1202 (FIG. 11). A high resolution ADC 1232 and a smart power management controller 1238 are also provided on the chip. A CORDIC processor 1236 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits and magnetic field information are transmitted over a standard serial communication interface such as an SPI interface 1234 to the controller 1104. The position sensor 1200 provides 12 or 14 bits of resolution. The position sensor 1200 may be an AS5055 chip provided in a small QFN 16-pin 4×4×0.85 mm package.

With reference to FIGS. 1-4 and 10-21, the position of the articulation joint 2270 and the position of the I-beam 178 (FIG. 4) can be determined with the absolute position feedback signal/value from the absolute positioning system 1100. In one aspect, the articulation angle can be determined fairly accurately based on the drive member 120 of the surgical instrument 10. As described above, the movement of the longitudinally movable drive member 120 (FIG. 2) can be tracked by the absolute positioning system 1100 wherein, when the articulation drive is operably coupled to the firing member 220 (FIG. 3) by the clutch assembly 400 (FIG. 3), for example, the absolute positioning system 1100 can, in effect, track the movement of the articulation system via the drive member 120. As a result of tracking the movement of the articulation system, the controller of the surgical instrument can track the articulation angle θ of the end effector 2300, such as the end effector 2300, for example. In various circumstances, as a result, the articulation angle θ can be determined as a function of longitudinal displacement DL of the drive member 120. Since the longitudinal displacement DL of the drive member 120 can be precisely determined based on the absolute position signal/value provided by the absolute positioning system 1100, the articulation angle θ can be determined as a function of longitudinal displacement DL.

In another aspect, the articulation angle θ can be determined by locating sensors on the articulation joint 2270. The sensors can be configured to sense rotation of the articulation joint 2270 using the absolute positioning system 1100 adapted to measure absolute rotation of the articulation joint 2270. For example, the sensor arrangement 1102 comprises a position sensor 1200, a magnet 1202, and a magnet holder 1204 adapted to sense rotation of the articulation joint 2270. The position sensor 1200 comprises one or more than one magnetic sensing elements such as Hall elements and is placed in proximity to the magnet 1202. The position sensor 1200 described in FIG. 12 can be adapted to measure the rotation angle of the articulation joint 2270. Accordingly, as the magnet 1202 rotates, the magnetic sensing elements of the position sensor 1200 determine the absolute angular position of the magnet 1202 located on the articulation joint 2270. This information is provided to the microcontroller 1104 to calculate the articulation angle of the articulation joint 2270. Accordingly, the articulation angle of the end effector 2300 can be determined by the absolute positioning system 1100 adapted to measure absolute rotation of the articulation joint 2270.

In one aspect, the firing rate or velocity of the I-beam 178 may be varied as a function of end effector 2300 articulation angle to lower the force-to-fire on the firing drive system 80 and, in particular, the force-to-fire of the I-beam 178, among other components of the firing drive system 80 discussed herein. To adapt to the variable firing force of the I-beam 178 as a function of end effector 2300 articulation angle, a variable motor control voltage can be applied to the motor 82 to control the velocity of the motor 82. The velocity of the motor 82 may be controlled by comparing the I-beam 178 firing force to different maximum thresholds based on articulation angle of the end effector 2300. The velocity of the electric motor 82 can be varied by adjusting the voltage, current, pulse width modulation (PWM), or duty cycle (0-100%) applied to the motor 82, for example.

Referring now to FIGS. 22-23 and 26-32, there are shown a variety of diagrams. The axes in each of these figures are normalized such that each axis represents a ratio between a minimum value and a maximum value, rather than set values. The minimum and maximum values of the variables represented in these graphs can vary according to different aspects of the surgical instrument. For example, the minimum articulation angle of the sweep range of the end effector can in various aspects include −65°, −60°, and −45° and the maximum articulation angle of the end effector of the sweep range of the end effector can in various aspects include +45°, +60°, and +65° relative to the longitudinal axis of the elongated shaft assembly. Furthermore, it can be understood that although the above examples were discussed in terms of degrees, angular position can additionally be represented in terms of radians or any other unit of angular position. As another example, the minimum and maximum position of the articulation driver can include 0.0m and 0.304m, respectively. Furthermore, it can be understood that although the above example was discussed in terms of meters, linear position can additionally be represented in terms of feet, inches, or any other unit of linear position.

Figure 22:
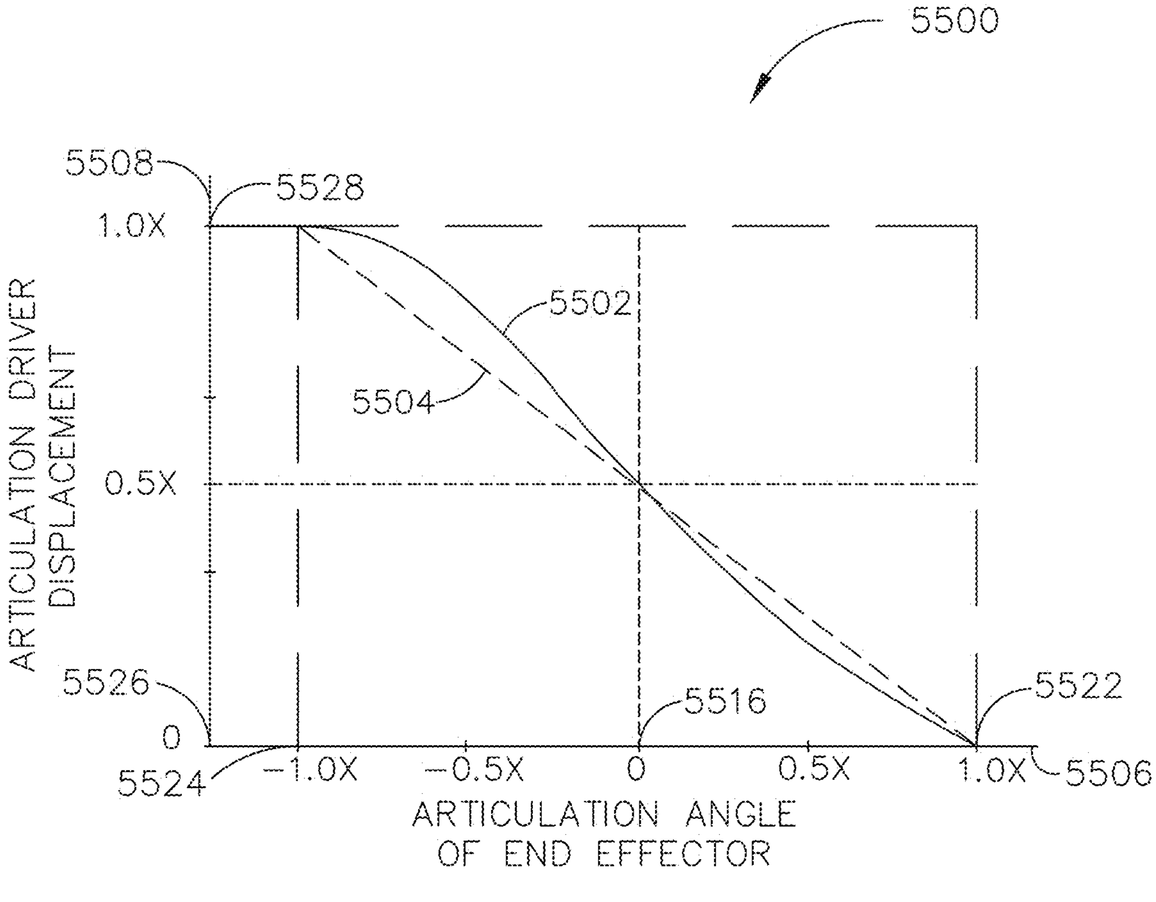
FIG. 22 is a diagram illustrating displacement of an articulation driver relative to end an effector articulation angle for constant articulation driver velocity and variable articulation drive velocity according to one aspect of this disclosure.

In some aspects of the surgical instrument wherein the angular displacement of the end effector through the articulation joint is driven by the displacement of the articulation driver, such as the aspect depicted in FIGS. 19-21, there exists a non-linear relationship between the displacement of the articulation driver 230 (FIG. 17) and the angular displacement of the end effector 2300 (FIGS. 19-21). Stated differently, there may not be a 1:1 relationship between the displacement of the articulation driver and the angular displacement of the end effector due to the kinematics of the linkage between the components. Referring specifically now to FIG. 22, there is shown a diagram 5500 illustrating articulation driver displacement 5508 relative to end an effector articulation angle 5506 for constant articulation driver velocity and variable articulation drive velocity according to one aspect of this disclosure. In some aspects of the surgical instrument, the articulation driver is driven from a first position 5526 to a second position 5528 at a constant rate, as depicted by line 5504, that is independent of the articulation angle of the end effector. In these aspects, the articulation velocity, i.e., rate of angular displacement of the end effector, varies according to the particular articulation angle of the end effector due to the non-linear relationship with the displacement of the articulation driver. Notably, the natural response of the linkage between the end effector and the articulation driver in some such aspects is to cause the articulation velocity of the end effector to increase from a midpoint 5516 towards the ends 5522, 5524 of the end effector articulation range, if the articulation driver is being translated at a constant rate. In some cases, it may be desired for the articulation velocity to remain constant throughout the entire articulation range of the end effector, i.e., from the first end 5522 to the second end 5524 of the articulation range. In such aspects where it is desired to compensate for the kinematics of the linkage between the articulation driver and the end effector, the articulation driver is driven at a variable rate, as depicted by line 5502, as a function of the articulation angle.

Figure 23:
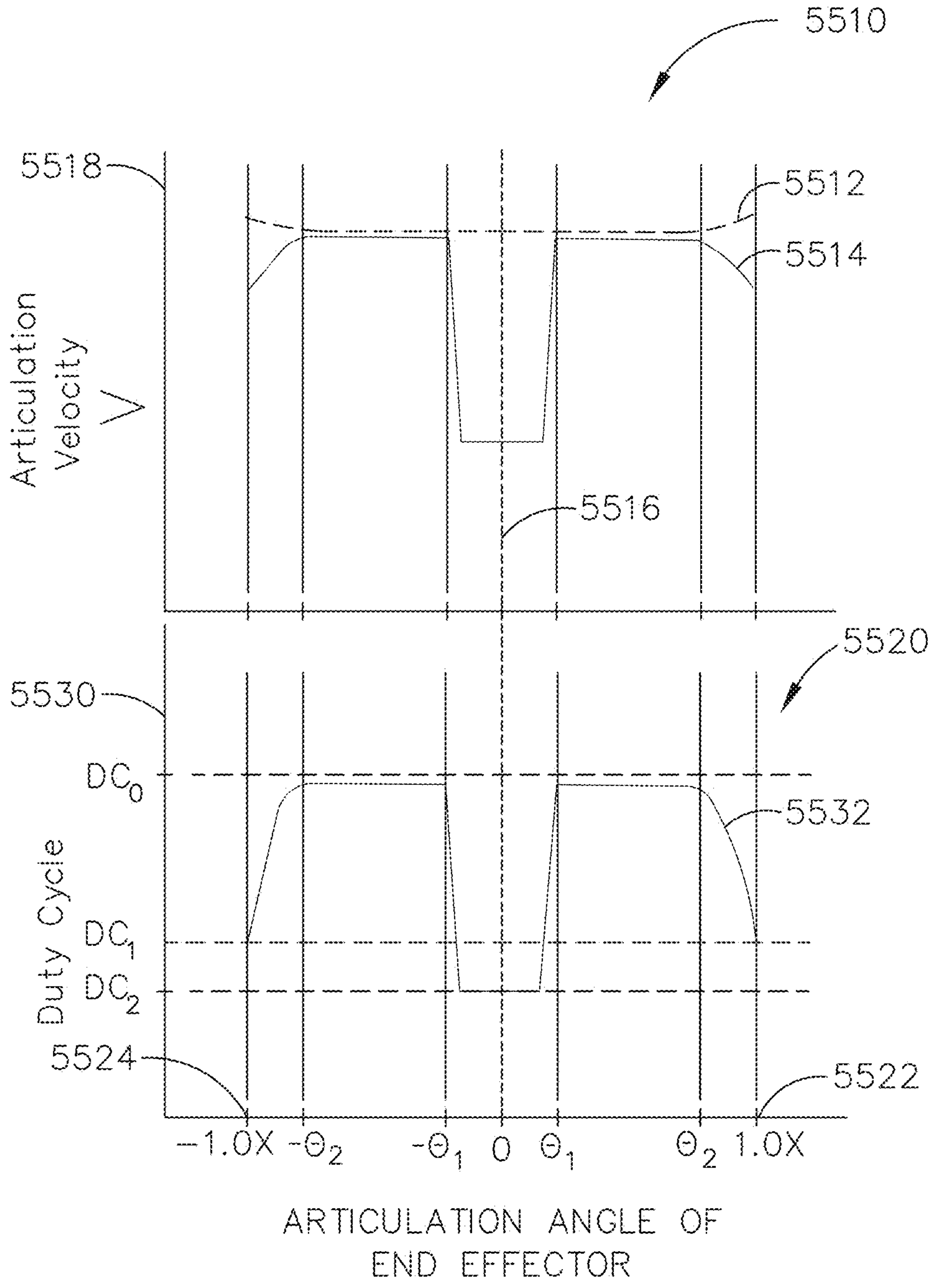
FIG. 23 is a first diagram illustrating articulation velocity relative to articulation angle of an end effector and a second diagram illustrating motor duty cycle relative to articulation angle of an end effector according to one aspect of this disclosure.

FIG. 23 depicts a first diagram 5510 illustrating articulation velocity 5518 relative to the articulation angle of the end effector 5506 and a second diagram 5520 illustrating motor duty cycle 5530 relative to the articulation angle of the end effector 5506. In addition to controlling the articulation of the end effector to provide a constant angular displacement rate over the articulation range of the end effector or a portion of the articulation range of the end effector, the articulation velocity can additionally be adjusted to a fixed value when the end effector is positioned at or near certain locations within the end effector articulation range. Stated differently, in certain aspects the articulation range can include a first zone, wherein the articulation velocity is a fixed value, and a second zone, wherein the articulation velocity is a function of the particular position or articulation angle of the end effector. Line 5514 exemplifies a control scheme for a surgical instrument that includes one or more zones wherein the articulation velocity is a fixed value. Comparatively, line 5512 exemplifies a control scheme for a surgical instrument wherein the displacement of the articulation driver is constant, as depicted by line 5504 in FIG. 22. As exemplified by line 5514, the end effector can be slowed when it reaches within a threshold distance from a predefined location. In one such aspect, the end effector is slowed to $V_2$, which is less than the default or steady state velocity, $V_0$, when the end effector falls within $\theta_1$ degrees of the home or default position. The home or default position can be, for example, the 0° position 5516, which is the position in which the end effector is aligned with the longitudinal axis of the shaft. Such an aspect wherein the end effector slows when it nears the home position can be beneficial in making it easier to remove the surgical instrument from a trocar through which the instrument is positioned. In another aspect, the end effector is slowed to $V_1$, which is less than the default or steady state velocity, $V_0$, when the end effector is positioned in excess of $\theta_2$ degrees from the default or home position. Such an aspect wherein the end effector slows near the ends 5522, 5524 of its articulation range can be useful in signaling to a user of the surgical instrument that the end effector is nearing the end of its effective range. Line 5532 in the second diagram 5520 indicating the change in the duty cycle at which the motor is driven corresponds to line 5514 in the first diagram 5510. In various aspects, the duty cycle at which the motor is driven can be adjusted according to the desired articulation velocity of the end effector. In various other aspects, the articulation velocity of the end effector can also be increased, as opposed to decreased as described above, relative to the default or steady state velocity according to the position of the end effector. Aspects utilizing combinations of positional ranges where the articulation velocity of the end effector is adjusted are also within the scope of the present disclosure.

There are several possible methods for controlling the angular velocity of the end effector by varying the velocity of the articulation driver 230 according to the articulation angle at which the end effector is positioned. One such method is varying the duty cycle of the motor driving the articulation driver 230, which is referred to as pulse width modulation (PWM). One aspect utilizing this method is illustrated as line 5532, which corresponds to line 5514 depicting the change in articulation velocity of the end effector 2502 as a function of the articulation angle. Another method is varying the magnitude of the voltage supplied to the motor driving the articulation driver. A third method is utilizing a combination of PWM and varying the magnitude of the voltage supplied to the motor. As the velocity at which the motor drives the articulation driver 230 corresponds to both the duty cycle at which the motor is operating and the magnitude of the voltage received by the motor, each of the aforementioned methods allows the surgical instrument to control the velocity of the articulation driver 230 and, thus, the angular velocity of the end effector.

Figure 24:
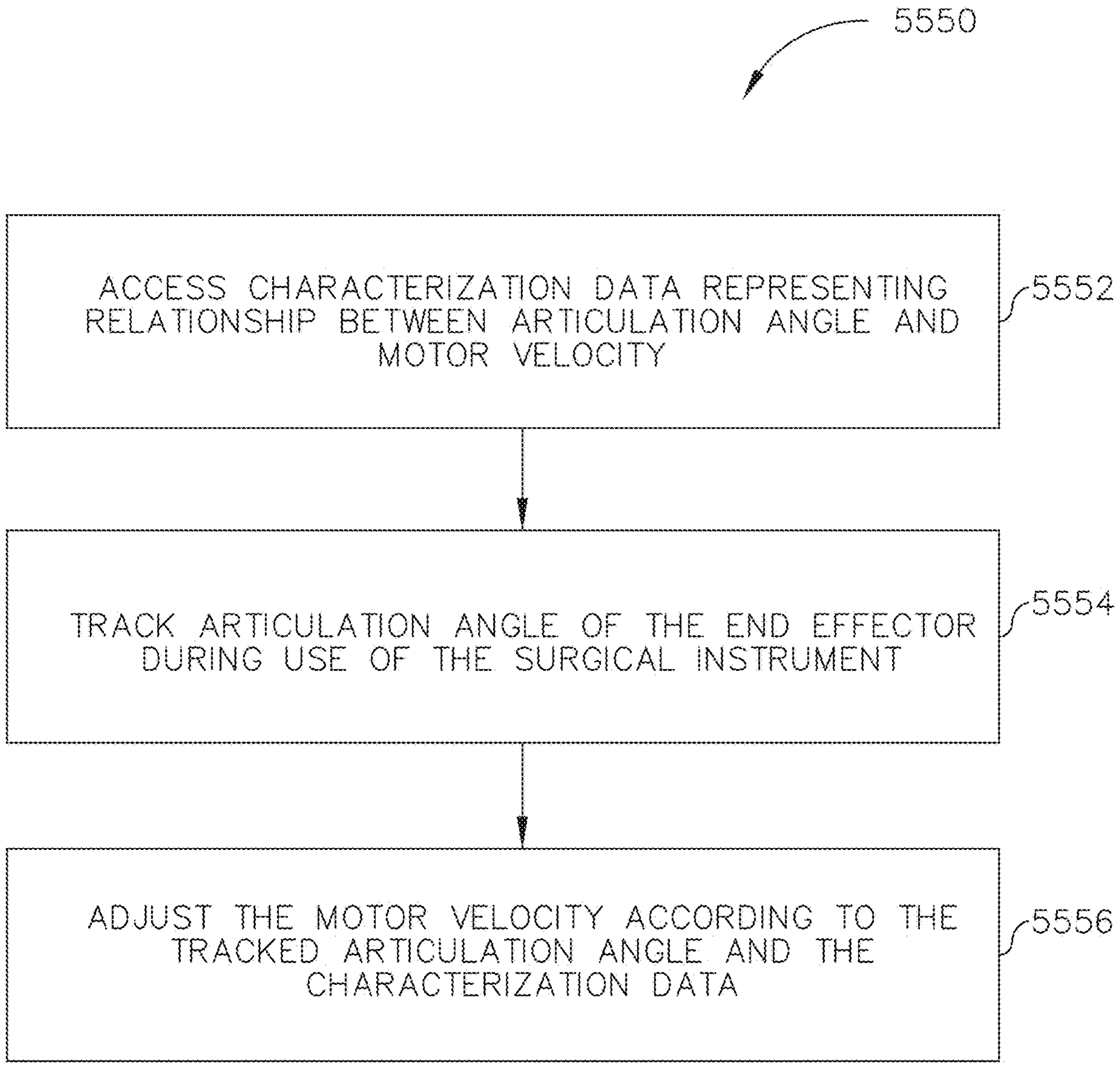
FIG. 24 is a logic flow diagram depicting a process of a control program or a logic configuration for controlling end effector articulation velocity according to one aspect of this disclosure.

FIG. 24 illustrates a logic flow diagram depicting a process of a control program or a logic configuration for controlling end effector articulation velocity according to one aspect of this disclosure. In the following description of the logic 5550 in FIG. 24, reference should also be made to FIG. 14-21. In one aspect of a logic 5550 for controlling the articulation velocity of the end effector 2502, the relationship between the articulation angle of the end effector 2502 and a property of the motor 2504 affecting the articulation velocity of the end effector 2502 is initially characterized and the characterization data is stored in the memory of the surgical instrument 2500. The property of the motor 2504 affecting the articulation velocity of the end effector 2502 can include the duty cycle of the motor, the magnitude of the voltage supplied to the motor, a combination thereof, or other such methods. In one aspect, the memory is a non-volatile memory such as flash memory, EEPROM, and the like. When the surgical instrument is being utilized, the control circuit 2510 accesses 5552 the characterization data stored in the memory. In aspects wherein the position of the articulation driver 230 is tracked by the articulation sensor arrangement as a proxy for the articulation angle of the end effector 2502, the relationship between the position of the articulation driver 230 and the property of the motor can instead be initially characterized in order to reduce the processing power that would otherwise be required to first translate the position of the articulation driver 230 to the angular position of the end effector 2502, prior to accessing 5552 the characterized data stored in the memory according to the translated angular position of the end effector 2502.

In one aspect, the output of the characterization process is an algorithm implemented in computer readable instructions stored in memory and executed by the control circuit 2510. Accordingly, in one aspect, the control circuit 2510 accesses 5552 the characterization data of the algorithm implemented in the memory, inputs either the angular position of the end effector 2502 (which is determined either directly or indirectly) or the position of the articulation driver 230, and then performs a run-time calculation to determine the output, which is the value the particular motor property is to be set at to effectuate the desired articulation velocity of the end effector 2502.

In one aspect, the output of the characterization process is a lookup table implemented in the memory. Accordingly, in one aspect, the control circuit 2510 accesses 5552 the characterization data from the lookup table implemented in the memory. In one aspect, the lookup table comprises an array that replaces runtime computation with a simpler array indexing operation. The savings in terms of processing time can be significant, since retrieving a value from the memory by the control circuit 2510 is generally faster than undergoing an "expensive" computation or input/output operation. The lookup table may be precalculated and stored in static program storage, calculated (or "pre-fetched") as part of a program's initialization phase (memorization), or even stored in hardware in application-specific platforms. In the instant application, the lookup table stores the output values of the characterization of the relationship between articulation angle of the end effector 2502 and the property of the motor 2504 dictating the articulation velocity of the end effector 2502. The lookup table stores these output values in an array and, in some programming languages, may include pointer functions (or offsets to labels) to process the matching input. Thus, for each unique value of the articulation angle of the end effector 2502 or the position of the articulation driver 230 (as a proxy for the articulation angle), there exists a corresponding motor 2504 duty cycle value. The corresponding motor 2504 duty cycle value is stored in the lookup table and is used by the control circuit 2510 to determine what duty cycle the motor 2504 should be set to according to the angular position of the end effector 2502. Other lookup table techniques are contemplated within the scope of the present disclosure.

In one aspect, the output of the characterization process is a best curve fit formula, linear or nonlinear. Accordingly, in one aspect, the control circuit 2510 is operative to execute computer readable instructions to implement a best curve fit formula based on the characterization data. Curve fitting is the process of constructing a curve, or mathematical function that has the best fit to a series of data points, possibly subject to constraints. Curve fitting can involve either interpolation, where an exact fit to the data is required. In one aspect, the curve represents the motor 2504 duty cycle at which the motor is to be set as a function of the articulation angle of the end effector 2502. The data points such as the articulation angle of the end effector 2502, the position of the articulation driver 230, and the motor 2504 duty cycle can be measured and used to generate a best fit curve in the form of an $n^{th}$ order polynomial (usually a $3^{rd}$ order polynomial would provide a suitable curve fit to the measured data). The control circuit 2510 can be programmed to implement the $n^{th}$ order polynomial. In use, the input of the $n^{th}$ order polynomial is the angular position of the end effector 2502 and/or the position of the articulation driver 230.

As the surgical instrument is operated, the surgical instrument tracks 5554 the articulation angle of the end effector 2502, either directly or indirectly, via an articulation sensor arrangement, as described above. As the articulation angle is tracked 5554, the surgical instrument adjusts 5556 one or more properties of the motor 2504, such as the duty cycle of the motor 2504, to in turn adjust the articulation velocity at which the motor 2504 drives the end effector 2502. The property (or properties) of the motor 2504 that is adjusted according to the characterization data to control the articulation velocity of the end effector 2502 includes, for example, varying the motor duty cycle, varying the magnitude of the voltage supplied to the motor, or a combination thereof. The logic 5550 therefore provides a dynamic system wherein the motor is controlled to continuously or regularly adjust the articulation velocity of the end effector 2502 according to the pre-characterized data.

In various aspects, the memory for storing the characterization may be a nonvolatile memory located on the on the shaft, the handle, or both, of the surgical instrument.

In one aspect, the characterization is utilized by control software of the microcontroller communicating with the non-volatile memory to gain access to the characterization.

Figure 25:
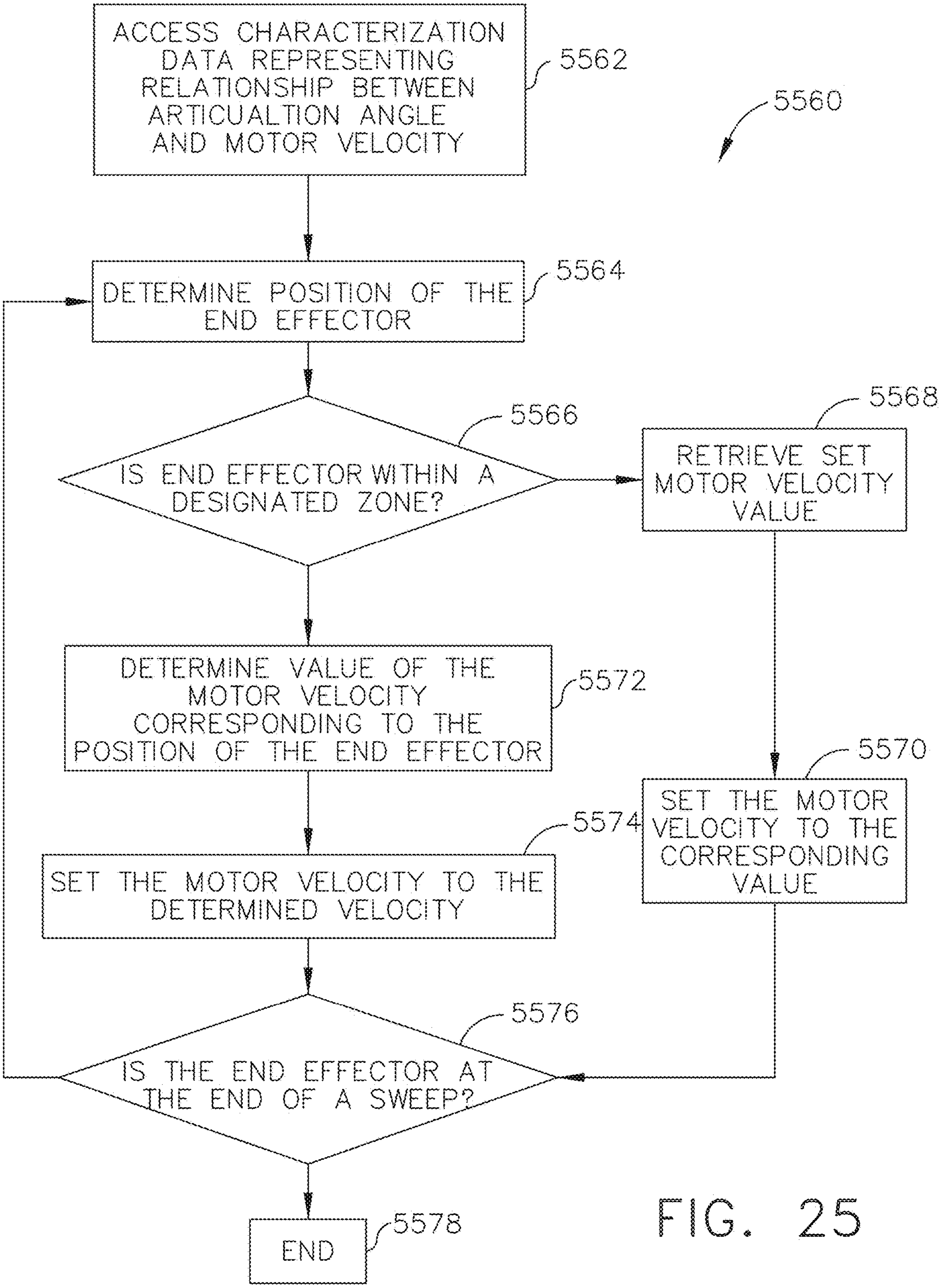
FIG. 25 is a logic flow diagram depicting a process of a control program or a logic configuration for controlling end effector articulation velocity according to one aspect of this disclosure.

FIG. 25 illustrates another aspect of a logic flow diagram depicting a process of a control program or a logic configuration for controlling the end effector articulation velocity. As above, in the following description of the logic 5560 in FIG. 25, reference should also be made to FIG. 14-21. In one aspect, the logic 5560 for controlling the articulation velocity of the end effector 2502 comprises accessing 5562 characterization data of the relationship between the articulation angle of the end effector 2502 and a property of the motor 2504 affecting the articulation velocity of the end effector 2502. The characterization data can be accessed 5562 prior to or during use of the surgical instrument 2500. The relationship between the articulation angle of the end effector 2502 and the property of the motor 2504 can initially be stored in the memory of the surgical instrument. The property of the motor 2504 affecting the articulation velocity of the end effector 2502 can include the duty cycle of the motor, the magnitude of the voltage received by the motor, and a combination thereof.

Once the characterization data is accessed 5562, the logic 5560 then determines 5564 the present position or articulation angle of the end effector 2502 via an articulation sensor arrangement. The logic 5560 then determines 5566 whether the end effector 2502 is positioned within one or more designated zones within the angular articulation range or sweep of the end effector 2502. The designated zones within the articulation range of the end effector 2502 correspond to areas where the end effector 2502 is driven at a certain fixed velocity, rather than at a velocity that corresponds to the articulation angle at which the end effector 2502 is positioned. In one aspect, a designated zone includes when the end effector 2502 is positioned within a threshold distance of a set position, as illustrated in FIG. 23. The designated zone or zones are also referred to collectively as a "first zone" and the remaining portion or portions of the articulation range of the end effector are also referred to collectively as a "second zone."

The first zone can include multiple discrete portions of the angular articulation range of the end effector 2502, as also illustrated in FIG. 23. If the end effector 2502 is within the first zone, the logic 5560 then retrieves 5568 a fixed value for the particular motor 2504 property and then sets 5570 the motor 2504 property to that value. The fixed value can be stored in, for example, a lookup table implemented in memory. In the aspect of the logic 5560 corresponding to FIG. 23, for example, if the end effector 2502 is within $\theta_1$ degrees of a position, then the logic 5560 retrieves 5568 the motor 2504 duty cycle value $DC_2$ and then sets 5570 the motor 2504 duty cycle to that value for the duration of the time that the end effector 2502 is within that particular portion of the first zone. In one aspect of the logic 5560, there can be multiple designated zones wherein a motor 2504 property, such as the duty cycle at which the motor 2504 is driven, is set to a fixed value. In the aspect of the logic 5560 corresponding to FIG. 23, for example, in addition to the motor being set to duty cycle $DC_2$ if it is within $\theta_1$ degrees of a position 5516, the sweep range can include additional zones where the motor is set to duty cycle $DC_1$ if the end effector 2502 is greater than $\theta_2$ degrees from a position 5516. If the end effector 2502 is not within the first zone, i.e., is in the second zone, the logic 5560 instead determines 5572 the value of the motor property corresponding to the particular position of the end effector 2502 and then sets 5574 the motor property to the determined value. The logic 5560 can determine 5572 the motor property value by accessing the output characterization data in a variety of manners, as described above.

Once the property of the motor 2504 has been set 5570 to a fixed value or set 5574 to a value that is a function of the position of the end effector 5572, the logic 5560 then determines 5576 whether the sweep of the end effector 2502 is completed or whether the operator is otherwise finished using the surgical instrument 2500. The logic 5560 can determine whether the end effector 2502 is no longer in use by, for example, monitoring whether the articulation lock 2810 is engaged. If the sweep of the end effector 2502 is completed, then the logic 5560 is likewise completed 5578 for the particular sweep of the end effector 2502. If the sweep of the end effector 2502 is not completed, then the logic 5560 continues monitoring the position of the end effector 2502 and adjusting the articulation velocity of the end effector 2502 until the sweep is completed 5578. In some aspects, the logic 5560 continuously monitors the position of the end effector. In other aspects, the logic 5560 implements a delay between instances of sampling the articulation angle of the end effector. The delay between instances of sampling the end effector 2502 position can be determined by, for example, a timer or counter circuit 2531.

Figure 26:
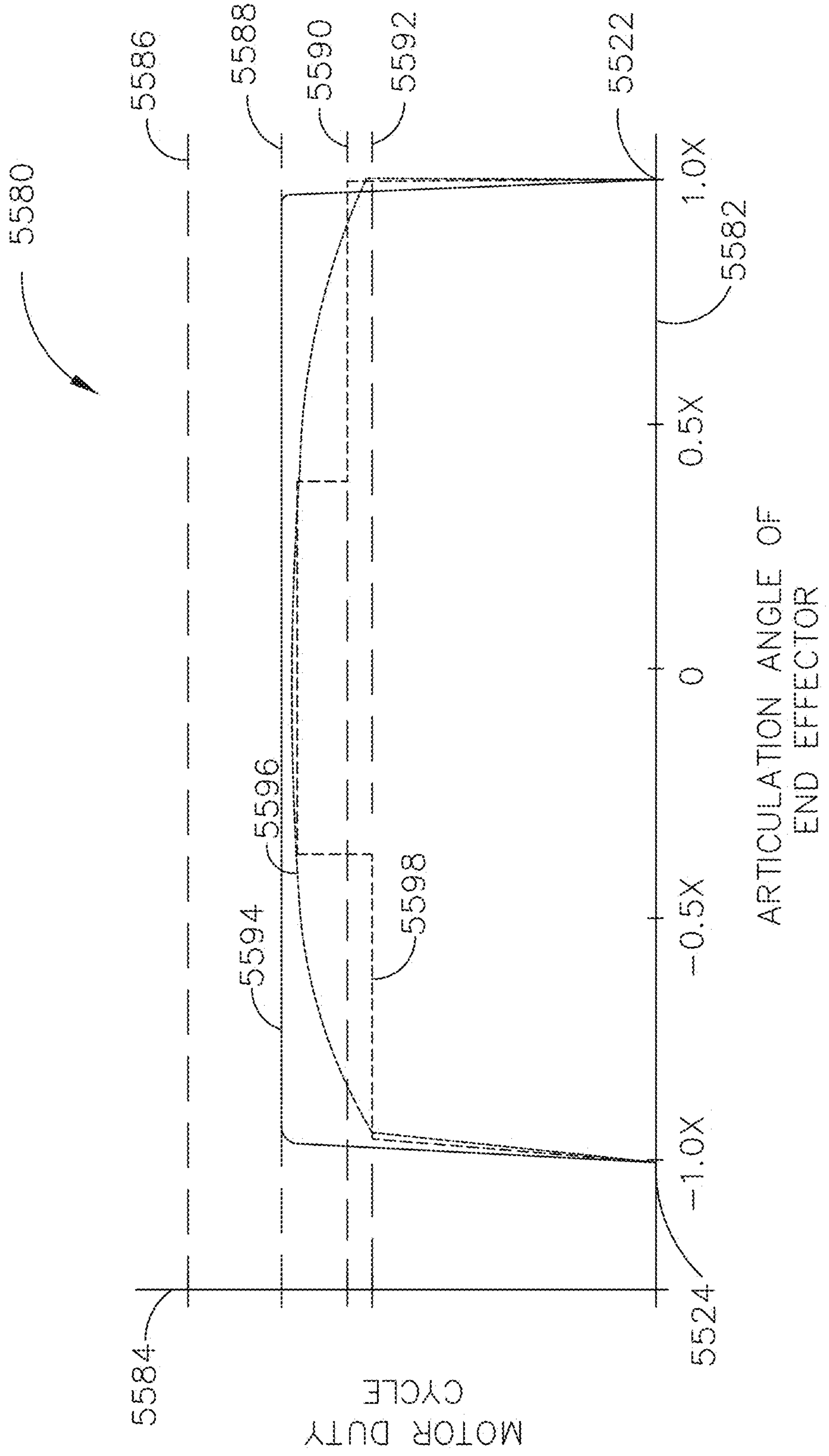
FIG. 26 is a diagram illustrating motor duty cycle relative to articulation angle of an end effector for aspects utilizing a constant motor duty cycle, a constantly variable motor duty cycle, and a discretely variable motor duty cycle according to one aspect of this disclosure.

FIG. 26 depicts a diagram 5580 illustrating the motor duty cycle 5584 relative to the articulation angle of the end effector for aspects utilizing a constant motor duty cycle, a constantly variable motor duty cycle, and a discretely variable motor duty cycle. In some aspects of the surgical instrument 2500, the duty cycle of the motor is held constant throughout the sweep of the end effector 2502, as represented by line 5594. In other words, the duty cycle of the motor 2504 is not a function of the position or articulation angle of the end effector 2502. The constant duty cycle 5588 can be less than or equal to a maximum duty cycle 5586 at which the motor 2504 can be driven. In other aspects, the motor 2504 duty cycle is varied according to the articulation angle of the end effector 2502. In one such aspect represented by line 5596, the articulation angle of the end effector 2502 is sampled continuously and the articulation sensor arrangement has a correspondingly high resolution that is able to detect the articulation angle of the end effector 2502 throughout its angular sweep. In this aspect, the motor 2504 duty cycle can be updated at a very high rate, illustrated by the smooth, continuous curvature of the line 5596. In another such aspect represented by line 5598, the articulation angle of the end effector 2502 is sampled at a relatively low rate and/or the articulation sensor arrangement has a relatively low resolution. In this aspect, the motor 2504 duty cycle is updated at discrete points, rather than continuously over the course of the angular sweep of the end effector 2502. Aspects that sample the position of the end effector 2502 at a high rate and update the motor 2504 duty cycle at a corresponding high rate can be computationally expensive, but can also produce smoother, more consistent movement for the end effector 2502 as it articulates.

Although the aspects illustrated in FIG. 26 were described in terms of the motor duty cycle, it is to be understood that the principles are equally applicable to aspects wherein either the magnitude of the voltage supplied to the motor is adjusted or a combination of the motor duty cycle and the motor duty cycle are adjusted as a function of the articulation angle of the end effector.

Figure 27:
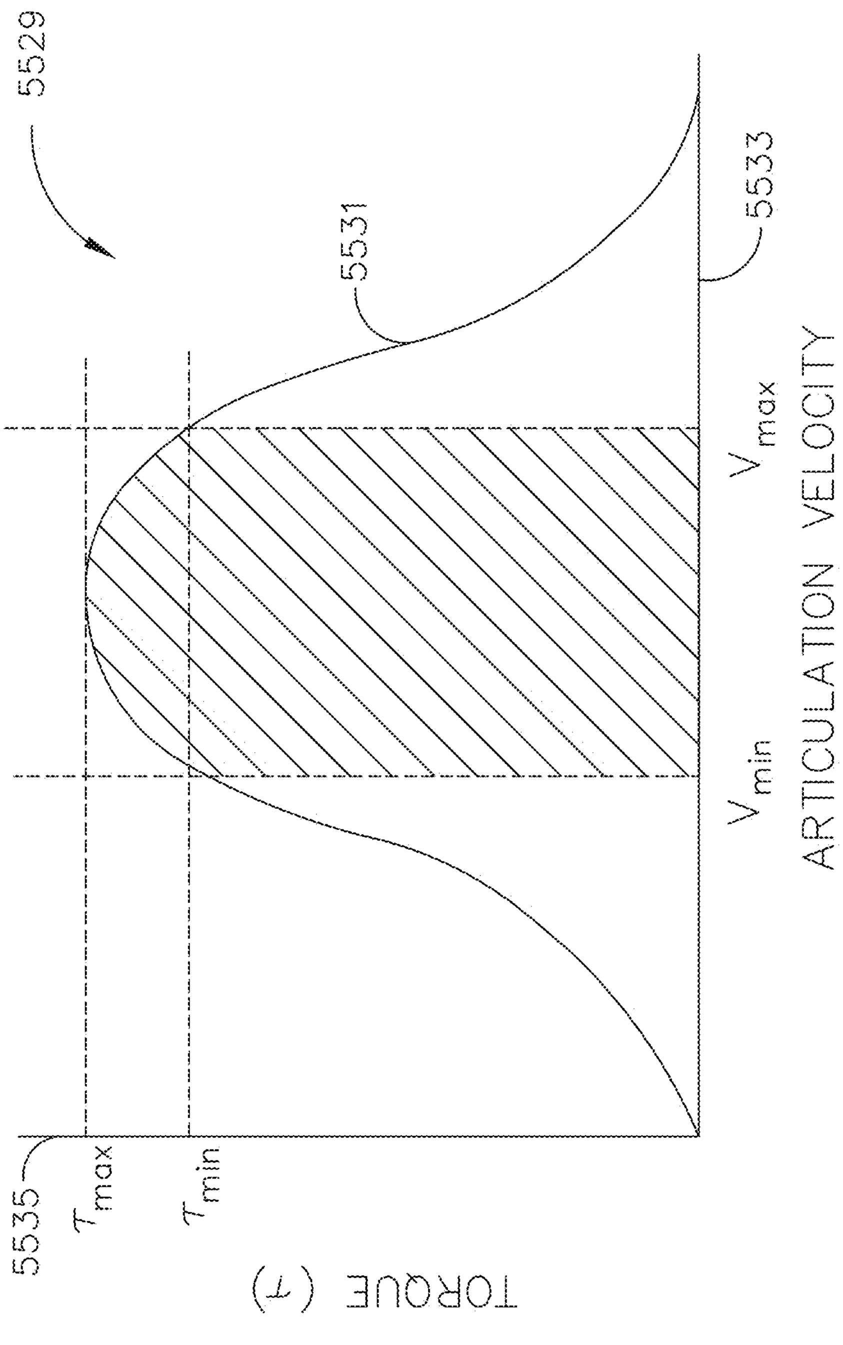
FIG. 27 is a diagram illustrating torque relative to articulation velocity of an end effector according to one aspect of this disclosure.

FIG. 27 shows a diagram 5529 illustrating torque 5535 relative to articulation velocity of an end effector 5533 according to one aspect of this disclosure. Line 5531 depicts the relationship between the articulation velocity of the end effector and the torque generated by the movement of the end effector. In some aspects, it can be beneficial to maintain the torque generated by the end effector between a first value $T_{min}$ and a second value $T_{max}$. Therefore, in order to maintain the torque generated by the articulation of the end effector between $T_{min}$ and $T_{max}$, the articulation velocity of the end effector is correspondingly maintained between a first value $V_{min}$ and a second value $V_{max}$. In such aspects, the logic executed by the surgical instrument can be configured to maintain the articulation velocity between $V_{min}$ and $V_{max}$ throughout the articulation range of the end effector. In aspects where the articulation velocity is set to certain fixed values within designated zones of the articulation range of the end effector, such as is depicted in FIG. 23, the fixed values can fall within the upper and lower bounds set by $V_{min}$ and $V_{max}$. In aspects where the end effector is articulated at a constant articulation velocity either throughout is articulation range or when the end effector is not located in one or more of the aforementioned designated zones, then the velocity at which the end effector is articulated can likewise fall within the upper and lower bounds set by $V_{min}$ and $V_{max}$.

Figure 28:
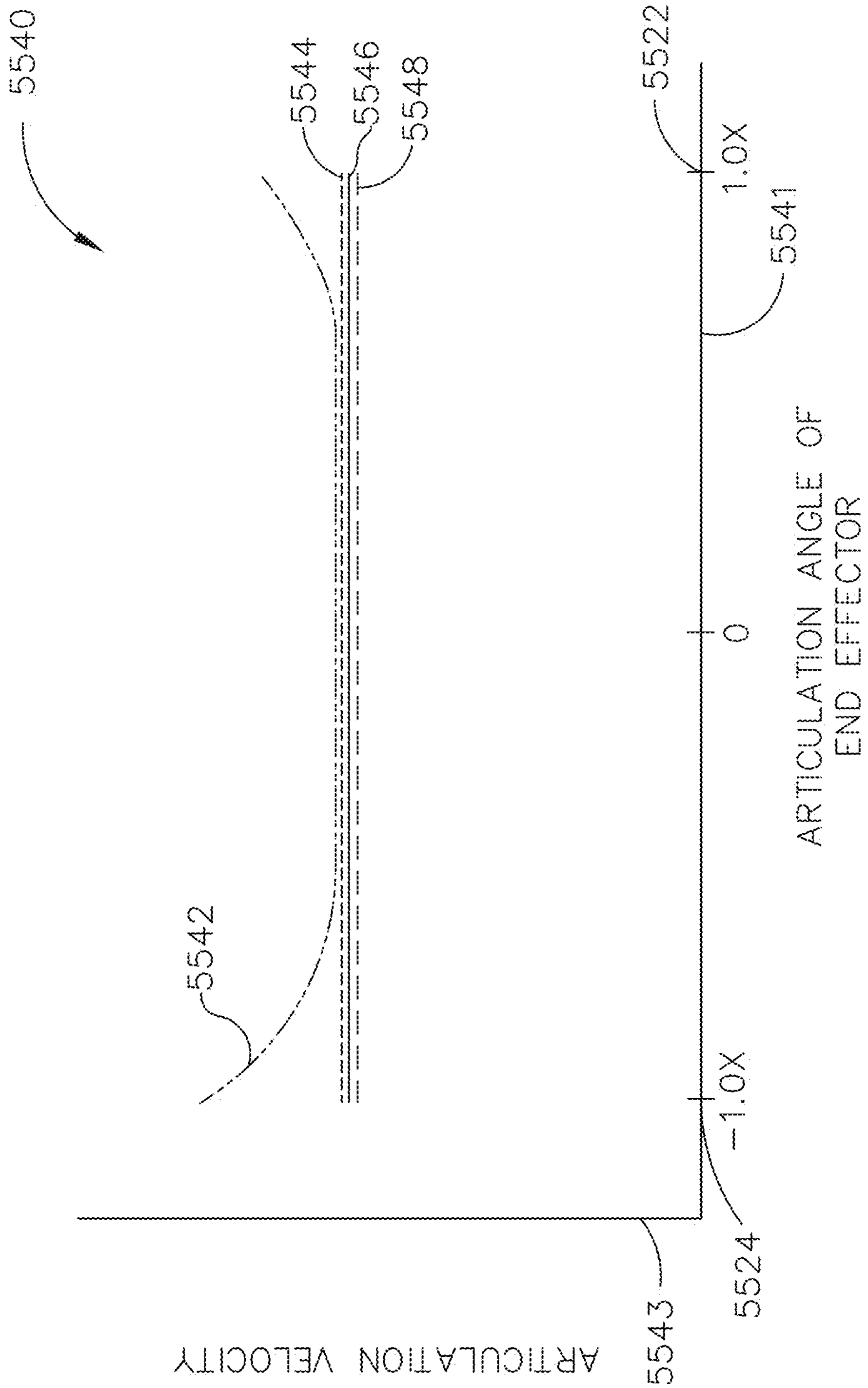
FIG. 28 is a diagram depicting articulation velocity of an end effector relative to articulation angle based on various control algorithms according to one aspect of this disclosure.
Figure 32:
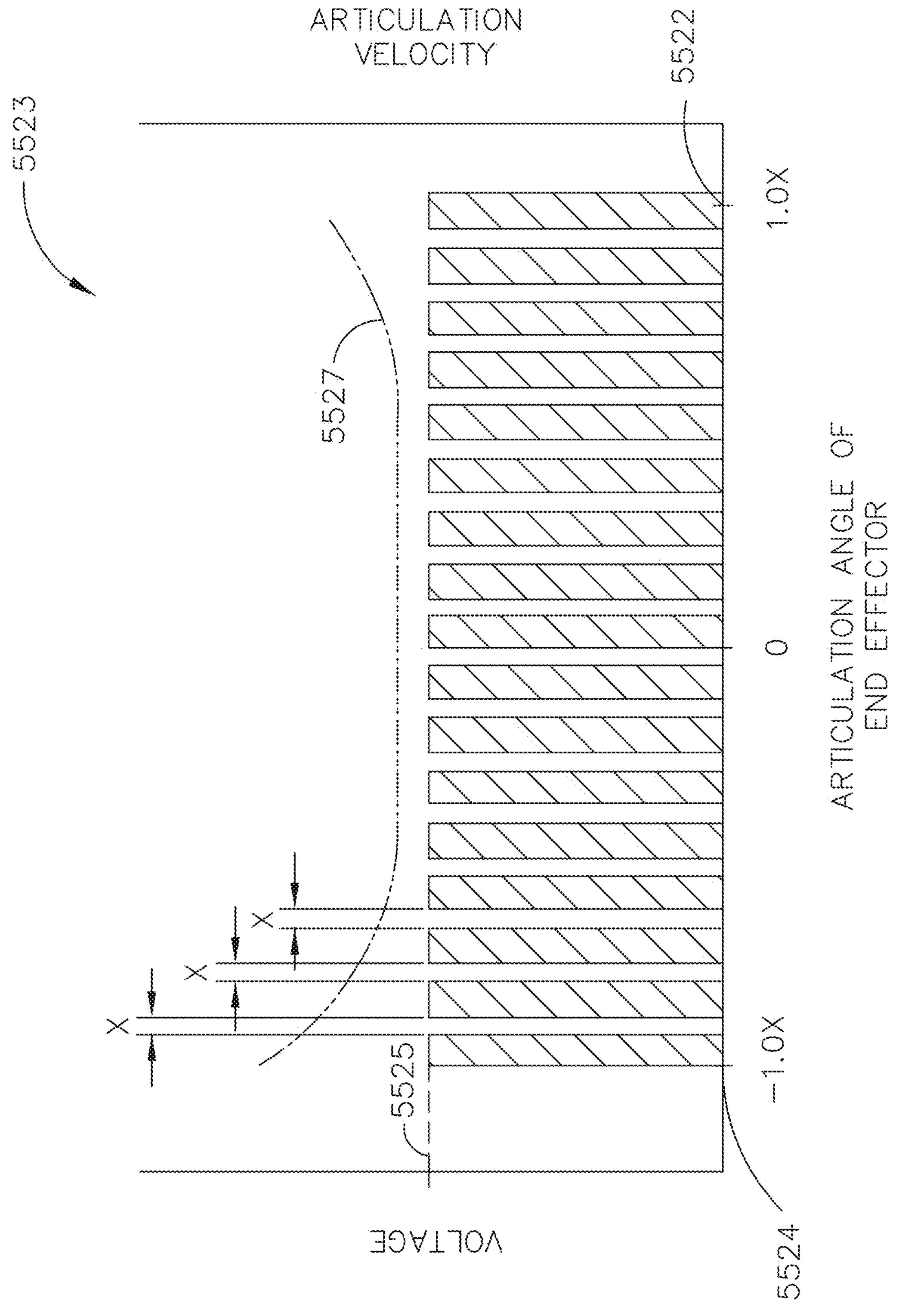

FIG. 28 shows a diagram 5540 depicting the articulation velocity 5543 of the end effector relative to the articulation angle 5541 according to various control algorithms according to one aspect of this disclosure. Line 5542 depicts an aspect of the surgical instrument wherein the articulation driver is driven by the motor at a constant rate, which causes the articulation velocity of the end effector to vary from a first end 5522 to a second end 5524 of its articulation range. In this aspect, the motor voltage and the motor duty cycle are held constant regardless of the articulation angle of the end effector, as illustrated in FIG. 32. FIG. 32 is a diagram 5523 that depicts a control algorithm for controlling an articulation velocity of an end effector utilizing constant voltage and no pulse width modulation. In this aspect, the motor is held at a constant voltage 5525, which results in the articulation velocity represented by line 5527 increasing towards the ends 5522, 5524 of the articulation range of the end effector.

Figure 29:
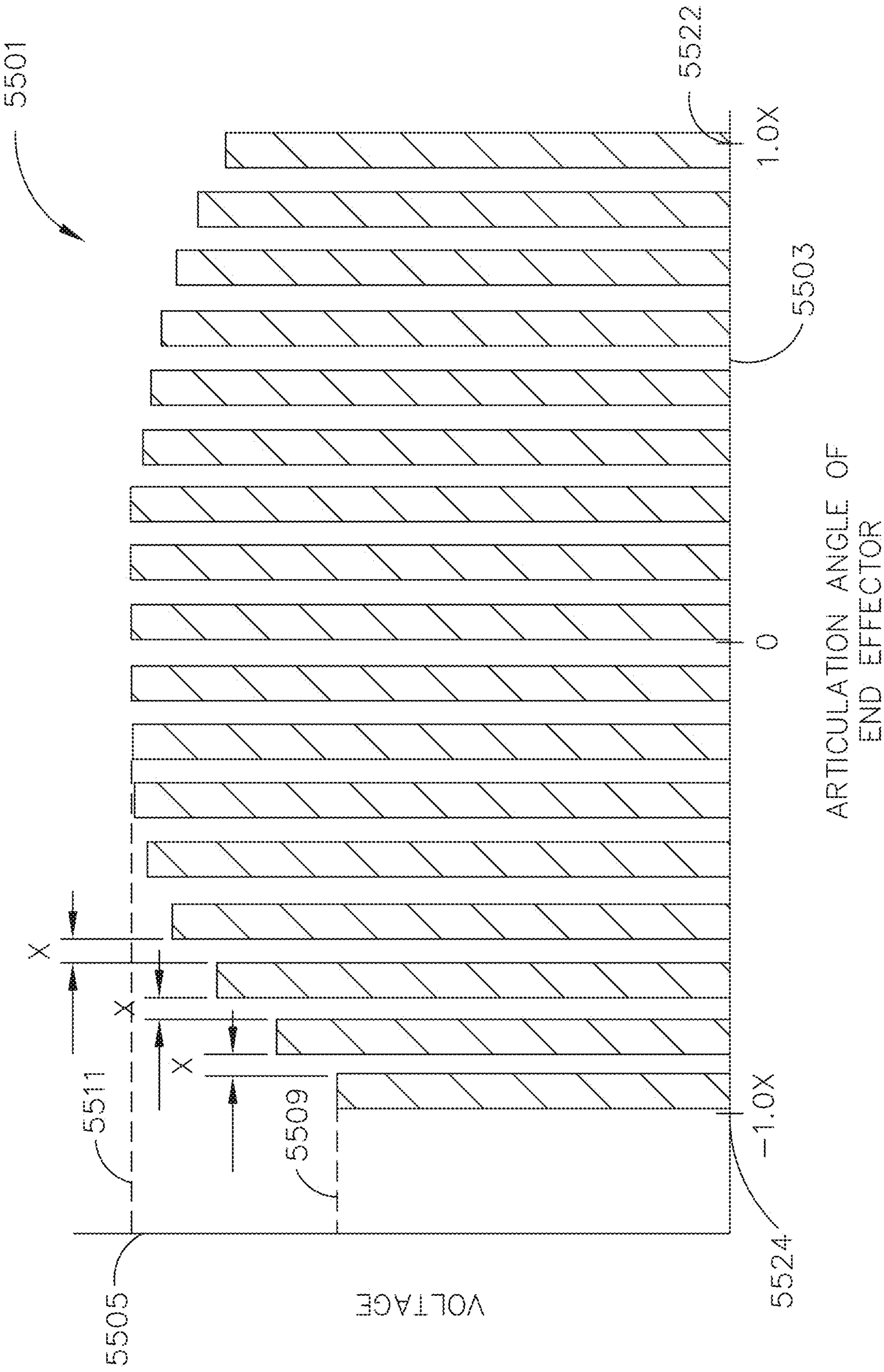
FIGS. 29-32 are diagrams depicting motor voltage and duty cycle relative to articulation angle of an end effector based on various control algorithms according to one aspect of this disclosure, where.

Conversely, lines 5544, 5546, 5548 in FIG. 28 depict aspects of the surgical instrument utilizing control algorithms, such as the logic described in FIGS. 24 and 25, to cause the end effector to have a constant articulation velocity throughout its entire range of movement. One such aspect is illustrated in FIG. 29. FIG. 29 is a diagram 5501 that depicts voltage 5505 relative to the articulation angle of the end effector 5503 for a control algorithm for controlling an articulation velocity of an end effector utilizing variable voltage and no pulse width modulation. In this aspect, the duty cycle is held constant, but the magnitude of the voltage supplied to the motor is varied as a function of the articulation angle of the end effector. For the particular linkage of the articulation pivot assembly described in FIGS. 14-21, the articulation velocity of the end effector tends to increase at the ends of the articulation range of movement. Therefore, to counteract this natural tendency and hold the articulation velocity of the end effector constant throughout the entire range of movement, the magnitude of the voltage supplied to the motor varies between a maximum voltage 5511 and a minimum voltage 5509, such that the voltage is decreased as the articulation angle of the end effector approaches the ends 5522, 5524 of the range of movement in order to slow the articulation driver and thus hold the articulation velocity constant. The voltage at each of the ends 5522, 5524 can be equal or unequal in various aspects of the surgical instrument.

Figure 30:
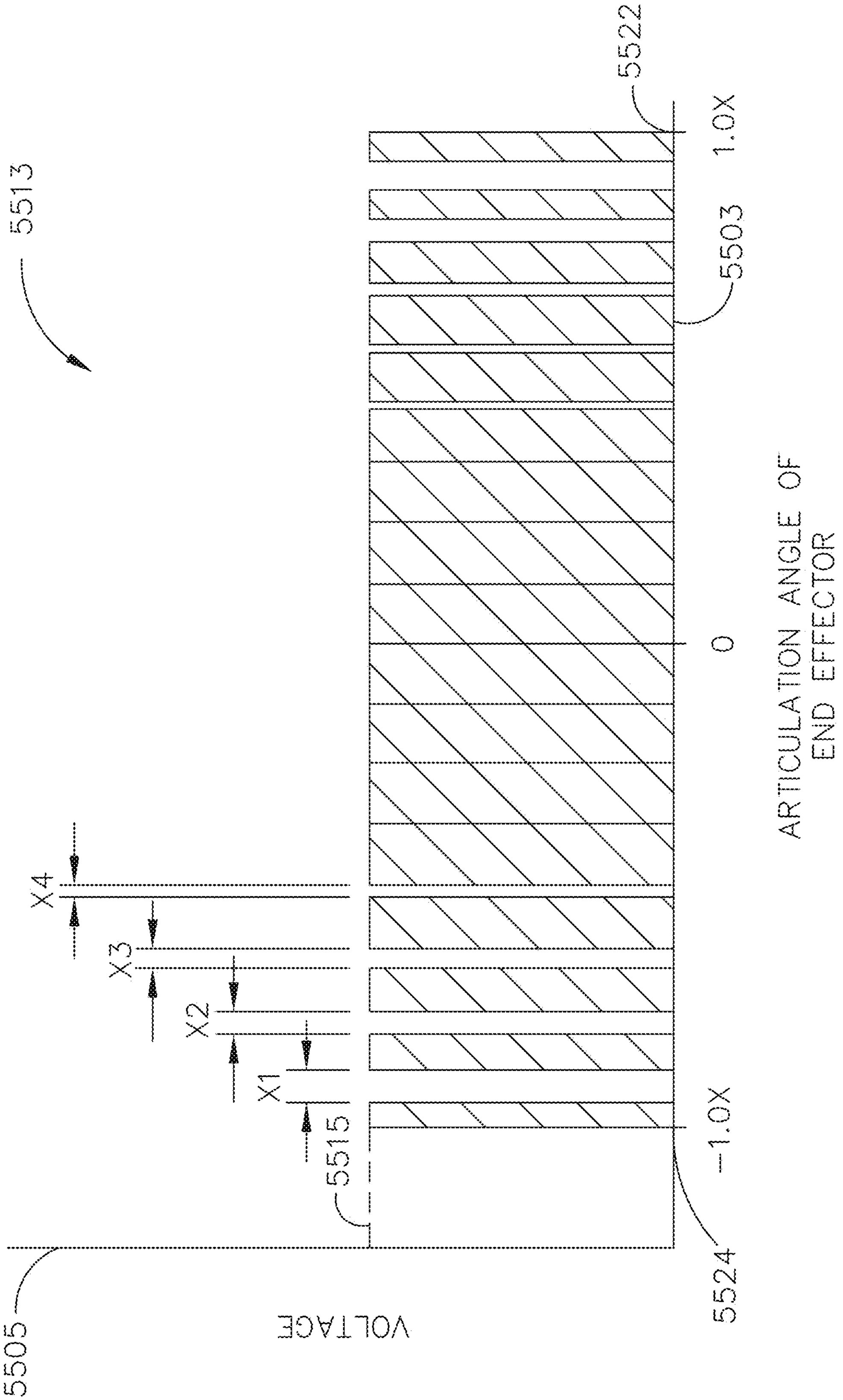
Figure 31:
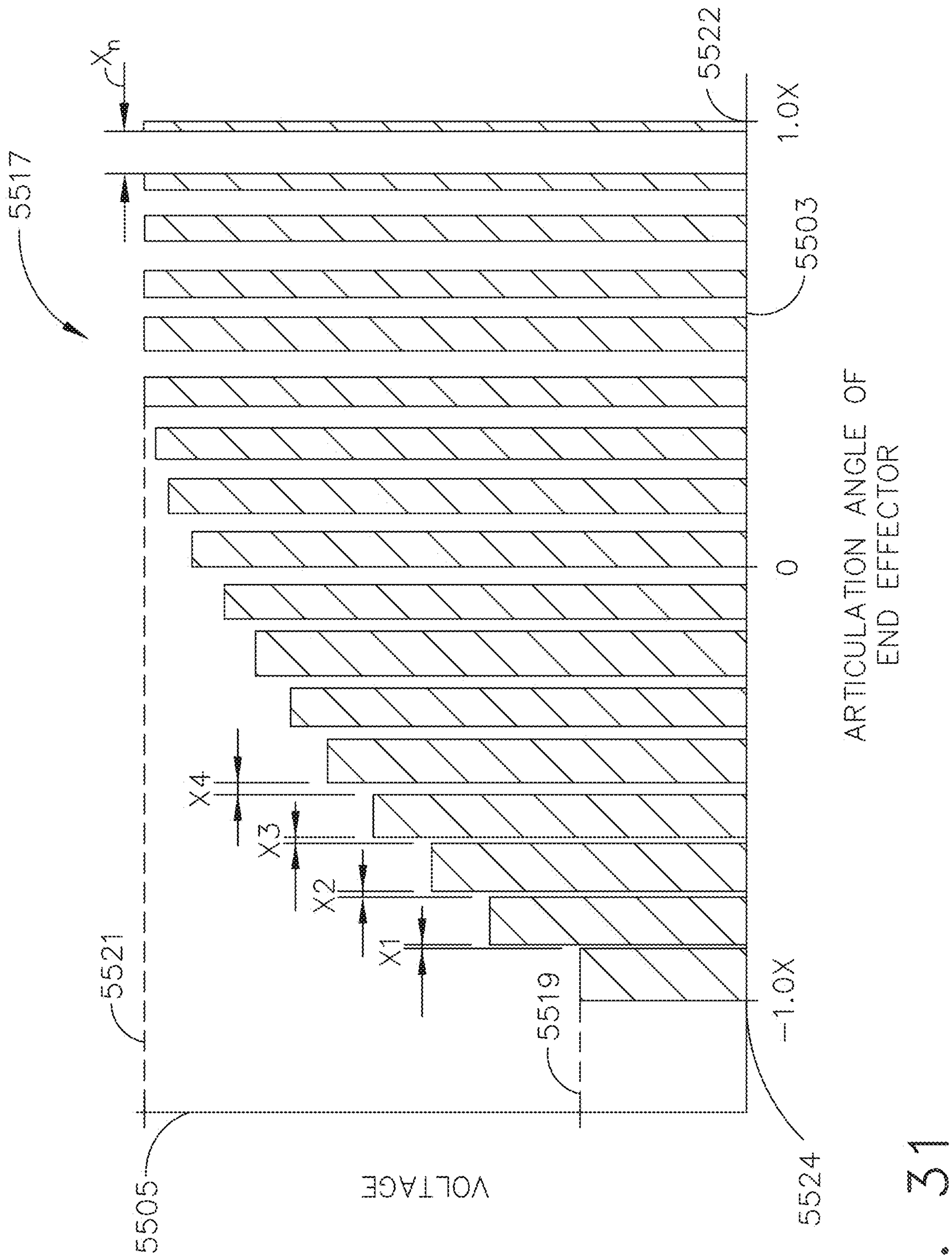

Another such aspect is illustrated in FIG. 30. FIG. 30 is a diagram 5513 that depicts voltage 5505 relative to the articulation angle of the end effector 5503 for a control algorithm for controlling an articulation velocity of an end effector utilizing constant voltage and pulse width modulation. In this aspect, the voltage supplied to the motor is held at a constant voltage 5515 and the duty cycle of the motor is decreased (such that $x_1>x_2>x_3$ and so on) as the articulation angle of the end effector approaches the ends 5522, 5524 of the range of movement in order to slow the articulation driver at the ends 5522, 5524 of the articulation range. Yet another such aspect is illustrated in FIG. 31. FIG. 31 is a diagram 5517 that depicts a control algorithm for controlling an articulation velocity of an end effector utilizing variable voltage and pulse width modulation. In this aspect, both the magnitude of the motor voltage and the motor duty cycle are varied as a function of the articulation angle of the end effector to the same general effect as was described with respect to FIGS. 29 and 30. The motor voltage is varied between a maximum voltage 5521 and a minimum voltage 5519. Accordingly, the duty cycle of the motor decreases (such that $x_1<x_2<x_3 \ldots <x_n$). The net effect between the varying motor voltage and the motor duty cycle is that the end effector is driven at a constant articulation velocity from the first end 5522 to the second end 5524 of its articulation range.

The functions or processes 5550, 5560 described herein may be executed by any of the processing circuits described herein, such as the control circuit 700 described in connection with FIGS. 5-6, the circuits 800, 810, 820 described in FIGS. 7-9, the microcontroller 1104 described in with FIGS. 10 and 12, and/or the control circuit 2510 described in FIG. 14.

Aspects of the motorized surgical instrument may be practiced without the specific details disclosed herein. Some aspects have been shown as block diagrams rather than detail. Parts of this disclosure may be presented in terms of instructions that operate on data stored in a computer memory. An algorithm refers to a self-consistent sequence of steps leading to a desired result, where a "step" refers to a manipulation of physical quantities which may take the form of electrical or magnetic signals capable of being stored, transferred, combined, compared, and otherwise manipulated. These signals may be referred to as bits, values, elements, symbols, characters, terms, numbers. These and similar terms may be associated with the appropriate physical quantities and are merely convenient labels applied to these quantities.

Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program which at least partially carries out processes and/or devices described herein, electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components. logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

Various aspects of the subject matter described herein are set out in the following numbered examples:

Example 1

A surgical instrument comprising: a motor configured to drive an end effector between an unarticulated position and an articulated position; a sensor configured to detect an articulation position of the end effector and provide a signal indicative of the articulation position of the end effector; and a control circuit coupled to the sensor and the motor, the control circuit configured to: determine the articulation position of the end effector via the signal provided by the sensor; and provide a drive signal to the motor to articulate the end effector at a velocity corresponding to the signal indicative of the articulation position of the end effector.

Example 2

The surgical instrument of Example 1, wherein the drive signal causes the motor to drive the end effector at a fixed velocity when the articulation position of the end effector is within a designated zone between the unarticulated position and the articulated position.

Example 3

The surgical instrument of Example 2, wherein the designated zone corresponds to a threshold distance from a position between the unarticulated position and the articulated position.

Example 4

The surgical instrument of Example 1 through Example 3, wherein the drive signal varies according to the articulation position of the end effector and the drive signal causes the motor to drive the end effector at a variable velocity according to the articulation position of the end effector.

Example 5

The surgical instrument of Example 1 through Example 4, wherein the drive signal has a variable duty cycle and the duty cycle varies according to the position of the end effector.

Example 6

The surgical instrument of Example 1 through Example 5, wherein the drive signal causes the motor to articulate the end effector at a constant velocity from the unarticulated position to the articulated position.

Example 7

A surgical instrument comprising: an articulation driver configured to drive an end effector that is articulatable between a first position and a second position, the articulation driver configured to drive the end effector from the first position to the second position; a motor coupled to the articulation driver, the motor configured to drive the articulation driver; a sensor configured to detect a position of the articulation driver and provide a signal indicative of the position of the articulation driver; and a control circuit coupled to the motor and the sensor, the control circuit configured to: determine a position of the articulation driver via the signal provided by the sensor; determine an angular position of the end effector according to the signal indicative of the position of the articulation driver; and provide a drive signal to the motor to drive the motor at a velocity corresponding to the angular position of the end effector.

Example 8

The surgical instrument of Example 7, wherein the drive signal causes the motor to drive the end effector at a fixed velocity when the angular position of the end effector is within a designated zone between the first position and the second position.

Example 9

The surgical instrument of Example 8, wherein the designated zone corresponds to a threshold distance from a position between the first position and the second position.

Example 10

The surgical instrument of Example 7 through Example 9, wherein the drive signal varies according to the position of the end effector and the drive signal causes the motor to drive the end effector at a variable velocity according to the position of the end effector.

Example 11

The surgical instrument of Example 7 through Example 10, wherein the drive signal has a variable duty cycle that varies according to the position of the end effector.

Example 12

The surgical instrument of Example 7 through Example 11, wherein the first position is aligned with a longitudinal axis of a shaft.

Example 13

The surgical instrument of Example 7 through Example 12, wherein the first position is a first end of an articulation range of the end effector and the second position is a second end of the articulation range of the end effector.

Example 14

A method of controlling a motor in a surgical instrument, the surgical instrument comprising a motor configured to drive an end effector between an unarticulated position and an articulated position, a sensor configured to detect an articulation position of the end effector and provide a signal indicative of the articulation position of the end effector, and a control circuit coupled to the sensor and the motor, the method comprising: determining, by the control circuit, the articulation position of the end effector via the signal provided by the sensor; and providing, by the control circuit, a drive signal to the motor to articulate the end effector at a velocity corresponding to the signal indicative of the articulation position of the end effector.

Example 15

The method of Example 14, driving, by the control circuit, the motor at a fixed velocity when the articulation position of the end effector is within a designated zone between the unarticulated position and the articulated position.

Example 16

The surgical instrument of Example 15, wherein the designated zone corresponds to a threshold distance from a position between the first position and the second position.

Example 17

The method of Example 14 through Example 16, driving, by the control circuit, the motor at a variable voltage according to the articulation position of the end effector.

Example 18

The method of Example 14 through Example 17, driving, by the control circuit, the motor at a variable duty cycle according to the articulation position of the end effector.

Example 19

The method of Example 14 through Example 18, driving, by the control circuit, the motor at a constant velocity from the first position to the second position.

The invention claimed is:

1. A surgical instrument comprising:

an articulation driver configured to drive an end effector that is articulatable between a first position and a second position, the articulation driver configured to drive the end effector from the first position to the second position;

a shaft assembly coupled to the end effector, wherein an end effector axis of the end effector is coaxially aligned or parallel with a shaft axis of the shaft assembly when the end effector is in the first position, and wherein the end effector axis intersects the shaft axis at a predetermined angle when the end effector is in the second position;

a motor coupled to the articulation driver, the motor configured to drive the articulation driver;

a sensor configured to detect a position of the articulation driver and provide a signal indicative of the position of the articulation driver during an articulation actuation motion; and a control circuit coupled to the motor and the sensor, the control circuit configured to:

determine a position of the articulation driver via the signal provided by the sensor;

determine an articulation angle of the end effector according to the signal indicative of the position of the articulation driver, wherein the articulation angle is an angle defined by the end effector axis and the shaft axis;

provide a drive signal to the motor during the articulation actuation motion to automatically drive the motor at a velocity corresponding to the determined articulation angle of the end effector to articulate the end effector at an articulation velocity corresponding to the determined articulation angle of the end effector; and automatically adjust the drive signal to adjust the articulation velocity of the end effector according to the articulation angle of the end effector.

2. The surgical instrument of claim 1, wherein the drive signal causes the motor to drive the end effector at a fixed articulation velocity when the determined articulation angle of the end effector is within a designated zone between the first position and the second position.

3. The surgical instrument of claim 2, wherein the designated zone corresponds to a threshold distance from a position between the first position and the second position.

4. The surgical instrument of claim 1, wherein the drive signal varies according to the position of the end effector and the drive signal causes the motor to drive the end effector at a variable articulation velocity according to the determined articulation angle of the end effector.

5. The surgical instrument of claim 1, wherein the drive signal has a variable duty cycle that varies according to the determined articulation angle of the end effector.

6. The surgical instrument of claim 1, wherein the end effector is further articulatable between the first position and a third position, wherein the articulation driver is configured to drive the end effector from the second position to the third position, and wherein the second position is a first end of an articulation range of the end effector and the third position is a second end of the articulation range of the end effector.

7. A surgical instrument, comprising:

a shaft;

an articulation joint; and an end effector attached to said shaft by way of said articulation joint, wherein said end effector is configured to be articulated between a plurality of angular positions, wherein said plurality of angular positions comprises an articulated position and a straight position, wherein an end effector axis of the end effector is coaxially aligned or parallel with a longitudinal axis of the shaft when the end effector is in the straight position, and wherein the end effector axis intersects the longitudinal axis of the shaft when the end effector is in the articulated position;

an articulation driver extending through said shaft to said articulation joint, wherein said articulation driver is actuatable to articulate said end effector between said articulated position and said straight position;

a motor coupled to the articulation driver;

a sensor configured to detect a position of the articulation driver and configured to provide a signal indicative of the position of the articulation driver during an articulation actuation motion; and a control circuit coupled to the motor and the sensor, wherein the control circuit is configured to:

receive the signal provided by the sensor;

determine the position of the articulation driver based on the received signal;

determine an articulation angle of the end effector based on the determined position of the articulation driver, wherein the articulation angle is an angle defined by the end effector axis and the longitudinal axis of the shaft;

provide a drive signal to the motor to articulate the end effector at an articulation velocity corresponding to the determined articulation angle of the end effector to adjust the articulation actuation motion of the end effector; and automatically adjust the drive signal to adjust the articulation velocity of the end effector according to the articulation angle of the end effector.

8. The surgical instrument of claim 7, wherein the drive signal causes the motor to articulate the end effector about said articulation joint at a fixed articulation velocity when the determined articulation angle of the end effector is within a designated zone between the articulated position and the straight position.

9. A surgical instrument, comprising:

a shaft;

an articulation joint; and an end effector attached to said shaft by way of said articulation joint, wherein said end effector is configured to be articulated relative to said shaft between a plurality of angular positions, wherein said plurality of angular positions comprises an articulated position and a non-articulated position, wherein an end effector axis of the end effector is coaxially aligned or parallel with a longitudinal axis of the shaft when the end effector is in the non-articulated position, and wherein the end effector axis intersects the longitudinal axis of the shaft when the end effector is in the articulated position;

an articulation drive member actuatable to articulate said end effector between said plurality of angular positions;

a motor coupled to the articulation drive member;

a sensor configured to detect a linear position of the articulation drive member and configured to provide a signal indicative of the linear position of the articulation drive member during an articulation actuation motion; and a control circuit coupled to the motor and the sensor, wherein the control circuit is configured to:

receive the signal provided by the sensor;

determine the linear position of the articulation drive member based on the received signal;

determine an articulation angle of the end effector based on the determined linear position of the articulation drive member, wherein the articulation angle is an angle defined by the end effector axis and the longitudinal axis of the shaft;

provide a drive signal to the motor to actuate the articulation drive member at a velocity corresponding to the determined articulation angle of the end effector to automatically adjust the articulation actuation motion of the end effector; and automatically adjust the drive signal to adjust an articulation velocity of the end effector according to the articulation angle of the end effector.

10. The surgical instrument of claim 9, wherein the drive signal causes the motor to articulate the end effector about said articulation joint at a fixed articulation velocity when the determined articulation angle of the end effector is within a designated zone between the articulated position and the straight position.

* * * * *